US009120081B2

(12) United States Patent
Liu et al.

(10) Patent No.: US 9,120,081 B2
(45) Date of Patent: Sep. 1, 2015

(54) TRANSITION METAL-CONTAINING CATALYSTS AND PROCESSES FOR THEIR PREPARATION AND USE AS OXIDATION AND DEHYDROGENATION CATALYSTS

(71) Applicant: Monsanto Technology LLC, St. Louis, MO (US)

(72) Inventors: Fuchen Liu, Ballwin, MO (US); Juan Arhancet, Creve Coeur, MO (US); James P. Coleman, Maryland Heights, MO (US); Martin P. McGrath, North Andover, MA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/190,989

(22) Filed: Feb. 26, 2014

(65) Prior Publication Data

US 2014/0235432 A1    Aug. 21, 2014

Related U.S. Application Data

(63) Continuation of application No. 13/049,496, filed on Mar. 16, 2011, now Pat. No. 8,697,904, which is a continuation of application No. 10/919,028, filed on Aug. 16, 2004, now Pat. No. 7,932,419.

(60) Provisional application No. 60/495,481, filed on Aug. 14, 2003.

(51) Int. Cl.

| | |
|---|---|
| *B01J 27/22* | (2006.01) |
| *B01J 27/24* | (2006.01) |
| *B01J 21/18* | (2006.01) |
| *B01J 35/02* | (2006.01) |
| *B01J 35/10* | (2006.01) |
| *B01J 37/08* | (2006.01) |
| *B82Y 30/00* | (2011.01) |
| *C07C 209/68* | (2006.01) |
| *C07C 249/02* | (2006.01) |
| *C07F 9/38* | (2006.01) |
| *B01J 23/40* | (2006.01) |
| *B01J 23/72* | (2006.01) |

(52) U.S. Cl.
CPC ........ *B01J 27/24* (2013.01); *B01J 21/18* (2013.01); *B01J 27/22* (2013.01); *B01J 35/023* (2013.01); *B01J 35/1023* (2013.01); *B01J 35/1028* (2013.01); *B01J 37/084* (2013.01); *B82Y 30/00* (2013.01); *C07C 209/68* (2013.01); *C07C 249/02* (2013.01); *C07F 9/3813* (2013.01); *B01J 23/40* (2013.01); *B01J 23/72* (2013.01)

(58) Field of Classification Search
CPC .................. B01J 27/24; C07C 2527/22
USPC ................................................. 502/177
See application file for complete search history.

(56) References Cited

U.S. PATENT DOCUMENTS

| | | |
|---|---|---|
| 2,384,817 A | 9/1945 | Chitwood |
| 3,143,511 A | 8/1964 | Bichard et al. |
| 3,799,758 A | 3/1974 | Franz |
| 3,871,998 A | 3/1975 | Rase et al. |
| 3,950,402 A | 4/1976 | Franz |
| 3,969,398 A | 7/1976 | Hershman |
| 4,264,776 A | 4/1981 | Hershman et al. |
| 4,325,842 A | 4/1982 | Slaugh et al. |
| 4,325,843 A | 4/1982 | Slaugh et al. |
| 4,326,992 A | 4/1982 | Slaugh et al. |
| 4,333,916 A | 6/1982 | Iwai et al. |
| 4,345,038 A | 8/1982 | McCandlish et al. |
| 4,476,102 A | 10/1984 | McCandlish et al. |
| 4,522,708 A | 6/1985 | Leclercq et al. |
| 4,579,689 A | 4/1986 | Hershman et al. |
| 4,582,650 A | 4/1986 | Felthouse |
| 4,624,937 A | 11/1986 | Chou |
| 4,696,772 A | 9/1987 | Chou |
| 4,775,498 A | 10/1988 | Gentilcore |
| 4,782,183 A | 11/1988 | Goto et al. |
| 4,853,159 A | 8/1989 | Riley et al. |
| 4,895,680 A | 1/1990 | Ellis, Jr. et al. |
| 5,023,369 A | 6/1991 | Fields, Jr. |
| 5,043,475 A | 8/1991 | Fields, Jr. |

(Continued)

FOREIGN PATENT DOCUMENTS

| | | |
|---|---|---|
| CN | 1349478 | 5/2005 |
| DE | 4336829 A1 | 5/1995 |

(Continued)

OTHER PUBLICATIONS

Markusse, A.P., et al., "Platinum Deactivation: in situ EXAFS During Aqueous Alcohol Oxidation Reaction," 1998, Catalysts Letters, 1998, pp. 141-145.

Mehn, D., et al., "A Comparison of Different Preparation Methods of Fe/Mo/Al2O3 Sol-Gel Catalyst for Synthesis of Single Wall Carbon Nanotubes," 2004, Chemical Physics Letters, 393:378-384.

Mordenti, D., et al., "New Synthesis of Mo2 14 nm in Average Size Supported on a High Specific Surface Area Carbon Material," 1998, Journal of Solid State Chemistry, 141:114-120.

Milad, I.K., et al., "A Comparison of Bulk Metal Nitride Catalysts for Pyridine Hydrodenitrogenation," 1998, Catalysis Letters, 52(1-2):113-119.

(Continued)

*Primary Examiner* — Porfirio Nazario Gonzalez
*Assistant Examiner* — Kofi Adzamli
(74) *Attorney, Agent, or Firm* — Senniger Powers LLP; Joseph A. Schaper

(57) ABSTRACT

This invention relates to the field of heterogeneous catalysis, and more particularly to catalysts including carbon supports having formed thereon compositions which comprise a transition metal in combination with nitrogen and/or carbon. The invention further relates to the fields of catalytic oxidation and dehydrogenation reactions, including the preparation of secondary amines by the catalytic oxidation of tertiary amines and the preparation of carboxylic acids by the catalytic dehydrogenation of alcohols.

21 Claims, 30 Drawing Sheets

(56) References Cited

U.S. PATENT DOCUMENTS

| | | |
|---|---|---|
| 5,138,111 A | 8/1992 | Kugler et al. |
| 5,179,228 A | 1/1993 | Martin Ramon et al. |
| 5,292,936 A | 3/1994 | Franczyk |
| 5,338,716 A | 8/1994 | Triplett et al. |
| 5,367,112 A | 11/1994 | Franczyk |
| 5,372,981 A | 12/1994 | Witherspoon |
| 5,427,761 A | 6/1995 | Grindatto et al. |
| 5,606,107 A | 2/1997 | Smith |
| 5,627,125 A | 5/1997 | Ebner et al. |
| 5,739,390 A | 4/1998 | Franczyk et al. |
| 5,989,648 A | 11/1999 | Phillips |
| 6,005,140 A | 12/1999 | Morgenstern et al. |
| 6,169,152 B1 | 1/2001 | Sakai |
| 6,265,339 B1 | 7/2001 | Bidell et al. |
| 6,329,478 B1 | 12/2001 | Katayama et al. |
| 6,376,708 B1 | 4/2002 | Morgenstern et al. |
| 6,417,133 B1 | 7/2002 | Ebner et al. |
| 6,436,816 B1 | 8/2002 | Lee et al. |
| 6,528,680 B1 | 3/2003 | Aust et al. |
| 6,586,621 B2 | 7/2003 | Leiber et al. |
| 6,603,039 B1 | 8/2003 | Ebner et al. |
| 6,632,770 B2 | 10/2003 | Holtcamp |
| 6,683,018 B1 | 1/2004 | Kristen et al. |
| 6,689,711 B2 | 2/2004 | Lefebvre |
| 6,696,384 B2 | 2/2004 | McCrae et al. |
| 6,706,662 B2 | 3/2004 | Morgenstern et al. |
| 6,764,874 B1 | 7/2004 | Zhang et al. |
| 6,808,746 B1 | 10/2004 | Dai et al. |
| 6,963,009 B2 | 11/2005 | Leiber et al. |
| 7,129,373 B2 | 10/2006 | Coleman et al. |
| 7,291,751 B2 | 11/2007 | Leiber et al. |
| 2002/0068836 A1 | 6/2002 | Haupfear et al. |
| 2002/0121460 A1 | 9/2002 | Moy et al. |
| 2003/0008772 A1* | 1/2003 | Ma et al. ............... 502/180 |
| 2003/0228972 A1 | 12/2003 | Birss et al. |

FOREIGN PATENT DOCUMENTS

| | | |
|---|---|---|
| EP | 0439445 A1 | 7/1991 |
| EP | 1236509 A1 | 9/2002 |
| FR | 2798079 A1 | 3/2001 |
| FR | 2798135 A1 | 3/2001 |
| WO | 9532150 A1 | 11/1995 |
| WO | 0062926 A1 | 10/2000 |
| WO | 0063115 | 10/2000 |
| WO | 0128679 A1 | 4/2001 |
| WO | 0146208 A2 | 6/2001 |
| WO | 0177052 A1 | 10/2001 |
| WO | 02098557 A1 | 12/2002 |
| WO | 03068387 A1 | 8/2003 |
| WO | WO 03068387 A1 * | 8/2003 |
| WO | 2005080269 A2 | 9/2005 |

OTHER PUBLICATIONS

Mukerjee, S., et al., "An In Situ X-Ray Absorption Spectroscopy Investigation of the Effect of Sn Additions to Carbon-Supported Pt Electrocatalysts," 1999, Journal of the Electrochemical Society, 146/2:600-606.

Murav'ev, V. I., "Carbonitriding in a Fluidized Bed of Carbon-Graphite Materials," 1976, Metal Science and Heat Treatment, 1976, 18/5-6:492-495.

Nagai, M., et al., "Catalytic Activity and Surface Properties of Nitride Molybdena-Alumina for Carbazole Hydrodenitrogenation," 2000, J Catal, 191:128-137.

Nishihara, H., et al., "Electrochemical Olefin Epoxidation with Manganese meso-Tetraphenylporphyrin Catalyst and Hydrogen Peroxide Generation at Polymer-Coated Electrodes," 1990, Inorganic Chemistry, 29/5:1000-1006.

Nhut, J.M., et al., "Synthesis and Catalytic Uses of Carbon and Silicon Carbide Nanostructures," 2002, Catalysis Today, 76:11-32.

Ohta, R., et al., "Origin of N 1s Spectrum in Amorphous Carbon Nitride Obtained by X-Ray Photoelectron Spectroscopy," 2003, Thin Solid Films, 434:296-302.

Okada, T., et al., "Oxygen Reduction Characteristics of Graphite Electrodes Modified with Cobalt Di-Quinolyldiamine Derivatives ," 2000, Electrochimica Acta, 2000, 45:4419-4428.

Okada, T., et al., "Oxygen Reduction Characteristics of Heat-Treated Catalysts Based on Cobalt-Porphyrin Ion Complexes," 1998, J. Electrochem. Soc.,145/3:815-822.

Oyama, S.T., "Preparation and Catalytic Properties of Transition Metal Carbides and Nitrides," 1992, Catalysis Today, 15:179-200.

Oyama, S.T., et al., "Preparation and Characterization of Early Transition-Metal Carbides and Nitrides," 1988, Industrial & Engineering Chemistry Research, 27/9:1639-1648.

Pinel, C., et al., "Effect of the Nature of Carbon Catalysts on Glyphosate Synthesis," 1999, Academic Press, pp. 515-519.

Sedunov, V. K., et al., "Structure and Phase Composition of Surface Zones of Carburized and Carbonitrided Layers," 1977, Metal Science and Heat Treatment, 1977, 19/9-10:742-745.

Singh, A., et al., "X-Ray Photoelectron Spectroscopy of Nitrogen-Implanted Cemented Tungsten Carbide (WC-Co)," 1990, J Mat Sci Ltrs, 9:1101-1102.

Soto, G., et al., "XPS, AES, and EELS Characterization of Nitrogen-Containing Thin Films," 2004, J Elect Spectro Related Phenomena,135:27-39.

Takano, I., et al., "Nitrogenation of Various Transition Metals by N2+-Ion Implantation," 1989, Applied Surface Science, 37:25-32.

Tang, C., et al., "Synthesis and Field Emission of Carbon Nanotubular Fibers Doped with High Nitrogen Content," 2003, Chem Commun., pp. 3050-3051.

Tavadyan, L., et al., "Catalysis of the Liquid-Phase Oxidation of Organic Compounds by Metal-Complex Compounds of Nitrogen-Containing Carbon: III. Oxidation of Benzaldehyde," 1997, Kinetics and Catalysis, 38/3:375-380.

Toda, T., et al., "Enhancement of the Electroreduction of Oxygen on Pt Alloys with Fe, Ni, and Co," 1999, Journal of the Electrochemical Society, 146/10:3750-3756, vol. 146, No. 10.

Torrens, Manuel A., "Mossbauer Studies on Oxo-Bridged Iron (III) Porphines," 1972, Journal of the Am Chem Soc, 94/12:4160-4162.

Van Der Putten, A., et al., "Oxygen Reduction on Pyrolysed Carbon-Supported Transition Metal Chelates," 1986, J Electroanalyl Chem Interfacial Electrochem, 205:233-244.

Van Veen, J.A.R., et al., "On the Effect of a Heat Treatment on the Structure of Carbon-Supported Metalloporphyrins and Phthalocyanines," 1988, Electrochimica Acta, 33/6:801-804.

Van Veen, J.A.R., et al., "Effect of Heat Treatment on the Performance of Carbon-supported Transition-metal Chelates in the Electrochemical Reduction of Oxygen," 1981, J. Chem Soc., Faraday Trans. 1, 77:2827-2843.

Wang, H., et al., "Effect of the Pre-Treatment of Carbon Black Supports on the Activity of Fe-Based Electocatalysts for the Reduction of Oxygen," 1999, Journal of Physical Chemistry B, 1999, 103:2042-2049.

Weng, L. T., et al., Characterization of Electrocatalysts for Oxygen Reduction by TOF SIMS, Secondary Ion Mass Spectrometry, Proceedings of the International Conference on Secondary Ion Mass Spectrometry, 9th, Yokohama, Nov. 7-12, 1994, pp. 442-445.

Weng, L.T., et al., "Surface Characterization by Time-of-Flight SIMS of a Catalyst for Oxygen Electroreduction: Pyrolyzed Cobalt Phthalocyanine-on-Carbon Black," 1995, Applied Surface Science, 84:9-21.

Applicants' Supplemental Information Disclosure Statement filed in U.S. Appl. No. 10/919,028, filed Aug. 6, 2005, 6 pages.

Applicants' Fourth Supplemental Information Disclosure Statement filed in U.S. Appl. No. 10/919,028, filed May 29, 2007, 2 pages.

Applicants' Sixth Supplemental Information Disclosure Statement filed in U.S. Appl. No. 10/919,028, filed Nov. 29, 2007, 18 pages; discussing inventorship issues, sequence of development of claimed subject matter, and related statutory prior art issues under 35 U.S.C. 102(a), 102(b), 102(e), and 102(g) (pp. 1-18).

Applicants' Seventh Supplemental Information Disclosure Statement filed in U.S. Appl. No. 10/919,028, filed Nov. 29, 2007, 3 pages.

Applicants' Supplemental Information Disclosure Statement filed in U.S. Appl. No. 10/919,028, filed Dec. 4, 2008, 2 pages.

Applicants' Supplemental Information Disclosure Statement filed in U.S. Appl. No. 10/919,028, filed Oct. 30, 2009, 2 pages.

(56) References Cited

OTHER PUBLICATIONS

Non-final Office action issued in U.S. Appl. No. 12/124,497, dated Dec. 26, 2008.
Final Office action issued in U.S. Appl. No. 11/274,555, dated May 12, 2009.
Non-final Office action issued in U.S. Appl. No. 10/366,947, dated May 14, 2004, 17 pages.
Amendment B submitted Oct. 14, 2004, in U.S. Appl. No. 10/366,947, in response to the Office action dated May 14, 2004, 11 pages.
Final Office action issued in U.S. Appl. No. 10/366,947, dated Jan. 24, 2005, 7 pages.
Amendment C submitted May 24, 2005, in U.S. Appl. No. 10/366,947, in response to the Office action dated Jan. 24, 2005, 28 pages.
Non-Final Office Action issued in U.S. Appl. No. 10/923,416, dated Jun. 25, 2007, 15 pages.
Amendment B submitted Nov. 29, 2007 in U.S. Appl. No. 10/923,416, in response to Office action dated Jun. 25, 2007, 18 pages.
Notice of Allowance dated Feb. 4, 2008 in connection with U.S. Appl. No. 10/923,416.
Supplemental Notice of Allowance dated Mar. 5, 2008 in connection with U.S. Appl. No. 10/923,416.
Supplemental Notice of Allowance dated Mar. 18, 2008 in connection with U.S. Appl. No. 10/923,416.
Supplemental Notice of Allowance dated May 19, 2008 in connection with U.S. Appl. No. 10/923,416.
Non-final Office action issued in U.S. Appl. No. 11/274,555, dated Oct. 29, 2008, 9 pages.
Final Office action issued in U.S. Appl. No. 11/274,555, dated May 12, 2009, 16 pages.
Non-Final Office action issued in U.S. Appl. No. 12/124,497, dated Dec. 26, 2008, 41 pages.
Parton R. D. et al., "Iron-Phthalocyanine Immobilized on Activated Carbon Black: A Selective Catalyst for Alkane Oxidation", Journal of Catalysis, 164, 1996, pp. 341-346.
Gojkovic S.Lj et al., "Heat-treated iron(III) tetramethoxyphenyl porphyrin chloride supported on high-area carbon as an electrocatalyst for oxygen reduction Part II. Kinetics of oxygen reduction", Journal of Electroanalytical Chemistry, 462, pp. 63-72, 1999.
Office Action dated Mar. 11, 2014, U.S. Appl. No. 13/450,909, 42 pages.
Alvarez-Merino, M., et al., "Tungsten Catalysis supported on Activated Carbon," 2000, J Catal, 192:363-373.
Allum, K.G., et al., "Supported Transition Metal Complexes IV. Rhodium Catalysts for the Liquid Phase Hydroformylation of Hexene-1," 1976, J Catal, 43:322-330.
Allum, K.G., et al., "Supported Transition Metal Complexes V. Liquid Phase Catalytic Hydrogenation of Hexene-1; Cyclohexene and Isoprene under Continuous Flow Conditions," 1976, J Catal, 43:331-338.
Alves, M.C. Martin, et al., "Characterization of New Systems for the Catalytic Electroreduction of Oxygen by Electrochemistry and X-Ray Absorption Spectroscopy," 1994, NATO ASI Series, Series C: Mathematical and Physical Sciences, Synchrotron Techniques in Interfacial Electrochemistry, 432:281-293.
Arana, C., et al., "Electrocatalytic Reduction of Carbon Dioxide with Iron, Cobalt, and Nickel Complexes of Terdentate Ligands," 1992, Inorg Chem, 31:3680-3682.
Berger, R., et al., "Magnetic Resonance of Superparamagnetic Iron-Containing Nanoparticles in Annealed Glass," 2000, J App Phys, 87/10:7389-7396.
Bett, J.S., et al., "Platinum-macrocycle co-catalysts for the Electrochemical Oxidation of Methanol ," 1998, Electrochimica Acta, 43/24:3645-3655.
Birss, V.I., et al., "Non-Noble Metal Catalysts for PEM Oxygen Reduction Based on Sol Gel Derived Cobalt Nigrogen Compounds," 2002, Electrochemical Society Proceedings, 2002-31:89-98.
Bouwkamp-Wijnoltz, A.L., et al., "On Active-Site Heterogeneity in Pyrolyzed Carbon-Supported Iron Porphyrin Catalysts for the Electrochemical Reduction of Oxygen: An In Situ Mossbauer Study," 2002, J Phys Chem, 106/50:12993-13001.
Bouwkamp-Wijnoltz, A.L., et al., "Electrochemical Reduction of Oxygen: An Alternative Method to Prepare Active CoN4 Catalysts," 1999, Electrochimica Acta., 45:379-386.
Bridgewater, A.J., et al., "Reactions of Carbon Monoxide with Hydrogen Over Molybdenum/Charcoal Catalysts," 1982, J Catal, 78:116-125.
Brunetta, A., et al., "Epoxidation Versus Baeyer—Villiger Oxidation: The Possible Role of Lewis Acidity in the Control of Selectivity in Catalysis by Transition Metal Complexes," 2004, Eur J Inorg Chem, 2004, pp. 1030-1038.
Collman, J.P., et al., "Electrode Catalysis of the Four-Electron Reduction of Oxygen to Water by Dicobalt Face-to-Face Porphyrins," 1980, J Amer Chem Soc, 102:6027-6036.
Cote, R., et al., "Non-Noble Metal-Based Catalysts for the Reduction of Oxygen in Polymer Electrolyte Fuel Cells," 1998, Journal of New Materials for Electrochemical Systems I, pp. 7-16.
Dandekar A., et al., "Carbon-Supported Copper Catalysts," 1999, J Catal, 183:131-154.
Deng, C.Z., et al., "Sputtered Cobalt—Carbon—Nitrogen Thin Films as Oxygen Reduction Electrocatalysts ," 1998, J. Electrochem. Soc., 145/10:3507-3512.
Dignard-Bailey, L. et al., "Graphitization and Particle Size Analysis of Pyrolyzed Cobalt Phthalocyanine/Carbon Catalysts for Oxygen Reduction in Fuel Cells," 1994, J of Mat Res, 9/12:3203-3209.
Durand, Richard R., et al., "Catalysis of Dioxygen Reduction at Graphite Electrodes by an Adsorbed Cobalt(II) Porphyrin," 1982, J Electroanaly Chem, 134(2):273-289.
Ewen, Richard J., et al., "X-Ray Photoelectron Spectroscopy of Clean and Gas-Doped Films of Phthalocyanines," 1991, J Physic Cond Mat, 3:S303-S310.
Faubert, G., et al., "Oxygen Reduction Catalysts for Polymer Electrolyte Fuel Cells from the Pyrolysis of FeII Acetate Absorbed on 3,4,9,10-Perylenetetracarboxylic Dianhydride," 1999, Electrochimica Acta, 44:2589-2603.
Faubert, G., et al., "Iron Catalysts Prepared by High-Temperature Pyrolysis of Tetraphenylporphyrins Adsorbed on Carbon Black for Oxygen Reduction in Polymer Electrolyte Fuel Cells," 1998, Electrochimica Acta., 43/3-4:341-353.
Faubert, G., et al., "Activation and Characterization of Fe-Based Catalysts for the Reduction of Oxygen in Polymer Electrolyte Fuel Cells," 1998, Electrochimica Acta., 43/14-15:1969-1984.
Faubert, G., et al., "Heat-Treated Iron and Cobalt Tetraphenylporphyrins Adsorbed on Carbon Black: Physical Characterization and Catalytic Properties of these Materials for the Reduction of Oxygen in Polymer Electrolyte Fuel Cells," 1996, Electrochimica Acta, 41/10:1689-1701.
Fournier, J., et al., "Activation of Various Fe-Based Precursors on Carbon Black and Graphite Supports to Obtain Catalysts for the Reduction of Oxygen in Fuel Cells," 1997, J Electrochem So., 144/1:218-226.
Franz, J. E., et al., "Glyphosate: A Unique Global Herbicide, Chapter 8—Methods of Preparing Glyphosate," 1997, Am Chem Soc, pp. 233-262.
Frostin-Rio, M., et al., "Oxidation of Phenols by Molecular Oxygen Catalysed by Transition Metal Complexes. Comparison between the Activity of various Cobalt and Manganese Complexes and the Role of Peroxy Intermediates," 1984, J Chem Soc Perkin Trans, 1:1971-1979.
Glerup, M., et al., "Synthesis of Highly Nitrogen-Doped Multi-Walled Carbon Nanotubes," 2003, Chem Comm, pp. 2542-2543.
Granger, P., et al., "Kinetics of the No and Co Reaction Over Platinum Catalysts," 1998, J Catal, pp. 304-314.
Gupta, S., et al., "Methanol-Tolerant Electrocatalysts for Oxygen Reduction in a Polymer Electrolyte Membrane Fuel Cell," 1998, J Appl Electrochem, 28/7:673-682.
He, P., et al., "Oxygen Reduction Catalysts for Polymer Electrolyte Fuel Cells From the Pyrolysis of Various Transition Metal Acetates Adsorbed on 3,4,9,10-Perylenetetracarboxylic Dianhydride," 1999, Journal of New Material for Electrochemical Systems, 2:243-251.

(56) References Cited

OTHER PUBLICATIONS

Hesse, D., et al., "Advantages and Problems in the Use of Transition-Metal Complexes as SLPC," 1985, Annual AlChE Meeting, Session 114, pp. 1-8.
Hirai, T., et al., "The Influence of Catalyst-Supporting Methods on Electrochemical Activity and the Resultant Stability of Air Electrodes Activated with Iron Pythalocyanine," 1985, J Appl Electrochem, pp. 441-445.
Jasinski, R., "Cobalt Phthalocyanine as a Fuel Cell Cathode," 1965, J Electrochem Soc, 112/5):526-528.
Kalvelage H., et al., "Electrochemical Reduction of Oxygen at Pyrolyzed Iron and Cobalt N4-Chelates on Carbon Black Supports," 2000, Chem Eng Techno, 2000, 23:803-807.
Kim, D-W., et al., "CoMo Bimetallic Nitride Catalysts for Thiophene HDS," 1997, Catalysis Letters, 43/1-2:91-95.
Kimbara, N., et al., "New Type of TiN Support for Hydroprocessing Catalyst Yst.," 1990, Catal Lett, 6:3-6.
Lalande, G., et al., "Chromium-Based Electrocatalysts for Oxygen Reduction in Polymer Electrolyte Fuel Cells, New Materials for Fuel Cell and Modern Battery Systems II," Jul. 6-10, 1997, Proceedings of the International Symposium on New Materials for Fuel Cell and Modern Battery Systems, 2nd Montreal, pp. 768-777.
Lalande, G., et al., "Electroreduction of Oxygen in Polymer Electrolyte Fuel Cells by Activated Carbon Coated Cobalt Nanocrystallites Produced by Electric Arc Discharge," 1997, Chem Mat, 9/3:784-790.
Lalande, G. et al., "Is Nitrogen Important in the Formulation of Fe-based Catalysts for Oxygen Reduction in Solid Polymer Fuel Cells? ," 1997, Electrochimica Acta., 42/9:1379-1388.
Lalande, G., et al., "Catalytic Activity and Stability of Heat-Treated Iron Phthalocyanines for the Electroreduction of Oxygen in Polymer Electrolyte Fuel Cells," 1996, J Power Sources, 61:227-237.
Lalande, G., et al., "Rotating Disk Electrode Measurements on the Electrocatalytic Activity of Heat-Treated Carbon Supported Cobalt Phthalocyanine Catalysts for Oxygen Reduction," 1994, Electrochemical Society Proceedings, pp. 418-429.
Lefévre, M., et al., "Molecular Oxygen Reduction in PEM Fuel Cells: Evidence for the Simultaneous Presence of Two Active Sites in Fe-Based Catalysts," 2002, Journal of Physical Chemistry, 106/34:8705-8713.
Lefévre, M., et al., "O2 Reduction in PEM Fuel Cells: Activity and Active Site Structural Information for Catalysts Obtained by the Pyrolysis at High Temperature of Fe Precursors," 2000, Journal of Physical Chemistry B, 104:11238-11247.
Lefévre, M., et al., "Functionalities of a Fe-Based Catalyst Evidenced by ToF-SIMS in Relation with the Electroreduction of Oxygen in Polymer Electrolyte Fuel Cells," Secondary Ion Mass Spectrometry, SIMS XII, Proceedings of the International Conference on Secondary Ion Mass Spectrometry, 1999, pp. 447-450.
Levy, R. B., et al., "Platinum-Like Behavior of Tungsten Carbide in Surface Catalysis," 1973, Science, 181:547-549.
Liang, C., et al., "Activated Carbon Supported Bimetallic CoMo Carbides Synthesized by Carbothermal Hydrogen Reduction," 2003, Carbon, 41:1833-1839.
Lin, C. A., et al., "Characterization of Boron—Nitride-Supported Pt Catalysts for the Deep Oxidation of Benzene," 2002, J Catal, 210:39-45.
Lin, W.-F., et al., "On-Line FTIR Spectroscopic Investigations of Methanol Oxidation in a Direct Methanol Fuel Cell," 1997, J. Electrochem. Soc., 144/6:1917-1922.
Liu et al., "Advances in CNx Nanotube Growth," 2003, Mat. Res. Soc. Symp. Proc., 772:M2.5.1-M2.5.7.
Marcotte, S., et al., "Electroreduction of Oxygen on Co-based Catalysts: Determination of the Parameters Affecting the Two-Electron Transfer Reaction in an Acid Medium," 2004, Electrochimica Acta, 50(1):179-188.
International Search Report issued in International Application No. PCT/US03/04578, dated Jun. 30, 2003, 3 pages.
Written Opinion issued in International Application No. PCT/US03/04578, dated Dec. 4, 2003, 9 pages.
International Preliminary Examination Report issued in International Application No. PCT/US03/04578, dated May 19, 2004, 18 pages.
International Search Report and Written Opinion issued in International Application No. PCT/US2004/026550, dated Jan. 24, 2005, 31 pages.
International Preliminary Report on Patentability issued in International Application No. PCT/US2004/026550, dated Nov. 18, 2005, 21 pages.
Non-Final Office Action issued in U.S. Appl. No. 11/357,900, dated Jun. 9, 2011, 7 pages.

\* cited by examiner

Cu + Mo

Cu

Mo

TRANSITION METAL-CONTAINING CATALYSTS AND PROCESSES FOR THEIR PREPARATION AND USE AS OXIDATION AND DEHYDROGENATION CATALYSTS

REFERENCE TO RELATED APPLICATION

This application is a continuation of U.S. patent application Ser. No. 13/049,496, filed Mar. 16, 2011, which issued Apr. 15, 2014 as U.S. Pat. No. 8,697,904 and which is a continuation of U.S. patent application No. 10/919,028 filed Aug. 16, 2004, which issued as U.S. Pat. No. 7,932,419 on Apr. 26, 2011 and which claims priority from U.S. Provisional Application Ser. No. 60/495,481 filed Aug. 14, 2003, the entire contents of which are incorporated herein by reference.

FIELD OF INVENTION

This invention relates to the field of heterogeneous catalysis, and more particularly to catalysts including carbon supports having formed thereon compositions which comprise a transition metal in combination with nitrogen and/or carbon. The invention further relates to the fields of catalytic oxidation and dehydrogenation reactions, including the preparation of secondary amines by the catalytic oxidation of tertiary amines and the preparation of carboxylic acids by the catalytic dehydrogenation of alcohols.

BACKGROUND OF INVENTION

Investigations to discover alternative materials for use in catalysis concerning various types of reactions have included evaluation of the suitability of carbide and nitride materials. Generally, carbide and nitride materials have been considered as possible alternatives for use in various types of catalysis since they exhibit "metal-like" properties (e.g., high melting points, hardness and strength). Levy & Boudart report that carbide and nitride materials exhibit catalytic properties similar to those of noble metals. See *Platinum-Like Behavior of Tungsten Carbide in Surface Catalysis* (Science, 181 (1973), 547-549).

Supported carbide and nitride catalysts have been described generally and reported as suitable for use in various types of reactions. Slaugh et al. describe a supported molybdenum carbide composition prepared by impregnating hexamolybdenum dodecachloride onto a porous aluminous (e.g., $Al_2O_3$), siliceous or carbonaceous (e.g., active carbon) support which is then heated in a carbiding atmosphere at a temperature of about 650° C. to about 750° C. See U.S. Pat. No. 4,325,842.

Leclercq et al. report a catalytic reforming process employing catalysts based on tungsten and molybdenum carbides supported on alumina and active carbon. See U.S. Pat. No. 4,522,708. These catalysts are prepared by successive impregnations of active carbon using ammonium molybdate and ammonium tungstate solutions which are evaporated to dryness in air, calcined in a nitrogen atmosphere which is followed by reduction of the tungsten and molybdenum oxides formed during calcination under a hydrogen atmosphere. These compounds are then heated under hydrogen to allow the active phase compounds to react with the carbon support to produce mixed carbides of tungsten and molybdenum.

Sherif et al. report carbon-supported Group VIB metal (e.g., Cr, Mo, W) carbide-containing catalysts formed by calcining a carbon support (e.g., activated carbon and acid washed activated carbon) which has been impregnated with a water-soluble precursor for the metal carbide. See International Publication No. WO 95/32150.

Oyama reports interstitial alloys formed by the incorporation of carbon, nitrogen, and oxygen into the lattices of early transition metals to produce a class of compounds with metallic character. See *Preparation and Catalytic Properties of Transition Metal Carbides and Nitrides* (Catalysis Today, 15, 179-200. 1992)

Iwai et al. report carbonitrides consisting of a carbide and nitride of the metals of Groups IV, V, and VI prepared by calcining a precursor obtained by reacting polyphenol with the reaction product of ammonia and the halide of a Group IV, V, or VI metal. The precursor may also be obtained by reacting the reaction product of polyphenol and the halide of a Group IV, V, or VI metal with ammonia. See U.S. Pat. No. 4,333,916.

Faubert et al. report on methods for preparing iron-containing catalysts containing iron carbide particles prepared by activation of a precursor consisting of Fe hydroxide adsorbed on carbon black by hydrogen reduction and pyrolysis in the presence of acetonitrile. See *Activation and characterization of Fe-based catalysts for the reduction of oxygen in polymer electrolyte fuel cells* (Electrochimica Acta, Vol. 43, Nos. 14-15, pp. 1969-1984, 1998)

Cote et al. report on methods for preparation of non-noble metal based catalysts prepared by pyrolysis of a transition metal hydroxide (e.g., vanadium, chromium, iron, cobalt hydroxide) on carbon black including reduction in the presence of hydrogen and heating in the presence of acetonitrile. See *Non-noble metal-based catalysts for the reduction of oxygen in polymer electrolyte fuel cells* (Journal of New Materials for Electrochemical Systems, 1, 7-16, 1998).

Catalysts containing carbides or nitrides may be advantageous in certain instances due to the absence of a costly noble metal. One such reaction in which an active catalyst which does not require the presence of a noble metal may be advantageous is the oxidation of a tertiary amine (e.g., N-(phosphonomethyl)iminodiacetic acid) to produce a secondary amine (e.g., N-(phosphonomethyl)glycine). N-(phosphonomethyl)glycine (known in the agricultural chemical industry as "glyphosate") is described in Franz, U.S. Pat. No. 3,799,758. N-(phosphonomethyl)glycine and its salts are conveniently applied as a post-emergent herbicide in an aqueous formulation. It is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for making N-(phosphonomethyl)glycine are known in the art. Franz (U.S. Pat. No. 3,950,402) teaches that N-(phosphonomethyl)glycine may be prepared by the liquid phase oxidative cleavage of N-(phosphonomethyl)iminodiacetic acid (sometimes referred to as "PMIDA") with oxygen in the presence of a catalyst comprising a noble metal deposited on the surface of an activated carbon support:

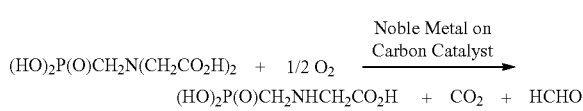

Other by-products also may form, such as formic acid, which is formed by the oxidation of the formaldehyde byproduct; and aminomethylphosphonic acid ("AMPA"), which is formed by the oxidation of N-(phosphonomethyl) glycine. Even though the Franz method produces an acceptable yield and purity of N-(phosphonomethyl)glycine, high losses of the costly noble metal into the reaction solution (i.e., "leaching") result because under the oxidation conditions of the reaction, some of the noble metal is oxidized into a more soluble form and both PMIDA and N-(phosphonomethyl) glycine act as ligands which solubilize the noble metal.

In U.S. Pat. No. 3,969,398, Hershman teaches that activated carbon alone, without the presence of a noble metal, may be used to effect the oxidative cleavage of PMIDA to form N-(phosphonomethyl)glycine. In U.S. Pat. No. 4,624,937, Chou further teaches that the activity of the carbon catalyst taught by Hershman may be increased by removing the oxides from the surface of the carbon catalyst before using it in the oxidation reaction. See also, U.S. Pat. No. 4,696,772, which provides a separate discussion by Chou regarding increasing the activity of the carbon catalyst by removing oxides from the surface of the carbon catalyst. Although these processes obviously do not suffer from noble metal leaching, they do tend to produce greater concentrations of formaldehyde by-product when used to effect the oxidative cleavage of N-(phosphonomethyl)iminodiacetic acid. This formaldehyde by-product is undesirable because it reacts with N-(phosphonomethyl)glycine to produce unwanted by-products (mainly N-methyl-N-(phosphonomethyl)glycine, sometimes referred to as "NMG") which reduce the N-(phosphonomethyl)glycine yield. In addition, the formaldehyde by-product itself is undesirable because of its potential toxicity. See Smith, U.S. Pat. No. 5,606,107.

It has been suggested that the formaldehyde be simultaneously oxidized to carbon dioxide and water as the PMIDA is oxidized to N-(phosphonomethyl)glycine in a single reactor, thus giving the following reaction:

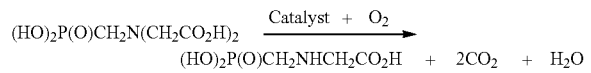

$$(HO)_2P(O)CH_2N(CH_2CO_2H)_2 \xrightarrow{\text{Catalyst} + O_2} (HO)_2P(O)CH_2NHCH_2CO_2H + 2CO_2 + H_2O$$

As the above teachings suggest, such a process requires the presence of both carbon (which primarily effects the oxidation of PMIDA to form N-(phosphonomethyl)glycine and formaldehyde) and a noble metal (which primarily effects the oxidation of formaldehyde to formic acid, carbon dioxide and water). Previous attempts to develop a stable catalyst for such an oxidation process, however, have not been entirely satisfactory.

Like Franz, Ramon et al. (U.S. Pat. No. 5,179,228) teach using a noble metal deposited on the surface of a carbon support. To reduce the problem of leaching (which Ramon et al. report to be as great as 30% noble metal loss per cycle), however, Ramon et al. teach flushing the reaction mixture with nitrogen under pressure after the oxidation reaction is completed to cause re-deposition of the noble metal onto the surface of the carbon support. According to Ramon et al., nitrogen flushing reduces the noble metal loss to less than 1%. Still, the amount of noble metal loss incurred with this method is unacceptable. In addition, re-depositing the noble metal can lead to loss of noble metal surface area which, in turn, decreases the activity of the catalyst.

Using a different approach, Felthouse (U.S. Pat. No. 4,582,650) teaches using two catalysts: (i) an activated carbon to effect the oxidation of PMIDA into N-(phosphonomethyl) glycine, and (ii) a co-catalyst to concurrently effect the oxidation of formaldehyde into carbon dioxide and water. The co-catalyst consists of an aluminosilicate support having a noble metal located within its pores. The pores are sized to exclude N-(phosphonomethyl)glycine and thereby prevent the noble metal of the co-catalyst from being poisoned by N-(phosphonomethyl)glycine. According to Felthouse, use of these two catalysts together allows for the simultaneous oxidation of PMIDA to N-(phosphonomethyl)glycine and of formaldehyde to carbon dioxide and water. This approach, however, suffers from several disadvantages: (1) it is difficult to recover the costly noble metal from the aluminosilicate support for re-use; (2) it is difficult to design the two catalysts so that the rates between them are matched; and (3) the carbon support, which has no noble metal deposited on its surface, tends to deactivate at a rate which can exceed 10% per cycle.

Ebner et al., in U.S. Pat. No. 6,417,133, describe a deeply reduced noble metal on carbon catalyst which is characterized by a CO desorption of less than 1.2 mmole/g, preferably less than 0.5 mmole/g, when a dry sample of the catalyst, after being heated at a temperature of about 500° C. for about 1 hour in a hydrogen atmosphere and before being exposed to an oxidant following the heating in the hydrogen atmosphere, is heated in a helium atmosphere from about 20° to about 900° C. at a rate of about 10° C. per minute, and then at about 900° C. for about 30 minutes. The catalyst is additionally or alternatively characterized as having a ratio of carbon atoms to oxygen atoms of at least about 20:1, preferably at least about 30:1, at the surface as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

The catalysts of U.S. Pat. No. 6,417,133 have proven to be highly advantageous and effective catalysts for the oxidation of N-(phosphonomethyl)iminodiacetic acid to N-(phosphonomethyl)glycine, and for the further oxidation of by-product formaldehyde and formic acid, and without excessive leaching of noble metal from the carbon support. It has further been discovered that these catalysts are effective in the operation of a continuous process for the production of N-(phosphonomethyl)glycine by oxidation of N-(phosphonomethyl)iminodiacetic acid.

Carbon and noble metal sites on the catalysts of U.S. Pat. No. 6,417,133 are highly effective for transfer of electrons in the oxidation of N-(phosphonomethyl)iminodiacetic acid, and the noble metal sites are especially effective for this purpose in the oxidation of formaldehyde and formic acid. However, it would be advantageous to have a multi-reaction catalyst and reaction process which oxidizes PMIDA to N-(phosphonomethyl)glycine while simultaneously exhibiting desired oxidation of formaldehyde to carbon dioxide and water (i.e., increased formaldehyde activity), and which does not require the presence of a noble metal (e.g., a carbide, nitride, or carbide-nitride containing catalyst). Additionally or alternatively, it would likewise be advantageous to have such a multi-reaction catalyst and reaction process which does not require costly noble metal, or which functions effectively with a reduced noble metal content relative to catalysts currently available for commercial manufacture of N-(phosphonomethyl)glycine or other secondary amines.

Salts of iminodiacetic acid may be phosphonomethylated to form PMIDA which, in turn, may be oxidized to form N-(phosphonomethyl)glycine in accordance with the above description.

See, e.g., Gentilcore, U.S. Pat. No. 4,775,498 (disclosing a method to phosphonomethylate a salt of iminodiacetic acid); Ebner, et al., U.S. Pat. No. 6,417,133 (disclosing methods for oxidizing PMIDA).

Salts of nitrilotriacetic acid, for example, are excellent chelating agents, and consequently may be used as detergent builders, water-softening agents, scouring aids, dyeing assistants, paper-coating agents, scale inhibitors, and agents for preventing soap degeneration. And many amino-carboxylic acid salts (e.g., salts of glycine, salts of iminodiacetic acid, etc.) may also be neutralized to their corresponding acids and then used, for example, as chelating agents; in food preparations; and as raw materials for making pharmaceuticals, agricultural chemicals, and pesticides. See, e.g., Franz, et al., *Glyphosate: A Unique Global Herbicide* (ACS Monograph 189, 1997) at pp. 234-41 (disclosing the use of glycine and iminodiacetic acid compounds as raw materials to form N-(phosphonomethyl)glycine).

It has long been known that a carboxylic acid salt may be prepared from a primary alcohol by dehydrogenating the alcohol using a copper-containing or silver-containing catalyst. In 1945, Chitwood first reported forming a carboxylic acid salt (specifically, the potassium salt of glycine) by oxidizing a primary alcohol (specifically, monoethanolamine) in an alkaline environment (specifically, in a mixture containing potassium hydroxide) using a copper-containing catalyst (specifically, copper metal or cupric oxide, which reportedly was reduced to copper metal under the reaction conditions) or a silver-containing catalyst (specifically, silver metal or silver oxide, which reportedly was reduced to silver metal under the reaction conditions). See Chitwood, U.S. Pat. No. 2,384,817. Chitwood, however, reported that copper-containing compounds are disadvantageous for this reaction because the copper coagulates over time, thereby causing the copper-containing compounds to have a short duration of maximum catalytic activity. Chitwood also reported that silver-containing compounds have relatively low activity (the silver oxide also reportedly coagulates over time).

In 1988, Goto et al. reported forming a carboxylic acid salt by oxidizing an ethanolamine compound in an alkaline solution (specifically, an aqueous solution containing the hydroxide of an alkali metal or an alkaline earth metal) using Raney copper. See Goto et al., U.S. Pat. No. 4,782,183. Goto et al. reported selectivities of at least 94.8% when dehydrogenating monoethanolamine, diethanolamine, and triethanolamine to form salts of glycine, iminodiacetic acid, and nitrilotriacetic acid, respectively. Raney copper, however, is disadvantageous because (like Chitwood's copper-containing compounds) Raney copper deactivates over time. See, e.g., Franczyk, U.S. Pat. No. 5,292,936, Table 1 (showing the reaction time for Raney copper to increase from 4 to 8 hours over 9 cycles).

Various developments have been reported which address the instability of copper-containing catalysts when used to dehydrogenate primary alcohols. Although these developments have made the use of copper catalysts more commercially viable, their results are still not entirely satisfactory.

Ebner et al. report using a catalyst comprising copper supported on an alkali-resistant support (particularly a carbon support) to dehydrogenate primary alcohols to make carboxylic acid salts. See Ebner et al., U.S. Pat. No. 5,627,125. This catalyst also comprises about 0.05 to about 10% by weight of a noble metal to anchor and disperse the copper to the support. Although the Ebner catalysts afford shorter reaction times relative to previously disclosed copper-containing catalysts, their catalyst may be relatively expensive due to the need for the noble metal to anchor the copper to the support.

Ebner et al.'s catalyst often loses activity over time with use (although the rate of deactivation is often less than the rate of deactivation of the Franczyk catalysts). See, e.g., Ebner et al., Table 1 (showing the reaction time increasing from 103 to 150 minutes over 9 cycles) and Table (showing the reaction time increasing from 61 to 155 minutes over 8 cycles). As with the Franczyk catalysts, this problem tends to arise particularly where the primary alcohol or the dehydrogenation salt product is a chelating agent.

Morgenstern et al. report a process for dehydrogenating a primary alcohol (e.g., amino alcohols such as diethanolamine) to make a carboxylic acid salt (e.g., disodium iminodiacetic acid) using a copper-containing or silver-containing catalyst including a metal support (e.g., a metal sponge support) coated with the copper or silver. See Morgenstern et al., U.S. Pat. No. 6,376,708. The catalyst described by Morgenstern et al. may further include a non-copper or non-silver metal deposited on the support and having the copper-containing or silver-containing catalyst active phase deposited thereon. The catalyst of Morgenstern et al. is an economical alternative to previously known copper-containing catalysts since it does not require an expensive noble metal such as those which are required in the catalyst described by Ebner et al. while exhibiting acceptable and potentially improved durability and activity. However, it has been discovered that the catalyst described by Morgenstern et al. may lead to the production of unwanted byproducts (e.g., sarcosine) which may have an adverse impact on processes incorporating a carboxylic acid salt produced using this catalyst.

Other reported copper-containing catalysts contain a non-carbon support, such as, $SiO_2$, $Al_2O_3$, $TiO_2$, $ZrO_2$, and the like. See, e.g., Akzo Nobel, WO 98/13140 (disclosing a catalyst consisting of copper on $ZrO_2$). These supports, however, tend to be vulnerable to attrition under the reaction conditions normally present when dehydrogenating a primary alcohol, and are therefore usually less suitable than Ebner et al.'s carbon supports. Vulnerability to attrition tends to also cause these supports to exhibit poor filtration characteristics.

Use of copper-containing and silver-containing catalysts in other types of oxidation reactions has also been reported. Applicants, however, are unaware of any such disclosures which address the problems associated with copper-containing or silver-containing catalysts in processes involving the dehydrogenation of primary alcohols to form carboxylic acid salts.

Thus, although positive advances have been reported for converting a primary alcohol to a carboxylic acid salt using a copper-containing catalyst, in particular carbon-supported copper-containing catalysts, there continues to be a need for a more economical catalyst that has high surface area, has high activity, exhibits stability (i.e., maintains its activity) over time with usage, and minimizes the production of unwanted byproducts. This need particularly exists where the primary alcohol substrate and/or carboxylic acid salt product is a chelating agent (e.g., a salt of iminodiacetic acid). A need remains for alternative catalysts for the dehydrogenation of alcohols, and in particular for the dehydrogenation of diethanolamine to iminodiacetic acid, or its salts. There is further need for such catalysts which do not require the presence of a noble metal for anchoring a copper active phase to a support. It is particularly desirous to provide such alternative catalysts which are effective for anaerobic dehydrogenation. The hydrogen produced by the dehydrogenation of primary alcohols can also be useful, particularly in the production of fuel cells. For example, W. H. Cheng, in Acc. Chem. Rev., vol. 32, 685-91 (1999), describes the conversion of primary alcohols such as methanol to hydrogen as a safe and readily transportable source of hydrogen fuel cells for a variety of applications, most notably automotive applications.

SUMMARY OF INVENTION

This invention provides catalysts and methods for preparing catalysts that are useful in various heterogeneous oxidation and dehydrogenation reactions, including the preparation of secondary amines by the catalytic oxidation of tertiary amines and the preparation of carboxylic acids by the catalytic dehydrogenation of primary alcohols. The catalysts include supports, particularly carbon supports, having formed thereon compositions which comprise a transition metal in combination with nitrogen and/or carbon and optionally a further metal deposited on the modified support. The oxidation catalysts disclosed herein are particularly useful in the oxidative cleavage of PMIDA reagents such as N-(phosphonomethyl)iminodiacetic acid to form an N-(phosphonomethyl)glycine product. In such reactions, the catalyst of the present invention have proven to be effective in catalyzing the further oxidation of the formaldehyde and formic acid by-products. The dehydrogenation catalysts of the present invention are particularly suited for the preparation of iminodiacetic acid compounds by the catalytic dehydrogenation of diethanolamine.

Briefly, therefore, the present invention is directed to a catalyst comprising a carbon support having formed thereon a transition metal composition comprising a transition metal, nitrogen, and carbon. In a first embodiment, the catalyst has a total Langmuir surface area of at least about 600 $m^2/g$. In a second embodiment, the total Langmuir surface area of the catalyst is at least about 60% of the total Langmuir surface area of the carbon support prior to formation of the transition metal composition thereon. In another embodiment, the micropore Langmuir surface area of the catalyst is at least about 750 $m^2/g$ and at least about 55% of the micropore Langmuir surface area of the carbon support prior to formation of the transition metal composition thereon. In another embodiment, the combined mesopore and macropore Langmuir surface area of the catalyst is at least about 175 $m^2/g$ and at least about 70% of the combined mesopore and macropore Langmuir surface area of the carbon support prior to formation of the transition metal composition thereon. In a still further embodiment, the transition metal composition is present on the carbon support in the form of discrete particles and at least about 95% by weight of the particles have a particle size, in their largest dimension, of less than about 1000 nm.

In another embodiment, the catalyst comprising a carbon support having formed thereon a transition metal composition comprising a transition metal, carbon and nitrogen further comprises carbon nanotubes at the surface of the carbon support. The carbon nanotubes have a diameter of at least about 0.01 μm. In an alternative embodiment, the carbon nanotubes have a diameter of less than about 1 μm.

In a further embodiment, the catalyst comprises a carbon support having formed thereon a transition metal composition comprising a transition metal and nitrogen. At least about 5% by weight of the transition metal is present in a non-zero oxidation state and the catalyst has a total Langmuir surface area of at least about 600 $m^2/g$.

In another embodiment, the catalyst comprises a carbon support having formed thereon a transition metal composition comprising a plurality of transition metals and nitrogen. The catalyst has a total Langmuir surface area of at least about 600 $m^2/g$.

In another embodiment, the catalyst comprises a modified carbon support comprising a carbon support having formed thereon a transition metal composition comprising a transition metal, carbon, and nitrogen. A metal selected from the group consisting of copper, nickel, cadmium, cobalt, and combinations thereof is deposited on the modified carbon support in a proportion of from about 2% to about 8% by weight of the catalyst.

In another embodiment, the catalyst comprises a modified carbon support comprising a carbon support having formed thereon a transition metal composition comprising a transition metal, carbon, and nitrogen. An active phase comprising copper is deposited on the modified carbon support.

In another embodiment of the present invention, the catalyst comprises a carbon support having formed thereon a transition metal composition comprising a transition metal, nitrogen, and carbon. The catalyst is further characterized by its effectiveness for catalyzing the oxidation of formaldehyde. More particularly, when a representative aqueous solution containing about 0.8% by weight formaldehyde and having a pH of about 1.5 is contacted with an oxidizing agent in the presence of such catalyst at a temperature of about 100° C., at least about 5% of the formaldehyde is converted to formic acid, carbon dioxide and/or water.

In yet another embodiment, the catalyst comprising a carbon support having formed thereon a transition metal composition comprising a transition metal, nitrogen, and carbon is characterized by its effectiveness for catalyzing the oxidation of formaldehyde in a representative aqueous solution containing about 0.8% by weight formaldehyde and about 6% by weight of N-(phosphonomethyl)iminodiacetic acid and having a pH of about 1.5. More particularly, at least about 50% of the formaldehyde is converted to formic acid, carbon dioxide and/or water when the representative aqueous solution is contacted with an oxidizing agent in the presence of the catalyst at a temperature of about 100° C.

In a further embodiment, the catalyst comprises a supporting structure selected from the group consisting of silica, alumina, and carbon supports. A transition metal composition comprising a transition metal, carbon, and nitrogen is formed on the support. At least about 5% by weight of the transition metal is present in a non-zero oxidation state and the catalyst has a total Langmuir surface area of at least about 600 $m^2/g$.

In a still further embodiment, the catalyst comprises a carbon support having formed thereon a composition comprising carbon, nitrogen, and an element selected from the group consisting of Group IIA, tellurium, selenium, and combinations thereof.

The present invention is further directed to processes for the oxidation of an organic substrate using the various embodiments of the oxidation catalysts described above. In such processes, the organic substrate is contacted with an oxidizing agent in the presence of the oxidation catalyst.

In a further embodiment, the process for oxidizing an organic substrate comprises contacting the organic substrate with an oxidizing agent in the presence of an oxidation catalyst comprising a carbon support having formed thereon a transition metal composition comprising a transition metal and nitrogen. The transition metal is selected from the group consisting of copper, silver, vanadium, chromium, molybdenum, tungsten, manganese, nickel, ruthenium, cerium, and combinations thereof.

The present invention is further directed to processes for the preparation of a catalyst comprising a transition metal composition comprising a transition metal and nitrogen on a porous carbon support. In one embodiment, the porous carbon support is in particulate form and a fixed or fluidized bed of the particulate porous carbon support having thereon a precursor of the transition metal composition is contacted with a vapor phase source of a nitrogen-containing compound. The bed of the particulate porous carbon support is heated while in contact with the nitrogen-containing compound to form the transition metal composition on the carbon support.

In accordance with another embodiment, the process for preparing the catalyst comprises contacting the porous carbon support having thereon a precursor of the transition metal composition with a vapor phase source of a nitrogen-containing compound. The porous carbon support is heated to a temperature of from about 600 to about 975° C. while in contact with the nitrogen-containing compound to form the transition metal composition on the carbon support.

A further aspect of the present invention provides dehydrogenation catalysts and processes for their preparation and use in catalyzing the dehydrogenation of a primary alcohol to produce a salt of a carboxylic acid.

In one embodiment, the catalyst comprises a modified carbon support comprising a carbon support having formed thereon a composition comprising carbon and a transition metal selected from tungsten and molybdenum. A metal selected from Group IB and Group VIII metals is deposited on the modified carbon support.

In another embodiment a modified carbon catalyst support is provided comprising a carbon support and a composition comprising nitrogen and a transition metal selected from the group consisting of molybdenum and tungsten formed on the carbon support. A catalyst may be formed by depositing a metal selected from Group IB and Group VIII metals onto such a modified carbon support.

The invention is further directed to a process for forming a catalyst comprising a transition metal composition comprising carbon and a transition metal selected from molybdenum and tungsten on a porous carbon support. The process comprises contacting a hydrocarbon and the porous carbon support having thereon a precursor of the transition metal composition, thereby producing a modified carbon support having the transition metal composition formed thereon. A metal selected from Group IB and Group VIII metals is deposited on the modified catalyst support.

Another embodiment of the invention provides a process for forming a catalyst comprising a transition metal composition comprising nitrogen and a transition metal selected from molybdenum and tungsten on a porous carbon support. The process comprises contacting a nitrogen-containing compound and the porous carbon support having thereon a precursor of the transition metal composition, thereby producing a modified carbon support having the transition metal composition formed thereon.

The invention is further directed to a process for preparing a salt of a carboxylic acid. The process comprises contacting a primary alcohol with a catalyst in an alkaline medium. The catalyst comprises a modified carbon support having copper deposited thereon. The modified carbon support comprises a carbon support having a transition metal composition formed thereon. The transition metal composition comprises a transition metal and nitrogen or a transition metal and carbon.

Other objects and features of this invention will be in part apparent and in part pointed out hereinafter.

DETAILED DESCRIPTION OF THE PREFERRED EMBODIMENTS

Figure 1:
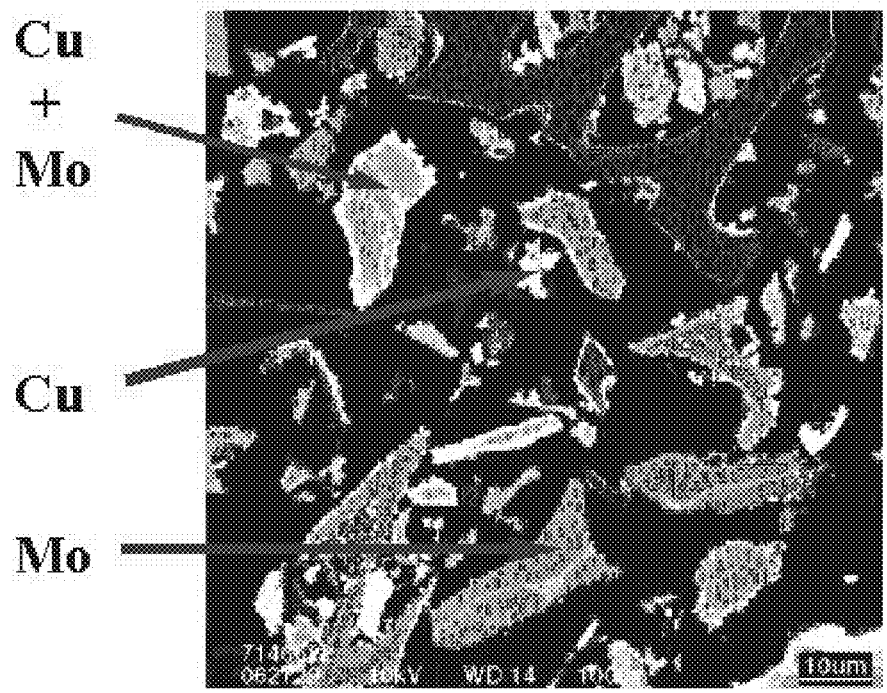
FIG. 1 is a Scanning Electron Microscopy (SEM) image of a carbon supported molybdenum carbide having copper deposited thereon.

Described herein are catalysts containing a transition metal composition formed on a carbon support. The catalyst generally comprises a transition metal composition comprising a transition metal and nitrogen, a transition metal and carbon, or a transition metal, nitrogen, and carbon. A transition metal composition comprising a transition metal and nitrogen preferably includes a transition metal nitride while a transition metal composition comprising a transition metal and carbon preferably includes a transition metal carbide. Transition metal compositions including a transition metal, nitrogen, and carbon may include both a transition metal nitride and a transition metal carbide, and/or a transition metal carbide-nitride.

In various embodiments, the catalyst comprises a transition metal/carbon composition which includes a transition metal carbide (e.g., molybdenum carbide). In other embodiments, the catalyst comprises a transition metal/nitrogen composition which includes a transition metal nitride (e.g., molybdenum nitride). In still other embodiments, the catalyst includes a transition metal carbide (e.g., cobalt carbide) and a transition metal nitride (e.g., cobalt nitride). In still further embodiments, the catalyst includes a transition metal carbide-nitride (e.g., cobalt carbide-nitride).

Catalysts of the present invention may be used to catalyze liquid phase (i.e., in an aqueous solution or an organic solvent) oxidation reactions and, in particular, the oxidation of a tertiary amine (e.g., N-(phosphonomethyl)iminodiacetic acid) to produce a secondary amine (e.g., N-(phosphonomethyl)glycine). Advantageously, the catalysts of the present invention including a transition metal composition formed on a carbon support also catalyze oxidation of the formaldehyde by-product that is formed in the oxidation of N-(phosphonomethyl)iminodiacetic acid) to N-(phosphonomethyl)glycine).

In certain embodiments, the catalyst of the present invention includes a noble metal deposited on a modified carbon support including a transition metal composition formed on a carbon support. Presence of the noble metal generally enhances the effectiveness of the catalyst in oxidation of the formaldehyde by-product of the oxidation of N-(phosphonomethyl)iminodiacetic acid to N-(phosphonomethyl)glycine). Although the catalysts of the present invention are advantageous in catalyzing the oxidation of tertiary amines such as N-(phosphonomethyl)iminodiacetic acid in the absence of a noble metal, and may also be effective for the oxidation of by-products such as formaldehyde, the presence of a noble metal active phase may be preferable in some instances. By evaluating experimental data for a particular substrate and process, applying standard economic principles, those skilled in the art can weigh the advantages of a noble metal-free catalyst against a noble metal catalyst with respect to yields, productivity, capital, depreciation, labor and materials expense.

Also described herein are catalysts useful for the conversion of a primary alcohol to a salt of a carboxylic acid using a catalyst including a metal-containing (e.g., copper-containing) active phase deposited over a modified carbon support including a transition metal composition formed on a carbon support. Such catalysts are suitable for converting a wide range of primary alcohols to carboxylic acid salts. The term "primary alcohol" refers to any alcohol comprising a hydroxy group attached to a carbon which is bound to two hydrogen atoms (e.g., R—CH$_2$OH). Dehydrogenation of the primary alcohol yields a carboxylic acid salt and hydrogen gas and is generally carried out in a heated reaction zone containing the primary alcohol, a base and a catalyst. In various embodiments, a catalyst of the present invention is used for the dehydrogenation of diethanolamine to disodium iminodiacetic acid.

Further described herein are processes for preparing transition metal compositions comprising a transition metal and nitrogen, a transition metal and carbon, or a transition metal, nitrogen, and carbon on a carbon support. Also detailed herein are processes for depositing a metal-containing active phase on a modified carbon support including a transition metal composition formed on a carbon support. Reference to deposition of a metal-containing "active" phase onto catalysts including a transition metal composition formed on a carbon support (e.g., a modified carbon support) should not be taken as exclusive of any catalytic activity of the transition metal composition formed on the carbon support, or of the carbon support itself. For example, the carbon support alone is known to catalyze the oxidation of tertiary amines to secondary amines, and the transition metal composition possesses catalytic properties as well.

Generally, the supporting structure may comprise any material suitable for formation of a transition metal composition thereon and/or depositing a metal-containing active phase onto a modified support including a transition metal composition formed on a carbon support. Preferably, the supporting structure is in the form of a carbon support. In particular, carbon supports are preferred for the conversion of primary alcohols to carboxylic acid salts due to their resistance to the alkaline environment of the reaction.

In general, the carbon supports used in the present invention are well known in the art. Activated, non-graphitized carbon supports are preferred. These supports are characterized by high adsorptive capacity for gases, vapors, and colloidal solids and relatively high specific surface areas. The support suitably may be a carbon, char, or charcoal produced by means known in the art, for example, by destructive distillation of wood, peat, lignite, coal, nut shells, bones, vegetable, or other natural or synthetic carbonaceous matter, but preferably is "activated" to develop adsorptive power. Activation usually is achieved by heating to high temperatures (800-900° C.) with steam or with carbon dioxide which brings about a porous particle structure and increased specific surface area. In some cases, hygroscopic substances, such as zinc chloride and/or phosphoric acid or sodium sulfate, are added before the destructive distillation or activation, to increase adsorptive capacity. Preferably, the carbon content of the carbon support ranges from about 10% for bone charcoal to about 98% for some wood chars and nearly 100% for activated carbons derived from organic polymers. The non-carbonaceous matter in commercially available activated carbon materials normally will vary depending on such factors as precursor origin, processing, and activation method. Many commercially available carbon supports contain small amounts of metals. In certain embodiments, carbon supports having the fewest oxygen-containing functional groups at their surfaces are most preferred.

The form of the carbon support is not critical. In certain embodiments, the support is a monolithic support. Suitable monolithic supports may have a wide variety of shapes. Such a support may be, for example, in the form of a screen or honeycomb. Such a support may also, for example, be in the form of a reactor impeller.

In a particularly preferred embodiment, the support is in the form of particulates. Because particulate supports are especially preferred, most of the following discussion focuses on embodiments which use a particulate support. It should be recognized, however, that this invention is not limited to the use of particulate supports.

Suitable particulate supports may have a wide variety of shapes. For example, such supports may be in the form of granules. Even more preferably, the support is in the form of a powder. These particulate supports may be used in a reactor system as free particles, or, alternatively, may be bound to a structure in the reactor system, such as a screen or an impeller.

Typically, a support which is in particulate form comprises a broad size distribution of particles. For powders, preferably at least about 95% of the particles are from about 2 to about 300 μm in their largest dimension, more preferably at least about 98% of the particles are from about 2 to about 200 μm in their largest dimension, and most preferably about 99% of the particles are from about 2 to about 150 μm in their largest dimension with about 95% of the particles being from about 3 to about 100 μm in their largest dimension. Particles being greater than about 200 μm in their largest dimension tend to fracture into super-fine particles (i.e., less than 2 μm in their largest dimension), which are difficult to recover.

In the following discussion, specific surface areas of carbon supports and the oxidation and dehydrogenation catalysts of the present invention are provided in terms of the well-known Langmuir method using $N_2$. However, such values generally correspond to those measured by the also well-known Brunauer-Emmett-Teller (B.E.T.) method using $N_2$.

The specific surface area of the carbon support, typically measured by the Langmuir method using $N_2$, is preferably from about 10 to about 3,000 $m^2/g$ (surface area of carbon support per gram of carbon support), more preferably from about 500 to about 2,100 $m^2/g$, and still more preferably from about 750 to about 2,100 $m^2/g$. In some embodiments, the most preferred specific area is from about 750 to about 1,750 $m^2/g$. In other embodiments, typically the particulate carbon support has a Langmuir surface area of at least about 1000 $m^2/g$ prior to formation of a transition metal composition on the carbon support, more typically at least about 1200 $m^2/g$ and, still more typically, at least about 1400 $m^2/g$. Preferably, the Langmuir surface area of the carbon support prior to formation of a transition metal composition on the carbon support is from about 1000 to about 1600 $m^2/g$ and, more preferably, from about 1000 to about 1500 $m^2/g$ prior to formation of a transition metal composition on the carbon support.

The Langmuir micropore surface area of the support (i.e., surface area of the support attributed to pores having a diameter less than 20 Å) is typically at least about 300 $m^2/g$, more typically at least about 600 $m^2/g$. Preferably, the Langmuir micropore surface area is from about 300 to about 1500 $m^2/g$ and, more preferably, from about 600 to about 1400 $m^2/g$. The Langmuir combined mesopore and macropore surface area of the support (i.e., surface area of the support attributed to pores having a diameter greater than 20 Å) is typically at least about 100 $m^2/g$, more typically at least about 150 $m^2/g$. Preferably, the combined Langmuir mesopore and macropore surface area is from about 100 to about 400 $m^2/g$, more preferably from about 100 to about 300 $m^2/g$ and, still more preferably, from about 150 to about 250 $m^2/g$.

For certain applications (e.g., hydrogenation, petroleum hydrotreating, and isomerization), non-carbon supports may be used with a catalyst containing a transition metal composition formed on the support as described herein. For example, silica and alumina supports having Langmuir surface areas of at least about 50 $m^2/g$. Typically, these supports will have Langmuir surface areas of from about 50 to about 300 $m^2/g$.

Generally, supports having high surface areas are preferred because they tend to produce a finished catalyst having a high surface area.

Finished catalysts exhibiting sufficient pore volume are desired so that reactants are able to penetrate the pores of the finished catalyst. The pore volume of the support may vary widely. Generally, the pore volume of the support is at least about 0.1 $cm^3/g$ (pore volume per gram of support) and, typically, at least about 0.5 $cm^3/g$. Typically, the pore volume is from about 0.1 to about 2.5 $cm^3/g$ and, more typically, from about 1.0 to about 2.0 $cm^3/g$. Preferably, the pore volume of the support is from about 0.2 to about 2.0 $cm^3/g$, more preferably from about 0.4 to about 1.7 $cm^3/g$ and, still more preferably, from about 0.5 to about 1.7 $cm^3/g$. Catalysts comprising supports with pore volumes greater than about 2.5 $cm^3/g$ tend to fracture easily. On the other hand, catalysts comprising supports having pore volumes less than 0.1 $cm^3/g$ tend to have small surface areas and therefore low activity.

Penetration of reactants into the pores of the finished catalysts is also affected by the pore size distribution of the support. Typically, at least about 60% of the pore volume of the support is made up of pores having a diameter of at least about 20 Å. Preferably, from about 60 to about 75% of the pore volume of the support is made up of pores having a diameter of at least about 20 Å.

Typically, at least about 20% of the pore volume of the support is made up of pores having a diameter of between about 20 and about 40 Å. Preferably, from about 20 to about 35% of the pore volume of the support is made of pores having a diameter of between about 20 and about 40 Å.

Typically, at least about 25% of the pore volume of the support is made up of pores having a diameter of at least about 40 Å. Preferably, from about 25 to about 60% of the pore volume of the support is made up of pores having a diameter of at least about 40 Å.

Typically, at least about 5% of the pore volume of the support is made up of pores having a diameter of between about 40 and about 60 Å. Preferably, from about 5 to about 20% of the pore volume of the support is made up of pores having a diameter of between about 40 and about 60 Å.

Carbon supports for use in the present invention are commercially available from a number of sources. The following is a listing of some of the activated carbons which may be used with this invention: Darco G-60 Spec and Darco X (ICI-America, Wilmington, Del.); Norit SG Extra, Norit EN4, Norit EXW, Norit A, Norit Ultra-C, Norit ACX, and Norit 4×14 mesh (Amer. Norit Co., Inc., Jacksonville, Fla.); G1-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar CN, Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); and Columbia SXAC (Union Carbide New York, N.Y.).

The transition metal composition formed on the carbon support generally comprises a transition metal and nitrogen, a transition metal and carbon, or a transition metal, nitrogen, and carbon. The transition metal is selected from the group consisting of Group IB, Group VB, Group VIB, Group VIIB, Group VIII, lanthanide series metals, and combinations thereof. Groups of elements as referred to herein are with reference to the Chemical Abstracts Registry (CAS) system for numbering the elements of the Periodic Table (e.g., Group VIII includes, among others, iron, cobalt, and nickel). In particular, the transition metal is selected from the group consisting of copper, silver, vanadium, chromium, molybdenum, tungsten, manganese, iron, cobalt, nickel, ruthenium, cerium, and combinations thereof. In certain embodiments, the transition metal composition includes a plurality of transition metals (e.g., cobalt and cerium).

In certain other embodiments, a catalyst of the present invention includes a composition comprising an element selected from Group IIA (e.g., magnesium) and Group VIA (e.g., tellurium, selenium), together with nitrogen, carbon, and/or nitrogen and carbon formed on a carbon support. For example, a catalyst of the present invention may include a composition comprising magnesium, nitrogen, and/or carbon and, in particular, magnesium nitride or magnesium carbide-nitride. It should be understood that the discussion herein regarding transition metal compositions applies to these compositions as well.

Generally, the transition metal compositions of the present invention include the transition metal in a non-metallic form (i.e., in a non-zero oxidation state) combined with nitrogen, carbon, or carbon and nitrogen in form of a transition metal nitride, carbide, or carbide-nitride, respectively. The transition metal compositions may further comprise free transition metal in its metallic form (i.e., in an oxidation state of zero). The transition metal compositions may also include carbide-nitride compositions having an empirical formula of $CN_x$ wherein x is from about 0.01 to about 0.7.

Typically, at least about 5% by weight of the transition metal is present in a non-zero oxidation state (e.g., as part of a transition metal nitride, transition metal carbide, or transition metal carbide-nitride), more typically at least about 20%, still more typically at least about 30% and, even more typically, at least about 40%. Preferably, from about 5 to about 50% by weight of the transition metal is in a non-zero oxidation state, more preferably from about 20 to about 40% by weight and still more preferably, from about 30 to about 40% by weight of the transition metal is in a non-zero oxidation state.

For catalysts including a transition metal composition (e.g., transition metal nitride) formed on a carbon support, generally the transition metal composition comprises at least about 0.1% by weight of the catalyst and, typically, at least about 0.5% by weight of the catalyst. Typically, the transition metal composition comprises from about 0.1 to about 20% by weight of the catalyst, more typically from about 0.5 to about 15% by weight of the catalyst, more typically from about 0.5 to about 10% by weight of the catalyst and, still more typically, from about 1 to about 12% by weight of the catalyst. In certain embodiments, the transition metal composition comprises from about 1 to about 2% by weight of the catalyst and, in others, from about 1 to about 1.5% by weight of the catalyst.

Typically, the transition metal component of the transition metal composition is present in a proportion of at least about 0.1% by weight of the catalyst, more typically at least about 0.5% by weight of the catalyst and, still more typically, at least about 1% by weight of the catalyst. Preferably, the transition metal component is present in a proportion of from about 0.1 to about 20% by weight of the catalyst, more preferably from about 0.5 to about 10% by weight of the catalyst, still more preferably from about 1 to about 2% by weight of the catalyst and, even more preferably, from about 1 to about 1.5% by weight of the catalyst.

The nitrogen component of transition metal compositions comprising a transition metal and nitrogen is typically present in a proportion of at least about 0.01% by weight of the catalyst, more typically at least about 0.1% by weight of the catalyst, still more typically at least about 0.5% by weight of the catalyst and, even more typically, in a proportion of at least about 1% by weight of the catalyst. Preferably, the nitrogen component is present in a proportion of from about 0.1 to about 5% by weight of the catalyst, more preferably from about 0.1 to about 3% by weight of the catalyst, even more preferably from about 1 to about 2% by weight of the catalyst and, still more preferably, from about 1 to about 1.5% by weight of the catalyst.

In certain embodiments, the transition metal/nitrogen composition comprises cobalt and nitrogen and, in various embodiments, cobalt nitride. Such cobalt nitride typically has an empirical formula of, for example, $CoN_x$ wherein x is typically from about 0.25 to about 4, more typically from about 0.25 to 2 and, still more typically, from about 0.25 to about 1. Typically, the total proportion of at least one cobalt nitride having such an empirical formula (e.g., $Co_2N$) is at least about 0.01% by weight of the catalyst. Typically, the total proportion of all cobalt nitride having such an empirical formula is at least about 0.1% by weight of the catalyst.

In such embodiments, cobalt is typically present in a proportion of at least about 0.1% by weight of the catalyst, more typically at least about 0.5% by weight of the catalyst and, more typically, at least about 1% by weight of the catalyst. Preferably, cobalt is present in a proportion of from about 0.5 to about 10% by weight of the catalyst, more preferably from about 1 to about 2% by weight of the catalyst and, even more preferably, from about 1 to about 1.5% by weight of the catalyst. In certain embodiment, cobalt is present in a proportion of from about 0.1 to about 3% by weight of the catalyst. Further in accordance with such embodiments, nitrogen is typically present in a proportion of at least about 0.01% by weight of the catalyst and, more typically, in a proportion of from about 0.5 to about 2% by weight of the catalyst.

In certain embodiments, the transition metal/nitrogen composition comprises iron and nitrogen and, in particular, iron nitride. Such iron nitride typically has an empirical formula of, for example, $FeN_x$ wherein x is typically from about 0.25 to about 4, more typically from about 0.25 to 2 and, still more typically, from about 0.25 to about 1. Typically, the total proportion of at least one iron nitride having such an empirical formula (e.g., FeN) is present in a proportion of at least about 0.01% by weight of the catalyst. Typically, the total proportion of all iron nitrides having such an empirical formula is at least about 0.1% by weight of the catalyst.

In such embodiments, iron is typically present in a proportion of at least about 0.01% by weight of the catalyst, more typically at least about 0.1% by weight of the catalyst and, more typically, at least about 0.2% by weight of the catalyst. Preferably, iron is present in a proportion of from about 0.1 to about 5% by weight of the catalyst, more preferably from about 0.1 to about 3% by weight of the catalyst, still more preferably from about 0.2 to about 1.5% by weight of the catalyst and, even more preferably, from about 0.5 to about 1% by weight of the catalyst. In certain embodiments, iron is present in a proportion of at from about 1 to about 2% by weight of the catalyst and, in others, from about 1 to about 1.5% by weight of the catalyst. Further in accordance with such embodiments, nitrogen is typically present in a proportion of at least about 0.01% by weight of the catalyst and, more typically, in a proportion of from about 0.1 to about 2% by weight of the catalyst.

In certain embodiments, transition metal/carbon compositions comprise cobalt and carbon and, in certain embodiments, cobalt carbide. Such cobalt carbide typically has an empirical formula of, for example, $CoC_x$ wherein x is typically from about 0.25 to about 4, more typically from about 0.25 to 2 and, still more typically, from about 0.25 to about 1. Typically, the total proportion of at least one cobalt carbide of such stoichiometric formula (e.g., $Co_2C$) is at least about 0.01% by weight of the catalyst. Typically, the total proportion of all cobalt carbide of such empirical formulae is at least about 0.1% by weight of the catalyst.

In such embodiments, cobalt is typically present in a proportion of at least about 0.1% by weight of the catalyst, more typically at least about 0.5% by weight of the catalyst and, more typically, at least about 1% by weight of the catalyst. Preferably, cobalt is present in a proportion of from about 0.5 to about 10% by weight of the catalyst, more preferably from about 1 to about 2% by weight of the catalyst and, still more preferably, from about 1 to about 1.5% by weight of the catalyst. In certain embodiments, cobalt is present in a proportion of from about 0.1 to about 3% by weight of the catalyst.

In certain embodiments, the transition metal/carbon composition comprises iron and carbon and, in particular, iron carbide. Such iron carbide typically has an empirical formula of, for example, $FeC_x$ wherein x is typically from about 0.25 to about 4, more typically from about 0.25 to 2 and, still more typically, from about 0.25 to about 1. Typically, the total proportion of at least one iron carbide of such stoichiometric formula (e.g., $Fe_3C$) is at least about 0.01% by weight of the catalyst. Typically, the total proportion of all iron carbides of such empirical formulae is at least about 0.1% by weight of the catalyst.

In such embodiments, iron is typically present in a proportion of at least about 0.01% by weight of the catalyst and, more typically, at least about 0.1% by weight of the catalyst. Preferably, iron is present in a proportion of from about 0.1 to about 5% by weight of the catalyst, more preferably from about 0.2 to about 1.5% by weight of the catalyst and, still more preferably, from about 0.5 to about 1% by weight of the catalyst.

It should be understood that the description of transition metal compositions containing iron and cobalt generally applies to transition metal compositions containing other transition metals (e.g., cerium) listed above.

In various embodiments, the transition metal composition includes a transition metal, nitrogen, and carbon. In certain embodiments, the transition metal composition comprises cobalt, carbon, and nitrogen and, in particular, cobalt carbide and cobalt nitride having empirical formula of $CoC_x$ or $CoN_x$, respectively, where x is typically from about 0.25 to about 4, more typically from about 0.25 to 2 and, still more typically, from about 0.25 to 1.

Typically, a cobalt carbide and nitride having such an empirical formula are each present in a proportion of at least about 0.01% by weight of the catalyst and, more typically, from about 0.1 to about 0.5% by weight of the catalyst. Typically, the total proportion of all cobalt carbides of such empirical formula is at least about 0.1% by weight of the catalyst while the total proportion of all cobalt nitrides of such empirical formula is typically at least about 0.1% by weight of the catalyst.

In such embodiments, cobalt is typically present in a proportion of at least about 0.1% by weight of the catalyst, more typically at least about 0.5% by weight of the catalyst and, more typically, at least about 1% by weight of the catalyst. Preferably, cobalt is present in a proportion of from about 0.5 to about 10% by weight of the catalyst, more preferably from about 1 to about 2% by weight of the catalyst and, still more preferably, from about 1 to about 1.5% by weight of the catalyst. In certain embodiments, cobalt is present in a proportion of from about 0.1 to about 3% by weight of the catalyst. Further in accordance with such embodiments, nitrogen is typically present in a proportion of at least about 0.1% by weight of the catalyst and, more typically, in a proportion of from about 0.5 to about 2% by weight of the catalyst.

In certain embodiments, the transition metal composition comprises iron, carbon, and nitrogen and, in particular, iron carbide and iron nitride having empirical formula of $FeC_x$ or $FeN_x$, respectively, where x is typically from about 0.25 to about 4, more typically from about 0.25 to 2 and, still more typically, from about 0.25 to about 1. For example, $Fe_3C$ may be present and, additionally or alternatively, FeN may also be present.

Typically, an iron carbide and nitride having such an empirical formula are each present in a proportion of at least about 0.01% by weight of the catalyst and, more typically, from about 0.1 to about 0.5% by weight of the catalyst. Typically, the total proportion of all iron carbides of such empirical formula is at least about 0.1% by weight of the catalyst while the total proportion of all iron nitrides of such empirical formula is typically at least about 0.1% by weight of the catalyst.

In such embodiments, iron is typically present in a proportion of at least about 0.1% by weight of the catalyst, more typically at least about 0.5% by weight of the catalyst and, more typically, at least about 1% by weight of the catalyst. Preferably, iron is present in a proportion of from about 0.5 to about 10% by weight of the catalyst, more preferably from about 1 to about 2% by weight of the catalyst and, still more preferably, from about 1 to about 1.5% by weight of the catalyst. In certain embodiments, iron is present in a proportion of from about 0.1 to about 3% by weight of the catalyst. Further in accordance with such embodiments, nitrogen is typically present in a proportion of at least about 0.1% by weight of the catalyst and, more typically, in a proportion of from about 0.5 to about 2% by weight of the catalyst.

In various other embodiments the transition metal composition comprising a transition metal, carbon, and nitrogen may include a transition metal carbide-nitride composition (e.g., cobalt carbide-nitride). For example, the transition metal composition may include cobalt carbide-nitride. In such embodiments, cobalt is typically present in a proportion of at least about 0.1% by weight of the catalyst, more typically at least about 0.5% by weight of the catalyst and, still more typically, at least about 1% by weight of the catalyst. Preferably, cobalt is present in a proportion of from about 0.5 to about 10% by weight of the catalyst, more preferably from about 1 to about 2% by weight of the catalyst and, still more preferably, from about 1 to about 1.5% by weight of the catalyst. In certain embodiments, the cobalt carbide-nitride may be present in a proportion of from about 0.1 to about 3% by weight of the catalyst. Further in accordance with such embodiments, nitrogen is typically present in a proportion of at least about 0.1% by weight of the catalyst and, more typically, in a proportion of from about 0.5 to about 2% by weight of the catalyst.

In various embodiments, the catalyst may comprise cobalt carbide, cobalt nitride, and cobalt carbide-nitride. In such embodiments, typically the total proportion of such carbide(s), nitride(s), and carbide-nitride(s) is at least about 0.1% by weight of the catalyst and, still more typically, from about 0.1 to about 20% by weight of the catalyst.

In various other embodiments, the transition metal composition may include iron carbide-nitride. In such embodiments, iron is typically present in a proportion of at least about 0.1% by weight of the catalyst, more typically at least about 0.2% by weight of the catalyst, still more typically at least about 0.5% by weight of the catalyst and, even more typically, at least about 1% by weight of the catalyst. Preferably, iron is present in a proportion of from about 0.1 to about 5% by weight of the catalyst, more preferably from about 0.1 to about 3% by weight of the catalyst, more preferably from about 0.2 to about 2% by weight of the catalyst and, still more preferably, from about 0.5 to about 1.5% by weight of the catalyst. Further in accordance with such embodiments, nitrogen is typically present in a proportion of at least about 0.1% by weight of the catalyst and, more typically, in a proportion of from about 0.5 to about 2% by weight of the catalyst.

In various embodiments, the catalyst may comprise iron carbide, iron nitride, and iron carbide-nitride. In such embodiments, typically the total proportion of such carbide(s), nitride(s), and carbide-nitride(s) is at least about 0.1% by weight of the catalyst and, still more typically, from about 0.1 to about 20% by weight of the catalyst.

In various other embodiments the transition metal composition comprises nickel cobalt-nitride, vanadium cobalt-nitride, chromium cobalt-nitride, manganese cobalt-nitride, copper cobalt-nitride, molybdenum carbide-nitride, and tungsten carbide-nitride.

Further in accordance with the present invention, the transition metal composition may include a plurality of transition metals selected from the group consisting of Group IB, Group VB, Group VIB, Group VIIB, Group VIII, lanthanide series metals, and combinations thereof. In particular, the transition metal composition may include a plurality of transition metals selected from the group consisting of copper, silver, vanadium, chromium, molybdenum, tungsten, manganese, iron, cobalt, nickel, ruthenium and cerium. For example, the transition metal composition may comprise cobalt-cerium nitride, cobalt-cerium carbide, and/or cobalt-cerium carbide-nitride. Other bi-metallic carbide-nitrides present in transition metal compositions in accordance with the present invention may be in the form of cobalt-iron carbide-nitride or cobalt-copper carbide-nitride. One of such bi-transition metal compositions (e.g., a bi-transition metal nitride) may be present in a total proportion of at least about 0.1% by weight and, more typically, in a proportion of from about 0.1 to about 20% by weight of the catalyst. One or more of such bi-transition metal compositions (e.g., nitride, carbide, and/or carbide-nitride) may be present in a total proportion of at least about 0.1% by weight and, more typically, in a proportion of from about 0.1 to about 20% by weight of the catalyst.

In certain embodiments, the transition metal composition formed on the carbon support generally comprises either or both of a composition comprising a transition metal and carbon (i.e., a transition metal/carbon composition) or a composition comprising a transition metal and nitrogen (i.e., a transition metal/nitrogen composition) in which the transition metal is selected from molybdenum and tungsten. Transition metal compositions formed on a carbon support containing molybdenum or tungsten are useful as oxidation catalysts; however, they are particularly useful as a modified carbon support for a dehydrogenation catalyst.

Thus, in certain of these embodiments, the transition metal/carbon composition comprises molybdenum and carbon and, in a preferred embodiment, comprises molybdenum carbide. Typically, molybdenum carbide formed on the carbon support as part of the transition metal composition comprises a compound having a stoichiometric formula of $Mo_2C$. In other embodiments, the transition metal/carbon composition comprises tungsten and carbon and, in a preferred embodiment, comprises tungsten carbide. Typically, tungsten carbide formed on the carbon support as part of the transition metal composition comprises a compound having a stoichiometric formula of $WC$ or $W_2C$.

Similarly, transition metal/nitrogen compositions may comprise molybdenum and nitrogen and, in a preferred embodiment, comprises molybdenum nitride. Typically, any molybdenum nitride formed on the carbon support as part of the transition metal composition comprises a compound having a stoichiometric formula of $Mo_2N$. Transition metal/nitrogen compositions formed on the carbon support may comprise tungsten and nitrogen and, in a preferred embodiment, comprises tungsten nitride. Typically, any tungsten nitride formed on the carbon support as part of the transition metal composition comprises a compound having a stoichiometric formula of $W_2N$.

In various embodiments including transition metal compositions comprising either or both of a transition metal/carbon composition or a transition metal/nitrogen composition in which the transition metal is selected from molybdenum and tungsten, generally the transition metal composition comprises at least about 5% by weight of a catalyst including a transition metal composition formed on a carbon support (i.e., a modified carbon support). Such modified carbon supports are particularly useful as modified carbon supports for dehydrogenation catalysts formed by depositing a metal-containing active phase on the modified carbon support. Typically, the transition metal composition comprises from about 5% to about 20% by weight of the catalyst, more typically from about 10% to about 15% by weight of the catalyst, and, still more typically, from about 10% to about 12% by weight of the catalyst. Generally, the transition metal component of the transition metal composition (i.e., molybdenum or tungsten and nitrogen and/or carbon) comprises at least about 5% by weight of the catalyst. Preferably, the transition metal component of the transition metal composition comprises from about 8 to about 15% by weight of the catalyst.

Transition metal compositions deposited on carbon supports in accordance with the above discussion may be incorporated into catalysts further containing a metal containing active phase deposited over a modified carbon support including such transition metal compositions formed on a carbon support.

In processes for forming a transition metal composition on the carbon support, a precursor of the transition metal composition is first formed on the carbon support by contacting the carbon support with a source compound comprising the transition metal to be deposited.

Generally, the source compound is in the form of a water-soluble transition metal salt selected from the group consisting of halides, sulfates, acetates, nitrates, ammonium salts, and combinations thereof. Typically, the source compound is in the form of a transition metal salt such as a transition metal halide. However, the selection of the transition metal salt is not critical. For example, to produce a transition metal composition comprising iron, the source compound may comprise an iron halide (e.g., $FeCl_3$), iron sulfate (e.g., $FeSO_4$), iron acetate, an ammonium salt of iron (e.g., $(NH_4)_4Fe(CN)_6$), or combinations thereof. Similarly, to produce a transition metal composition comprising cobalt, the source compound may comprise a cobalt halide (e.g., $CoCl_2$), cobalt sulfate (e.g., $CoSO_4$), cobalt acetate, or combinations thereof. Similarly, to produce a transition metal composition comprising molybdenum or tungsten, the molybdenum or tungsten-containing salts are preferably water-soluble and generally selected from the sodium, potassium and ammonium salts. The salt may contain molybdenum as an anion, for example, in the form of ammonium molybdate $((NH_4)_2MoO_4^{-2})$ or sodium molybdate $(Na_2MoO_4)$. In the case of a transition metal composition comprising tungsten, the transition metal salt may be selected from tungsten salts including, for example, sodium tungstate and tungstophosphoric acid.

To form the precursor, a source compound is contacted with the carbon support or a mixture may be prepared comprising the source compound, for example an aqueous solution of a salt comprising the transition metal, and the carbon support is contacted with such mixture. Advantageously, this may be accomplished by preparing an aqueous slurry of a particulate carbon support in a liquid medium (e.g., water), and adding to the slurry an aqueous solution containing the salt which comprises the transition metal. Alternatively, an aqueous slurry containing the particulate carbon support can be added to an aqueous solution containing the salt comprising the transition metal.

The amount of source compound contacted with the carbon support or present in a slurry contacted with the carbon support is not narrowly critical. Overall, a suitable amount of source compound should be added to any slurry containing the carbon support to provide sufficient transition metal deposition. Typically, the source compound is added to the carbon support slurry at a rate of at least about 0.00005 moles/minute and, more typically, at a rate of from about 0.00005 to about 0.0005 moles/minute. Typically, the source compound is present in a suspension or slurry containing the source compound and a liquid medium in a proportion of at least about 0.01 g/liter and, more typically, from about 0.1 to about 10 g/liter. The carbon support is typically present in the suspension of slurry in a proportion of at least about 1 g/liter and, more typically, from about 1 to about 50 g/liter. Preferably, the source compound and carbon support are present in the suspension or slurry at a weight ratio of transition metal/carbon in the range of from about 0.1 to about 20. More preferably, the source compound and carbon support are present in the suspension or slurry at a weight ratio of transition metal/carbon in the range of from about 0.5 to about 10.

The rate of addition of the transition metal-containing salt to a slurry containing the carbon support is not narrowly critical but, generally, is at least about 0.05 L/hour per L slurry (0.01 gal./hour per gal. of slurry) of salt is added to the slurry. Preferably, from about 0.05 L/hour per L slurry (0.01 gal./hour per gal. of slurry) to about 0.4 L/hour per L slurry (0.1 gal./hour per gal. of slurry) and, more preferably, from about 0.1 L/hour per L of slurry (0.026 gal./hour per gal. of slurry) to about 0.2 L/hour per L of slurry (0.052 gal./hour per gal. of slurry) of salt is added to the slurry containing the carbon support.

In certain embodiments in which the transition metal composition formed on the carbon support includes either or both of a composition comprising molybdenum or tungsten and carbon or a composition comprising molybdenum or tungsten and nitrogen, the method of precursor deposition generally proceeds in accordance with the above discussion. Typically, an aqueous solution of a salt containing molybdenum or tungsten is added to an aqueous slurry of a particulate carbon support. Typically, the salt is added to the carbon support slurry at a rate of at least about 0.00005 moles/minute and, more typically, at a rate of from about 0.00005 to about 0.0005 moles/minute. Typically, the salt is present in a suspension or slurry containing the salt and a liquid medium in a proportion of at least about 0.1 g/liter and, more typically, from about 0.1 to about 5 g/liter. The carbon support is typically present in the suspension of slurry in a proportion of at least about 1 g/liter and, more typically, from about 5 to about 20 g/liter. Preferably, the molybdenum or tungsten-containing salt and carbon support are present in the suspension or slurry at a weight ratio of molybdenum/carbon or tungsten/carbon in the range of from about 0.1 to about 20. More preferably, the molybdenum or tungsten-containing salt and carbon support are present in the suspension or slurry at a weight ratio of molybdenum/carbon or tungsten/carbon in the range of from about 1 to about 10. Generally, at least about 0.001 L of the molybdenum or tungsten-containing salt solution per gram of carbon support is added to the slurry. Preferably, from about 0.001 L to about 0.05 L transition metal salt per gram of carbon support is added to the slurry. The salt is typically present in the aqueous medium in such concentrations at the outset of precursor deposition in which a carbon support slurry is added to a solution or suspension containing the source compound. Alternatively, such concentrations of source compound generally represent the cumulative total of source compound added to the carbon support slurry in those embodiments in which the solution or suspension of source compound is added to the carbon support slurry.

The rate of addition of the molybdenum or tungsten-containing salt to the slurry in such embodiments is not narrowly critical but, generally, is at least about 0.05 L/hour per L slurry (0.01 gal./hour per gal. of slurry) of salt is added to the slurry. Preferably, from about 0.05 L/hour per L slurry (0.01 gal./hour per gal. of slurry) to about 0.4 L/hour per L slurry (0.1 gal./hour per gal. of slurry) and, more preferably, from about 0.1 L/hour per L of slurry (0.026 gal./hour per gal. of slurry) to about 0.2 L/hour per L of slurry (0.052 gal./hour per gal. of slurry) of salt is added to the slurry.

It is believed that the pH of the transition metal salt and carbon support mixture relative to the zero charge point of carbon (i.e., in mixtures having pH of 3, for example, carbon exhibits a charge of zero whereas in mixtures having a pH greater than 3 or less than 3 carbon exhibits a negative charge and positive charge, respectively) may affect transition metal-containing precursor formation. A transition metal salt having a metal component (e.g., molybdenum) exhibiting a positive or negative charge may be selected to provide bonding between the carbon and the metal based on the pH of the support slurry. For example, in the case of ammonium molybdate, the majority of the molybdenum will exist as $MoO_4^{2-}$, regardless of pH. However, the pH of the slurry may affect adsorption of $MoO_4^{2-}$ on the carbon surface. For example, when the carbon in the slurry has a zero charge point at pH 3, a greater proportion of $MoO_4^{2-}$ will be adsorbed on the carbon in a slurry having a pH 2 than would be adsorbed in a slurry having a pH of 5. In the case of ammonium tungstate or ammonium molybdate in a slurry having a pH of from about 2 to about 3, substantially all of the transition metal is adsorbed on the carbon support (i.e., less than about 0.001% of the transition metal remains in the salt solution). The pH of the slurry may be controlled by addition of an acid or base either concurrently with the transition metal salt or after addition of the transition metal salt to the slurry is complete.

Alternatively, the pH of the slurry of the source compound and carbon support and, accordingly, the charge of the carbon support may be controlled depending on whether the transition metal component is present as the cation or anion of the source compound. Thus, when the transition metal is present as the cation of the source compound the pH of the slurry is preferably maintained above 3 to promote adsorption of transition metal on the carbon support surface. In certain embodiments, the pH of the liquid medium is maintained at 7.5 or above.

In various embodiments, transition metal is present in the source compound as the cation (e.g., $FeCl_3$ or $CoCl_2$). As the pH of the liquid medium increases, the transition metal cation of the source compound becomes partially hydrolyzed. For example, in the case of $FeCl_3$, iron hydroxide ions such as $Fe(OH)_2^{+1}$ or $Fe(OH)^{+2}$ may form and such ions are adsorbed onto the negatively charged carbon support surface. Preferably, the ions diffuse into the pores and are adsorbed and dispersed throughout the surface of the carbon support, including within the surfaces of pores. However, if the pH of the liquid medium is increased too rapidly, iron hydroxide ($Fe(OH)_3$) will precipitate in the liquid medium and conversion of the iron ions to neutral iron hydroxide removes the electrostatic attraction between iron and the carbon support surface and reduces deposition of iron on the support surface. Precipitation of iron hydroxide into the liquid medium may also impede dispersion of iron ions throughout the pores of the carbon support surface. Thus, preferably the pH of the liquid medium is controlled to avoid rapid precipitation of transition metal hydroxides before the occurrence of sufficient deposition of transition metal onto the carbon support surface by virtue of the electrostatic attraction between transition metal ions and the carbon support surface. After sufficient deposition of iron onto the carbon support surface, the pH of the liquid medium may be increased at a greater rate since a reduced proportion of iron remains in the bulk liquid phase.

The temperature of the liquid medium also affects the rate of precipitation of transition metal, and the attendant deposition of transition metal onto the carbon support. Generally, the rate of precipitation increases as the temperature of the medium increases. Typically, the temperature of the liquid medium during introduction of the source compound is maintained in a range from about 10 to about 30° C. and, more typically, from about 20 to about 25° C.

Further in accordance with embodiments in which the transition metal is present as the cation of the source compound, after addition of the source compound to the liquid medium is complete, both the pH and temperature of the liquid medium may be increased. In certain embodiments, the pH of the liquid medium is increased to at least about 8.5, in others to at least about 9.0 and, in still other embodiments, to at least about 9.0. Generally, the temperature of the liquid medium is increased to at least about 40° C., more generally to at least about 45° C. and, still more generally, to at least about 50° C. Typically, the temperature is increased at a rate of from about 0.5 to about 10° C./min and, more typically, from about 1 to about 5° C./min.

After an increase of the temperature and/or pH of the liquid medium, typically the medium is maintained under these conditions for a suitable period to time to allow for sufficient deposition of transition metal onto the carbon support surface. Typically, the liquid medium is maintained at such conditions for at least about 2 minutes, more typically at least about 5 minutes and, still more typically, at least about 10 minutes.

In certain embodiments, the temperature of the liquid medium is about 25° C. and the pH of the liquid medium is maintained at from about 7.5 to about 8.0 during addition of the source compound. After addition of the source compound is complete, the liquid medium is agitated by stirring for from about 25 to about 35 minutes while its pH is maintained at from about 7.5 to about 8.5. The temperature of the liquid medium is then increased to a temperature of from about 40 to about 50° C. at a rate of from about 1 to about 5° C./min while the pH of the liquid medium is maintained at from about 7.5 to about 8.5. The medium is then agitated by stirring for from about 15 to about 25 minutes while the temperature of the liquid medium is maintained at from about 40 to about 50° C. and the pH at from about 7.5 to about 8.0. The slurry is then heated to a temperature of from about 50 to about 55° C. and its pH adjusted to from about 8.5 to about 9.0, with these conditions being maintained for approximately 15 to 25 minutes. Finally, the slurry is heated to a temperature of from about 55 to about 65° C. and its pH adjusted to from about 9.0 to about 9.5, with these conditions maintained for approximately 10 minutes.

Regardless of the presence of the transition metal in the source compound as an anion or cation, to promote contact of the support with the transition metal source compound, and mass transfer from the liquid phase, the slurry may be agitated concurrently with additions of source compound to the slurry or after addition of the transition metal salt to the slurry is complete. The liquid medium may likewise be agitated prior to, during, or after operations directed to increasing its temperature and/or pH. Suitable means for agitation include, for example, by stirring or shaking the slurry.

For transition metal compositions comprising a plurality of metals, typically a single source compound comprising all of the metals, or a plurality of source compounds each containing at least one of the metals is contacted with the carbon support in accordance with the preceding discussion. Deposition of precursors of the component transition metals may be carried out concurrently (i.e., contacting the carbon support with a plurality of source compounds, each containing a transition metal for deposition of a precursor) or sequentially (deposition of one precursor followed by deposition of one or more additional precursors) in accordance with the above discussion.

After the transition metal salt has contacted the support for a time sufficient to ensure sufficient deposition of the source compound(s) and/or formation of its (their) derivative(s), the slurry is filtered, the support is washed with an aqueous solution and allowed to dry. Typically, the salt contacts the support for at least about 0.5 hours and, more typically, from about 0.5 to about 5 hours. Generally, the impregnated support is allowed to dry for at least about 2 hours. Preferably, the impregnated support is allowed to dry for from about 5 to about 12 hours. Drying may be accelerated by contacting the impregnated carbon support with air at temperatures generally from about 80 to about 150° C.

A source compound or derivative may also be formed on the carbon support by vapor deposition methods in which the carbon support is contacted with a mixture comprising a vapor phase source of a transition metal. In chemical vapor deposition the carbon support is contacted with a volatile metal compound generally selected from the group consisting of halides, carbonyls, and organometallic compounds which decomposes to produce a transition metal suitable for formation on the carbon support. Examples of suitable metal carbonyl compounds include $Mo(CO)_6$, $W(CO)_6$, $Fe(CO)_5$, and $Co(Co)_4$.

Decomposition of the compound generally occurs by subjecting the compound to light or heat. In the case of decomposition using heat, temperatures of at least about 100° C. are typically required for the decomposition.

It may be noted that the precursor compound may be the same as the source compound, or it may differ as a result of chemical transformation occurring during the process of deposition and/or otherwise prior to contact with a nitrogen-containing compound, carbon-containing compound (e.g., a hydrocarbon), or nitrogen and carbon-containing compound. For example, where a porous carbon support is impregnated with an aqueous solution of a source compound comprising ammonium molybdate, the precursor is ordinarily the same as the source compound. But where vapor deposition techniques are used with a source compound such as a molybdenum halide, the precursor formed may be metallic molybdenum or molybdenum oxide.

Regardless of the method for formation of the source compound or its derivative on the carbon support, in certain embodiments the pretreated carbon support is then subjected to further treatment (e.g., temperature programmed treatment) to form a transition metal composition comprising a transition metal and nitrogen, a transition metal and carbon, or a transition metal, nitrogen, and carbon on the carbon support. Generally, the pretreated carbon support is contacted with a nitrogen-containing, carbon-containing, or nitrogen and carbon-containing compound under certain conditions (e.g, elevated temperature). Generally, a fixed or fluidized bed comprising carbon support having the precursor deposited thereon is contacted with a nitrogen and/or carbon-containing compound. Preferably, the carbon support is established in a fixed bed reactor and a vapor-phase nitrogen-containing, carbon-containing, or nitrogen and carbon-containing compound is contacted with the support by passage over and/or through the bed of carbon support.

When a transition metal composition comprising a transition metal and nitrogen is desired, typically the pretreated carbon support is contacted with any of a variety of nitrogen-containing compounds which may include ammonia, an amine, a nitrile, a nitrogen-containing heterocyclic compound, or combinations thereof. Such nitrogen-containing compounds are typically selected from the group consisting of ammonia, dimethylamine, ethylenediamine, isopropylamine, butylamine, melamine, acetonitrile, propionitrile, picolonitrile, pyridine, pyrrole, and combinations thereof.

Typically, the carbon support having a precursor of the transition metal composition deposited thereon is contacted with a nitriding atmosphere which comprises a vapor phase nitrogen-containing compound as set forth above. In a preferred embodiment, the nitrogen-containing compound comprises acetonitrile. Typically, the nitriding atmosphere comprises at least about 5% by volume of nitrogen-containing compound and, more typically, from about 5 to about 20% by volume of the nitrogen-containing compound. Generally, at least about 100 liters of nitrogen-containing compound per kg of carbon per hour (at least about 3.50 ft$^3$ of carbon-containing compound per lb of carbon per hour) are contacted with the carbon support. Preferably, from about 200 to about 500 liters of nitrogen-containing compound per kg of carbon per hour (from about 7.0 to about 17.7 ft$^3$ of carbon-containing compound per lb of carbon per hour) are contacted with the carbon support.

The nitriding atmosphere optionally includes additional components selected from the group consisting of hydrogen and inert gases such as argon. Hydrogen, where present, generally may be present in a proportion of at least about 1% by volume hydrogen or, more generally, from about 1 to about 10% by volume hydrogen. Additionally or alternatively, the nitriding atmosphere typically comprises at least about 75% by volume argon and, more typically, from about 75 to about 95% by volume argon. In certain embodiments, the nitriding atmosphere comprises at least about 10 liters of hydrogen per kg of carbon support per hour (at least about 0.35 ft$^3$ of hydrogen per lb of carbon support). Preferably, such a nitriding atmosphere comprises from about 30 to about 50 liters of hydrogen per kg of carbon support per hour (from about 1.05 to about 1.8 ft$^3$ of hydrogen per lb of carbon support per hour). In various other embodiments, the nitriding atmosphere comprises at least about 900 liters of argon per kg of carbon support per hour (at least about 31.5 ft$^3$ of argon per lb of carbon support). Preferably, such a nitriding atmosphere comprises from about 1800 to about 4500 liters of argon per kg of carbon support per hour (from about 63 to about 160 ft$^3$ of argon per lb of carbon support per hour). In further embodiments, the nitriding atmosphere comprises at least about 10 liters of hydrogen per kg of carbon support per hour (at least about 0.35 ft$^3$ of hydrogen per lb of carbon support) and at least about 900 liters of argon per kg of carbon support per hour (at least about 31.5 ft$^3$ of argon per lb of carbon support).

The carbon support having a precursor of the transition metal composition thereon is typically contacted with the nitrogen-containing compound in a nitride reaction zone under a total pressure of no greater than about 15 psig. Typically, the nitride reaction zone is under a pressure of from about 2 to about 15 psig. The nitrogen-containing compound partial pressure of the nitride reaction zone is typically no greater than about 2 psig and, more typically, from about 1 to about 2 psig. The partial pressure of any hydrogen present in the nitriding zone is typically less than about 1 psig and, more typically, from about 0.1 to about 1 psig.

When a transition metal composition comprising a transition metal and carbon is desired, typically the pretreated carbon support is contacted with a carbiding atmosphere containing a carbon-containing compound including, for example, hydrocarbons such as methane, ethane, propane, butane, and pentane.

Typically, the carbon support having a precursor of the transition metal composition deposited thereon is contacted with a carbiding atmosphere which comprises a vapor phase carbon-containing compound. In a preferred embodiment, the carbon-containing compound comprises methane. Typically, the carbiding atmosphere comprises at least about 5% by volume of carbon-containing compound and, more typically, from about 5 to about 50% by volume of the carbon-containing compound. Generally, at least about 100 liters of carbon-containing compound per kg of carbon per hour (at least about 3.50 ft$^3$ of carbon-containing compound per lb of carbon per hour) are contacted with the carbon support. Preferably, from about 200 to about 500 liters of carbon-containing compound per kg of carbon per hour (from about 7.0 to about 17.7 ft$^3$ of carbon-containing compound per lb of carbon per hour) are contacted with the carbon support.

The carbiding atmosphere optionally includes additional components selected from the group consisting of hydrogen and inert gases such as argon and nitrogen. Hydrogen, where present, generally is present in a proportion of at least about 1% by volume or, more generally, from about 1 to about 50% by volume. In certain embodiments, the carbiding atmosphere comprises at least about 10 liters of hydrogen per kg of carbon support per hour (at least about 0.35 ft$^3$ of hydrogen per lb of carbon support). Preferably, such a carbiding atmosphere comprises from about 30 to about 50 liters of hydrogen per kg of carbon support per hour (from about 1.05 to about 1.8 ft$^3$ of hydrogen per lb of carbon support per hour).

In various other embodiments, the carbiding atmosphere comprises at least about 900 liters of argon per kg of carbon support per hour (at least about 31.5 ft$^3$ of argon per lb of carbon support). Preferably, such a carbiding atmosphere comprises from about 1800 to about 4500 liters of argon per kg of carbon support per hour (from about 63 to about 160 ft$^3$ of argon per lb of carbon support per hour).

In further embodiments, the carbiding atmosphere comprises at least about 10 liters of hydrogen per kg of carbon support per hour (at least about 0.35 ft$^3$ of hydrogen per lb of carbon support) and at least about 900 liters of argon per kg of carbon support per hour (at least about 31.5 ft$^3$ of argon per lb of carbon support).

In various other embodiments, the carbiding atmosphere comprises at least about 900 liters of nitrogen per kg of carbon support per hour (at least about 31.5 ft$^3$ of nitrogen per lb of carbon support). Preferably, such a carbiding atmosphere comprises from about 1800 to about 4500 liters of nitrogen per kg of carbon support per hour (from about 63 to about 160 ft³ of nitrogen per lb of carbon support per hour).

The carbon support having a precursor of the transition metal composition thereon is typically contacted with the carbon-containing compound in a carbide reaction zone under a total pressure of no greater than about 15 psig. Typically, the carbide reaction zone is under a pressure of from about 2 to about 15 psig. The carbon-containing compound partial pressure of the carbide reaction zone is typically no greater than about 2 psig and, more typically, from about 1 to about 2 psig. The partial pressure of any hydrogen present in the carbide reaction zone is typically less than about 2 psig and, more typically, from about 0.1 to about 2 psig.

In certain embodiments, the pretreated carbon support, having a precursor transition metal compound thereon, may be treated to form a transition metal composition comprising both carbon and nitrogen and the transition metal on the carbon support. In such embodiments, the precursor compound on the support may be contacted with a "carbiding-nitriding atmosphere." One method involves contacting the pretreated carbon support with a carbon and nitrogen-containing compound. Suitable carbon and nitrogen-containing compounds include amines, nitriles, nitrogen-containing heterocyclic compounds, or combinations thereof. Such carbon and nitrogen-containing compounds are generally selected from the group consisting of dimethylamine, ethylenediamine, isopropylamine, butylamine, melamine, acetonitrile, propionitrile, picolonitrile, pyridine, pyrrole, and combinations thereof.

Typically, the carbon support having a precursor of the transition metal composition deposited thereon is contacted with a carbiding-nitriding atmosphere which comprises a vapor phase carbon and nitrogen-containing compound. Typically, the carbiding-nitriding atmosphere comprises at least about 5% by volume of carbon and nitrogen-containing compound and, more typically, from about 5 to about 20% by volume of the carbon and nitrogen-containing compound. Generally, at least about 100 liters of carbon and nitrogen-containing compound per kg of carbon per hour (at least about 3.50 ft³ of carbon and nitrogen-containing compound per lb of carbon per hour) are contacted with the carbon support. Preferably, from about 200 to about 500 liters of carbon and nitrogen-containing compound per kg of carbon per hour (from about 7.0 to about 17.7 ft³ of carbon and nitrogen-containing compound per lb of carbon per hour) are contacted with the carbon support.

The carbiding-nitriding atmosphere optionally includes additional components selected from the group consisting of hydrogen and inert gases such as argon. Hydrogen, where present, is generally present in a proportion of at least about 1% by volume or, more generally, from about 1 to about 5% by volume. In certain embodiments, the carbiding-nitriding atmosphere comprises at least about 10 liters of hydrogen per kg of carbon support per hour (at least about 0.35 ft³ of hydrogen per lb of carbon support). Preferably, such a carbiding-nitriding atmosphere comprises from about 30 to about 50 liters of hydrogen per kg of carbon support per hour (from about 1.05 to about 1.8 ft³ of hydrogen per lb of carbon support per hour).

In various other embodiments, the carbiding-nitriding atmosphere comprises at least about 900 liters of argon per kg of carbon support per hour (at least about 31.5 ft³ of argon per lb of carbon support). Preferably, such a carbiding-nitriding atmosphere comprises from about 1800 to about 4500 liters of argon per kg of carbon support per hour (from about 63 to about 160 ft³ of argon per lb of carbon support per hour).

In further embodiments, the carbiding-nitriding atmosphere comprises at least about 10 liters of hydrogen per kg of carbon support per hour (at least about 0.35 ft³ of hydrogen per lb of carbon support) and at least about 900 liters of argon per kg of carbon support per hour (at least about 31.5 ft³ of argon per lb of carbon support).

The carbon support having a precursor of the transition metal composition thereon is typically contacted with the carbon and nitrogen-containing compound in a carbide-nitride reaction zone under a total pressure of no greater than about 15 psig. Typically, the carbide-nitride reaction zone is under a pressure of from about 2 to about 15 psig. The carbon and nitrogen-containing compound partial pressure of the carbide-nitride reaction zone is typically no greater than about 2 psig and, more typically, from about 1 to about 2 psig. The partial pressure of any hydrogen present in the carbide-nitride reaction zone is typically less than about 1 psig and, more typically, from about 0.1 to about 1 psig.

Additionally or alternatively, a transition metal composition comprising a transition metal, carbon, and nitrogen may be formed by contacting the support and precursor with a nitrogen-containing compound as described above with the carbon of the transition metal composition derived from the supporting structure.

In further embodiments, the support and precursor of the transition metal composition may be contacted with a nitrogen-containing compound (e.g., ammonia) and a carbon-containing compound (e.g., methane) as set forth above to form a transition metal composition comprising a transition metal, carbon, and nitrogen on the carbon support.

In still further embodiments the carbon support is contacted with a compound comprising a transition metal, nitrogen, and carbon to form a precursor of the transition metal composition thereon (i.e., the source compound and carbon and nitrogen-containing compound are provided by one composition) and heated in accordance with the following description to form a transition metal composition comprising a transition metal, nitrogen, and carbon on a carbon support. Typically, such compositions comprise a co-ordination complex comprising nitrogen-containing organic ligands including, for example, nitrogen-containing organic ligands including five or six membered heterocyclic rings comprising nitrogen. Generally, such ligands are selected from the group consisting of porphyrins, porphyrin derivatives, polyacrylonitrile, phthalocyanines, pyrrole, substituted pyrroles, polypyrroles, pyridine, substituted pyridines, bipyridyls, phthalocyanines, imidazole, substituted imadazoles, pyrimidine, substituted pyrimidines, acetonitrile, o-phenylenediamines, bipyridines, salen ligands, p-phenylenediamines, cyclams, and combinations thereof. In certain embodiments, the co-ordination complex comprises phthalocyanine (e.g., a transition metal phthalocyanine) or a phthalocyanine derivative. Certain of these co-ordination complexes are also described in International Publication No. WO 03/068387 A1 and U.S. Application Publication No. 2004/0010160 A1, the entire disclosures of which are hereby incorporated by reference.

To deposit the transition metal composition precursor in such embodiments, typically a suspension is prepared comprising the carbon support and the co-ordination complex which is agitated for a time sufficient for adsorption of the co-ordination compound on the carbon support. Typically, the suspension contains the carbon support in a proportion of from about 5 to about 20 g/liter and the co-ordination compound in a proportion of from about 2 to about 5. Preferably, the carbon support and co-ordination compound are present in a weight ratio of from about 2 to about 5 and, more preferably, from about 3 to about 4.

Formation of a transition metal composition on the carbon support proceeds by heating the support and precursor in the presence of an atmosphere described above (i.e., in the presence of a nitrogen-containing, carbon-containing, or nitrogen and carbon-containing compound). Typically, the carbon support having the precursor thereon is heated using any of a variety of means known in the art including, for example, an electrical resistance furnace or an induction furnace.

Generally, the transition metal composition precursor may contain a transition metal salt, partially hydrolyzed transition metal, and/or a transition metal oxide. For example, in the case of iron, the precursor may comprise $FeCl_3$, $Fe(OH)_3$, $Fe(OH)_2^{+1}$, $Fe(OH)^{+2}$, and/or $Fe_2O_3$. Generally, heating the carbon support having a precursor of the transition metal composition thereon forms the transition metal composition by providing the energy necessary to replace the bond between the transition metal and the other component of the precursor composition(s) with a bond between the transition metal and nitrogen, carbon, or carbon and nitrogen. Additionally or alternatively, the transition metal composition may be formed by reduction of transition metal oxide to transition metal which combines with the carbon and/or nitrogen of the composition present in the nitriding, carbiding, or carbiding-nitriding atmosphere with which the carbon support is contacted to form the transition metal composition.

Typically, the support is heated to a temperature of at least about 600° C., more typically to a temperature of at least about 700° C., still more typically to a temperature of at least about 800° C. and, even more typically, to a temperature of at least about 850° C. to produce the transition metal composition.

The maximum temperature to which the support is heated is not narrowly critical as long as it is sufficient to produce a transition metal nitride, transition metal carbide, or transition metal carbide-nitride. The support can be heated to temperatures greater than 1000° C., greater than 1250° C., or up to about 1500° C. It has been observed, however, that graphitization of the carbon support may occur if the support is heated to temperatures above 900° C. or above 1000° C. Graphitization may have a detrimental effect on the activity of the catalyst. Thus, preferably, the support is heated to a temperature of no greater than about 1000° C. However, active catalysts can be prepared by heating the support and precursor to temperatures in excess of 1000° C., regardless of any graphitization which may occur. Preferably, the support is heated to a temperature of from about 600° C. to about 1000° C., more preferably, from about 600 to about 975° C., more preferably from about 700 to about 975° C., even more preferably from about 800 to about 975° C., still more preferably from about 850 to about 975° C. and especially to a temperature of from about 850° C. to about 950° C.

In the case of a carbiding atmosphere comprising a hydrocarbon (e.g., methane), it has been observed that heating the carbon support to temperatures above 700° C. may cause polymeric carbon to form on the carbon support. Thus, in certain embodiments in which a transition metal composition comprising a transition metal and carbon is desired, it may be preferable to form such a composition by heating the support to temperatures of from about 600 to about 700° C. However, it should be understood that formation of a transition metal composition comprising a transition metal and carbon proceeds at temperatures above 700° C. and such a method produces suitable modified carbon supports for use in accordance with the present invention provided $T_{max}$ is sufficient for carbide formation (e.g., at least 500° C. or at least 600° C.).

The rate of heating is likewise not narrowly critical. Typically, the support having a precursor deposited thereon is heated at a rate of at least about 2° C./minute, more typically at least about 5° C./minute, still more typically at least about 10° C./minute and, even more typically, at a rate of at least about 12° C./minute. Generally, the support having a precursor deposited thereon is heated at a rate of from about 2 to about 15° C./minute and, more generally, at a rate of from about 5 to about 15° C./minute.

A carbon support having a transition metal/nitrogen and/or transition metal/carbon composition formed thereon may serve as a modified carbon support for a metal-containing active phase effective for promoting the dehydrogenation of an alcohol. In various embodiments, the metal-containing active phase comprises copper.

In certain embodiments of the present invention it may be desired to form a transition metal composition comprising carbon or nitrogen (i.e., a transition metal carbide or nitride) comprising molybdenum or tungsten (i.e., molybdenum carbide, tungsten carbide, molybdenum nitride, or tungsten nitride). One method for forming such carbides and nitrides involves temperature programmed reduction (TPR) which includes contacting the support and the transition metal precursor with a carbiding (i.e., carbon-containing) or nitriding (i.e., nitrogen-containing) atmosphere under the conditions described below. It should be understood that the following discussion regarding forming molybdenum and tungsten-containing transition metal compositions does not limit the discussion set forth above regarding forming catalytically active transition metal compositions comprising at least one of numerous transition metals (including molybdenum and tungsten).

In embodiments in which molybdenum carbide or tungsten carbide is desired, typically, a carbiding atmosphere comprises a hydrocarbon having from 1 to 5 carbons. In a preferred embodiment, the carbon-containing compound comprises methane. Typically, the carbiding atmosphere comprises at least about 5% by volume of carbon-containing compound and, more typically, from about 5 to about 50% by volume of the carbon-containing compound. Generally, at least about 100 liters of carbon-containing compound per kg of carbon per hour (at least about 3.50 ft³ of carbon-containing compound per lb of carbon per hour) are contacted with the carbon support. Preferably, from about 200 to about 500 liters of carbon-containing compound per kg of carbon per hour (from about 7.0 to about 17.7 ft³ of carbon-containing compound per lb of carbon per hour) are contacted with the carbon support.

The carbiding atmosphere optionally includes additional components selected from the group consisting of hydrogen and inert gases such as argon or nitrogen. Hydrogen, where present, is generally present in a proportion of at least about 1% by volume hydrogen or, more generally, from about 1 to about 50% by volume hydrogen. In one such embodiment, the carbiding atmosphere comprises at least about 10 liters of hydrogen per kg of carbon support per hour (at least about 0.35 ft³ of hydrogen per lb of carbon support per hour). Preferably, such a carbiding atmosphere comprises from about 30 to about 50 liters of hydrogen per kg of carbon support per hour (from about 1.05 to about 1.8 ft³ of hydrogen per lb of carbon support per hour).

In such embodiments in which molybdenum nitride or tungsten nitride is desired, a nitriding atmosphere generally comprises a nitrogen-containing compound such as ammonia and may also include inert gases such as argon and nitrogen. Typically, the nitriding atmosphere comprises at least about 5% by volume of nitrogen-containing compound and, more typically, from about 5 to about 20% by volume of the nitrogen-containing compound. Generally, at least about 100 liters of nitrogen-containing compound per kg of carbon per hour (at least about 3.50 ft³ of nitrogen-containing compound per lb of carbon) are contacted with the carbon support. Preferably, from about 200 to about 500 liters of nitrogen-containing compound per kg of carbon per hour (from about 7.1 to about 17.7 ft³ of nitrogen-containing compound per lb of carbon per hour) are contacted with the carbon support. Hydrogen, where present, generally is present in a proportion of at least about 1% by volume hydrogen or, more generally, from about 1 to about 5% by volume hydrogen.

In various embodiments in which a transition metal composition comprising molybdenum or tungsten is desired, the temperature of the atmosphere is increased to a temperature $T_1$ having a value of at least about 250° C., more typically 300° C., over a period of time, $t_1$. Preferably, the temperature of the atmosphere is increased to from about 250 to about 350° C. and, more preferably, increased to from about 275 to about 325° C. during $t_1$. This period of time ($t_1$) necessary for increasing the temperature from $T_0$ to $T_1$ is generally at least about 5 minutes. Typically, $t_1$ is from about 5 to about 30 minutes and, more typically, from about 10 to about 15 minutes. The rate of temperature increase during $t_1$ is not narrowly critical and generally is less than 150° C./min. Typically, the rate of temperature increase during $t_1$ is from about 10 to about 100° C./min and, more typically, from about 20 to about 50° C.

During $t_1$ the source compound or derivative transition metal carbide or nitride may be transformed to an intermediate oxide formed on the surface of the support. The intermediate oxide formed during $t_1$ generally have an empirical formula of $A_xO_y$, wherein A is molybdenum or tungsten, depending on the desired make-up of the transition metal composition. Typically, the ratio of x to y is at least about 0.33:1 and preferably from about 0.33:1 to about 1:1.

For example, in the formation of a transition metal composition comprising molybdenum, an oxide intermediate may be formed in accordance with the following methods:

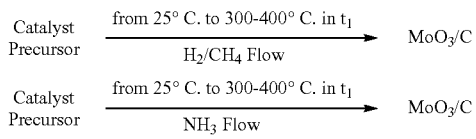

Dehydrogenations which may be promoted by catalysts including a modified carbon support (i.e., a carbon support having a transition metal/nitrogen and/or transition metal/carbon composition formed thereon) having a metal-containing (e.g., copper-containing) active phase deposited thereon are typically conducted in an alkaline environment. Transition metal oxide precursor unconverted to a carbide or nitride may react with an alkaline component of such a dehydrogenation system or alkaline component of a metal plating solution to form a transition metal salt due to the instability of the oxide, thus resulting in removal of transition metal from the surface of the carbon support. For example, $MoO_3$ unconverted to molybdenum carbide may react with sodium hydroxide in accordance with the following:

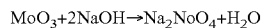

Removal of the transition metal salt from the surface of the carbon support is undesired because it may compromise the catalytic properties of the transition metal composition as such, and/or result in reduced deposition of a metal-containing active phase onto the transition metal composition.

Thus, in accordance with the above considerations, it is desired to convert as great a proportion of any transition metal oxide formed during a carbiding or nitriding operation as possible. Typically, at least about 80% and, more typically, from about 80% to about 95% of the transition metal oxide is converted to the transition metal composition. Preferably, no more than about 5% by weight of the oxide precursor remains unconverted, more preferably, no more than about 3% by weight of the oxide precursor remains unconverted and, still more preferably, no more than about 1% by weight of the oxide precursor remains unconverted.

Considerations concerning the initial temperature ($T_0$), rate of increase from $T_0$ to $T_1$ ($t_1$), the value of $T_1$, and precursor formation are generally the same regarding formation of carbides and nitrides from the precursor or intermediate oxide. However, the remainder of the temperature programmed reduction method differs in certain important respects based on whether a carbide or nitride is desired.

The following discussion relates to preparation of modified carbon supports which may serve as the support for a metal-containing active phase in a catalyst useful for promoting the dehydrogenation of an alcohol. After the initial period of temperature increase, $t_1$, which typically results in formation of transition metal oxide precursor, the temperature of a carbiding (i.e., carburization) atmosphere is elevated from $T_1$ to a maximum temperature ($T_{max}$) during which time a transition metal carbide containing molybdenum or tungsten is formed on the surface of the carbon support by reduction of the transition metal oxide precursor.

Typically, $T_{max}$ is at least about 500° C., more typically at least about 600° C., still more typically at least about 700° C. and, even more typically, at least about 800° C. or at least about 850° C. Preferably, $T_{max}$ is from about 600° C. to about 1000° C. and, more preferably, from about 850° C. to about 950° C.

In the case of a carbiding atmosphere comprising a hydrocarbon (e.g., methane), it has been observed that heating the carbon support to temperatures above 700° C. may cause polymeric carbon to form on the carbon support. Thus, in certain embodiments in which a transition metal composition comprising a transition metal and carbon is desired, it may be preferable to form such a composition by heating the support to temperatures of from about 600 to about 700° C. However, it should be understood that formation of a transition metal composition comprising a transition metal and carbon proceeds at temperatures above 700° C. and such a method produces suitable modified carbon supports for use in accordance with the present invention provided $T_{max}$ is sufficient for carbide formation (e.g., at least 500° C. or at least 600° C.).

In certain embodiments for carbiding atmospheres comprising, for example, methane, the precursor is heated to 650° C. at a rate of at least about 2° C./min. While not narrowly critical, typically the precursor is heated to $T_{max}$ over a period of time ($t_2$) of at least about 10 minutes and, more typically, from about 15 to about 150 minutes and, still more typically, from about 30 to about 60 minutes. The rate at which the temperature increases from $T_1$ to $T_{max}$ is not narrowly critical but generally is at least about 2° C./min. Typically, this rate is from about 2 to about 40° C./min and, more typically, from about 5 to about 10° C./min.

After the atmosphere contacting the oxide-containing precursor reaches $T_{max}$, the temperature of the atmosphere is generally maintained at $T_{max}$ for a time sufficient to ensure the desired reduction of the transition metal oxide to form the transition metal carbide. Typically, this holding time at $T_{max}$, $t_3$, during which the temperature remains at $T_{max}$ is at least about 1 hour and may be from about 1 to about 8 hours; however, care is preferably taken to ensure that $t_3$ is not of a duration such that polymeric carbon forms on the carbon support in amounts that adversely affect catalyst activity. Preferably, $t_3$ is from about 1 to about 4 hours and, more preferably, from about 2 to about 3 hours.

Generally, the intermediate transition metal oxide is contacted with the hydrocarbon under conditions which substantially avoid the production of polymeric carbon on the surface of the transition metal carbide.

The transition metal oxide is typically contacted with the hydrocarbon in a carbide reaction zone under a total pressure of no greater than about 15 psig. Typically, the carbide reaction zone is under a pressure of from about 2 to about 15 psig. The hydrocarbon partial pressure of the carbide reaction zone is typically no greater than about 2 psig and, more typically, from about 1 to about 2 psig.

Both $T_{max}$ and the holding time at $T_{max}$, $t_3$, directly affect carbide formation with each condition being controlled in order to provide sufficient carbide formation. However, ensuring that both conditions are within a preferred range provides even more preferred conditions for carbide formation. Thus, in a particularly preferred embodiment, $T_{max}$ is from about 625 to about 675° C. while $t_3$ is from about 2 to about 3 hours.

After the initial period of temperature increase, $t_1$, which typically results in formation of a transition metal oxide, the temperature of a nitriding (i.e., nitridation) atmosphere is elevated from $T_1$ to a maximum temperature ($T_{max}$) in order to form the transition metal nitride containing molybdenum or tungsten. In contrast to the method described above for carbide formation, the temperature of a nitriding atmosphere is then elevated from $T_1$ to a maximum temperature ($T_{max}$) of at least about 700° C. to produce the nitride since it has been observed that at temperatures below 700° C. the nitride formation is not substantially complete. However, as the nitriding atmosphere approaches temperatures of from about 900° C. and above the metal nitride may be reduced by hydrogen produced by decomposition of the nitriding gas. Thus, $T_{max}$ is preferably from about 700 to about 900° C., more preferably from about 700 to about 850° C. and, still more preferably, from about 725 to about 800° C. While not narrowly critical, typically the oxide-containing precursor is heated to $T_{max}$ over a period of time ($t_2$) of at least about 15 minutes, more typically from about 15 to about 250 minutes and, still more typically, from about 30 to about 60 minutes. The rate at which the temperature increases from $T_1$ to $T_{max}$ is not narrowly critical but generally is at least about 2° C./min. Typically, this rate is from about 2 to about 40° C./min and, more typically, from about 5 to about 10° C./min.

After the atmosphere contacting the oxide-containing precursor reaches $T_{max}$, the temperature of the atmosphere is generally maintained at $T_{max}$ for a time sufficient to ensure the desired reduction of the transition metal oxide to a transition metal nitride. Typically, this period of time, $t_3$, during which the temperature remains at $T_{max}$ is at least about 1 hour. Preferably, $t_3$ is preferably from about 1 to about 5 hours and, more preferably, from about 3 to about 4 hours.

As with carbide formation, both $T_{max}$ and the holding time at $T_{max}$, $t_3$, directly affect nitride formation with each condition being controlled in order to provide sufficient nitride formation. However, ensuring that both conditions are within a preferred range provides even more preferred conditions for nitride formation. Thus, in a particularly preferred embodiment, $T_{max}$ is from about 725 to about 800° C. while $t_3$ is from about 1 to about 5 hours.

It has been observed that during temperature programmed reduction used to produce a transition metal nitride in which the nitrogen-containing atmosphere comprises ammonia, the transition metal nitride thus formed (e.g., molybdenum nitride) may be reduced to form free transition metal.

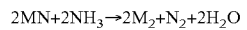

This reaction typically occurs when the nitridation reaction is complete (i.e., substantially all of the oxide precursor has been reduced to the nitride) and is likely to occur when $T_{max}$ reaches higher temperatures (i.e., above 900° C.). Even though these reactions may result in producing the desired transition metal nitride by the forward reaction between free transition metal and ammonia, the conditions for direct ammonia nitridation of free transition metal are preferably avoided because of the possibility of the reverse reduction of the nitride by hydrogen. This is typically controlled by maintaining $T_{max}$ during nitridation below that which accelerates decomposition of ammonia to form hydrogen, thereby preventing the reverse formation of free transition metal by the reduction of the nitride by hydrogen.

The contact of either a carbiding or nitriding atmosphere with the support may occur via a gas phase flow within a fluid bed reaction chamber at a space velocity of at least about 0.01 sec$^{-1}$. The gas phase flow of the carbiding or nitriding atmosphere within a fluid bed reaction chamber is not narrowly critical and may exhibit a space velocity of from about 0.01 to about 0.50 sec$^{-1}$. While carbide and nitride formation proceeds readily over a wide range of gas phase flow rates, the flow rate may be increased to initially increase diffusion of the source compound into the pores of the support to accelerate formation of the carbide or nitride and reduce the time necessary to hold the temperature at $T_{max}$ to ensure sufficient carbide or nitride formation.

In addition to temperature programmed reduction, other methods for producing a transition metal (e.g., molybdenum or tungsten) carbide may be used. For example, a carbon support having a precursor formed on its surface in accordance with the above description may be contacted with an inert gas at temperatures ranging from about 500 to about 1400° C. It is believed that the precursor is reduced by the carbon support under the high temperature conditions and the precursor reacts with the carbon support to form a carbide on the surface of the support. The inert gas may be selected from the group consisting of argon, nitrogen, and helium.

Another method includes contacting a volatile metal compound and a carbon support at temperatures ranging from about 500 to about 1400° C. to reduce the volatile metal compound which then reacts with the carbon support to form a carbide. The volatile metal compound is generally an organometallic compound.

A carbon support having a precursor formed on its surface may also be contacted with hydrogen at a temperature of from about 500 to about 1200° C. (typically, about 800° C.) to reduce the precursor which reacts with the carbon support to form a carbide on the surface of the carbon support.

The time to reach the maximum temperature, the maximum temperature itself or time for holding the temperature at the maximum are not narrowly critical and may vary widely in accordance with either of these methods.

It has been observed that the yield and stability (e.g., resistance to leaching under alkaline dehydrogenation or metal plating conditions) of a carbide produced using the alternatives to temperature programmed reduction described above are reduced as compared to carbides produced using temperature programmed reduction. Thus, temperature programmed reduction is the preferred method for carbide formation.

Formation of a transition metal (e.g., molybdenum or tungsten) carbide and nitride on the surface of a carbon support may proceed generally in accordance with the above discussion. An exemplary preparation is formation of a transition metal (i.e., molybdenum or tungsten) carbide and nitride on the surface of a carbon support having a molybdenum or tungsten-containing precursor deposited thereon as described above. One such method involves subjecting a carbon support to high temperatures (e.g., from about 600 to about 1000° C.) in the presence of an organic ligand containing carbon and nitrogen to form both a carbide and nitride on the support surface. Possible ligands include, for example, a transition metal porphyrin or a nitrogen-containing molybdenum organometallic compound (e.g., a molybdenum pyridine compound).

In a further alternative process for preparing a modified carbon support comprising a transition metal carbide and a transition metal nitride, a transition metal-containing (e.g., molybdenum or tungsten-containing) nitride is formed according to any of the process schemes described above for that purpose, after which the nitride is contacted with a hydrocarbon or a mixture comprising a hydrocarbon and hydrogen. Thus, a composition containing both a carbide and a nitride is formed on the surface of the carbon support by virtue of the conversion of only a certain portion of the nitride. Remainder of a portion of the nitride is assured by maintaining conditions under which conversion of nitride to carbide is incomplete, for example, by limiting $T_{max}$ or limiting the hold time at $T_{max}$.

In the transition metal/nitrogen composition, or transition metal/nitrogen/carbon composition, it is believed that the transition metal is bonded to nitrogen atoms by co-ordination bonds. In at least certain embodiments of the process for preparing the catalyst, a nitrogen-containing compound may be reacted with the carbon substrate, and the product of this reaction further reacted with a transition metal source compound or precursor compound to produce a transition metal composition in which the metal is co-ordinated to the nitrogen. Reaction of the nitrogen-containing compound with the carbon substrate is believed to be incident to many if not most embodiments of the process for preparing the transition metal composition, but can be assured by initially contacting a carbon substrate with the nitrogen-containing compound under pyrolysis conditions in the absence of the transition metal or source thereof, and thereafter cooling the pyrolyzed N-containing carbon, impregnating the cooled N-containing carbon with a transition metal precursor compound, and pyrolyzing again. According to this alternative process, during the first pyrolysis step the carbon may be contacted with a nitrogen-containing gas such as ammonia or acetonitrile at greater than 700° C., typically about 900° C. The second pyrolysis step may be conducted in the presence of an inert or reducing gas (e.g., hydrogen and/or additional nitrogen-containing compound) under the temperature conditions described herein for preparation of a transition metal/nitrogen composition or transition metal/nitrogen/carbon composition on a carbon support. Conveniently, both pyrolysis steps may be conducted by passing a gas of appropriate composition through a fixed or fluid bed comprising a particulate carbon substrate.

Where nitrogen is combined with the carbon substrate, the nitrogen atoms on the carbon support are understood to be typically of the pyridinic-type wherein nitrogen contributes one n electron to carbon of the support, e.g., to the graphene plane of the carbon, leaving an unshared electron pair for co-ordination to the transition metal. It is further preferred that the concentration of transition metal on the support be not substantially greater than that required to saturate the nitrogen atom co-ordination sites on the carbon. Increasing the transition metal concentration beyond that level may result in the formation of zero valence (metallic form) of the transition metal, which is believed to be catalytically inactive for at least certain reactions. The formation of zero valence transition metal particles on the surface may also induce graphitization around the metal particles. Although the graphite may itself possess catalytic activity for certain reactions, graphitization reduces effective surface area, an effect that, if excessive, may compromise the activity of the catalyst.

In the case of catalysts further including a metal-containing active phase formed on a modified carbon support (i.e., a carbon support having a transition metal composition formed thereon), a modified carbon support having a high surface area is desired in order to provide a high surface area suitable for metal deposition. Thus, modified carbon supports typically have a Langmuir surface area of at least about 500 m$^2$/g prior to deposition of a metal thereon. Preferably, the Langmuir surface area of a modified carbon support is at least about 600 m$^2$/g and, more preferably, from about 600 to about 800 m$^2$/g prior to deposition of a metal thereon. Preferably, the surface area of the modified support is at least about 30% of the surface area of the support prior to formation of the transition metal composition thereon and, more preferably, from about 40 to about 70% of the surface area of the support prior to formation of the transition metal composition on the carbon support.

The micropore surface area of modified carbon supports of the present invention (i.e., surface area attributed to pores having a diameter less than 20 Å) is typically at least about 200 m$^2$/g and, more typically, from about 200 to about 400 m$^2$/g. Preferably, the Langmuir micropore surface area of the modified support is at least about 20% of the surface area of the support prior to formation of the transition metal composition thereon, more preferably from about 20 to about 50% and, still more preferably, from about 30 to about 50% of the Langmuir micropore surface area of the support prior to formation of the transition metal composition on the carbon support.

The combined Langmuir mesopore and macropore surface area of modified carbon supports of the present invention (i.e., surface area attributed to pores having a diameter greater than 20 Å) is typically at least about 200 m$^2$/g and, more typically, from about 200 to about 400 m$^2$/g. Preferably, the combined Langmuir micropore and mesopore surface area of the modified support is at least about 40% of the surface area of the support prior to formation of the transition metal composition thereon and, more preferably, from about 50 to about 70% of the surface area of the support prior to formation of the transition metal composition on the carbon support.

Modified carbon supports prepared in accordance with the process of the present invention likewise preferably exhibit pore volumes sufficient to allow for diffusion of reactants into the pores of the finished catalyst. Thus, preferably a modified carbon support comprising a transition metal/carbon composition (i.e., a transition metal carbide) has a total pore volume of at least about 0.50 cm$^3$/g and, more preferably, a pore volume of at least about 0.60 cm$^3$/g.

In addition to overall pore volume, the pore volume distribution of modified carbon supports of the present invention preferably conduces to diffusion of reactants into the pores of the finished catalyst. Preferably, pores having a diameter of less than about 20 Å make up no more than about 45% of the overall pore volume of the modified carbon support and, more preferably, no more than about 30% of the overall pore volume. Pores having a diameter of greater than about 20 Å preferably make up at least about 60% of the overall pore volume of the modified carbon support and, more preferably, at least about 65% of the overall pore volume.

It has been observed that "mesopores" (i.e., pores having a diameter of from about 20 to about 50 Å) allow suitable diffusion of reactants into the pores of a modified carbon support. Thus, preferably mesopores make up at least about 25% of the overall pore volume and, more preferably, at least about 30% of the overall pore volume. Macro pores (i.e., pores having a diameter larger than about 50 Å) also allow suitable diffusion of reactants into the pores of the modified carbon support. Thus, preferably, these pores make up at least about 5% of the overall pore volume and, more preferably, at least about 10% of the overall pore volume of the catalyst.

Catalysts of the present invention may include a metal-containing active phase suitable for catalyzing reactions such as, for example, the dehydrogenation of primary alcohols deposited on a modified carbon support prepared as described above. Such a metal-containing active phase may comprise a metal selected from the group consisting of Group IB and Group VIII. In various embodiments, the metal is selected from the group consisting of copper, nickel, platinum, and palladium with nickel, platinum, or palladium acting as a support for an active phase containing copper.

In the case of dehydrogenation of a primary alcohol, the metal-containing active phase preferably comprises copper. The following discussion focuses on copper-containing catalysts. Nevertheless, it should be recognized that this discussion generally applies to catalysts containing other metals (e.g., nickel, platinum, and palladium).

Copper may be deposited onto the modified carbon support (i.e., the carbon support having a transition metal composition as described above formed thereon) surface via different methods including, for example, electroless plating and electrolytic plating.

Electrolytic plating generally involves passing an electric current through a plating solution comprising the metal to be plated in contact with a cathode comprising the modified carbon support. One alternative method for electrolytic metal plating involves the use of a "slurry electrode" such as that described by Kastening et al. See *Design of a slurry electrode reactor system*, (Journal of Applied Electrochemistry (1997), 27, 147-152). Plating using a slurry electrode proceeds using a metal (e.g., copper) anode and a slurry cathode comprising a feeder electrode in a slurry of the modified carbon support. Plating proceeds by oxidation of the copper anode caused by release of electrons to the external circuit and reduction of the resulting copper ions by electrons supplied by the feeder cathode.

The following discussion focuses on electroless plating since it is the preferred technique due to its simplicity and low cost. Electroless plating proceeds by the reduction of metal ions (e.g., copper ions) to metal by an external reducing agent in a solution in contact with the modified carbon support. In accordance with the present invention, the plating solution generally comprises an aqueous plating medium comprising a water-soluble salt of the metal to be deposited, a reducing agent, and a retardant which inhibits reduction of metal ions (e.g., cupric ions) prior to contact with the modified carbon support. The retardant may, for example, be a chelating agent (i.e., a co-ordination compound) which inhibits reduction of metal ions by forming a co-ordination compound with the metal ions to be deposited in order to delay their reduction by the reducing agent until the metal salt is contacted with the modified carbon support. The plating solution may contain other ingredients including, for example, an alkaline hydroxide and other formulation additives such as stabilizers, surfactants, and brightness and wetting agents. The plating solution is typically stable (i.e., remains as a well-dispersed mixture) for extended periods of time (e.g., a week or longer) and, thus, provides the advantage of being suitable for use in multiple plating operations. Typically, the pH of the aqueous medium is from about 7 to about 14.

In the case of copper, the water-soluble salts of the aqueous medium are preferably selected from the group consisting of copper chloride, copper nitrate, and copper sulfate salts. In a preferred embodiment the water-soluble salt comprises copper sulfate. While the concentration of water-soluble salt in the aqueous medium is not narrowly critical, to help ensure sufficient metal deposition while preventing excess precipitation, typically the salt concentration in the aqueous medium is no more than about 20% by weight. Preferably, the salt concentration in the aqueous medium is from about 1% to about 10% by weight and, more preferably, from about 8% to about 10%. Generally, the aqueous medium comprises at least about 0.2 g of copper salt per g of modified carbon support contacted with the aqueous medium and no more than about 1.5 g of copper salt per g of modified carbon support contacted with the aqueous medium.

A wide variety of reducing agents may be used including, for example, sodium hypophosphite ($NaH_2PO_2$), formaldehyde ($CH_2O$) and other aldehydes, formic acid (HCOOH), salts of formic acid, salts of borohydride (e.g., sodium borohydride ($NaBH_4$)), salts of substituted borohydrides (e.g., sodium triacetoxyborohydride ($Na(CH_3CO_2)_3BH$)), sodium alkoxides, dimethylborane (DMAB), and hydrazine ($H_2NNH_2$). In a preferred embodiment, the reducing agent comprises formaldehyde. Reducing agent is generally present in the aqueous medium in an amount stoichiometrically required for reduction of all or a substantial portion of the metal ions present in the aqueous medium. The concentration of the reducing agent in the aqueous medium is typically no more than about 1% by weight of the overall plating solution and, more typically, no more than about 0.5% by weight.

The reducing agent may be present in an amount in excess of that stoichiometrically required for reduction of all or a substantial portion of the metal ions present in the aqueous medium. If present in an excess amount, typically no more than about 400% excess reducing agent is present.

Suitable retardants (i.e., chelating agents or co-ordination ligands) for incorporation in the aqueous medium for use in electroless plating include, for example, aminopolycarboxylic ligands, aminopolyhydroxylic ligands, polyhydroxylic ligands, and polycarboxy-polyhydroxylic ligands. In particular, the retardant or, co-ordination ligand, may be selected from the group consisting of ethylenediaminetetraacetic acid (EDTA); diethylenetriaminepentaaectic acid; N,N,N',N'-tetrakis-(2-hydroxypropyl)-ethylenediamine; glycerol; and tartaric acid. In a preferred embodiment, the retardant comprises sodium potassium tartrate and, in another, EDTA.

In certain embodiments, the modified carbon support is contacted with the aqueous medium comprising a water-soluble salt of the metal to be deposited, a reducing agent, and a retardant which inhibits reduction of metal ions (e.g., cupric ions) prior to contact with the transition metal composition of the modified carbon support. The transition metal composition (e.g., transition metal carbide or nitride) catalyzes the reduction reaction and overcomes the retardant effect of the chelating agent or other retardant.

As the reducing agent reduces the metal ions in the solution to metal, the metal forms a coating on the surface of the supported transition metal composition which has been formed on the modified carbon support and/or on any transition metal free portion of the carbon support surface. The mechanism of the electroless plating is shown below in which the anodic reaction is the decomposition of the reducing agent (as shown below, formaldehyde) and the cathodic reaction is the reduction of the metal complex.

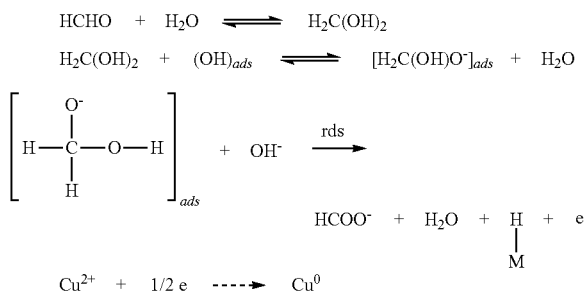

It has been observed that a reducing agent comprising formaldehyde functions more effectively in an alkaline environment. This is because the formaldehyde exists as methylene glycol in the aqueous medium. The presence of an alkaline component facilitates the deprotonation of methylene glycol; thus, the aqueous medium typically also comprises an alkaline component. Typically, the concentration of the alkaline component in the aqueous medium is at least about 0.1% by weight. Preferably, the concentration of the alkaline component in the aqueous medium is from about 0.5 to about 5% by weight and, more preferably, from about 1 to about 3% by weight.

When the aqueous medium does include an alkaline component, care should be taken to avoid formation of precipitates, which may result from reaction between cations of the metal to be deposited and the hydroxide ions. Precipitation is preferably avoided since any precipitates formed may consume metal that may otherwise deposit on the carbon support; and the catalytically inactive precipitates (e.g., $Cu(OH)_2$) may also deposit on the surface of the modified support. Such precipitation may prevent deposition of transition metal within the pores of the carbon support. The presence of a retardant which inhibits reduction of metal ions (e.g., cupric ions) prior to contact with the transition metal composition of the modified carbon support generally sufficiently inhibits this precipitation. Thus, an alkaline component in the aqueous medium is not detrimental to the plating process.

The electroless plating deposition of metal onto the supported transition metal composition may in some circumstances proceed too rapidly, thus preventing sufficient diffusion of the metal into the carbon structure (i.e., sufficient diffusion of the metal into the pores of the carbon support) and, accordingly, preventing uniform deposition of the metal throughout the carbon-supported transition metal composition. The rate of plating is directly proportional to the plating temperature; thus, one way to control the plating rate is to control the plating temperature. It has been discovered that operating the plating process at moderate temperature improves diffusion of the metal to be deposited into the pores of the supported transition metal composition (e.g., carbide, nitride, or carbide-nitride) and, accordingly, the uniformity of metal deposition. Thus, typically the plating is carried out (i.e., the modified carbon support is contacted with the aqueous medium) at temperatures from about 1 to about 50° C. and, more typically, from about 2 to about 25° C. Typically, the modified carbon support remains in contact with the aqueous medium for at least about 0.5 hours and, more typically, for from about 0.5 to about 3 hours.

While plating of copper onto the transition metal composition surface proceeds readily, unfortunately a portion of the transition metal may be removed or, leached, from the transition metal/nitrogen, transition metal/carbon or transition metal/carbon/nitrogen composition on the carbon support during the plating process.

Leaching of transition metal from the support surface may be due to oxidation of the transition metal composition (i.e., nitride, carbide-nitride or carbide) by ions of the metal to be deposited on the transition metal composition which are present in the aqueous medium/plating solution. For example, an oxidized carbide is unstable and, thus, transition metal is more likely to be leached from the surface of the carbon support where the transition metal composition comprises a significant fraction of transition metal carbide. One explanation for the instability of an oxidized carbide may be that it causes oxidation of the transition metal and its removal from the oxide matrix. The oxidation rate of the nitride, carbide-nitride or carbide is directly proportional to the plating temperature; thus, this consideration may generally be addressed by plating at low temperature in accordance with the discussion set forth above regarding plating temperature. Leaching of transition metal due to oxidation of a carbide or nitride is also controlled, in part, by the presence of the reducing agent which contributes to maintaining the surface of the transition metal carbide or nitride in a well-reduced state.

In addition to controlling and/or reducing transition metal leaching, preventing oxidation of the carbide or nitride is also advantageous because metal generally does not plate onto an oxidized carbide or nitride or, if it plates at all, does not produce a metal phase stable under reaction (e.g., dehydrogenation) conditions. This is believed to be due, at least in part, to a much weaker interaction between oxidized carbide and copper.

As stated, the retardant is present in the aqueous medium in order to prevent reduction of metal ions prior to contact with the metal to be plated, and where the retardant is a chelating agent, it may perform this function by forming a co-ordination compound with the metal to be plated. Typically, the concentration of retardant in the aqueous medium is at least about 3% by weight. Preferably, the concentration of retardant in the aqueous medium is from about 3 to about 6% by weight. However, if too great a proportion of retardant is present in the aqueous medium, transition metal may leach from the surface of the carbon support due to formation of a co-ordination compound between the retardant and transition metal.

Thus, the preferred proportion of retardant present in the aqueous medium also depends on the concentration of metal salt present in the aqueous medium. It has been discovered that controlling the ratio of these components contributes to optimal plating considerations. That is to say, including an amount of retardant sufficient to ensure that a sufficient portion of metal is plated while maintaining the retardant concentration below that which may contribute to leaching as discussed above. In accordance with the present invention, the molar ratio of moles of retardant to moles of metal present in the aqueous medium is at least about 1:1, typically at least about 1.5:1, more typically at least about 2.0:1 and, still more typically, at least about 2.5:1. However, the molar ratio of moles of retardant to moles of metal present in the aqueous medium is preferably no more than about 3:1 in order to avoid formation of an excessive amount of co-ordination compound between the retardant and the transition metal.

In addition to plating temperature and retardant concentration, the manner of introduction to the aqueous medium of one or more of its components may be modified to control the plating rate and leaching from the surface of the support. FIG. 1 is a SEM image of a carbon supported molybdenum carbide having copper deposited thereon in accordance with the method described above in which the reducing agent is present at the outset of the electroless plating. As shown in FIG. 1, it has been observed that plating in accordance with the method described above in which the reducing agent is present at the outset of the electroless plating in the case of a carbon-supported molybdenum carbide results in appreciable metal cluster formation and less than desired plating within the pores of the carbon support. This method does, however, result in very little transition metal leaching.

It has been discovered, for example, that introducing the reducing agent into the aqueous medium after the modified carbon support has been contacted with the aqueous medium comprising a metal salt and a retardant provides increased diffusion of the metal to be deposited into the pores of the carbon support since the plating rate is slowed down by virtue of the delay in introduction of the reducing agent; thus resulting in more uniform metal deposition as compared to that observed when the reducing agent is present where the modified carbon support is contacted with the aqueous medium.

Figure 2:
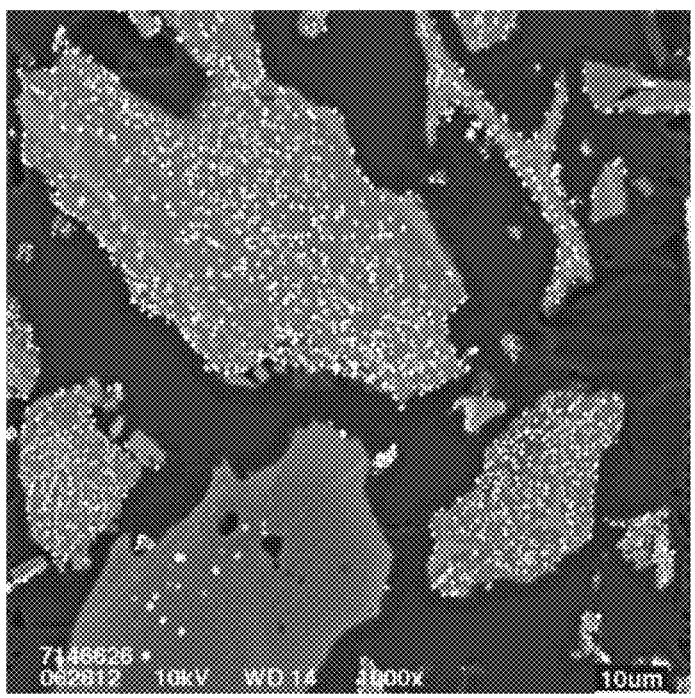
FIG. 2 is a SEM image of a carbon supported molybdenum carbide having copper deposited thereon.

FIG. 2 is a SEM image of a carbon supported molybdenum carbide having copper deposited thereon in accordance with this method (i.e., delaying introduction of the reducing agent until the support has been contacted with the aqueous medium). As shown in FIG. 2, uniform copper plating (i.e., no appreciable formation of copper clusters) and sufficient plating within the pores of the carbon support are observed using this method. On the other hand, introduction of the modified support to the aqueous medium in the absence of the reducing agent may result in high transition metal leaching from the support surface due to oxidation of carbide or nitride surface due to the instability of oxidized carbides and nitrides. For example, molybdenum leaching of as high as 20% was observed in the case of the copper plated carbon supported molybdenum carbide shown in FIG. 2.

Figure 3:
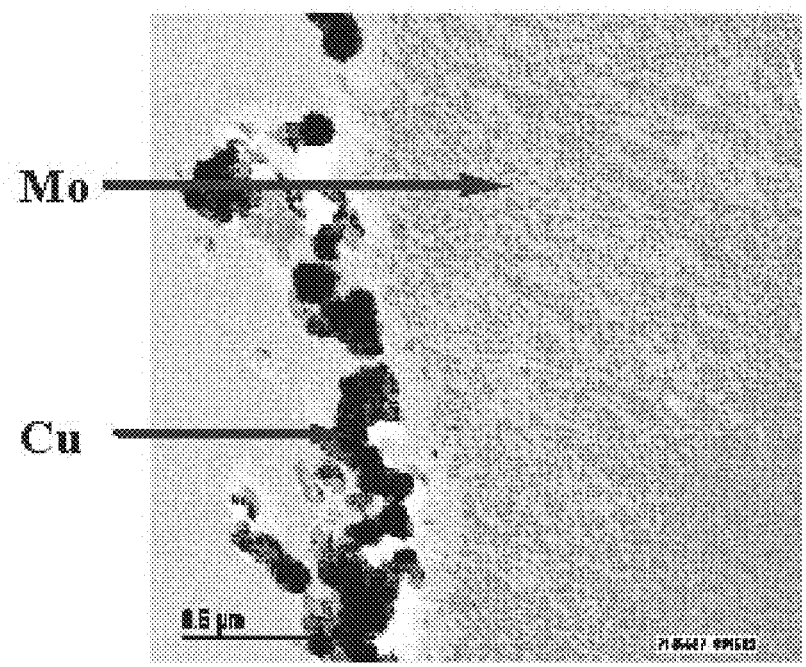
FIG. 3 is a Transmission Electron Microscopy (TEM) image of a carbon supported molybdenum carbide having copper deposited thereon.

Introducing the metal salt into the aqueous medium after the modified carbon support has been contacted with the aqueous medium comprising a reducing agent and a retardant has also been considered. Plating in this manner provides reduced leaching (e.g., as low as 5% of the transition metal formed on the carbon support) caused by oxidation of the carbide or nitride surface since the reducing agent is present to ensure that the carbide or nitride surface remains well reduced. However, plating can proceed too rapidly because the entire stoichiometric amount of reducing agent and salt are present when the carbon support is initially contacted with the aqueous medium. FIG. 3 is a TEM image of a carbon supported molybdenum carbide having copper deposited thereon in accordance with this method (i.e., delaying introduction of the metal salt into the aqueous medium after the modified carbon support has been contacted with the aqueous medium). As shown in FIG. 3, this method may not provide uniform distribution (i.e., appreciable formation of copper clusters occurs) or insufficient plating within the pores of the carbon support. Thus, even though leaching may be reduced as compared to those methods described above, this method, while acceptable in some instances, is not preferred. Deposition of metal per this alternative is usually not as uniform as that achieved using the method described above wherein introduction of a portion of the reducing agent is delayed.

Thus, preferably, the often conflicting considerations of plating rate, which directly affects the uniformity and quality of plating, and oxidation of the carbide or nitride are both addressed by controlling the manner of introduction of each of its components and the modified carbon support to the aqueous medium.

Figure 4:
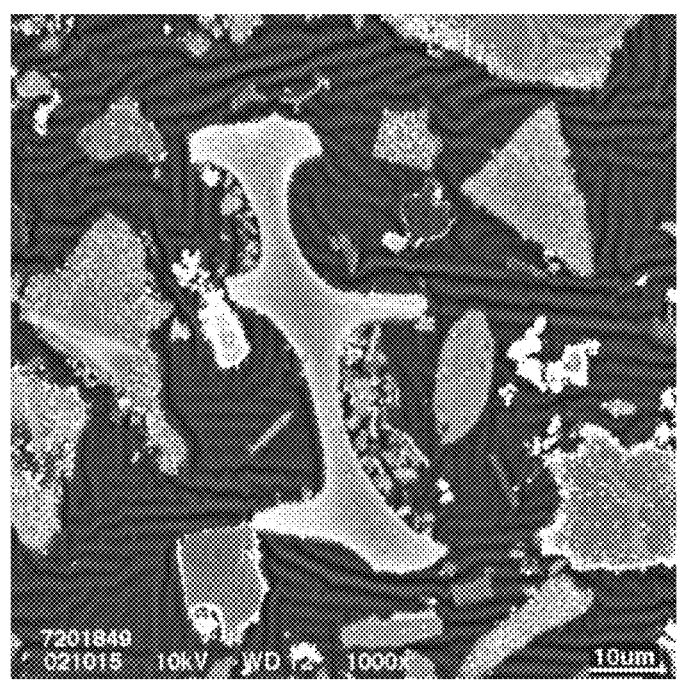
FIG. 4 is a SEM image of a carbon supported molybdenum carbide having copper deposited thereon.

Having reducing agent present in an amount stoichiometrically less than that required for reduction of the metal ions to the metal to be plated in the aqueous medium when the support is initially contacted with the aqueous medium followed by introduction of additional reducing agent to the aqueous medium solution after the support has been contacted with the aqueous medium has also been investigated. The slurry may be agitated as copper metal is deposited on the support. Delaying introduction of a portion of the reducing agent to the aqueous medium in this manner to form a primary electroless plating slurry comprising the less than stoichiometrically required amount of reducing agent reduces the plating rate and, accordingly, allows increased diffusion of the metal to be deposited into the pores of the carbon support, resulting in more uniform metal deposition. The initial portion of reducing agent is sufficient to reduce metal ions while also sufficient to provide a well-reduced carbide or nitride surface to control leaching caused by oxidation of carbide and nitride surface. FIG. 4 is a SEM image of a carbon supported molybdenum carbide having copper deposited thereon in accordance with this method (i.e., delaying introduction of a portion of the reducing agent until the support has been contacted with the aqueous medium). As shown in FIG. 4, uniform deposition of copper is achieved using this method. In addition, low molybdenum leaching (e.g., no more than about 5% by weight) occurs with this method. In certain embodiments, the electroless plating slurry comprises no more than about 2% of the stoichiometric amount of reducing agent required for reduction of the metal ions to be plated while in others the electroless plating slurry comprises from about 2 to about 10% of the stoichiometric amount of reducing agent necessary for reduction of the metal ions to be plated.

Delaying introduction of a portion of the reducing agent to the aqueous medium also serves to minimize decomposition of the reducing agent. For example, in the case of a reducing agent comprising formaldehyde, its decomposition to form hydrogen is delayed.

Even though each of the above methods provides metal deposition on the carbide or nitride surface, the preferred method is that in which introduction of a portion of the reducing agent is delayed since both considerations of plating rate and oxidation of the carbide or nitride are most adequately addressed. As previously discussed, the plating temperature preferably is used to control the plating rate and, accordingly, provide uniform metal deposition. Thus, it is further preferred to combine the beneficial effect of a low plating temperature along with delaying introduction of a portion of the reducing agent to the aqueous medium. Accordingly, in a preferred embodiment the plating temperature is no more than about 2° C. and no more than about 5% of the amount of reducing agent stoichiometrically required for reduction of the metal ions to be plated is introduced to the aqueous medium to form the electroless plating slurry. In various embodiments, however, the plating temperature may range from about 1 to about 20° C., from about 1 to about 10° C., or from about 1 to about 5° C.

Plating of metal on the modified carbon support generally proceeds until the pH of the aqueous medium reaches a predetermined pH based on consumption of the hydroxide ion. Thus, the rate of pH drop is directly related to the plating rate and accordingly is controlled within a suitable range based on the considerations set forth above for controlling the plating process. Typically, plating begins with the aqueous medium at a pH of about 13 and is typically discontinued when the pH of the aqueous medium is about 8. In accordance with the methods set forth above for controlling the plating rate (e.g., temperature and introduction of the reducing agent), preferably the rate of pH drop is no more than about 0.5/min.

Based on the foregoing, it can be seen that numerous factors influence the plating operation. For example, the concentration of metal, retardant, reducing agent, and hydroxide component in the aqueous medium. Thus, preferably the concentrations of each of these components are maintained within a suitable range.

For dehydrogenation catalysts of the present invention, metal deposited on a modified carbon support typically makes up at least about 5% by weight of the catalyst. Preferably, the metal deposited on the modified carbon support makes up from about 5% to about 30% by weight of the catalyst and, more preferably, from about 15% to about 25% by weight of the catalyst and, still more preferably, from about 18% to about 23% by weight of the catalyst. In embodiments in which the catalyst comprises copper deposited on a modified carbon support, the catalyst typically comprises at least about 10% by weight copper and, more typically, at least about 15% by weight copper. Preferably, the catalyst comprises from about 10 to about 30% by weight copper, more preferably from about 15 to about 25% by weight copper and, still more preferably, from about 18 to about 23% by weight copper. In certain embodiments, preferably the copper-containing catalyst comprises no more than about 3% by weight of a noble metal (e.g., platinum) deposited as described below, more preferably, no more than about 1% by weight of a noble metal and, still more preferably, no more than about 0.5% by weight of a noble metal. In other embodiments, preferably the copper-containing catalyst of the present invention comprises no more than about 1% by weight nickel, more preferably, no more than about 1% by weight nickel and, still more preferably, no more than about 0.5% by weight nickel.

Oxidation catalysts of the present invention including a transition metal composition formed on a carbon support may further comprise a noble metal-containing active phase. Catalysts containing an active phase comprising a noble metal are effective for the oxidation of a tertiary amine (e.g., N-(phosphonomethyl)iminodiacetic acid), and also for the oxidation byproducts of this reaction (e.g., formaldehyde and formic acid). In an embodiment of the catalyst of the present invention comprising a noble metal (e.g., platinum) deposited on a modified carbon support, the noble metal is typically deposited in accordance with a well-known method. These include, for example, liquid phase methods such as reaction deposition techniques (e.g., deposition via reduction of noble metal compounds and deposition via hydrolysis of noble metal compounds), ion exchange techniques, excess solution impregnation, and incipient wetness impregnation; vapor phase methods such as physical deposition and chemical deposition; precipitation; and electrochemical displacement deposition methods such as electroless and electrolytic deposition.

Preferably, the noble metal is deposited onto the surface of the modified carbon support via an impregnation method comprising contacting the modified carbon support with a solution comprising a salt of the noble metal to be deposited followed by hydrolysis of the salt. Generally, the salt of the noble metal to be deposited is selected from the group consisting of hydrogen, sodium, potassium, and ammonium salts. One example of a platinum salt suitable for use in solution deposition which is also relatively inexpensive is hexachloroplatinic acid ($H_2PtCl_6$).

The noble metal may also be deposited onto the surface of the modified carbon support using a solution comprising a salt of the noble metal in one of its more reduced oxidation states. For example, instead of using a salt of Pt(IV) (e.g., $H_2PtCl_6$), a salt of Pt(II) is used. In another embodiment, platinum in its elemental state (e.g., colloidal platinum) is used. Using these more reduced metal precursors leads to less oxidation of the modified carbon support and, therefore, less oxygen-containing functional groups being formed at the surface of the support while the noble metal is being deposited on the surface. One example of a Pt(II) salt is $K_2PtCl_4$. Another potentially useful Pt(II) salt is diamminedinitrito platinum(II).

Suitable methods for deposition of the noble metal are discussed in U.S. Pat. No. 6,417,133, the entire disclosure of which is hereby incorporated by reference.

For oxidation catalysts of the present invention, platinum is typically present in a proportion of at least about 0.5% by weight of the catalyst and, more typically, at least about 1% by weight of the catalyst. Preferably, platinum is present in a proportion of from about 1 to about 10% by weight of the catalyst, more preferably from about 2 to about 8% by weight of the catalyst and, still more preferably, from about 2 to about 5% by weight of the catalyst.

In addition to the noble metal, at least one promoter may be at the surface of the carbon support. Although the promoter typically is deposited onto the surface of the carbon support, other sources of promoter may be used (e.g., the carbon support itself may naturally contain a promoter). A promoter tends to increase catalyst selectivity, activity, and/or stability. A promoter additionally may reduce noble metal leaching.

The promoter may, for example, be an additional noble metal(s) at the surface of the carbon support. For example, ruthenium and palladium have been found to act as promoters on a catalyst comprising platinum deposited at a carbon support surface. The promoter(s) alternatively may be, for example, a metal selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn), cerium (Ce), and zirconium (Zr). Preferably, the promoter is selected from the group consisting of bismuth, iron, tin, and titanium. In a particularly preferred embodiment, the promoter is tin. In another particularly preferred embodiment, the promoter is iron. In an additional preferred embodiment, the promoter is titanium. In a further particularly preferred embodiment, the catalyst comprises both iron and tin. Use of iron, tin, or both generally (1) reduces noble metal leaching for a catalyst used over several cycles, and (2) tends to increase and/or maintain the activity of the catalyst when the catalyst is used to effect the oxidation of PMIDA. Catalysts comprising iron generally are most preferred because they tend to have the greatest activity and stability with respect to formaldehyde and formic acid oxidation.

In one preferred embodiment, the promoter is more easily oxidized than the noble metal. A promoter is "more easily oxidized" if it has a lower first ionization potential than the noble metal. First ionization potentials for the elements are widely known in the art and may be found, for example, in the *CRC Handbook of Chemistry and Physics* (CRC Press, Inc., Boca Raton, Fla.).

The amount of promoter at the surface of the carbon support (whether associated with the carbon surface itself, metal, or a combination thereof) may vary within wide limits depending on, for example, the noble metal and promoter used. Typically, the weight percentage of the promoter is at least about 0.05% ([mass of promoter÷total mass of the catalyst]×100%). The weight percent of the promoter preferably is from about 0.05 to about 10%, more preferably from about 0.1 to about 10%, still more preferably from about 0.1 to about 2%, and most preferably from about 0.2 to about 1.5%. When the promoter is tin, the weight percent most preferably is from about 0.5 to about 1.5%. Promoter weight percentages less than 0.05% generally do not promote the activity of the catalyst over an extended period of time. On the other hand, weight percents greater than about 10% tend to decrease the activity of the catalyst.

The molar ratio of noble metal to promoter may also vary widely, depending on, for example, the noble metal and promoter used. Preferably, the ratio is from about 1000:1 to about 0.01:1; more preferably from about 150:1 to about 0.05:1; still more preferably from about 50:1 to about 0.05:1; and most preferably from about 10:1 to about 0.05:1. For example, a catalyst comprising platinum and iron preferably has a molar ratio of platinum to iron of about 3:1.

In certain embodiments, the noble metal (e.g., platinum) is alloyed with at least one promoter (e.g., tin or iron) to form alloyed metal particles.

One feature of a carbon support having a transition metal composition formed thereon (i.e., a modified carbon support) which affects the surface area of transition metal composition available for deposition of copper, noble metal, or other metal active phase thereon is the resistance of the transition metal composition to removal from the surface of the carbon support under certain conditions (e.g., alkaline metal plating conditions and contact with cations of the metal to be plated on the modified carbon support). Thus, preferably no more than about 20% by weight of a transition metal composition of the present invention is removed from the surface of a carbon support when contacted with an alkaline aqueous plating medium under alkaline metal plating conditions for at least about 3 hours. In addition, preferably no more than about 5% by weight of a transition metal composition of the present invention is removed from the surface of a carbon support when contacted with cations of a metal to be deposited on a modified carbon support for at least about 3 hours.

Generally, it is preferred for the oxidation catalysts of the present invention to have a high surface area. Formation of the transition metal/nitrogen, transition metal/carbon or transition metal/carbon/nitrogen composition typically is associated with some reduction in Langmuir surface area. Loss of surface area may be a result of coating of the carbon surface with a transition metal composition of relatively lower surface area, e.g., in the form of an amorphous film and/or relatively large particles of the transition metal composition. Amorphous transition metal composition may be in the form of either amorphous particles or an amorphous film. Preferably, the sacrifice in surface area is not greater than about 40%. Where the transition metal composition is formed under the preferred conditions described above, the loss in total Langmuir surface area is typically between about 20 and about 40%. Thus, generally, the surface area of the catalyst is at least about 60% of the surface area of the carbon support prior to formation of the transition metal composition thereon and, more generally, from about 60 to about 80%.

Typically, the catalyst has a total Langmuir surface area of at least about 500 $m^2/g$, more typically at least about 600 $m^2/g$. Preferably, the total Langmuir surface area of the catalyst is at least about 800 $m^2/g$, more preferably at least about 900 $m^2/g$. It is generally preferred that the total Langmuir surface area of the catalyst remains at a value of at least about 1000 $m^2/g$, more preferably at least about 1100 $m^2/g$, even more preferably at least about 1200 $m^2/g$, after the transition metal composition has been formed. Generally, the catalyst has a total Langmuir surface area of from about 600 to about 1500 $m^2/g$, typically from about 600 to about 1400 $m^2/g$. In certain embodiments, the catalyst has a total Langmuir surface area of from about 800 to about 1200 $m^2/g$. Preferably, the catalyst has a total Langmuir surface area of from about 1000 to about 1400 $m^2/g$, more preferably from about 1100 to about 1400 $m^2/g$ and, even more preferably, from about 1200 to about 1400 $m^2/g$.

Where the transition metal composition is formed in accordance with a preferred method, it is believed that the composition comprises a substantial fraction of very fine particles, e.g., wherein at least about 20 wt. % of the transition metal is in amorphous form or in the form of particles of less than 15 nm, more typically less than 5 nm, more typically 2 nm, as determined by X-ray diffraction.

It is further preferred that, as compared to the carbon support, the micropore Langmuir surface area be reduced by not more than 45%, more preferably not more than about 40%. Thus, the micropore Langmuir surface area of oxidation catalysts is generally at least about 55% of the micropore Langmuir surface area of the carbon support prior to formation of the transition metal composition thereon, more generally at least about 60% and, still more generally, at least about 80%. Typically, the micropore Langmuir surface area of the catalyst is from about 55 to about 80% of the micropore Langmuir surface area of the carbon support prior to formation of the transition metal composition thereon, more typically from about 60 to about 80% and, still more typically, from about 70 to about 80%.

The Langmuir surface area of an oxidation catalyst of the present invention attributed to pores having a diameter of less than 20 Å (i.e., micropores) is typically at least about 750 $m^2/g$, more typically at least 800 $m^2/g$, still more typically at least about 800 $m^2/g$ and, even more typically, at least about 900 $m^2/g$. Preferably, the micropore Langmuir surface area of the oxidation catalyst is from about 750 to about 1100 $m^2/g$ and, more preferably, from about 750 to about 1000 $m^2/g$.

In addition to the preferred reduction in micropore surface area, it is further generally preferred that the combined mesopore and macropore Langmuir surface area be reduced by not more than about 30%, more preferably not more than about 20%, as a result of the formation of the transition metal composition on the carbon support. Thus, generally, the combined mesopore and macropore Langmuir surface area of oxidation catalysts is generally at least about 70% of the combined mesopore and macropore Langmuir surface area of the carbon support prior to formation of the transition metal composition thereon and, more generally, at least about 80%. Typically, the combined mesopore and macropore Langmuir surface area of the catalyst is from about 70 to about 90% of the combined mesopore and macropore Langmuir surface area of the carbon support prior to formation of the transition metal composition thereon.

Generally, the combined mesopore and macropore surface area is at least about 175 $m^2/g$ and, more generally, at least 200 $m^2/g$. Preferably, the combined mesopore and macropore Langmuir surface area of the oxidation catalyst is from about 175 to about 300 $m^2/g$ and, more preferably, from about 200 to about 300 $m^2/g$. In certain embodiments, the combined mesopore and macropore surface area is from about 175 to about 250 $m^2/g$.

Additionally or alternatively, it is preferred that the micropore Langmuir surface area of the catalyst remain at a value of at least about 750 m$^2$/g, more preferably at least about 800 m$^2$/g, and the combined mesopore and macropore Langmuir surface area of the catalyst remain at a value of at least about 175 m$^2$/g, more preferably at least about 200 m$^2$/g, after the transition metal composition has been formed.

In various particularly preferred embodiments of the invention, X-ray diffraction analysis at a detection limit of 1 nm does not detect any significant portion of transition metal composition particles. Thus, it is currently believed that the transition metal composition particles are present on the surface of the carbon support in the form of discrete particles having a particle size of less than 1 nm or are present on the surface of the carbon support in the form of an amorphous film. However, based on the decrease in surface area after formation of the transition metal composition on the carbon support, it is reasonable to infer the transition metal composition may be present at least in part as an amorphous film since an increase in surface area would be expected in the case of deposition of crystallites having a particle size below 1 nm.

It is likewise preferred for dehydrogenation catalysts of the present invention (i.e., modified carbon supports having a metal-containing active phase deposited thereon) to have a high surface area. Typically, the catalyst has a Langmuir surface area of at least about 500 m$^2$/g, more typically at least about 600 m$^2$/g and, still more typically, from about 500 to about 1200 m$^2$/g. Generally, the catalyst has a Langmuir surface area of from about 600 to about 1000 m$^2$/g and, more generally, from about 600 to about 800 m$^2$/g.

A further advantageous feature of the oxidation and dehydrogenation catalysts of the present invention is a pore volume sufficient to allow for diffusion of reactants into the pores of the catalyst. Thus, preferably, catalysts of the present invention including a transition metal composition formed on a carbon support typically have a pore volume of at least about 0.1 cm$^3$/g and, more typically at least about 0.5 cm$^3$/g. Generally, such catalysts have a pore volume of from about 0.1 to about 2 cm$^3$/g and, more generally, from about 0.5 to about 1.5 cm$^3$/g.

In addition to overall pore volume, the pore volume distribution of the oxidation and dehydrogenation catalysts of the present invention preferably conduces to diffusion of reactants into the pores of the finished catalyst. Preferably, pores having a diameter of less than about 20 Å make up no more than about 45% of the overall pore volume of the catalyst and, more preferably, no more than about 30% of the overall pore volume. Pores having a diameter of greater than about 20 Å preferably make up at least about 60% of the overall pore volume of the catalyst and, more preferably, at least about 65% of the overall pore volume.

It has been observed that "mesopores" (i.e., pores having a diameter of from about 20 to about 40 Å) allow suitable diffusion of reactants into the pores of the catalyst. Thus, preferably mesopores make up at least about 25% of the overall pore volume and, more preferably, at least about 30% of the overall pore volume. Macro pores (i.e., pores having a diameter larger than about 40 Å) also allow suitable diffusion of reactants into the pores of the catalyst. Thus, preferably, these pores make up at least about 5% of the overall pore volume and, more preferably, at least about 10% of the overall pore volume of the catalyst.

It is generally preferred for the transition metal composition (e.g., the transition metal carbide or transition metal nitride) to be uniformly distributed substantially over the surface of the pore walls and interstitial passages of the catalyst particles (i.e., all surfaces accessible to fluid with which the catalyst is contacted). Particle size of the transition metal composition, as determined, for example, by X-ray diffraction, affects such uniform distribution and it has been observed that the smaller the size of the particulate crystals of the transition metal composition, the more uniform its deposition.

For oxidation catalysts of the present invention including a transition metal composition deposited on a carbon support, generally, at least about 95% by weight of the transition metal composition particles have a particle size, in their largest dimension, of less than about 1000 nm. Typically, at least about 80% by weight of the transition metal composition particles have a particle size, in their largest dimension, of less than about 250 nm. More typically, at least about 70% by weight of the transition metal composition particles have a particle size, in their largest dimension, of less than about 200 nm. Still more typically, at least about 60% by weight of the transition metal composition particles have a particle size, in their largest dimension, of less than about 18 nm. Even more typically, at least about 20% by weight, preferably at least about 55% by weight of the transition metal composition particles have a particle size, in their largest dimension, of less than about 15 nm. Preferably, at least about 20% by weight of the transition metal composition particles have a particle size, in their largest dimension, of less than about 5 nm, more preferably, less than about 2 nm, and even more preferably, less than about 1 nm. More preferably, from about 20 to about 95% by weight of the transition metal composition particles have a particle size, in their largest dimension, of less than about 1 nm and, more preferably, from about 20 to about 100% by weight.

Generally, at least about 75%, on a number basis, of the transition metal composition particles have a particle size, in their largest dimension, of less than about 1000 nm. Typically, at least about 60%, on a number basis, of the transition metal composition particles have a particle size, in their largest dimension, of less than about 250 nm. More typically, at least about 50%, on a number basis, of the transition metal composition particles have a particle size, in their largest dimension, of less than about 200 nm. Still more typically, at least about 40%, on a number basis, of the transition metal composition particles have a particle size, in their largest dimension, of less than about 18 nm. Even more typically, at least about 35%, on a number basis, of the transition metal composition particles have a particle size, in their largest dimension, of less than about 15 nm.

For dehydrogenation catalysts including a metal-containing (e.g., copper-containing) active deposited on a modified carbon support including a transition metal composition comprising molybdenum or tungsten formed on a carbon support, typically at least about 99% of the particles of the transition metal composition formed on the carbon support exhibit a particle size of less than about 100 nm, thereby contributing to uniform distribution of the transition metal composition throughout the carbon support since it has been observed that a greater proportion of particles of such a size provide a uniform coating of transition metal composition on the carbon support. More preferably, at least about 95% of the particles of the carbide or nitride formed on the carbon support exhibit a particle size of from about 5 nm to about 50 nm.

It has been observed that uniform distribution of the transition metal composition on the carbon support (i.e., reduced clustering of the transition metal and/or suitable distribution of the transition metal composition throughout the pores of the carbon support) may improve catalytic activity of catalysts including a transition metal composition deposited on a carbon support and/or may allow for improved coating of a metal-containing active phase on the modified carbon support in the case of a dehydrogenation catalyst.

Figure 5:
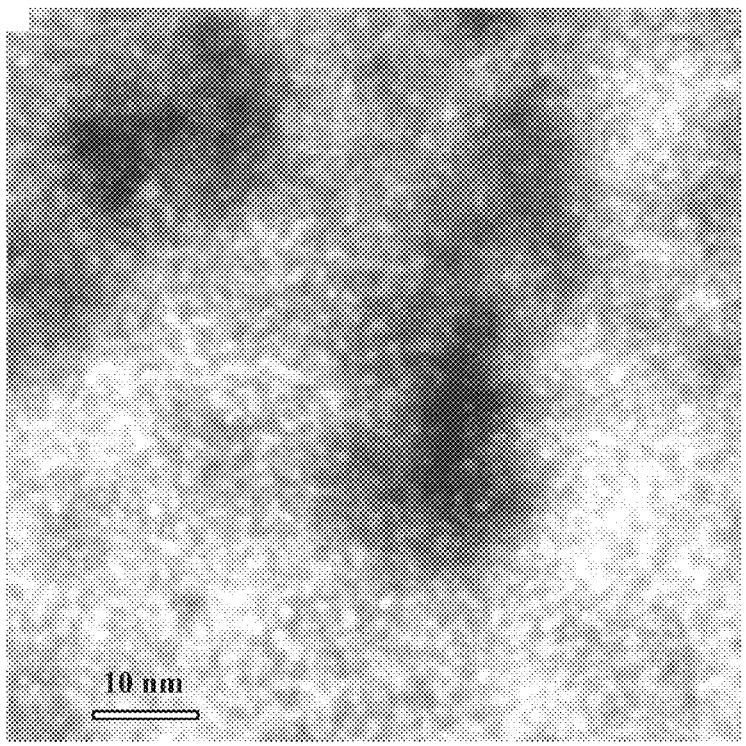
FIG. 5 is a High Resolution Transmission Electron Microscopy (HRTEM) image of a carbon-supported molybdenum carbide.

FIG. 5 is a High Resolution Transmission Electron Microscopy (HRTEM) image of a carbon-supported molybdenum carbide prepared in accordance with the above methods in which molybdenum carbide is present in a proportion of 15% by weight. As shown, a carbon support having molybdenum carbide formed thereon prepared in accordance with the methods described above exhibits uniform dispersion of molybdenum carbide throughout the carbon support.

Figure 6:
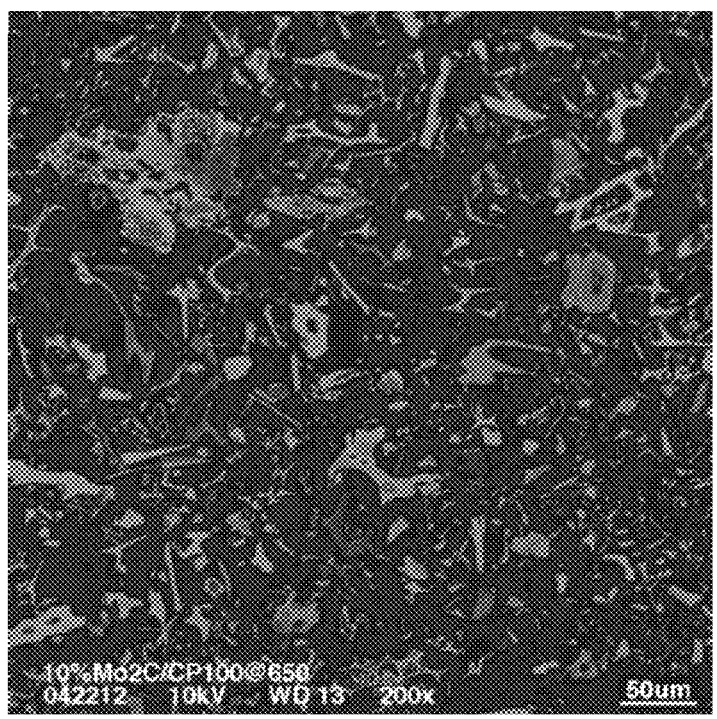
FIG. 6 is a SEM image of a carbon supported molybdenum carbide.

FIG. 6 is a Scanning Electron Microscopy (SEM) image of a carbon supported molybdenum carbide prepared in accordance with the above methods in which the carbide is present in a proportion of 10% by weight. As shown, a carbon support having molybdenum carbide formed thereon in a proportion of 10% by weight of the modified carbon support in accordance with the methods described above exhibits uniform distribution of molybdenum throughout the carbon support.

Figure 7:
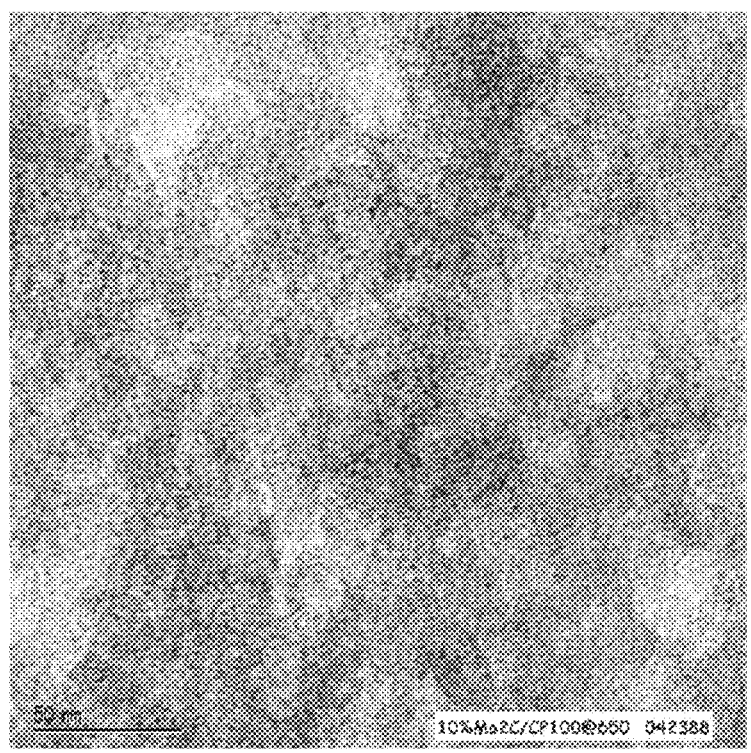
FIG. 7 is a TEM image of a carbon supported molybdenum carbide.

FIG. 7 is a Transmission Electron Microscopy (TEM) image of a carbon supported molybdenum carbide prepared in accordance with the above methods in which the carbide is present in a proportion of 10% by weight. As shown, a carbon support having molybdenum carbide formed thereon in a proportion of 10% by weight of the modified carbon support in accordance with the above methods exhibits uniformity of molybdenum carbide distribution throughout believed to be due, at least in part, to the particle size distribution of molybdenum carbide.

Uniform distribution may be indicated by the percentage of surface area of the carbon support covered with the transition metal composition. Preferably in certain embodiments (e.g., transition metal compositions including molybdenum or tungsten carbide or nitride), a suitable portion of the surface area of the carbon support is coated with transition metal composition. Generally, at least about 20% and, more generally, at least about 50% of the surface area of the carbon support is coated with a transition metal composition (e.g., a transition metal carbide or nitride). Typically, from about 20 to about 80% and, more typically, from about 50% to about 80% of the surface area of the carbon support is coated with a transition metal composition (e.g., a transition metal carbide or nitride).

Oxidation catalysts of the present invention may exhibit one or more properties described in Ebner et al., U.S. Pat. No. 6,417,133, the entire disclosure of which was incorporated by reference above. Such characteristics may be found, for example, at column 3, line 6 to column 7, line 23; column 8, line 27 to column 9, line 24; column 10, lines 53-57; column 11, line 49 to column 14, line 18; column 14, line 50 to column 16, line 3; column 17, line 14 to column 21, line 2; column 26 (Example 2); column 27, lines 21-34 (Example 4); and column 30, line 21 to column 40, line 61 (Examples 7 to 19).

Oxidation catalysts of the present invention may include carbon nanotubes on the surface of the carbon support which may contain a certain proportion of the transition metal contained in the catalyst. Additionally or alternatively, the carbon nanotubes may contain a portion of the nitrogen of the transition metal composition. Typically, any such transition metal is present at the root or the tip of the nanotube, however, transition metal may also be present along the length of the nanotube. The carbon nanotubes typically have a diameter of at least about 0.01 µm and, more typically, have a diameter of at least about 0.1 µm. In certain embodiments, the carbon nanotubes have a diameter of less than about 1 µm and, in other embodiments, have a diameter of less than about 0.5 µm.

Certain embodiments of the above-described catalyst (e.g., catalysts comprising a transition metal composition deposited on a carbon support and such catalysts further including a noble metal) may be used for liquid phase oxidation reactions. Examples of such reactions include the oxidation of alcohols and polyols to form aldehydes, ketones, and acids (e.g., the oxidation of 2-propanol to form acetone, and the oxidation of glycerol to form glyceraldehyde, dihydroxyacetone, or glyceric acid); the oxidation of aldehydes to form acids (e.g., the oxidation of formaldehyde to form formic acid, and the oxidation of furfural to form 2-furan carboxylic acid); the oxidation of tertiary amines to form secondary amines (e.g., the oxidation of nitrilotriacetic acid ("NTA") to form iminodiacetic acid ("IDA")); the oxidation of secondary amines to form primary amines (e.g., the oxidation of IDA to form glycine); and the oxidation of various acids (e.g., formic acid or acetic acid) to form carbon dioxide and water.

The oxidation catalyst disclosed herein is particularly suited for catalyzing the liquid phase oxidation of a tertiary amine to a secondary amine, for example in the preparation of glyphosate and related compounds and derivatives. For example, the tertiary amine substrate may correspond to a compound of Formula II having the structure:

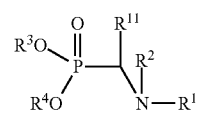

[Formula II]

wherein $R^1$ is selected from the group consisting of $R^5OC(O)CH_2$— and $R^5OCH_2CH_2$—, $R^2$ is selected from the group consisting of $R^5OC(O)CH_2$—, $R^5OCH_2CH_2$—, hydrocarbyl, substituted hydrocarbyl, acyl, —$CHR^6PO_3R^7R^8$, and —$CHR^9SO_3R^{10}$, $R^6$, $R^9$ and $R^{11}$ are selected from the group consisting of hydrogen, alkyl, halogen and —$NO_2$, and $R^3$, $R^4$, $R^5$, $R^7$, $R^8$ and $R^{10}$ are independently selected from the group consisting of hydrogen, hydrocarbyl, substituted hydrocarbyl and a metal ion. Preferably, $R^1$ comprises $R^5OC(O)CH_2$—, $R^{11}$ is hydrogen, $R^5$ is selected from hydrogen and an agronomically acceptable cation and $R^2$ is selected from the group consisting of $R^5OC(O)CH_2$—, acyl, hydrocarbyl and substituted hydrocarbyl. As noted above, the oxidation catalyst of the present invention is particularly suited for catalyzing the oxidative cleavage of a PMIDA substrate such as N-(phosphonomethyl)iminodiacetic acid or a salt thereof to form N-(phosphonomethyl)glycine or a salt thereof. In such an embodiment, the catalyst is effective for oxidation of byproduct formaldehyde to formic acid, carbon dioxide and/or water.

The above-described catalysts are especially useful in liquid phase oxidation reactions at pH levels less than 7, and in particular, at pH levels less than 3. One such reaction is the oxidation of PMIDA or a salt thereof to form N-(phosphonomethyl)glycine or a salt thereof in an environment having pH levels in the range of from about 1 to about 2. This reaction is often carried out in the presence of solvents which solubilize noble metals and, in addition, the reactants, intermediates, or products often solubilize noble metals. Certain catalysts of the present invention avoid these problems due to the absence of a noble metal. Advantageously, however, the catalysts of the present invention containing a noble metal have been found to be useful in such environments.

The description below discloses with particularity the use of catalysts described above containing a transition metal composition (e.g., a transition metal nitride, transition metal carbide or transition metal carbide-nitride) acting as the catalyst or further containing a noble metal-containing active phase to effect the oxidative cleavage of PMIDA or a salt thereof to form N-(phosphonomethyl)glycine or a salt thereof. It should be recognized, however, that the principles disclosed below are generally applicable to other liquid phase oxidative reactions, especially those at pH levels less than 7 and those involving solvents, reactants, intermediates, or products which solubilize noble metals.

To begin the PMIDA oxidation reaction, it is preferable to charge the reactor with the PMIDA reagent (i.e., PMIDA or a salt thereof), catalyst, and a solvent in the presence of oxygen. The solvent is most preferably water, although other solvents (e.g., glacial acetic acid) are suitable as well.

The reaction may be carried out in a wide variety of batch, semi-batch, and continuous reactor systems. The configuration of the reactor is not critical. Suitable conventional reactor configurations include, for example, stirred tank reactors, fixed bed reactors, trickle bed reactors, fluidized bed reactors, bubble flow reactors, plug flow reactors, and parallel flow reactors.

When conducted in a continuous reactor system, the residence time in the reaction zone can vary widely depending on the specific catalyst and conditions employed. Typically, the residence time can vary over the range of from about 3 to about 120 minutes. Preferably, the residence time is from about 5 to about 90 minutes, and more preferably from about 5 to about 60 minutes. When conducted in a batch reactor, the reaction time typically varies over the range of from about 15 to about 120 minutes. Preferably, the reaction time is from about 20 to about 90 minutes, and more preferably from about 30 to about 60 minutes.

In a broad sense, the oxidation reaction may be practiced in accordance with the present invention at a wide range of temperatures, and at pressures ranging from sub-atmospheric to super-atmospheric. Use of mild conditions (e.g., room temperature and atmospheric pressure) have obvious commercial advantages in that less expensive equipment may be used. However, operating at higher temperatures and super-atmospheric pressures, while increasing capital requirements, tends to improve phase transfer between the liquid and gas phase and increase the PMIDA oxidation reaction rate.

Preferably, the PMIDA reaction is conducted at a temperature of from about 20 to about 180° C., more preferably from about 50 to about 140° C., and most preferably from about 80 to about 110° C. At temperatures greater than about 180° C., the raw materials tend to begin to slowly decompose.

The pressure used during the PMIDA oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient such that the PMIDA oxidation is not limited due to an inadequate oxygen supply. The pressure preferably is at least equal to atmospheric pressure. More preferably, the pressure is from about 30 to about 500 psig, and most preferably from about 30 to about 130 psig.

The catalyst concentration preferably is from about 0.1 to about 10 wt. % ([mass of catalyst÷total reaction mass]× 100%). More preferably, the catalyst concentration preferably is from about 0.1 to about 5 wt. %, still more preferably from about 0.2 to about 5 wt. % and, most preferably, from about 0.3 to about 1.5 wt. %. Concentrations greater than about 10 wt. % are difficult to filter. On the other hand, concentrations less than about 0.1 wt. % tend to produce unacceptably low reaction rates.

The present invention is further directed to a catalyst system comprising a combination of transition metal composition on carbon catalysts of the present invention, preferably substantially devoid of a noble metal active phase, with a noble-metal containing bifunctional catalyst (i.e., a catalyst which oxidizes PMIDA while further providing oxidation of formaldehyde and formic acid byproducts) as described in U.S. Pat. No. 6,417,133 to Ebner et al., the entire disclosure of which was incorporated by reference above. Such a catalyst system including the catalysts described by Ebner et al. and transition metal containing catalysts of the present invention is advantageous since it is effective for oxidizing PMIDA, formaldehyde, and formic acid, but not all of the catalyst available for PMIDA oxidation requires the presence of a costly noble metal. Thus, such a catalyst system may potentially provide a more economical process. Typically, such a catalyst system comprises at least about 10% by weight of a catalyst as described in U.S. Pat. No. 6,417,133, more typically at least about 20% by weight and, most typically from about 10 to about 50% by weight.

Additionally or alternatively, the catalyst system comprises at least about 10% by weight of a transition metal composition-containing catalyst of the present invention, more typically at least about 20% by weight and, most typically, from about 20 to about 50% by weight of a transition metal composition-containing catalyst of the present invention.

The concentration of PMIDA reagent in the feed stream is not critical. Use of a saturated solution of PMIDA reagent in water is preferred, although for ease of operation, the process is also operable at lesser or greater PMIDA reagent concentrations in the feed stream. If the catalyst is present in the reaction mixture in a finely divided form, it is preferred to use a concentration of reactants such that all reactants and the -(phosphonomethyl)glycine product remain in solution so that the catalyst can be recovered for re-use, for example, by filtration. On the other hand, greater concentrations tend to increase reactor through-put. Alternatively, if the catalyst is present as a stationary phase through which the reaction medium and oxygen source are passed, it may be possible to use greater concentrations of reactants such that a portion of the N-(phosphonomethyl)glycine product precipitates.

It should be recognized that, relative to many commonly-practiced commercial processes, this invention allows for greater temperatures and PMIDA reagent concentrations to be used to prepare N-(phosphonomethyl)glycine while minimizing by-product formation. In the commonly practiced commercial processes using a carbon-only catalyst, it is economically beneficial to minimize the formation of the NMG by-product, which is formed by the reaction of N-(phosphonomethyl)glycine with the formaldehyde by-product. In processes based on carbon catalysts, temperatures are typically maintained between about 60 to 90° C., and PMIDA reagent concentrations are typically maintained below about 9.0 wt. % ([mass of PMIDA reagent÷total reaction mass]$_{x100}$%) to achieve cost effective yields and to minimize the generation of waste. At such temperatures, the maximum N-(phosphonomethyl)glycine solubility typically is less than 6.5%. However, with the oxidation catalyst and reaction process of this invention, formaldehyde is effectively oxidized, thereby allowing for reaction temperatures as high as 180° C. or greater with PMIDA reagent solutions and slurries of the PMIDA reagent. The use of higher temperatures and reactor concentrations permits reactor throughput to be increased, reduces the amount of water that must be removed before isolation of the solid N-(phosphonomethyl)glycine, and reduces the cost of manufacturing N-(phosphonomethyl)glycine. This invention thus provides economic benefits over many commonly-practiced commercial processes.

Normally, a PMIDA reagent concentration of up to about 50 wt. % ([mass of PMIDA reagent÷total reaction mass]× 100%) may be used (especially at a reaction temperature of from about 20 to about 180° C.). Preferably, a PMIDA reagent concentration of up to about 25 wt. % is used (particularly at a reaction temperature of from about 60 to about 150° C.). More preferably, a PMIDA reagent concentration of from about 12 to about 18 wt. % is used (particularly at a reaction temperature of from about 100 to about 130° C.). PMIDA reagent concentrations below 12 wt. % may be used, but are less economical because a relatively low payload of N-(phosphonomethyl)glycine product is produced in each reactor cycle and more water must be removed and energy used per unit of N-(phosphonomethyl)glycine product produced. Relatively low reaction temperatures (i.e., temperatures less than 100° C.) often tend to be less advantageous because the solubility of the PMIDA reagent and N-(phosphonomethyl)glycine product are both relatively low at such temperatures.

The oxygen source for the PMIDA oxidation reaction may be any oxygen-containing gas or a liquid comprising dissolved oxygen. Preferably, the oxygen source is an oxygen-containing gas. As used herein, an "oxygen-containing gas" is any gaseous mixture comprising molecular oxygen which optionally may comprise one or more diluents which are non-reactive with the oxygen or with the reactant or product under the reaction conditions.

Examples of such gases are air, pure molecular oxygen, or molecular oxygen diluted with helium, argon, nitrogen, or other non-oxidizing gases. For economic reasons, the oxygen source most preferably is air, oxygen-enriched air, or pure molecular oxygen.

Oxygen may be introduced by any conventional means into the reaction medium in a manner which maintains the dissolved oxygen concentration in the reaction mixture at a desired level. If an oxygen-containing gas is used, it preferably is introduced into the reaction medium in a manner which maximizes the contact of the gas with the reaction solution. Such contact may be obtained, for example, by dispersing the gas through a diffuser such as a porous frit or by stirring, shaking, or other methods known to those skilled in the art.

The oxygen feed rate preferably is such that the PMIDA oxidation reaction rate is not limited by oxygen supply. If the dissolved oxygen concentration is too high, however, the catalyst surface tends to become detrimentally oxidized, which, in turn, tends to lead to more leaching of noble metal present in the catalyst and decreased formaldehyde activity (which, in turn, leads to more NMG being produced). Generally, it is preferred to use an oxygen feed rate such that at least about 40% of the oxygen is utilized. More preferably, the oxygen feed rate is such that at least about 60% of the oxygen is utilized. Even more preferably, the oxygen feed rate is such that at least about 80% of the oxygen is utilized. Most preferably, the rate is such that at least about 90% of the oxygen is utilized. As used herein, the percentage of oxygen utilized equals: (the total oxygen consumption rate÷oxygen feed rate)×100%. The term "total oxygen consumption rate" means the sum of: (i) the oxygen consumption rate ("$R_i$") of the oxidation reaction of the PMIDA reagent to form the N-(phosphonomethyl)glycine product and formaldehyde, (ii) the oxygen consumption rate ("$R_{ii}$") of the oxidation reaction of formaldehyde to form formic acid, and (iii) the oxygen consumption rate ("$R_{iii}$") of the oxidation reaction of formic acid to form carbon dioxide and water.

In various embodiments of this invention, oxygen is fed into the reactor as described above until the bulk of PMIDA reagent has been oxidized, and then a reduced oxygen feed rate is used. This reduced feed rate preferably is used after about 75% of the PMIDA reagent has been consumed. More preferably, the reduced feed rate is used after about 80% of the PMIDA reagent has been consumed. Where oxygen is supplied as pure oxygen or oxygen-enriched air, a reduced feed rate may be achieved by purging the reactor with (non-enriched) air, preferably at a volumetric feed rate which is no greater than the volumetric rate at which the pure molecular oxygen or oxygen-enriched air was fed before the air purge. The reduced oxygen feed rate preferably is maintained for from about 2 to about 40 minutes, more preferably from about 5 to about 20 minutes, and most preferably from about 5 to about 15 minutes. While the oxygen is being fed at the reduced rate, the temperature preferably is maintained at the same temperature or at a temperature less than the temperature at which the reaction was conducted before the air purge. Likewise, the pressure is maintained at the same or at a pressure less than the pressure at which the reaction was conducted before the air purge. Use of a reduced oxygen feed rate near the end of the PMIDA reaction allows the amount of residual formaldehyde present in the reaction solution to be reduced without producing detrimental amounts of AMPA by oxidizing the N-(phosphonomethyl)glycine product.

In embodiments in which the catalyst includes a noble metal, reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof are used. Experiments conducted in accordance with this invention indicate that if small amounts of formic acid, formaldehyde, or a combination thereof are added to the reaction solution, the catalyst will preferentially effect the oxidation of the formic acid or formaldehyde before it effects the oxidation of the PMIDA reagent, and subsequently will be more active in effecting the oxidation of formic acid and formaldehyde during the PMIDA oxidation. Preferably from about 0.01 to about 5.0 wt. % ([mass of formic acid, formaldehyde, or a combination thereof÷total reaction mass]× 100%) of sacrificial reducing agent is added, more preferably from about 0.01 to about 3.0 wt. % of sacrificial reducing agent is added, and most preferably from about 0.01 to about 1.0 wt. % of sacrificial reducing agent is added.

In certain embodiments, unreacted formaldehyde and formic acid are recycled back into the reaction mixture for use in subsequent cycles. In this instance, an aqueous recycle stream comprising formaldehyde and/or formic acid also may be used to solubilize the PMIDA reagent in the subsequent cycles. Such a recycle stream may be generated by evaporation of water, formaldehyde, and formic acid from the oxidation reaction mixture in order to concentrate and/or crystallize product N-(phosphonomethyl)glycine. Overheads condensate containing formaldehyde and formic acid may be suitable for recycle.

As noted above, the oxidation catalysts of the present invention including a transition metal composition comprising a transition metal, nitrogen, and carbon formed on a carbon support as described herein, preferably substantially devoid of a noble metal active phase, are effective for the oxidation of formaldehyde to formic acid, carbon dioxide and water. In particular, oxidation catalysts of the present invention are effective for the oxidation of byproduct formaldehyde produced in the oxidation of N-(phosphonomethyl)iminodiacetic acid. More particularly, such catalysts are characterized by their effectiveness for catalyzing the oxidation of formaldehyde such that when a representative aqueous solution containing about 0.8% by weight formaldehyde and having a pH of about 1.5 is contacted with an oxidizing agent in the presence of said catalyst at a temperature of about 100° C., at least about 5%, preferably at least about 10%, more preferably at least about 15%, even more preferably at least about 20% or even at least about 30% by weight of said formaldehyde is converted to formic acid, carbon dioxide and/or water.

The oxidation catalysts of the present invention including a transition metal composition comprising a transition metal, nitrogen, and carbon formed on a carbon support as described herein, preferably substantially devoid of a noble metal active phase, is particularly effective in catalyzing the liquid phase oxidation of formaldehyde to formic acid, carbon dioxide and/or water in the presence of a PMIDA reagent such as N-(phosphonomethyl)iminodiacetic acid. More particularly, such catalyst is characterized by its effectiveness for catalyzing the oxidation of formaldehyde such that when a representative aqueous solution containing about 0.8% by weight formaldehyde and about 6% by weight of N-(phosphonomethyl)iminodiacetic acid and having a pH of about 1.5 is contacted with an oxidizing agent in the presence of said catalyst at a temperature of about 100° C., at least about 50%, preferably at least about 60%, more preferably at least about 70%, even more preferably at least about 80%, and especially at least about 90% by weight of said formaldehyde is converted to formic acid, carbon dioxide and/or water.

Typically, the concentration of N-(phosphonomethyl)glycine in the product mixture may be as great as 40% by weight, or greater. Preferably, the N-(phosphonomethyl)glycine concentration is from about 5 to about 40%, more preferably from about 8 to about 30%, and still more preferably from about 9 to about 15%. Concentrations of formaldehyde in the product mixture are typically less than about 0.5% by weight, more preferably less than about 0.3%, and still more preferably less than about 0.15%.

Following the oxidation, the catalyst preferably is subsequently separated by filtration. The N-(phosphonomethyl) glycine product may then be isolated by precipitation, for example, by evaporation of a portion of the water and cooling.

In certain embodiments (e.g., those in which the catalyst includes a noble metal), it should be recognized that the catalyst of this invention has the ability to be reused over several cycles, depending on how oxidized its surface becomes with use. Even after the catalyst becomes heavily oxidized, it may be reused by being reactivated. To reactivate a catalyst having a heavily oxidized surface, the surface preferably is first washed to remove the organics from the surface. It then preferably is reduced in the same manner that a catalyst is reduced after the noble metal is deposited onto the surface of the support, as described above.

A process incorporating a catalyst of the present invention which includes a transition metal composition formed on a carbon support and further including a copper-containing active phase may generally be used to convert any primary alcohol to a carboxylic acid salt. As used herein, a "primary alcohol" is any alcohol comprising a hydroxy group attached to a carbon which is bound to two hydrogen atoms, i.e., $R-CH_2OH$. Such a process dehydrogenates a primary alcohol to yield both a carboxylic acid salt and hydrogen gas. Typically, this reaction is carried out in a heated reaction zone containing an alkaline medium containing the primary alcohol, a base, and a catalyst prepared in accordance with the present invention. An example of this reaction is the dehydrogenation of monoethanolamine in a heated reaction zone containing KOH to form hydrogen gas and the potassium salt of glycine:

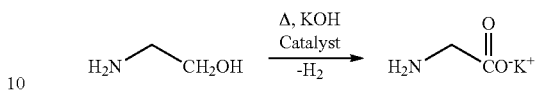

Another example of this reaction is the dehydrogenation of diethanolamine (sometimes described in the art as "DEA") in a heated reaction zone containing NaOH to form hydrogen gas and disodium iminodiacetic acid (sometimes described in the art as "DSIDA"):

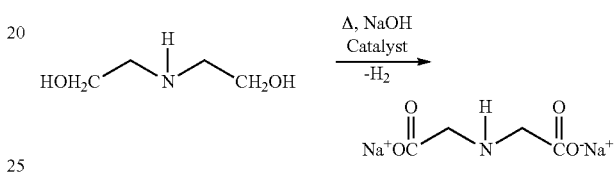

An additional example is the dehydrogenation of an N-alkyl-monoethanolamine to form a salt of an N-alkyl-glycine. The alkyl group can be, for example, methyl ($-CH_3$). In that instance, the dehydrogenation product would be a salt of N-methyl-glycine (i.e., a salt of sarcosine):

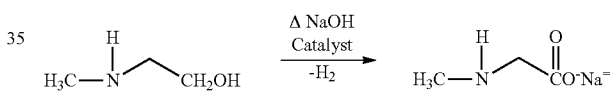

A further example is the dehydrogenation of triethanolamine to form a salt of nitrilotriacetic acid:

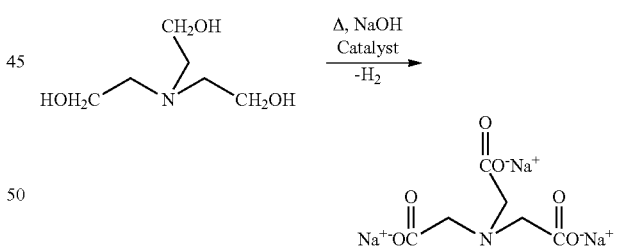

Although effective and useful in the dehydrogenation of essentially any primary alcohol, the process of the invention is particularly advantageous for primary alcohols which contain amino groups or other functionalities which are reactive and susceptible to side reactions. In particular, β-amino alcohols are susceptible to dehydrogenation of the C—N bond and subsequent dealkylation, consequently leading to the formation of usually undesirable side products. In various preferred embodiments of this invention, the primary alcohol is an alkanolamine (i.e., a compound wherein the nitrogen of an amine functionality is bonded directly to the carbon of an alkyl alcohol). In this embodiment, the primary alcohol preferably has formula (I):

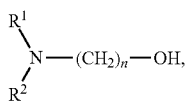

(I)

wherein n is an integer ranging from 2 to 20; and $R^1$ and $R^2$ are independently hydrogen, hydrocarbyl, or substituted hydrocarbyl.

A hydrocarbyl may be any group consisting exclusively of carbon and hydrogen. The hydrocarbyl may be branched or unbranched, may be saturated or unsaturated, and may comprise one or more rings. Suitable hydrocarbyl groups include alkyl, alkenyl, alkynyl, and aryl groups. They also include alkyl, alkenyl, alkynyl, and aryl groups substituted with other aliphatic or cyclic hydrocarbyl groups, such as alkaryl, alkenaryl, and alkynaryl.

A substituted hydrocarbyl may be any hydrocarbyl wherein a carbon atom of the hydrocarbyl group has been substituted with an atom other than hydrogen or a group of atoms containing at least one atom other than hydrogen. For example, a hydrogen atom may be substituted with a halogen atom, such as a chlorine or fluorine atom. Alternatively, one or more hydrogen atoms may be replaced with a substituent comprising an oxygen atom or a group containing an oxygen atom to form, for example, a hydroxy group, an ether, an ester, an anhydride, an aldehyde, a ketone, or a carboxylic acid. The hydrogen atom also may be replaced with a group containing a nitrogen atom to form, for example, an amide or a nitro group. In addition, a hydrogen atom may be replaced with a substituent group containing a sulfur atom to form, for example, —$SO_3H$.

Typically, $R^1$ and $R^2$ are independently either: hydrogen; —$(CH_2)_x$—$(CH_3)_m$, x being an integer ranging from 0 to about 19 (particularly from 1 to 6, and even more particularly 1), m being 1; —$(CH_2)_y$—OH, y being an integer ranging from 1 to about 20 (especially from 2 to 6); $(CH_2)_z$—COOH, z being an integer ranging from 1 to about 19 (especially from 1 to 5); or phosphonomethyl.

In some preferred embodiments, $R^1$ and $R^2$ are both hydrogen (i.e., the amine functionality shown in formula (I) is a primary amine). An example of such an alcohol is monoethanolamine.

In other preferred embodiments, $R^1$ is hydrogen and $R^2$ is hydrocarbyl or substituted hydrocarbyl (i.e., the amine functionality shown in formula (I) is a secondary amine). Examples of primary alcohols in which $R^2$ is hydrocarbyl include N-methylethanolamine, N-ethylethanolamine, N-isopropylethanolamine, N-butylethanolamine, and N-nonylethanolamine. Examples of primary alcohols in which $R^2$ is a substituted hydrocarbyl include primary alcohols wherein $R^2$ is —$(CH_2)_y$—OH and y is an integer ranging from 1 to about 20 (more preferably from 1 to 6). An example of such an alcohol is diethanolamine. Other examples of primary alcohols wherein $R^2$ is a substituted hydrocarbyl include N-(2-aminoethyl)ethanolamine, N-(3-aminopropyl)ethanolamine, N-(carboxymethyl)ethanolamine, and N-(phosphonomethyl) ethanolamine. N-substituted ethanolamines, for example, may be prepared using the various methods known in the art. For example, a ketone may be condensed with monoethanolamine in the presence of $H_2$, a solvent, and a noble metal catalyst. This reaction is described in, for example, Cope, A. C. and Hancock, E. M. J. Am. Chem. Soc., 64, 1503-6 (1942). N-substituted ethanolamines also may be prepared by combining a mono-substituted amine (such as methylamine) and ethylene oxide to form the mono-substituted ethanolamine. This reaction is described by, for example, Y. Yoshida in Japanese Patent Application No. 95-141575.

In yet other preferred embodiments, both $R^1$ and $R^2$ are independently hydrocarbyl or substituted hydrocarbyl (i.e., the amine functionality shown in formula (I) is a tertiary amine). Examples of primary alcohols in which $R^1$ and $R^2$ are independently hydrocarbyl include N,N-dimethylethanolamine, N,N-diethylethanolamine, and N,N-dibutylethanolamine. Examples of primary alcohols in which $R^1$ is hydrocarbyl and $R^2$ is substituted hydrocarbyl include primary alcohols wherein $R^2$ is —$(CH_2)_y$—OH and y is an integer ranging from 1 to about 20 (more preferably from 1 to 6). Such alcohols include, for example, N-methyldiethanolamine, N-ethyldiethanolamine, N-isopropyldiethanolamine, and N-butyldiethanolamine. Other examples of primary alcohols in which $R^1$ is hydrocarbyl and $R^2$ is substituted hydrocarbyl include N-ethyl, N-(2-aminoethyl)ethanolamine; N-ethyl, N-(2-aminoethyl)ethanolamine; and N-methyl, N-(3-aminopropyl)ethanolamine. Examples of primary alcohols in which $R^1$ and $R^2$ are independently substituted hydrocarbyl include primary alcohols wherein $R^1$ and $R^2$ are independently —$(CH_2)_y$—OH and y is an integer ranging from 1 to about 20 (more preferably from 1 to 6). An example of such an alcohol is triethanolamine. Other examples of primary alcohols in which $R^1$ and $R^2$ are independently substituted hydrocarbyl include tetra(2-hydroxyethyl)ethylenediamine and N-(phosphonomethyl)-N-(carboxymethyl)ethanolamine.

In a particularly preferred embodiment, the primary alcohol comprises diethanolamine and the dehydrogenation proceeds as set forth above to form disodium iminodiacetic acid and hydrogen. One important consideration in this embodiment is the formation of unwanted byproducts such as sarcosine (i.e., N-methyl-glycine) which tend to impact downstream processes incorporating the dehydrogenation product (e.g., a process in which disodium iminodiacetic acid is converted to N-(phosphonomethyl)iminodiacetic which is then converted to N-(phosphonomethyl)glycine). It has been discovered that use of the catalyst of the present invention for the dehydrogenation of diethanolamine to disodium iminodiacetic produces no significant amount of sarcosine due to absence of nickel in the catalyst. For example, typically the product of the dehydrogenation of diethanolamine using the catalyst of the present invention contains no more than about 10% by weight of byproducts including sarcosine, glycine and oxalic acid. As an added benefit, the catalyst of the present invention does not require the presence of an expensive noble metal.

The dehydrogenation reaction is conducted in an alkaline environment (i.e., a basic environment) by contacting the primary alcohol with a catalyst in a heated reaction (i.e., dehydrogenation) zone containing an alkaline medium containing the catalyst. More specifically, this reaction is typically conducted in the presence of a strong base having a $pK_a$ value of at least about 11, more preferably at least about 12, and even more preferably at least about 13. Suitable bases include, for example, alkali metal hydroxides (LiOH, NaOH, KOH, RbOH, or CsOH), alkaline-earth metal hydroxides (e.g., $Mg(OH)_2$ or $Ca(OH)_2$), NaH, and tetramethyl ammonium hydroxide. Of these bases, alkali metal hydroxides (particularly NaOH and KOH, and even more particularly NaOH) are often preferred because of their solubility in water under the reaction conditions, as well as their ready commercial availability and ease of handling.

The preferred amount of base introduced into the reaction zone depends on, for example, the moles of primary alcohol groups introduced into the reaction zone. Preferably, at least about one molar equivalent of base is introduced per mole of primary alcohol hydroxy groups. Thus, for example, if the base is NaOH and the primary alcohol is monoethanolamine, preferably at least about 1 mole of NaOH is introduced per mole of monoethanolamine. If, on the other hand, the primary alcohol is diethanolamine, preferably at least 2 moles of NaOH are introduced per mole of diethanolamine. In a particularly preferred embodiment, from about 1.05 to about 2.0 molar equivalents of base per alcohol hydroxyl group are introduced. The hydroxide may, for example, be in the form of flakes, powder, pellets, or an aqueous solution.

The reaction is normally conducted in a liquid medium comprising the alcohol and usually a solvent for the alcohol and/or the base. Alcohol, base and catalyst are introduced into the liquid medium, and reaction proceeds in the liquid medium within the reaction zone. An alkali metal or alkaline earth metal hydroxide may be introduced into the reaction medium in various forms, for example, be in the form of flakes, powder, pellets, or an aqueous solution.

Preferably, the solvent is present in the liquid reaction medium in a proportion sufficient to dissolve essentially all (more preferably, all) the base. The solvent also preferably is present in a proportion sufficient to maintain the primary alcohol substrate and carboxylic acid salt product in a solubilized form.

Water is normally the preferred solvent due to its low cost, widespread availability, and ease of handling. Alcohol, base and solvent are preferably combined in relative proportions such that, at the outset of a batch reaction cycle or the upstream end of a flow reactor, the reaction medium contains at least about 1 moles of alcohol per liter of reaction medium, typically between about 1.8 and about 2.5 moles of alcohol per liter of reaction medium, and at least about 3 moles of base per liter of reaction medium, typically between about 4 and about 5 moles of alcohol per liter of base. The molar ratio of solvent to base and solvent to alcohol is typically between about 0.7 and about 1.2 and between about 0.8 and about 2.0, respectively, more typically between about 0.85 and about 1 and between about 1 and about 1.8, respectively. In a continuous back mixed reaction system, solvent, base and alcohol are preferably introduced into the reaction medium in relative proportions equivalent to the above concentrations and ratios.

Conveniently, the catalyst is slurried in the liquid reaction medium. Alternatively, the reaction medium containing base and alcohol can flow through a fixed bed of catalyst bodies. In a slurry catalyst system, the preferred catalyst loading (i.e., the preferred concentration of catalyst in the liquid reaction medium) depends on, for example, the initial concentration of the primary alcohol substrate therein or the relative rates at which solvent, catalyst and base are introduced into the reaction zone. Typically, the catalyst loading in a batch or continuous flow reactions system is at least about 1% by weight relative to the initial primary alcohol substrate content of the reaction medium (i.e., [mass of catalyst÷mass of primary alcohol substrate]×100%). More preferably, the catalyst loading is from about 1% to about 70% (still more preferably from about 10% to about 40%) by weight of the primary alcohol substrate. In a continuous back mixed reaction system, catalyst and primary alcohol are preferably introduced into the reactor in these same or similar relative proportions.

The preferred catalyst loading also depends on, for example, the total mass of the alkaline liquid medium in which the catalyst is slurried. Typically, the catalyst loading is at least about 0.1% by weight of the total mass of the alkaline medium (i.e., [mass of catalyst÷total mass of alkaline medium]×100%) and, more typically, at least about 5% by weight of the total mass of the alkaline liquid medium. More preferably, the catalyst loading is from about 0.1% to about 10% (even more preferably from about 3.5% to about 10%, and still even more preferably from about 3.5% to about 5%) by weight of the total mass of the alkaline liquid medium. Concentrations of greater than about 10 wt. % can be difficult to filter. On the other hand, concentrations of less than about 0.1 wt. % tend to produce less than optimal reaction rates.

In a preferred embodiment of the invention, particulate catalyst may be charged to an aqueous alkaline medium to form a slurry for contacting diethanolamine with the catalyst to produce a dehydrogenation reaction product slurry comprising catalyst and disodium iminodiacetic acid. Typically, in such an embodiment, the slurry comprises at least about 3.5% by weight of catalyst and, more typically, from about 3.5% to about 10% by weight. Disodium iminodiacetic acid is then recovered from the reaction product slurry.

Regardless of whether the reaction is conducted in a batch or continuous mode, it is preferably driven substantially to completion, e.g., to a conversion of at least about 90%, more preferably at least about 95%, more preferably at least about 98%. Alternatively, however, the reaction system may be operated at lower conversions, with unreacted alcohol separated from the reaction mixture, e.g., by distillation, and recycled as part of the feed to the reactor. Where the reactor is operated at significantly less than quantitative conversion of alcohol, it may be preferable to seek a higher conversion of base, since it may be less feasible to separate and recycle the base, especially an inorganic base such as NaOH or KOH. In such instance the ratio of base to alcohol introduced into the reactor may be significantly less than 1.0. For example if conversion is only 60%, the ratio of base to alcohol may be only 0.55 to 0.65.

The reaction typically is conducted at a temperature of at least about 70° C., preferably from about 120° to about 220° C., more preferably from about 140° to about 200° C., even more preferably from about 145° to about 155° C., and still even more preferably at about 150° C. (particularly when the primary alcohol is diethanolamine and the desired product is the salt of iminodiacetic acid). Although reaction temperatures outside of these ranges may be used, the results are typically less than optimal. For example, at temperatures of less than about 120° C., the reaction rate tends to be slow. And at temperatures greater than about 220° C., the catalyst normally begins to lose selectivity. To illustrate, as the reaction temperature exceeds about 150° C. (and particularly as the temperature exceeds about 220° C.), the dehydrogenation reaction of diethanolamine will tend to form more glycine salt byproduct, and, therefore, be less selective toward forming the desired iminodiacetic acid salt product.

The reaction is preferably conducted under pressure. More specifically, the reaction is normally conducted under a pressure which is sufficient to prevent boiling of the mixture at the reaction temperature. At reaction temperatures of from about 120° to about 220° C., the pressure preferably is at least about 5 kg/cm$^2$, more preferably from about 5 to about 30 kg/cm$^2$, even more preferably from about 5 to about 20 kg/cm$^2$, still even more preferably from about 8 to about 11 kg/cm$^2$ (i.e., from about 115 to about 155 psig), and most preferably about 9.4 kg/cm$^2$ (i.e., 135 psig). Although greater pressures may be used, they are normally less desirable because pressures above about 30 kg/cm$^2$ tend to reduce the reaction rate. In certain embodiments, the dehydrogenation reaction zone is under a total pressure of not greater than about 9.5 kg/cm$^2$ (135 psig) with the hydrogen partial pressure being from about 0 kg/cm$^2$ (0 psig) at the outset of the reaction to about 9.5 kg/cm$^2$ (135 psig) (i.e., the total pressure) at the peak of the reaction.

The dehydrogenation reaction preferably is conducted under a non-oxidizing atmosphere (preferably, an atmosphere containing a noble gas and/or $N_2$, and more preferably $N_2$ when the reaction is conducted on a commercial level) to avoid oxidation of the catalyst surface (the atmosphere will also contain $H_2$ which evolves during the dehydrogenation). This preference stems from the fact that oxidation of the copper near the surface of the catalyst tends to reduce the activity and selectivity of the catalyst.

The dehydrogenation reaction may be carried out in a wide variety of batch, semi-batch, and continuous reactor systems. The configuration of the reactor is not critical. Suitable conventional reactor configurations include, for example, stirred-tank reactors, fixed bed reactors, trickle bed reactors, fluidized bed reactors, bubble flow reactors, plug flow reactors, and parallel flow reactors. Often, the more preferred reactor configurations are stirred-tank reactors. However, for when the hydrogen produced in the dehydrogenation reaction is fed to a fuel cell, the preferred reactor configuration comprises a fixed bed reactor followed by gas-liquid adsorption.

During a batch reaction cycle, typically at least about 200 g of diethanolamine per kg of alkaline medium are introduced to a dehydrogenation reaction zone for each reaction cycle. Preferably, at least about 225 g of diethanolamine per kg of alkaline medium are introduced to a dehydrogenation reaction zone for each reaction cycle. Typically, at least about 5% of the diethanolamine present in the dehydrogenation reaction zone is converted to disodium iminodiacetic acid.

Generally, a primary alcohol will be converted to a salt of a carboxylic acid at an ultimate turnover ratio of at least about 2 moles of salt produced per mole of copper. Preferably, diethanolamine is converted to disodium iminodiacetic acid within the dehydrogenation reaction zone at an ultimate turnover ratio of at least about 1 mole of diethanolamine per mole of copper.

In a slurry reaction system the reaction mixture is preferably filtered for separation of the catalyst from the liquid medium. Preferably the separated catalyst is recycled to the reactor for further conversion of alcohol to carboxylic acid. In a slurried catalyst reaction system, the turnover ratio per cycle or pass through the reactor is generally at least about 1 mole of diethanolamine per mole of copper. Typically, the turnover ratio per cycle or pass through the reactor is at least about 10 moles of diethanolamine per mole of copper, more typically at least about 15 moles of diethanolamine per mole of copper and, still more typically, from about 15 to about 20 moles of diethanolamine per mole of copper. The preferred turnover ratios described hereinabove are realized by multiple recycles of catalyst mass or multiple passes of catalyst through the reactor. In a fixed or fluid bed reaction system, the ultimate turnover ratio reflects the frequency with which the catalyst mass or catalyst bodies are removed from the reaction system and/or regenerated for further use, and the volume of reactants and products flowing through the bed between successive catalyst regeneration or removal operations.

Diethanolamine may be introduced to the dehydrogenation reaction zone continuously or intermittently to be contacted with the catalyst to form a product mixture comprising disodium iminodiacetic acid. Likewise, product mixture my be continuously or intermittently withdrawn from the product mixture.

When the catalyst is recycled and/or reused through multiple reaction cycles or passes, migration of the metal deposited on the carbon support tends to occur during one or more of the initial reaction cycles or passes. In a continuous fixed or fluid bed system, such migration tends to occur during the early hours of operation. Generally, deposited metal particles tend to migrate from less stable to more stable portions of the surface of the carbon support. This migration due to instability of one or more sites is generally complete after the initial (i.e., first and second) reaction cycles of a batch system, or the early passes or other operation of a continuous system, thereby providing a catalyst which exhibits suitable stability throughout multiple reaction cycles, passes, etc.

When the dehydrogenation is conducted in a continuous reactor system, the residence time in the reaction zone can vary widely depending on the specific catalyst and conditions employed. Likewise, when the dehydrogenation is conducted in a batch reactor, the reaction time typically will also vary widely depending on such factors. Normally, the dehydrogenation behaves as a first order reaction, particularly toward the end of the reaction. Thus, the preferred residence time in a continuous reaction zone (or the preferred reaction time in a batch reaction zone) will also depend on the desired degree of conversion.

Various iminodiacetic acid compounds (preferably alkali metal salts of iminodiacetic acid, and even more preferably a sodium salt of iminodiacetic acid) produced using the dehydrogenation catalyst of this invention may be used as raw materials to prepare N-(phosphonomethyl)glycine and agronomically acceptable salts of N-(phosphonomethyl)glycine. Salts of iminodiacetic acid, for example, may be phosphonomethylated in a reaction zone containing HCl, phosphorous acid ($H_3PO_3$), and formaldehyde ($CH_2O$) to form N-(phosphonomethyl)iminodiacetic acid as disclosed for example in U.S. Pat. No. 4,775,498 (Gentilcore). The N-(phosphonomethyl)iminodiacetic acid may, in turn, be contacted with oxygen in the presence of the oxidation catalyst disclosed herein to oxidatively cleave a carboxymethyl group to form N-(phosphonomethyl)glycine. Moreover, N-(phosphonomethyl)glycine prepared in accordance with the present invention may be further processed in accordance with many well-known methods in the art to produce agronomically acceptable salts of N-(phosphonomethyl)glycine commonly used in herbicidal glyphosate compositions. As used herein, an "agronomically acceptable salt" is defined as a salt which contains a cation(s) that allows agriculturally and economically useful herbicidal activity of an N-(phosphonomethyl)glycine anion. Such a cation may be, for example, an alkali metal cation (e.g., a sodium or potassium ion), an ammonium ion, an isopropyl ammonium ion, a tetra-alkylammonium ion, a trialkyl sulfonium ion, a protonated primary amine, a protonated secondary amine, or a protonated tertiary amine.

The present invention is illustrated by the following examples which are merely for the purpose of illustration and not to be regarded as limiting the scope of the invention or the manner in which it may be practiced.

EXAMPLES

Example 1

Electroless Copper Plating on Bulk Metal Carbides and Nitrides

This example details electroless copper plating on bulk metal carbides and nitrides.

Bulk molybdenum carbide (20.0 g) (Aldrich Chemical Co., Milwaukee, Wis.) was added to a 2 l flask containing deionized water (200 ml) and a magnetic stirring bar to form a slurry.

A copper plating solution was prepared by adding reagent grade sodium potassium tartrate ($NaKC_4H_4O_6 \cdot 4H_2O$) (29.99 g) (Aldrich Chemical Co., Milwaukee, Wis.), copper sulfate ($CuSO_4 \cdot 5H_2O$) (11.79 g) (Aldrich Chemical Co., Milwaukee, Wis.), a 50 wt. % solution of sodium hydroxide (NaOH) (13.60 g) (Aldrich Chemical Co., Milwaukee, Wis.) and 37 wt. % formaldehyde ($CH_2O$) (11.35 ml) (Aldrich Chemical Co., Milwaukee, Wis.) to deionized water (950 ml) to form approximately 1 liter of plating solution in a 2 liter flask.

Plating solution was added to the carbide slurry incrementally over the course of about 40 minutes with approximately 60 ml of the plating solution added to the slurry every 2.5 minutes. Addition of plating solution to the carbide slurry and the plating reaction were carried out in a nitrogen atmosphere formed by flowing $N_2$ above the reaction solution.

The pH of the plating solution was monitored using a pH meter to detect reductions in the pH of the plating slurry caused by consumption of sodium hydroxide. Plating was allowed to proceed until the pH of the slurry reached approximately 8.0. After plating was complete, the slurry was filtered under the nitrogen atmosphere and the resulting wet cake was dried in a nitrogen purged vacuum for approximately 8 hours.

The wet cake was then weighed to determine the plating of copper on the bulk molybdenum carbide. The weight gain of the bulk molybdenum carbide indicated copper plating of from 90% to approximately 100% of the copper present in the plating solution.

Example 2

Synthesis of a Precursor for Use in Preparing Carbon-Supported Molybdenum Carbides ($Mo_2C/C$) and Carbon-Supported Molybdenum Nitrides ($Mo_2N/C$)

This example details the preparation of a precursor for use in preparing carbon-supported molybdenum carbides and nitrides.

A carbon support (20.0 g) having a B.E.T. surface area of 1067 $m^2/g$ (Degussa Corporation) was added to a 1 l beaker containing deionized water (300 ml) and a magnetic stirring bar to form a slurry.

A solution (60 ml) containing ammonium molybdate (($NH_4$)$_2MoO_4$) (4.236 g) (Aldrich Chemical Co., Milwaukee, Wis.) in deionized water was added to the carbon slurry using a MasterFlex® meter pump (MasterFlex® L/S®) manufactured by Cole-Parmer Instrument Company (Vernon Hills, Ill.). The slurry was agitated by a mechanical stirrer while the molybdenum solution was added to the carbon slurry at a rate of 2.0 ml/min over the course of about 30-40 minutes. During addition of the molybdenum solution to the carbon slurry, the pH of the resulting mixture was maintained at approximately 4.0 by co-addition of diluted nitric acid (approximately 5-10 ml) (Aldrich Chemical Co., Milwaukee, Wis.). The carbon slurry was agitated during the deposition process and acid was added in 5-10 ml increments when the pH of the slurry was above 4.0.

After addition of the molybdenum solution to the carbon slurry was complete, the slurry was agitated for approximately 30 minutes. The pH of the mixture was then adjusted to around 3.0 by addition of diluted nitric acid (2-5 ml) (Aldrich Chemical Co., Milwaukee, Wis.) and once again agitated for approximately 30 minutes.

The resulting mixture was filtered and washed with approximately 800 ml of deionized water and the wet cake was dried in a nitrogen purged vacuum oven at 120° C. overnight.

Example 3

Synthesis of Carbon-Supported Molybdenum Carbide Containing 15% by Weight Molybdenum Carbide (15% $Mo_2C/C$)

This example details preparation of a carbon-supported molybdenum carbide using a carbon-supported molybdenum carbide precursor prepared in accordance with the procedure set forth above in Example 2.

The carbide precursor (8.0 g) was charged into a Hastelloy C tube reactor packed with high temperature insulation material which was purged with argon introduced to the reactor at 100 $cm^3$/min at about 20° C. for approximately 15 minutes. A thermocouple was inserted into the center of the reactor for charging of the precursor material.

The temperature of the reactor was then raised to about 300° C. over the course of 30 minutes during which time a 50%/50% (v/v) mixture of methane and hydrogen (Airgas Co., St. Louis, Mo.) was introduced to the reactor at a rate of about 100 $cm^3$/min.

The temperature of the reactor was then increased to approximately 650° C. at a rate of approximately 2° C./min. The reactor was maintained at this temperature and under a flow of 50%/50% (v/v) mixture of methane and hydrogen (Airgas Co., St. Louis, Mo.) was introduced to the reactor at a rate of about 100 $cm^3$/min for approximately 4 hours. During this period of constant temperature a molybdenum carbide composition was formed on the carbon support.

The resulting carbide was then cleaned by contact with a 20%/80% (v/v) flow of a mixture of hydrogen and argon introduced to the reactor at a rate of about 100 $cm^3$/min. The temperature of the reactor was maintained at about 650° C. for approximately another 30 minutes after which time the reactor was cooled to approximately 20° C. over the course of 90 minutes under a flow of argon at 100 $cm^3$/min.

Example 4

Synthesis of Carbon-Supported Molybdenum Nitride Containing 15% by Weight Molybdenum Nitride (15% $Mo_2N/C$)

This example details preparation of a carbon-supported molybdenum nitride using a 15% carbon-supported molybdenum nitride precursor prepared in accordance with the procedure set forth above in Example 2.

The nitride precursor (10.0 g) was charged into a Hastelloy C tube reactor packed with high temperature insulation material which was purged with argon introduced to the reactor at 100 $cm^3$/min at about 20° C. for approximately 15 minutes.

The temperature of the reactor was then raised to about 300° C. over the course of 30 minutes during which time ammonia (Airgas Co., St. Louis, Mo.) was introduced to the reactor at a rate of about 100 $cm^3$/min.

The temperature of the reactor was then increased to approximately 800° C. at a rate of approximately 2° C./min. The reactor was maintained at this temperature and under a flow of ammonia at a rate of about 100 $cm^3$/min for approximately 4 hours. During this period of constant temperature, the reactor was maintained under flow of ammonia introduced to the reactor at a rate of about 100 $cm^3$/min.

A molybdenum nitride composition was formed on the carbon support. The reactor was cooled to approximately 20° C. over the course of 90 minutes under flow of 100 $cm^3$/min of argon.

Example 5

Quality of Plating of Copper on Carbon Supported Nitride

The quality of plating of copper on carbon supported metal nitride prepared in accordance with the method set forth above in Example 4 was examined as determined by the percent of molybdenum leaching from the carbon support. The carbon supported nitride prepared contained 10% by weight nitride. A nitriding operation as described above in Example 4 was performed using different maximum temperatures ($T_{max}$) at a constant holding time of 1 hour. The results are summarized below in Table 1.

TABLE 1

Results of Cu plating and Mo leaching at varying $T_{max}$ and a holding time of 1 hour

| | $T_{max}$ (° C.) | | | | |
|---|---|---|---|---|---|
| | 700 | 750 | 800 | 850 | 900 |
| Cu plating yield (%) | >99 | >99 | >99 | >99 | >99 |
| Weight gain in % of Cu | 66 | 73 | 77 | 85 | 83 |
| Mo leaching (%) | 44 | 45 | 23 | 40 | 32 |

Example 6

Quality of Copper Plating on Carbon Supported Nitride

The quality of plating of copper on a carbon-supported metal nitride prepared in accordance with the method set forth above in Example 4 was examined as determined by the percent of molybdenum leaching from the carbon support. The carbon supported metal nitride prepared contained 10% by weight nitride. A nitriding operation as described above in Example 4 was carried out using a maximum temperature ($T_{max}$) of 800° C. and a holding time of 4 hours. The results are summarized below in Table 2.

TABLE 2

Results of Cu plating and Mo leaching at $T_{max}$ of 800° C. and a holding time of 4 hours

| Cu Plating yield (%) | >99 |
|---|---|
| Weight Gain in % of Cu | 93 |
| Mo Leaching (%) | 7 |

Example 7

Quality of Copper Plating on Carbon Supported Carbide

The quality of plating of copper on carbon-supported metal carbides prepared in accordance with the method set forth above in Example 3 was examined as determined by the percent of molybdenum leaching from the carbon support. The carbon supported carbide prepared contained 10% by weight carbide. A carbiding operation as described above in Example 3 was performed using different maximum temperatures ($T_{max}$) at a constant holding time of 1 hour. The results are summarized below in Table 3.

TABLE 3

Results of Cu plating and Mo leaching at varying $T_{max}$ and a holding time of 1 hour

| | $T_{max}$ (° C.) | | | | |
|---|---|---|---|---|---|
| | 600 | 650 | 700 | 750 | 800 |
| Cu plating yield (%) | 98 | >99 | <5 | <5 | 0 |
| Weight gain in % of Cu | 47 | 67 | 0 | 0 | |
| Mo leach (%) | 58 | 53 | | | |

Example 8

Quality of Copper Plating on Carbon Supported Carbide

The quality of plating of copper on a carbon-supported metal carbide prepared in accordance with the method set forth above in Example 3 was examined as determined by the percent of molybdenum leaching from the carbon support. The carbon supported carbide contained 10% by weight carbide. A carbiding operation as described above in Example 3 was carried out using a maximum temperature ($T_{max}$) of 650° C. and a holding time of from 1 to 8 hours. The results are summarized below in Table 4.

TABLE 4

Results of Cu plating and Mo leaching at $T_{max}$ of 650° C. and varying holding times

| | Holding Time | | | |
|---|---|---|---|---|
| | 1 | 2 | 4 | 8 |
| Cu plating yield (%) | >99 | >99 | >99 | |
| Weight gain in % of Cu | 67 | 100 | | |
| Mo leaching (%) | 53 | 1 | 7 | |

Example 9

Stability of Carbon-Supported Carbides Under Conditions Suitable to Dehydrogenate Diethanolamine to Form Disodium Iminodiacetic Acid Carbon-supported carbides prepared in accordance with the methods set forth above using each of four carbon supports were tested in accordance using the procedure set forth below.

The supports may be described as follows:

| Support | Surface Area (m²/g) |
|---|---|
| No. 1 | 1041 |
| No. 2 | 1150 |
| No. 3 | 1067 |
| No. 4 | 1567 |

Dehydrogenation of diethanolamine was conducted in a 300 ml autoclave reactor constructed of Hastelloy C (high strength nickel-based alloy) and equipped with a back pressure regulator, $H_2$ mass flow meters, and a charge pot which allowed reagents and rinse water to be added to the reactor under inert gas.

To test the stability of the various carbon-supported carbide compositions during the dehydrogenation conditions, a catalyst containing 22% Cu by weight, 3% Pt by weight on a carbon support was charged to the reactor along with the carbon-supported carbide compositions.

The reactor was first flushed with argon (when conducting this reaction on a commercial scale, $N_2$ would be preferred). A mixture containing a 50 wt. % solution of sodium hydroxide (99.81 g) (Aldrich Chemical Co., Milwaukee, Wis.), diethanolamine (62.50 g) (Huntsman Chemicals) and deionized water (75 ml) was sparged with $N_2$ and introduced into the reactor along with $N_2$-sparged deionized water (40 ml). The reactor was then sealed and flushed with $N_2$. During the reaction, the mixture was continuously stirred, the pressure was maintained at 135 psig using the back pressure regulator, and the temperature was maintained at about 150° C.

The reaction was allowed to proceed for approximately 3 hours and samples were removed from the reactor at the outset, after the reaction was allowed to proceed for 1.5 hours, and after the reaction had proceeded for 3 hours.

The samples were analyzed to determine the stability of the carbon-supported carbide under the dehydrogenation conditions based on the amount of molybdenum leached from the carbide as determined by the amount of molybdenum present in the samples removed from the reactor determined using Inductively Coupled Plasma-Mass Spectrometry.

The carbon-supported carbide catalysts are referred to according to its support. For example, Catalyst No. 1 refers to a carbon-supported carbide catalyst including Support No. 1. One dehydrogenation cycle was run to test each of Catalyst No. 1, Catalyst No. 2, and Catalyst No. 3 while two dehydrogenation cycles were run to test Catalyst No. 4. The first run to test the stability of Catalyst No. 4 was carried out using only the carbon-supported carbide catalyst while the second run included the 22% Cu by weight, 3% Pt by weight on a carbon support.

The results are shown in Table 5. The percentage of leaching measured at a reaction time of 0 is substantially due to reaction of unconverted molybdenum oxide with sodium hydroxide. The percentage of leaching at a reaction time of 90 minutes and 3 hours includes that present at reaction time of 0 along with possible leaching from the carbide formed during the reaction. For example, as shown below in Table 5 for Catalyst No. 1, molybdenum leaching corresponding to 2.1% of the weight percent of total molybdenum during the first 90 minutes of reaction was from the surface of the carbide formed during that time. While in certain instances the leaching at a reaction time of 3 hours appears to be reduced, based on experimental error these results indicate that the amount of leaching remained substantially constant after a reaction time of 1.5 hours.

TABLE 5

Stability of carbon-supported molybdenum carbides under dehydrogenation conditions

| Catalyst | Molybdenum Leaching (wt. % of total Mo) | | |
|---|---|---|---|
| | t = 0 | t = 1.5 hours | t = 3 hours |
| No. 1 | 1.6% | 3.7% | 4.5% |
| No. 2 | 4.4% | 6.7% | 4.5% |
| No. 3 | 3.3% | 4.5% | 4.4% |
| No. 4 (cycle 1) | 4.9% | 14.5% | |
| No. 4 (cycle 2) | 1.6% | 0.9% | 0.9% |

Table 6 shows the composition of the reactor at the sampling times.

TABLE 6

| Reaction time (hours) | DEA (wt. %) | HEG (wt. %) | IDA (wt. %) | DSIDA (wt. %) |
|---|---|---|---|---|
| 0 | 22.88 | 0.00 | 0.00 | 0.00 |
| 1.5 | 17.59 | 6.50 | 1.50 | 2.00 |
| 3 | 5.51 | 15.09 | 6.87 | 9.14 |

Reactor sample components:
Diethanolamine (DEA)
N-(2-hydroxyethyl)glycine (HEG)
Iminodiacetic acid (IDA)
Disodium iminodiacetic acid (DSIDA)

Example 10

Stability of Carbon-Supported Nitrides Under Conditions Suitable to Dehydrogenate Diethanolamine to Form Disodium Iminodiacetic Acid Carbon-supported nitrides prepared in accordance with the methods set forth above using two different carbon supports were tested in accordance with the procedure set forth below. The supports may be described as follows:

| Support | Surface Area ($m^2/g$) |
|---|---|
| No. 1 | 1041 |
| No. 2. | 1150 |

Dehydrogenation of diethanolamine was conducted in a 300 ml autoclave reactor constructed of Hastelloy C (high strength nickel-based alloy) and equipped with a back pressure regulator, $H_2$ mass flow meters, and a charge pot which allowed reagents and rinse water to be added to the reactor under inert gas.

To test the stability of the carbon-supported nitride compositions during the dehydrogenation conditions, a catalyst containing 22% Cu by weight, 3% Pt by weight on a carbon support was charged to the reactor along with the carbon-supported carbide compositions.

The reactor was first flushed with argon (when conducting this reaction on a commercial scale, $N_2$ would be preferred). A mixture containing a 50 wt. % solution of sodium hydroxide (99.81 g) (Aldrich Chemical Co., Milwaukee, Wis.), diethanolamine (62.50 g) (Huntsman Chemicals) and deionized water (75 ml) was sparged with $N_2$ and introduced into the reactor along with $N_2$-sparged deionized water (40 ml). The reactor was then sealed and flushed with $N_2$. During the reaction, the mixture was continuously stirred, the pressure was maintained at 135 psig using the back pressure regulator and the temperature was maintained at about 150° C. When the $H_2$ generation from the reaction decreased to cm³/min, the reactor was cooled, and $N_2$-sparged deionized water (80 ml) was added to the reactor.

The reaction was allowed to proceed for approximately 3 hours and samples were removed from the reactor at the outset, after the reaction was allowed to proceed for 1.5 hours, and after the reaction had proceeded for 3 hours.

The samples were analyzed to determine the stability of the carbon-supported nitrides under the dehydrogenation conditions based on the amount of molybdenum leached from the nitride as determined by the amount of molybdenum present in the samples removed from the reactor.

The carbon-supported nitride catalysts are referred to according to its support. For example, Catalyst No. 1 refers to a carbon-supported nitride catalyst including Support No. 1. One dehydrogenation cycle was run to test Catalyst No. 1 and No. 2. The results are shown in Table 7.

TABLE 7

Stability of carbon-supported molybdenum nitrides under dehydrogenation conditions

| Nitride | Molybdenum Leaching (wt. % of total Mo) | | |
|---|---|---|---|
| | t = 0 | t = 1.5 hours | t = 3 hours |
| No. 1 | ~5% | 6.0% | 4.4% |
| No. 2 | ~5% | 10.1% | 7.5% |

The percentage of leaching measured at a reaction time of 0 is substantially due to reaction of unconverted molybdenum oxide with sodium hydroxide. The percentage of leaching at a reaction time of 90 minutes and 3 hours includes that present at reaction time of 0 along with possible leaching from the nitride formed during the reaction. For example, as shown for Catalyst No. 1, molybdenum leaching corresponding to approximately 0.9% of the weight percent of total molybdenum during the first 90 minutes of reaction was from the surface of the carbide formed during that time. While in certain instances the leaching at a reaction time of 3 hours appears to be reduced, based on experimental error these results indicate that the amount of leaching remained substantially constant after a reaction time of 1.5 hours.

Example 11

Preparation of Catalyst Containing Copper on Carbon-Supported Molybdenum Carbide This example details preparation of a catalyst containing a carbon-supported molybdenum carbide and copper.

A carbon-supported molybdenum carbide (6.70 g) prepared in accordance with the method set forth above in Example 3 and containing 15% by weight molybdenum carbide was added to deionized water (200 ml) in a 1 liter flask containing a magnetic stirring bar to form a slurry.

A copper plating solution (total volume approximately 500 ml) was prepared by adding reagent grade sodium potassium tartrate ($NaKC_4H_4O_6 \cdot 4H_2O$) (15 g) (Aldrich Chemical Co., Milwaukee, Wis.), copper sulfate ($CuSO_4 \cdot 5H_2O$) (5.90 g) (Aldrich Chemical Co., Milwaukee, Wis.), a 50 wt. % solution of sodium hydroxide (NaOH) (6.80 g) (Aldrich Chemical Co., Milwaukee, Wis.) and 37 wt. % formaldehyde ($CH_2O$) (5.70 ml) (Aldrich Chemical Co., Milwaukee, Wis.) to deionized water (450 ml) in a 1 liter flask.

The carbide slurry and plating solution were both cooled to about 2° C. in a nitrogen ($N_2$) atmosphere while stirred with a magnetic stirring bar. After cooling, plating solution was added to the carbide slurry under the nitrogen atmosphere incrementally over the course of approximately 30 minutes with 16 ml of plating solution being added to the carbide slurry every minute. After addition of the plating solution to the carbide slurry was complete, the resulting mixture was agitated for about 2 hours at approximately 3° C. using a magnetic stirring bar. Plating was monitored using by the drop in pH of the mixture caused by consumption of sodium hydroxide. The pH of the mixture is monitored using a pH meter and plating continued until the pH of the mixture dropped below 8. The mixture was filtered under the nitrogen atmosphere which produced a wet cake. The resulting wet cake was washed with water (200 ml), packed, and dried in a nitrogen purged vacuum oven at 120° C. for approximately 8 hours.

Based on metal analysis of the resulting filtrate, the resulting solid was determined to have a composition of 18 wt. % copper, 11 wt. % carbide with the balance consisting of the carbon support. (18% Cu-11% $Mo_2C$/C).

Example 12

Preparation of Catalyst Containing Copper on Carbon-Supported Molybdenum Carbide This example details preparation of a catalyst containing a carbon-supported molybdenum carbide and copper.

A carbon-supported molybdenum carbide (6.97 g) prepared in accordance with the method set forth above in Example 3 and containing 15% by weight molybdenum carbide was added to deionized water (200 ml) in a 1 liter flask containing a magnetic stirring bar to form a slurry.

A copper plating solution (total volume approximately 500 ml) was prepared by adding reagent grade sodium potassium tartrate ($NaKC_4H_4O_6 \cdot 4H_2O$) (15 g) (Aldrich Chemical Co., Milwaukee, Wis.), copper sulfate ($CuSO_4O_5H_2O$) (5.90 g) (Aldrich Chemical Co., Milwaukee, Wis.), and a 50 wt. % solution of sodium hydroxide (NaOH) (6.80 g) (Aldrich Chemical Co., Milwaukee, Wis.) to deionized water (450 ml) in a 1 liter flask.

The carbide slurry and plating solution were both cooled to from about 0-2° C. in a nitrogen ($N_2$) atmosphere. After cooling, the plating solution and carbide slurry were mixed under the nitrogen atmosphere and agitated for approximately 30 minutes using a magnetic stirring bar. Following the agitation, a mixture of 37 wt. % formaldehyde ($CH_2O$) (5.70 ml) (Aldrich Chemical Co., Milwaukee, Wis.) in 20 ml deionized water was added to the slurry at approximately 3° C. for approximately 30 minutes using MasterFlex® meter pump.

The temperature of the mixture was then raised to approximately 13° C. over the course of approximately one hour and maintained at this temperature until the mixture became substantially colorless. This took from 10 to 15 minutes after which time the mixture was filtered under the nitrogen atmosphere which produced a wet cake. The resulting wet cake was washed with water (200 ml), packed wet, and dried in a nitrogen purged vacuum oven at 120° C. for approximately 8 hours.

Based on metal analysis of the resulting filtrate, the resulting solid was determined to have a composition of 19 wt. % copper, 10 wt. % carbide with the balance consisting of the carbon support. (19% Cu-10% Mo$_2$C/C)

Example 13

Preparation of Catalyst Containing Copper on Carbon-Supported Molybdenum Carbide This example details preparation of a catalyst containing a carbon-supported molybdenum carbide and copper.

A carbon-supported molybdenum carbide (6.30 g) prepared in accordance with the method set forth above in Example 3 and containing 13% by weight molybdenum carbide was added to deionized water (200 ml) in a 1 liter flask containing a magnetic stirring bar to form a slurry.

A copper plating solution (total volume approximately 500 ml) was prepared by adding reagent grade ethylenediaminetetraacetic acid (EDTA, C$_{10}$H$_{16}$O$_8$N$_2$) (13.74 g) (Aldrich Chemical Co., Milwaukee, Wis.), copper sulfate (CuSO$_4$.5H$_2$O) (5.90 g) (Aldrich Chemical Co., Milwaukee, Wis.), and a 50 wt. % solution of sodium hydroxide (NaOH) (6.80 g) (Aldrich Chemical Co., Milwaukee, Wis.) and 37 wt. % formaldehyde (CH$_2$O) (0.15 ml) to deionized water (450 ml) in a 1 liter flask.

The carbide slurry and plating solution were both cooled to from about 0-2° C. in a nitrogen (N$_2$) atmosphere. After cooling, the plating solution and carbide slurry were mixed under the nitrogen atmosphere and agitated for approximately 15 minutes using a magnetic stirring bar. Following the agitation, a mixture of 37 wt. % formaldehyde (CH$_2$O) (5.70 ml) (Aldrich Chemical Co., Milwaukee, Wis.) in deionized water was added to the mixture which was agitated at approximately 2° C. for approximately 10 minutes using a magnetic stirring bar.

The temperature of the mixture was then raised to approximately 18° C. over the course of approximately 20 minutes and maintained at this temperature until the mixture became substantially colorless. This took from about 10 to 15 minutes after which time the mixture was filtered under the nitrogen atmosphere which produced a wet cake. The resulting wet cake was washed with water (200 ml), packed wet, and dried in a nitrogen purged vacuum oven at 120° C. for approximately 8 hours.

Based on metal analysis of the resulting filtrate, the resulting solid was determined to have a composition of 19 wt. % copper, 10 wt. % carbide with the balance consisting of the carbon support. (19% Cu-10% Mo$_2$C/C)

Example 14

Use of a Catalyst Containing Copper Deposited on a Carbon-Supported Molybdenum Carbide for the Dehydrogenation of Diethanolamine to Disodium Iminodiacetic Acid This example details use of the catalyst prepared in accordance with the procedure set forth above in Example 11 for the dehydrogenation of diethanolamine to produce disodium iminodiacetic acid over the course of 8 reaction cycles The dehydrogenation was conducted in a 300 ml Parr autoclave continuous stirred tank reactor able to be operated in a batch or continuous manner. The reactor was operated batchwise for each of the 8 reaction cycles of the present example. The reactor was constructed of Hastelloy C (high strength nickel-based alloy) and equipped with a back pressure regulator, H$_2$ mass flow meters, and a charge pot which allowed reagents and rinse water to be added to the reactor under inert gas.

Catalyst (7.0 g) prepared in accordance with the method set forth above in Example 7, 50 wt. % sodium hydroxide (55.90 g) (Aldrich Chemical Co., Milwaukee, Wis.), diethanolamine (35.11 g) (Huntsman Chemicals) and water (42.44 g) were charged in this sequence to the reactor to form a mixture.

The reactor was set at a maximum volume of approximately 170 ml and the total amount of mixture charged (140.45 g) provided proper hydrogen disengagement. High-pressure bottle N$_2$ at a pressure of 3000 psig was used to inert the reaction headspace and bring the reaction to the starting pressure of approximately 135 psig.

During the reaction, the mixture was continuously stirred and the pressure maintained at approximately 135 psig using a control valve manufactured by Badger Research. Reaction temperature was maintained at about 150° C. during the entire reaction.

The reaction was allowed to proceed for approximately 3 hours during which time a Brooks onstream thermal mass flow sensor (Model No. 58601A13VB2EA) was used to monitor the reaction based on the amount of hydrogen generated in the reaction mixture.

After the reaction was allowed to proceed for approximately 3 hours, the reaction mass was cooled to approximately 90° C. and the reactants were separated from the catalyst in situ using a 0.5 μm metal sintered frit (Mott Corporation, Hartford, Conn.). Samples of the reaction mass were analyzed using high pressure liquid chromatography ("HPLC").

Seven additional dehydrogenation cycles were conducted in accordance with the above conditions with similar amounts of diethanolamine being charged to the reactor.

The extent of reaction in terms of hydroxide conversion was determined for reaction cycles 1-7 by comparing the actual amount of hydrogen generated to the theoretical amount of hydrogen to be generated in the reaction mixture based on the amount of diethanolamine charged to the reactor. The results are shown below in Table 8.

The compositions of the product samples from reaction cycles 1 and 2 analyzed using HPLC are summarized below in Table 9.

TABLE 8

| | Reaction Cycle | | | | | | | |
|---|---|---|---|---|---|---|---|---|
| | 1 | 2 | 3 | 4 | 5 | 6 | 7 | 8 |
| Amount of DEA charged to reactor | 35.11 | 35.09 | 35.10 | 35.09 | 35.00 | 35.10 | 35.09 | 35.10 |
| Theoretical H$_2$ generation (mol) | 1.34 | 1.33 | 1.34 | 1.33 | 1.33 | 1.34 | 1.33 | 1.34 |
| Actual H$_2$ generation (mol) | 0.66 | 0.64 | 0.55 | 0.55 | 0.53 | 0.44 | 0.56 | |
| Hydroxide conversion (%) | 49.49 | 48.27 | 41.48 | 41.51 | 39.99 | 32.88 | 41.87 | |

TABLE 9

Composition of Dehydrogenation Product Samples

| | Cycle No. | |
|---|---|---|
| | 1 | 2 |
| DEA (mol %) | 10.77 | 11.73 |
| HEG (mol %) | 50.59 | 62.47 |
| Glycine (mol %) | 1.55 | 1.92 |
| IDA (mol %) | 20.09 | 23.92 |
| OH conversion (%) | 55 | 56 |

Product Sample Components:
Diethanolamine (DEA)
N-(2-Hydroxyethyl)glycine (HEG)
Iminodiacetic acid (IDA)

Example 15

Use of a Catalyst Containing Copper on a Carbon-Supported Molybdenum Carbide for the Dehydrogenation of Diethanolamine to Disodium Iminodiacetic Acid

Catalyst (7.2 g) prepared in accordance with the method set forth above in Example 12, 50 wt. % sodium hydroxide (54.95 g) (Aldrich Chemical Co., Milwaukee, Wis.), diethanolamine (35.04 g) (Huntsman Chemicals) and water (46.74 g) were charged in this sequence to the reactor described above in Example 14 to form a mixture. Dehydrogenation of diethanolamine was conducted using the same reaction conditions as in Example 14.

6 dehydrogenation cycles were conducted with similar amounts of diethanolamine charged to the reactor during each cycle. The results for the extent of reaction during each of the 6 reaction cycles were determined based on the hydroxide conversion in accordance with the method set forth above in Example 14 and are summarized below in Table 10.

TABLE 10

| | Cycle No. | | | | | |
|---|---|---|---|---|---|---|
| | 1 | 2 | 3 | 4 | 5 | 6 |
| DEA (g) | 35.04 | 35.10 | 35.05 | 35.08 | 35.04 | 35.05 |
| Theoretical $H_2$ generation (mol) | 1.33 | 1.34 | 1.33 | 1.33 | 1.33 | 1.33 |
| Actual $H_2$ generation (mol) | 0.56 | 0.54 | 0.39 | 0.43 | 0.38 | 0.29 |
| Hydroxide conversion (%) | 41.92 | 40.77 | 29.51 | 32.47 | 28.85 | 22.09 |

Diethanolamine (DEA)

Example 16

Use of a Catalyst Containing Copper on a Carbon-Supported Molybdenum Carbide for the Dehydrogenation of Diethanolamine to Disodium Iminodiacetic Acid

Catalyst (7.0 g) prepared in accordance with the method set forth above in Example 13, 50 wt. % sodium hydroxide (60.52 g) (Aldrich Chemical Co., Milwaukee, Wis.), diethanolamine (39.16 g) (Huntsman Chemicals) and water (49.40 g) were charged in this sequence to the reactor described above in Example 14 to form a mixture.

Dehydrogenation of diethanolamine was conducted using the same reaction conditions as in Example 10. 3 dehydrogenation cycles during which the reaction was allowed to proceed for about 4, 4.5 and 6 hours, respectively. Similar amounts of diethanolamine charged to the reactor during each cycle. The results for the extent of reaction during each of the 3 reaction cycles were determined based on the hydroxide conversion in accordance with the method set forth above in Example 13 and are summarized below in Table 11.

TABLE 11

| | Cycle No. | | |
|---|---|---|---|
| | 1 | 2 | 3 |
| Reaction time | 4.0 hours | 4.5 hours | 6.0 hours |
| DEA (g) | 39.16 | 39.50 | 39.33 |
| Theoretical $H_2$ generation (mol) | 1.49 | 1.50 | 1.50 |
| Actual $H_2$ generation (mol) | 0.85 | 1.06 | 0.84 |
| Hydroxide conversion (%) | 56.89 | 70.40 | 55.89 |

Example 17

Use of a Catalyst Containing Copper Deposited on a Carbon-Supported Molybdenum Carbide for the Dehydrogenation of Diethanolamine to Disodium Iminodiacetic Acid

This example details use of 12% Cu-13% $Mo_2C$/D1015 catalyst prepared in accordance with the procedure set forth above in Example 14 for the dehydrogenation of diethanolamine to produce disodium iminodiacetic acid over the course of 3 reaction cycles.

The dehydrogenation was conducted in a 300 ml Parr autoclave continuous stirred tank reactor able to be operated in a batch or continuous manner. The reactor was operated batchwise for each of the 3 reaction cycles of the present example. The reactor was constructed of Hastelloy C (high strength nickel-based alloy) and equipped with a back pressure regulator, $H_2$ mass flow meters, and a charge pot which allowed reagents and rinse water to be added to the reactor under inert gas.

Catalyst (7.5 g) prepared in accordance with the method set forth above in Example 7 (12% by weight copper and 13% by weight molybdenum carbide and the balance support having a surface area of 1067 $m^2$/g), 50 wt. % sodium hydroxide (59.6 g) (Aldrich Chemical Co., Milwaukee, Wis.), diethanolamine (37.45 g) (Huntsman Chemicals) and deionized water (36.10 g) were charged in this sequence to the reactor to form a mixture.

The reactor was set at a maximum volume of approximately 170 ml and the total amount of mixture charged (140.64 g) provided proper hydrogen disengagement. High-pressure bottle $N_2$ at a pressure of 3000 psig was used to inert the reaction headspace and bring the reaction to the starting pressure of approximately 135 psig.

During the reaction, the mixture was continuously stirred and the pressure maintained at approximately 135 psig using a control valve manufactured by Badger Research. Reaction temperature was maintained at about 150° C. during each of the reaction cycles.

The reaction was allowed to proceed for approximately 3 hours during which time a Brooks onstream thermal mass flow sensor (Model No. 58601A13VB2EA) was used to monitor the reaction based on the amount of hydrogen generated in the reaction mixture.

The extent of reaction in terms of hydroxide conversion was determined by comparing the actual amount of hydrogen generated to the theoretical amount of hydrogen to be generated in the reaction mixture based on the amount of diethanolamine charged to the reactor. The results for the extent of reaction during each of the 3 reaction cycles are summarized below in Table 12.

TABLE 12

| | Reaction Cycle | | |
|---|---|---|---|
| | 1 | 2 | 3 |
| Theoretical $H_2$ Generation (liters) | 32.1 l | 32.1 l | 32.3 l |
| Actual $H_2$ Generation (liters) | 19.9 l | | 17.1 |
| Hydroxide conversion (%) | 62% | | 53% |
| Molybdenum leaching (wt % of total Mo) | 7.1% | 1.9% | 0.6% |

Example 18

Use of Molybdenum Carbide in the Oxidation of N-(Phosphonomethyl)Iminodiacetic Acid A 8.2% by weight solution of N-(phosphonomethyl)iminodiacetic acid (PMIDA) (11.48 g) in water (127.8 ml) was charged to a 1 L Parr reactor together with molybdenum carbide at a loading of 1.3% (1.84 g). Prior to being charged to the reactor the molybdenum carbide was subjected to a helium atmosphere at a temperature of approximately 800° C. for approximately 1 hour.

The reactor was pressurized to 60 psig in the presence of a nitrogen atmosphere and the reaction mixture was heated to 100° C. The reaction was allowed to proceed for approximately 1 hour under a flow of 100 cc/min of pure oxygen.

Samples of the reaction product were removed from the reactor and analyzed to determine the conversion of N-(phosphonomethyl)iminodiacetic acid. HPLC analysis indicated a conversion of PMIDA to N-(phosphonomethyl) glycine of approximately 18.2% and a conversion of formaldehyde to formic acid of approximately 33.9%.

Example 19

Preparation of Carbon-Supported Molybdenum Catalyst

This example details preparation of a carbon-supported molybdenum catalyst.

Activated carbon (10.2 g) was added to water (160 ml) at a temperature of approximately 20° C. The mixture was stirred for approximately 40 minutes to form a slurry of the carbon support.

Phosphomolybdic acid ($H_3Mo_{12}O_{40}P$) (0.317 g) was dissolved in water (30 ml) to form a solution which was added to the support slurry. The mixture containing the phosphomolybdic acid was then stirred for 30 minutes after which time the solid was filtered, washed with deionized water and dried in a vacuum at 120° C. for approximately 8 hours.

The dried carbon-supported molybdenum compound was then subjected to a reduction operation in a 5% hydrogen in helium atmosphere at a temperature of from about 800 or 900° C.

Example 20

Use of a Carbon-Supported Molybdenum Carbide Catalyst in the Oxidation of N-(Phosphonomethyl) Iminodiacetic Acid This example details use of a carbon-supported molybdenum catalyst prepared in accordance with the method set forth above in Example 19 in the oxidation of N-(phosphonomethyl) iminodiacetic acid.

A 4.1% by weight solution of N-(phosphonomethyl) iminodiacetic acid (PMIDA) (5.74 g) in water (133.8 g) was charged to a 1 L Parr reactor together with the carbon-supported molybdenum catalyst at a loading of 0.309% (0.432 g). The reactor was pressurized to 60 psig in a nitrogen atmosphere and the reaction mixture was heated to approximately 100° C.

The reaction was allowed to proceed for approximately 80 minutes under a flow of 100 cc/min of pure oxygen. Four reaction cycles were performed and catalyst from the previous cycle was used in each of the final 3 cycles.

Samples from the reaction mixtures produced during the third and fourth reaction cycles were analyzed. HPLC analysis of these samples indicated conversions of PMIDA to N-(phosphonomethyl)glycine during the third and fourth cycles were approximately 86.2% and 86.9%, respectively. The conversions of formaldehyde to formic acid during the third and fourth cycles were approximately 30.0% and 34.4%, respectively.

Example 21

Use of Carbon-Supported Molybdenum in the Oxidation of N-(Phosphonomethyl)Iminodiacetic Acid This example details the use of carbon-supported molybdenum catalyst prepared in accordance with the method set forth above in Example 19 in the oxidation of N-(phosphonomethyl)iminodiacetic acid.

A 4.11% by weight solution of N-(phosphonomethyl) iminodiacetic acid (PMIDA) (5.74 g) in water (133.8 g) was charged to a 1 L Parr reactor together with the carbon-supported molybdenum catalyst at a loading of 0.155% (0.216 g).

The reactor was pressurized to 60 psig in a nitrogen atmosphere and the reaction mixture was heated to approximately 100° C. The reaction was allowed to proceed for approximately 15 minutes under a flow of 100 cc/min of pure oxygen.

A sample was removed from the reaction mixture and analyzed. HPLC analysis indicated a conversion of PMIDA to N-(phosphonomethyl)glycine of approximately 6.8% and a conversion of formaldehyde to formic acid of approximately 17.4%.

Example 22

This example details the preparation of a carbon-supported iron-containing catalyst precursor.

A particulate carbon support (10.0 g) having a Langmuir surface area of approximately 1500 m²/g was added to a 1 liter flask containing deionized water (400 ml) to form a slurry. The pH of the slurry was approximately 8.0 and the temperature approximately 20° C.

Iron chloride ($FeCl_3.6H_2O$) (0.489 g) was added to a 100 ml beaker containing deionized water (30 ml) to form a clear solution. The iron solution was added incrementally over the course of 15 minutes (i.e., at a rate of approximately 2 ml/minute). The pH of the carbon slurry was maintained at from about 4 to about 4.4 by co-addition of a 0.1 wt. % solution of sodium hydroxide (Aldrich Chemical Co., Milwaukee, Wis.). Approximately 5 ml of 0.1 wt. % sodium hydroxide solution was added to the carbon slurry during addition of the iron solution. The pH of the slurry was monitored using a pH meter (Thermo Orion Model 290).

After addition of the iron solution to the carbon slurry was complete, the slurry was stirred for 30 minutes using a mechanical stirring rod (at 50% output) (IKA-Werke RW16 Basic) with pH of the slurry monitored using the pH meter and maintained at approximately 4.4 by dropwise addition of 0.1 wt. % sodium hydroxide or 0.1 wt. % $HNO_3$.

The slurry was then heated under a nitrogen blanket to 70° C. at a rate of about 2° C. per minute while its pH was maintained at 4.4. Upon reaching 70° C., the slurry pH was slowly raised by addition of 0.1 wt. % sodium hydroxide (5 ml) according to the following pH profile: the pH was maintained at approximately 5.0 for 10 minutes, increased to 5.5, maintained at 5.5 for approximately 20 minutes at pH 5.5, and stirred for approximately 20 minutes during which time a constant pH of 6.0 was reached.

The resulting mixture was filtered and washed with a plentiful amount of deionized water (approximately 500 ml) and the wet cake was dried for approximately 16 hours in a vacuum oven at 120° C. The precursor contained approximately 1.0% by weight iron.

Example 23

This example details the preparation of a carbon-supported iron-containing catalyst using a precursor prepared in accordance with the procedure set forth above in Example 22.

Iron-containing precursor (5.0 g) was charged into a Hastelloy C tube reactor packed with high temperature insulation material. The reactor was purged with argon introduced to the reactor at a rate of approximately 100 cm³/min at approximately 20° C. for approximately 15 minutes. A thermocouple was inserted into the center of the reactor for charging the precursor material.

The temperature of the reactor was then raised to approximately 300° C. over the course of approximately 15 minutes during which time a 10%/90% (v/v) mixture of acetonitrile and argon (Airgas, Inc., Radnor, Pa.) was introduced to the reactor at a rate of approximately 100 cm³/minute. The temperature of the reactor was then increased to approximately 950° C. over the course of 30 minutes during which time the 10%/90% (v/v) mixture of acetonitrile and argon flowed through the reactor at a rate of approximately 100 cm³/minute. The reactor was maintained at approximately 950° C. for approximately 120 minutes. The reactor was cooled to approximately 20° C. over the course of 90 minutes under a flow of argon at approximately 100 cm³/minute.

The resulting catalyst contained approximately 1% by weight iron.

Example 24

This example details the use of various of various noble-metal and non-noble-metal-containing catalysts in the oxidation of PMIDA to N-(phosphonomethyl)glycine.

A 0.5% by weight iron containing catalyst was prepared in accordance with the procedure set forth above in Example 23. Its precursor was prepared in accordance with the procedure set forth above in Example 22 ($FeCl_3.6H_2O$) using a solution containing iron chloride ($FeCl_3.6H_2O$) (0.245 g) in deionized water (60 ml) which was contacted with the carbon support slurry.

Figure 8:
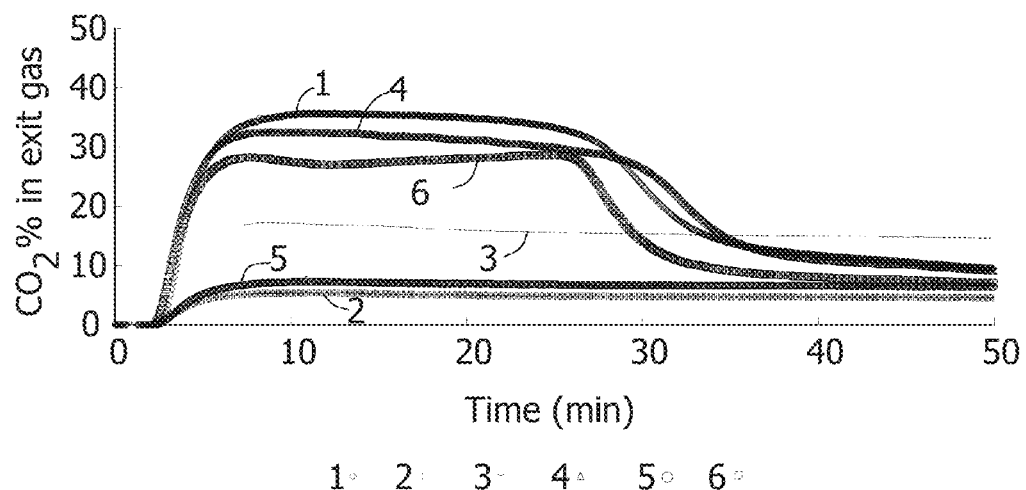
FIG. 8 shows the percentage of carbon dioxide in the exit gas produced during N-(phosphonomethyl)iminodiacetic acid (PMIDA) oxidation carried out using various catalysts as described in Example 24.

The 0.5% by weight iron catalyst was used to catalyze the oxidation of PMIDA to glyphosate (curve 6 of FIG. 8). Its performance was compared to: (1) 2 samples of a 5% platinum, 0.5% iron particulate carbon catalyst prepared in accordance with Ebner et al., U.S. Pat. No. 6,417,133, Samples 1 and 2 (curves 1 and 4, respectively, of FIG. 8); (2) a particulate carbon catalyst designated MC-10 prepared in accordance with Chou, U.S. Pat. No. 4,696,772 (curve 3 of FIG. 8); (3) a 1% Fe containing catalyst precursor prepared in accordance with the procedure set forth above in Example 22 treated in accordance with the catalyst preparation procedure described in Example 23 using argon in place of acetonitrile (curve 2 of FIG. 8); and (4) a particulate carbon support having a Langmuir surface area of approximately 1500 m²/g which was treated with acetonitrile in accordance with the procedure set forth above in Example 23 used to prepare the 1% by weight iron catalyst (curve 5 of FIG. 8).

In each instance, the PMIDA oxidation was conducted in a 200 ml glass reactor containing a total reaction mass (200 g) which included 5.74% by weight PMIDA (11.48 g) and 0.11% catalyst (0.22 g). The oxidation was conducted at a temperature of 100° C., a pressure of 60 psig, a stir rate of 100 revolutions per minute (rpm), and an oxygen flow rate of 150 cm³/minute for a run time of 50 minutes.

The maximum $CO_2$ percentage in the exit gas and cumulative $CO_2$ generated were used as indicators of the degree of oxidation of PMIDA, formaldehyde, and formic acid during the reaction.

FIG. 8 shows the percentage of $CO_2$ in the exit gas during a first reaction cycle carried out using the six different catalysts.

As shown in FIG. 8, the 0.5% by weight iron catalyst exhibited greater activity than the MC10 catalyst and exhibited comparable activity as compared to 5% Pt/0.5% Fe/C catalysts. Also shown in FIG. 8, the acetonitrile-treated carbon support and argon-treated precursor showed little activity. Table 13 shows the $CO_2$ in the exit gas and cumulative $CO_2$ generated in the reaction cycle using each of the 6 catalyst samples.

TABLE 13

Cumulative $CO_2$ number after 50 minute runtime

| Catalyst | Maximum $CO_2$ % in exit gas | Cumulative $CO_2$ (cm³) |
|---|---|---|
| 5% Pt/0.5% Fe/C, Sample 1 | 41.45 | 2140 |
| 5% Pt/0.5% Fe/C, Sample 2 | 37.4 | 2021 |
| MC-10 | 20.02 | 1255 |
| Ar treated 1% Fe/C | 6.29 | 373 |
| $CH_3CN$ treated carbon | 8.79 | 533 |
| 0.5% FeCN/C | 33.34 | 1742 |

Example 25

The performance of iron containing catalysts of varying iron loadings (0.5%, 0.75%, 1%, and 2% by weight iron) was tested in the oxidation of PMIDA to N-(phosphonomethyl) glycine.

The 0.5% by weight iron catalyst prepared in accordance with Example 24 and the 1% by weight iron catalyst prepared in accordance with Example 23 were tested along with a 0.75% by weight iron catalyst and 2% by weight iron catalyst.

The precursors of the 0.75% and 2% iron catalysts were prepared in accordance with the procedure set forth above in Example 22 using varying amounts of iron chloride ($FeCl_3 \cdot 6H_2O$), depending on the desired catalyst loading. For the catalyst containing 0.75% by weight iron, a solution containing iron chloride (0.366 g) in deionized water (60 ml) was prepared and contacted with the carbon support slurry.

For the catalyst containing 2.0% by weight iron, a solution containing iron chloride (0.988 g) in deionized water (60 ml) was prepared and contacted with the carbon support slurry.

Each of the catalysts was tested under the PMIDA oxidation reaction conditions as set forth in Example 24.

Figure 9:
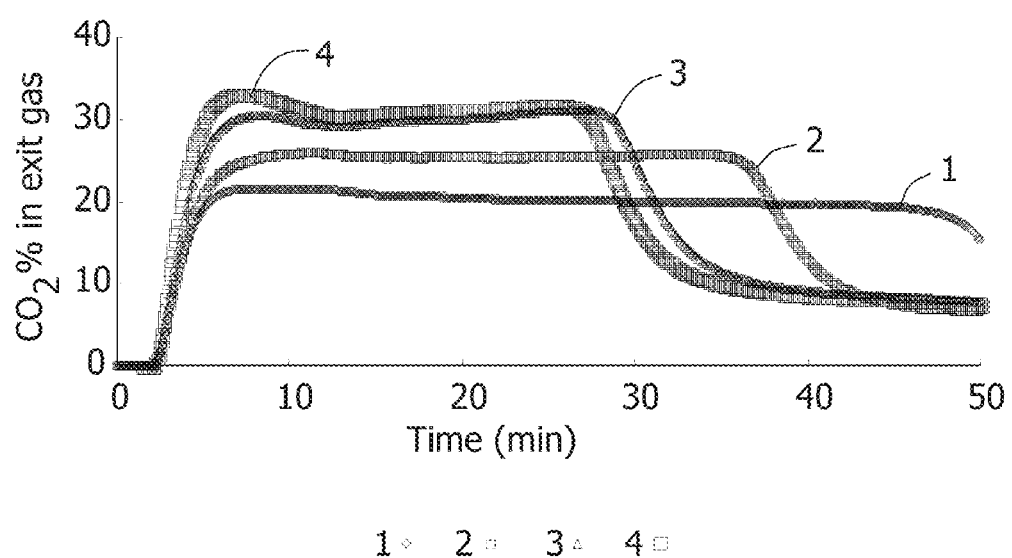
FIG. 9 shows carbon dioxide profiles of PMIDA oxidation carried out using various catalysts as described in Example 25.

FIG. 9 shows the first cycle $CO_2$ profiles for the various catalysts. Curve 1 of FIG. 9 corresponds to the first cycle using the 2% Fe catalyst, curve 2 of FIG. 9 corresponds to the first cycle using the 1% Fe catalyst, curve 3 of FIG. 9 corresponds to the first cycle using the 0.75% Fe catalyst, and curve 4 of FIG. 9 corresponds to the first cycle using the 0.5% Fe catalyst. As shown, the catalyst containing 0.5% by weight iron demonstrated the highest activity.

Table 14 shows HPLC results for the product mixtures of the reactions carried out using the 1% by weight iron catalyst prepared as in Example 23 and a 5% platinum, 0.5% iron catalyst prepared in accordance with Ebner et al., U.S. Pat. No. 6,417,133. The table shows the N-(phosphonomethyl) iminodiacetic acid (PMIDA), N-(phosphonomethyl) glycine (Gly), formaldehyde (FM), formic acid (FA), iminodiacetic acid (IDA), aminomethylphosphonic acid and methyl aminomethylphosphonic acid ((M)AMPA), N-methyl-N-(phosphonomethyl) glycine (NMG), imino-bis-(methylene)-bis-phosphonic acid (iminobis), and phosphate ion ($PO_4$) content of the reaction mixture.

TABLE 14

HPLC results for 5% platinum, 0.5% iron 6,417,133 catalyst and 1% FeCN/C catalyst after 50 minute runtime

|  | 5% Pt/0.5% Fe/C | 1% FeCN/C |
| --- | --- | --- |
| PMIDA (%) | 0.0108 | ND |
| Gly (%) | 3.76 | 3.63 |
| FM (ppm) | 1427 | 6115 |
| FA (ppm) | 3030 | 2100 |
| IDA (%) | 0.0421 | 0.0058 |
| AMPA/MAMPA (ppm) | 758 | 2231 |
| NMG (ppm) | 78 | 138 |
| Iminobis (ppm) | 230 | 256 |
| $PO_4$ (ppm) | 385 | 107 |

Example 26

This example details preparation of a carbon-supported cobalt-containing catalyst precursor containing 1% by weight cobalt.

A particulate carbon support (10.0 g) having a Langmuir surface area of approximately 1500 m²/g was added to a 1 liter flask containing deionized water (400 ml) to form a slurry. The pH of the slurry was approximately 8.0 and the temperature approximately 20° C.

Cobalt chloride ($CoCl_2 \cdot 2H_2O$) (0.285 g) (Sigma-Aldrich, St. Louis, Mo.) was added to a 100 ml beaker containing deionized water (60 ml) to form a clear solution. The cobalt solution was added to the carbon slurry incrementally over the course of 30 minutes (i.e., at a rate of approximately 2 ml/minute). The pH of the carbon slurry was maintained at from about 7.5 and about 8.0 during addition of the cobalt solution by co-addition of a 0.1 wt % solution of sodium hydroxide (Aldrich Chemical Co., Milwaukee, Wis.). Approximately 1 ml of 0.1 wt. % sodium hydroxide solution was added to the carbon slurry during addition of the cobalt solution. The pH of the slurry was monitored using a pH meter (Thermo Orion, Model 290).

After addition of the cobalt solution to the carbon slurry was complete, the slurry was stirred using a mechanical stirring rod operating at 50% of output (Model IKA-Werke RW16 Basic) for approximately 30 minutes; the pH of the slurry was monitored using the pH meter and maintained at about 8.0 by dropwise addition of 0.1 wt. % sodium hydroxide (1 ml) or 0.1 wt. % $HNO_3$ (1 ml). The slurry was then heated under a nitrogen blanket to 45° C. at a rate of about 2° C. per minute while maintaining the pH at 8.0 by dropwise addition of 0.1 wt. % sodium hydroxide (1 ml) or 0.1 wt. % $HNO_3$ (1 ml). Upon reaching 45° C., the slurry was stirred using the mechanical stirring bar described above for 20 minutes at constant temperature of 45° C. and a pH of 8.0. The slurry was then heated to 50° C. and its pH was adjusted to 8.5 by addition of 0.1 wt. % sodium hydroxide solution (5 ml); the slurry was maintained at these conditions for approximately 20 minutes. The slurry was then heated to 60° C., its pH adjusted to 9.0 by addition of 0.1 wt. % sodium hydroxide solution (5 ml) and maintained at these conditions for approximately 10 minutes.

The resulting mixture was filtered and washed with a plentiful amount of deionized water (approximately 500 ml) and the wet cake was dried for approximately 16 hours in a vacuum oven at 120° C. The precursor contained approximately 1.0% by weight cobalt.

Example 27

This example details the preparation of a carbon-supported cobalt-containing catalyst using a precursor prepared in accordance with the procedure set forth above in Example 26.

Cobalt-containing catalyst precursor prepared as described above in Example 26 (5.0 g) was charged into a Hastelloy C tube reactor packed with high temperature insulation material. The reactor was purged with argon introduced to the reactor at a rate of approximately 100 cm³/min at approximately 20° C. for approximately 15 minutes. A thermocouple was inserted into the center of the reactor for charging the precursor material.

The temperature of the reactor was then raised to approximately 700° C. during which time a 50%/50% (v/v) mixture of hydrogen and methane (Airgas, Inc., Radnor, Pa.) was introduced to the reactor at a rate of approximately 20 cm³/minute and argon at a rate of approximately 100 cm³/min. The reactor was maintained at approximately 700° C. for approximately 120 minutes.

The reactor was cooled to approximately 20° C. over the course of 90 minutes under a flow of argon at approximately 100 cm³/minute.

The resulting catalyst contained approximately 1% by weight cobalt.

A 1% cobalt-containing catalyst from the precursor prepared as described in Example 26 was also prepared as described in Example 23 using acetonitrile.

Example 28

The performance of cobalt containing catalysts of varying cobalt loadings (0.75%, 1%, 1.5%, and 2%) were tested in the oxidation of PMIDA under the conditions described above in Example 24. The 1% cobalt-containing catalyst was prepared as described in Example 27 using acetonitrile.

The precursors of the 0.5%, 0.75%, and 2% by weight cobalt catalysts were prepared in accordance with the procedure set forth above in Example 26 using varying amounts of cobalt chloride ($CoCl_2.2H_2O$), depending on the desired catalyst loading. The catalysts were then prepared in accordance with the procedure described in Example 27 using acetonitrile.

For the catalyst containing 0.75% by weight cobalt, a solution containing cobalt chloride (0.214 g) in deionized water (60 ml) was prepared and contacted with the carbon support slurry.

For the catalyst containing 1.5% by weight cobalt, a solution containing cobalt chloride (0.428 g) in deionized water (60 ml) was prepared and contacted with the carbon support slurry.

For the catalyst containing 2.0% by weight cobalt, a solution containing cobalt chloride (0.570 g) was prepared and contacted with the carbon support slurry.

Figure 10:
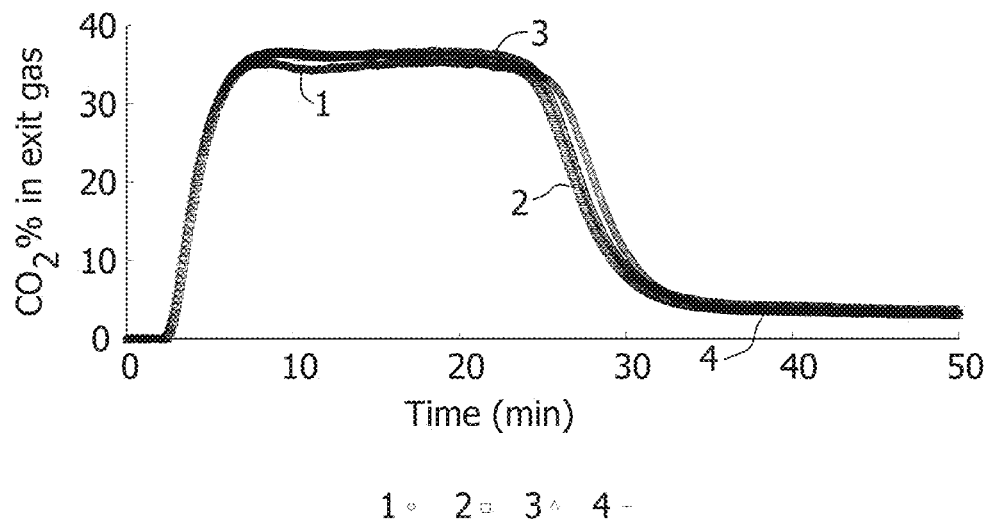
FIG. 10 shows carbon dioxide profiles of PMIDA oxidation carried out using various catalysts as described in Example 28.

FIG. 10 shows the first cycle $CO_2$ profiles using the various catalysts. Curve 1 of FIG. 10 corresponds to the first cycle using the 0.75% Co catalyst, curve 2 of FIG. 10 corresponds to the first cycle using the 1% Co catalyst, curve 3 of FIG. 10 corresponds to the first cycle using the 1.50% Co catalyst, and curve 4 of FIG. 10 corresponds to the first cycle using the 2.0% Co catalyst.

As shown in FIG. 10, catalysts containing from 1-1.5% cobalt demonstrated the highest activity.

The HPLC results for the product streams of the four PMIDA reaction cycles using the 1% cobalt catalyst and first four reaction cycles using the 5% Pt/0.5% Fe/C catalyst prepared in accordance with Ebner et al., U.S. Pat. No. 6,417,133 described are summarized below in Table 15.

The table shows the N-(phosphonomethyl) iminodiacetic acid (GI), N-(phosphonomethyl)glycine (Gly), formaldehyde (FM), formic acid (FA), iminodiacetic acid (IDA), aminomethylphosphonic acid and methyl aminomethylphosphonic acid ((M)AMPA), N-methyl-N-(phosphonomethyl) glycine (NMG), imino-bis-(methylene)-bis-phosphonic acid (iminobis), and phosphate ion (PO4) content of the reaction mixture for the various cycles.

Pat. No. 6,417,133, and a particulate carbon catalyst designated MC-10 prepared in accordance with Chou, U.S. Pat. No. 4,696,772.

Each of the catalysts were used in PMIDA oxidation under the conditions described above in Example 24 for multiple reaction cycles.

Figure 11:
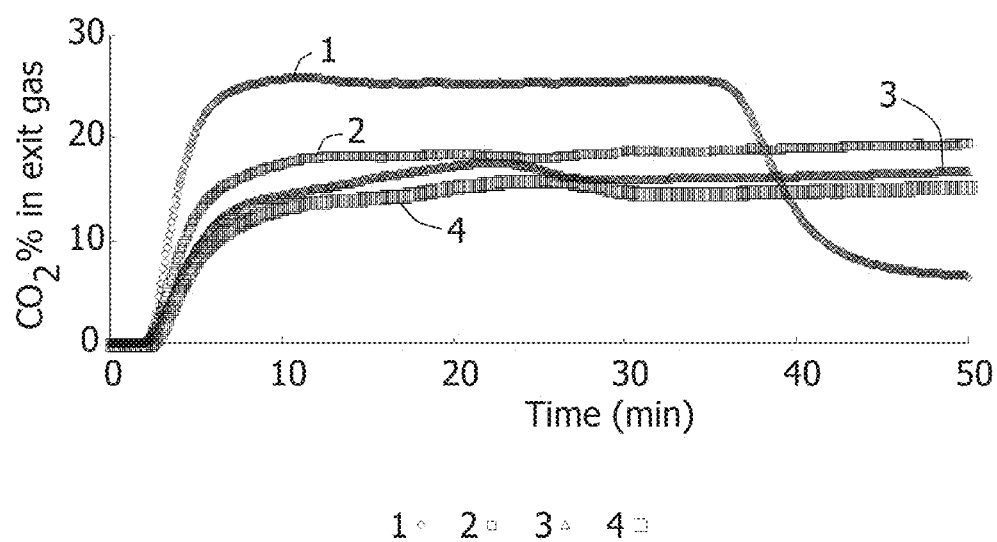
FIG. 11 shows the carbon dioxide percentage in the exit gas produced during PMIDA oxidation as described in Example 29.

FIG. 11 shows the $CO_2$ percentage in the exit gas during each of four reaction cycles (labeled accordingly) carried out using the 1% iron catalyst.

Figure 12:
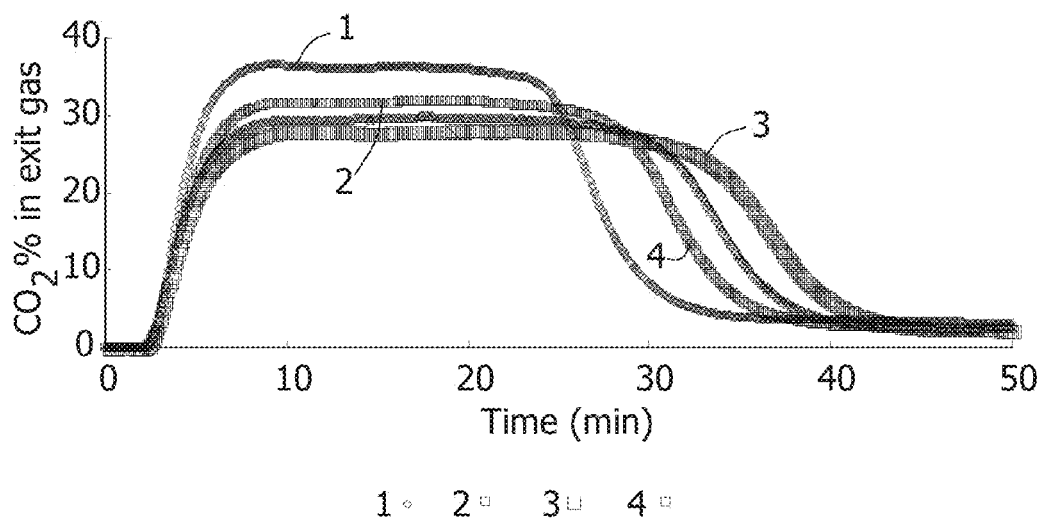
FIG. 12 shows the carbon dioxide percentage in the exit gas produced during PMIDA oxidation as described in Example 29.

FIG. 12 shows the $CO_2$ percentage in the exit gas during each of four reaction cycles (labeled accordingly) carried out using the 1% cobalt catalyst.

Figure 13:
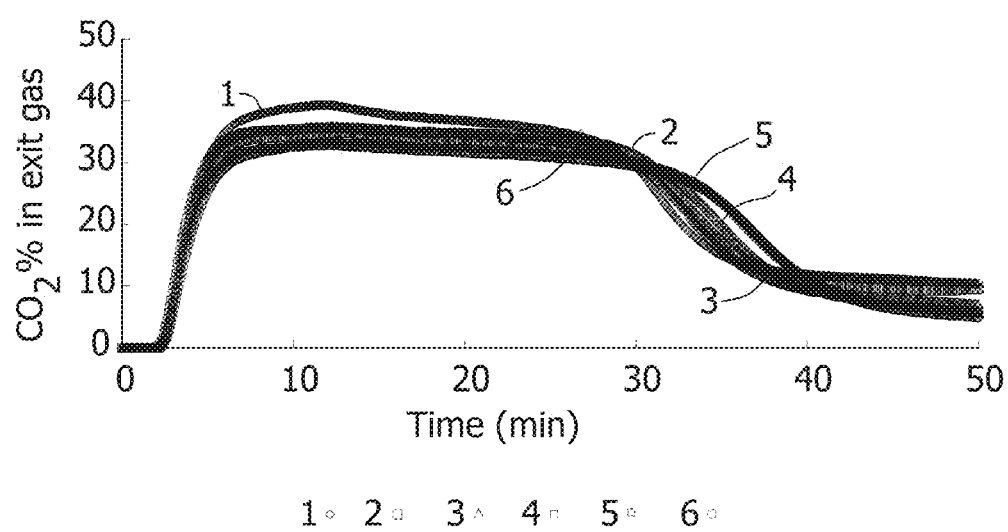
FIG. 13 shows the carbon dioxide percentage in the exit gas produced during PMIDA oxidation as described in Example 29.

FIG. 13 shows the $CO_2$ percentage in the exit gas during each of six reaction cycles (labeled accordingly) carried out using the 5% Pt/0.5% Fe/C catalyst.

Figure 14:
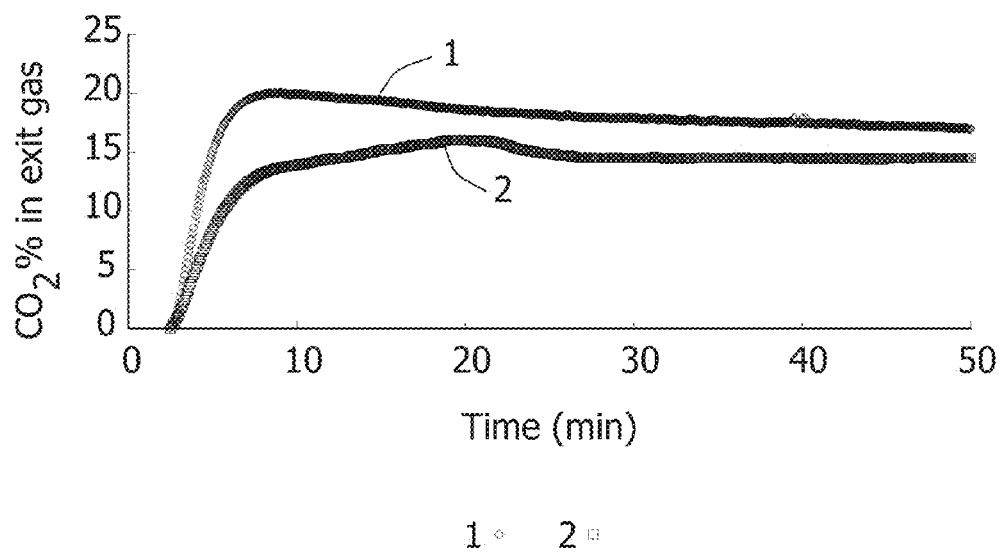
FIG. 14 shows the carbon dioxide percentage in the exit gas produced during PMIDA oxidation as described in Example 29.

FIG. 14 shows the $CO_2$ percentage in the exit gas during each of two reaction cycles (labeled accordingly) carried out using the MC-10 catalyst.

The iron-containing catalyst exhibited a drop in activity after the first cycle, possibly due to overoxidation of the catalyst. Minor deactivations were observed in later cycles where the catalyst was not overoxidized. The 5% Pt/0.5% Fe/C was the most stable. The 1% cobalt catalyst showed similar stability to the 5% Pt/0.5% Fe/C catalyst. The MC10 catalyst exhibited the worst stability, even in the absence of overoxidation of the catalyst.

Example 30

This example details the preparation of various carbon-supported metal-containing catalysts.

Precursors were prepared for catalysts containing vanadium, tellurium, molybdenum, tungsten, ruthenium, and cerium generally in accordance with Example 22 disclosure detailing preparation of an iron-containing catalyst precursor with variations in the pH and heating schedule depending the metal to be deposited.

Preparation of vanadium precursor: $Na_3VO_4O_4.10H_2O$ (0.721 g) was added to a 100 ml beaker containing deionized water (60 ml) to form a solution which was contacted with the carbon support slurry. The pH of the carbon support slurry was maintained at from about 3.4 to about 3.7 by co-addition of a 0.1 wt. % solution of nitric acid. Approximately 5 ml of nitric acid was added to the carbon slurry during addition of

TABLE 15

HPLC results for 5% Pt/0.5% Fe/C and 1% CoCN/C catalysts after 50 minute runtime

| | Cycle | PMIDA (%) | Gly (%) | FM (ppm) | FA (ppm) | IDA (%) | (M) AMPA (ppm) | NMG (ppm) | Iminobis (ppm) | PO$_4$ (ppm) |
|---|---|---|---|---|---|---|---|---|---|---|
| 5% Pt/ | 1 | 0.0108 | 3.76 | 1427 | 3030 | 0.0421 | 758 | 78 | 230 | 385 |
| 0.5% Fe/C | 2 | 0.0088 | 3.57 | 1554 | 3336 | 0.0261 | 643 | 128 | 228 | 258 |
| | 4 | 0.0135 | 3.91 | 2094 | 4057 | 0.0133 | 632 | 259 | 227 | 171 |
| | 6 | 0.0149 | 3.80 | 2257 | 3942 | 0.0099 | 510 | 313 | 240 | 150 |
| 1% CoCN/C | 1 | 0.0160 | 3.81 | 1551 | 8243 | | 1245 | 167 | 236 | 294 |
| | 2 | 0.0171 | 3.86 | 1316 | 8669 | | 860 | 180 | 225 | 381 |
| | 3 | 0.0205 | 4.03 | 1263 | 9174 | | 737 | 174 | 230 | 444 |
| | 4 | 0.0177 | 4.05 | 1239 | 9340 | | 653 | 214 | 232 | 471 |

Example 29

This example compares the stability of a 1% iron catalyst prepared as described in Example 23, a 1% cobalt catalyst prepared as described in Example 27 using acetonitrile, a particulate carbon catalyst containing 5% by weight Pt, 0.5% by weight iron prepared in accordance with Ebner et al., U.S.

the vanadium solution. After addition of the vanadium solution to the carbon slurry was complete, the slurry was stirred for 30 minutes using mechanical stirring rod operating at 50% of output (Model IKA-Werke RW16 Basic) with pH of the slurry monitored using the pH meter described above and maintained at approximately 3.6 by addition of nitric acid (0.1 wt. % solution) (2 ml).

The resulting mixture was filtered and washed with a plentiful amount of deionized water (approximately 500 ml) and the wet cake was dried for approximately 16 hours in a vacuum oven at 120° C. The precursor contained approximately 1% by weight vanadium.

Preparation of tellurium precursor: $Te(OH)_6$ (0.092 g) was added to a 100 ml beaker containing deionized water (60 ml) to form a solution which was contacted with the carbon support slurry. The pH of the carbon support slurry was maintained at from about 6.5 to about 6.9 by co-addition of a 0.1 wt. % solution of sodium hydroxide. Approximately 2 ml of 0.1 wt. % sodium hydroxide solution was added to the carbon slurry during addition of the tellurium solution. After addition of the tellurium solution to the carbon slurry was complete, the slurry was stirred for 30 minutes with pH of the slurry monitored using the pH meter and maintained at approximately 6.7 by addition of 0.1 wt. % sodium hydroxide solution (1-2 ml).

The pH was maintained at pH of 6.0, 5.0, 4.0, 3.0, 2.0, and 1.0 for 10 minutes each.

The resulting mixture was filtered and washed with a plentiful amount of deionized water (approximately 500 ml) and the wet cake was dried for approximately 16 hours in a vacuum oven at 120° C. The precursor contained approximately 1% by weight tellurium.

Preparation of molybdenum precursor: $(NH_4)_2MoO_4$ (0.207 g) was added to a 100 ml beaker containing deionized water (50 ml) to form a solution which was contacted with the carbon support slurry. The pH of the carbon support slurry was maintained at from about 1.5 to about 2.0 by co-addition of a 0.1 wt. % solution of nitric acid. Approximately 5 ml of 0.1 wt. % nitric acid was added to the carbon slurry during addition of the molybdenum solution. After addition of the molybdenum solution to the carbon slurry was complete, the slurry was stirred for 30 minutes with pH of the slurry monitored using the pH meter and maintained at approximately 2.0 by addition of 0.1 wt. % nitric acid. The pH was then increased to 3.0 by addition of 0.1 wt. % sodium hydroxide, maintained at 3.0 for 20 minutes, increased to 4.0 by addition of 0.1 wt. % sodium hydroxide solution, and maintained at 4.0 for 20 minutes.

The resulting mixture was filtered and washed with a plentiful amount of deionized water (approximately 500 ml) and the wet cake was dried for approximately 16 hours in a vacuum oven at 120° C. The precursor contained approximately 1% by weight molybdenum.

Preparation of tungsten precursor: $(NH_4)_6W_{12}O_{39}.2H_2O$ (0.135 g) was added to a 100 ml beaker containing deionized water (60 ml) to form a solution which was contacted with the carbon support slurry. The pH of the carbon support slurry was maintained at from about 3.0 to about 3.2 by co-addition of a 0.1 wt. % solution of sodium hydroxide. Approximately 2 ml of nitric acid was added to the carbon slurry during addition of the tungsten solution. After addition of the tungsten solution to the carbon slurry was complete, the slurry was stirred for 30 minutes with pH of the slurry monitored using the pH meter and maintained at approximately 3.0 by addition of 0.1 wt. % nitric acid solution.

The pH was then decreased to 2.5 by addition of 0.1 wt. % nitric acid solution, maintained at 2.5 for 10 minutes, decreased to 2.0 by addition of 0.1 wt. % nitric acid solution, and maintained at 2.0 for 10 minutes.

The resulting mixture was filtered and washed with a plentiful amount of deionized water (approximately 500 ml) and the wet cake was dried for approximately 16 hours in a vacuum oven at 120° C. The precursor contained approximately 1% by weight tungsten.

Preparation of ruthenium precursor: $RuCl_3.2H_2O$ (0.243 g) was added to a 100 ml beaker containing deionized water (50 ml) to form a solution which was contacted with the carbon support slurry. The pH of the carbon support slurry was maintained at from about 3.0 to about 3.5 by co-addition of a 0.1 wt. % solution of sodium hydroxide. Approximately 1 ml of sodium hydroxide was added to the carbon slurry during addition of the ruthenium solution. After addition of the ruthenium solution to the carbon slurry was complete, the slurry was stirred for 30 minutes with pH of the slurry monitored using the pH meter and maintained at approximately 3.5 by addition of 0.1 wt. % nitric acid solution.

The pH was then increased to 4.2 by addition of 0.1 wt. % sodium hydroxide (1 ml), maintained at 4.2 for 10 minutes, increased to 5.0 by addition of 0.1 wt. % sodium hydroxide solution (1 ml), maintained at 5.0 for 10 minutes, increased to 5.7 by addition of 0.1 wt. % sodium hydroxide (1 ml), and maintained at 5.7 for 10 minutes.

The resulting mixture was filtered and washed with a plentiful amount of deionized water (approximately 500 ml) and the wet cake was dried for approximately 16 hours in a vacuum oven at 120° C. The precursor contained approximately 1% by weight ruthenium.

Preparation of cerium precursor: $Ce(NO_3)_3.6H_2O$ (0.117 g) was added to a 100 ml beaker containing deionized water (50 ml) to form a solution which was contacted with the carbon support slurry. The pH of the carbon support slurry was maintained at from about 7.0 to about 7.5 by co-addition of a 0.1 wt. % solution of sodium hydroxide. Approximately 1 ml of sodium hydroxide was added to the carbon slurry during addition of the cerium solution. After addition of the cerium solution to the carbon slurry was complete, the slurry was stirred for 30 minutes with pH of the slurry monitored using the pH meter and maintained at approximately 7.5 by addition of 0.1 wt. % sodium hydroxide solution (1 ml).

The pH was then increased to 8.0 by addition of 0.1 wt. % sodium hydroxide (1 ml), maintained at 8.0 for 20 minutes, increased to 9.0 by addition of 0.1 wt. % sodium hydroxide (1 ml), maintained at 9.0 for 20 minutes, increased to 10.0 by addition of 0.1 wt. % sodium hydroxide solution (1 ml), and maintained at 10.0 for 20 minutes.

The resulting mixture was filtered and washed with a plentiful amount of deionized water (approximately 500 ml) and the wet cake was dried for approximately 16 hours in a vacuum oven at 120° C. The precursor contained approximately 1% by weight cerium.

Precursors were also prepared for catalysts containing nickel, chromium, manganese, magnesium, copper, and silver generally in accordance with Example 26 disclosure detailing preparation of a cobalt-containing catalyst precursor with variations in the pH and heating schedule depending on the metal to be deposited.

Preparation of nickel precursor: $NiCl_2.6H_2O$ (0.409 g) was added to a 100 ml beaker containing deionized water (60 ml) to form a solution which was contacted with the carbon support slurry. The pH of the carbon support slurry was maintained at from about 7.5 to about 8.0 by co-addition of a 0.1 wt. % solution of sodium hydroxide. Approximately 2 ml of sodium hydroxide was added to the carbon slurry during addition of the nickel solution. After addition of the nickel solution to the carbon slurry was complete, the slurry was stirred for 30 minutes with pH of the slurry monitored using the pH meter and maintained at approximately 8.0 by addition of 0.1 wt. % sodium hydroxide solution (1 ml). The slurry was then heated under a nitrogen blanket to 40° C. at a rate of about 2° C. per minute while maintaining its pH at 8.5 by addition of 0.1 wt. % sodium hydroxide solution. Upon reaching 60° C., the slurry was stirred for 20 minutes at constant temperature of 40° C. and a pH of 8.5. The slurry was then heated to 50° C. and its pH was adjusted to 9.0 by addition of sodium hydroxide solution (2 ml); the slurry was maintained at these conditions for approximately 20 minutes. The slurry was then heated to 60° C., its pH adjusted to 10.0 by addition of sodium hydroxide solution (2 ml) and maintained at these conditions for approximately 20 minutes.

The resulting mixture was filtered and washed with a plentiful amount of deionized water (approximately 500 ml) and the wet cake was dried for approximately 16 hours in a vacuum oven at 120° C. The precursor contained approximately 1% by weight nickel.

Preparation of chromium precursor: $CrCl_3 \cdot 6H_2O$ (0.517 g) was added to a 100 ml beaker containing deionized water (50 ml) to form a solution which was contacted with the carbon support slurry. The pH of the carbon support slurry was maintained at from about 7.0 to about 7.5 by co-addition of a 0.1 wt. % solution of sodium hydroxide. Approximately 1 ml of sodium hydroxide was added to the carbon slurry during addition of the chromium solution. After addition of the chromium solution to the carbon slurry was complete, the slurry was stirred for 30 minutes with pH of the slurry monitored using the pH meter and maintained at approximately 7.5 by addition of sodium hydroxide. The slurry was then heated under a nitrogen blanket to 60° C. at a rate of about 2° C. per minute while maintaining its pH at 8.0 by addition of 2 ml of 0.1 wt. % sodium hydroxide.

The resulting mixture was filtered and washed with a plentiful amount of deionized water (approximately 500 ml) and the wet cake was dried for approximately 16 hours in a vacuum oven at 120° C. The precursor contained approximately 1% by weight chromium.

Preparation of manganese precursor: $MnCl_2 \cdot 4H_2O$ (0.363 g) was added to a 100 ml beaker containing deionized water (60 ml) to form a solution which was contacted with the carbon support slurry. The pH of the carbon support slurry was maintained at from about 7.5 to about 8.0 by co-addition of a 0.1 wt. % solution of sodium hydroxide. Approximately 1 ml of sodium hydroxide solution was added to the carbon slurry during addition of the manganese solution. After addition of the manganese solution to the carbon slurry was complete, the slurry was stirred for 30 minutes with pH of the slurry monitored using the pH meter and maintained at approximately 7.4 by addition of sodium hydroxide. The slurry was then heated under a nitrogen blanket to 45° C. at a rate of about 2° C. per minute while maintaining its pH at 8.0 by addition of 2 ml of 0.1 wt. % sodium hydroxide solution. Upon reaching 60° C., the slurry was stirred for 20 minutes at constant temperature of 50° C. and a pH of 8.5. The slurry was then heated to 55° C. and its pH was adjusted to 9.0 by addition of sodium hydroxide solution (2 ml); the slurry was maintained at these conditions for approximately 20 minutes. The slurry was then heated to 60° C., its pH adjusted to 9.0 by addition of sodium hydroxide solution (1 ml) and maintained at these conditions for approximately 20 minutes.

The resulting mixture was filtered and washed with a plentiful amount of deionized water (approximately 500 ml) and the wet cake was dried for approximately 16 hours in a vacuum oven at 120° C. The precursor contained approximately 1% by weight manganese.

Preparation of magnesium precursor: $MgCl_2 \cdot 6H_2O$ (0.420 g) was added to a 100 ml beaker containing deionized water (50 ml) to form a solution which was contacted with the carbon support slurry. The pH of the carbon support slurry was maintained at from about 8.5 to about 9.0 by co-addition of a 0.1 wt. % solution of sodium hydroxide. Approximately 5 ml of sodium hydroxide solution was added to the carbon slurry during addition of the magnesium solution. After addition of the magnesium solution to the carbon slurry was complete, the slurry was stirred for 30 minutes with pH of the slurry monitored using the pH meter and maintained at approximately 8.5 by addition of 0.1 wt. % sodium hydroxide solution (1 ml).

The pH of the slurry was then increased to 9.0 by addition of 0.1 wt. % sodium hydroxide solution (1 ml) and maintained at 9.0 for 30 minutes.

The resulting mixture was filtered and washed with a plentiful amount of deionized water (approximately 500 ml) and the wet cake was dried for approximately 16 hours in a vacuum oven at 120° C. The precursor contained approximately 1% by weight magnesium.

Preparation of copper precursor: $CuCl_2$ (1.11 g) was added to a 100 ml beaker containing deionized water (60 ml) to form a solution which was contacted with the carbon support slurry. The pH of the carbon support slurry was maintained at from about 6.0 to about 6.5 by co-addition of a 0.1 wt. % solution of sodium hydroxide. Approximately 1 ml of sodium hydroxide was added to the carbon slurry during addition of the copper solution. After addition of the copper solution to the carbon slurry was complete, the slurry was stirred for 30 minutes with pH of the slurry monitored using the pH meter and maintained at approximately 6.5 by addition of sodium hydroxide. The slurry was then heated under a nitrogen blanket to 40° C. at a rate of about 2° C. per minute while maintaining its pH at 7.0 by addition of 0.1 wt. % sodium hydroxide solution. Upon reaching 40° C., the slurry was stirred for 20 minutes at constant temperature of 40° C. and a pH of 7.0 The slurry was then heated to 50° C. and its pH was adjusted to 7.5 by addition of 0.1 wt. % sodium hydroxide solution (1 ml); the slurry was maintained at these conditions for approximately 20 minutes. The resulting mixture was filtered and washed with a plentiful amount of deionized water (approximately 500 ml) and the wet cake was dried for approximately 16 hours in a vacuum oven at 120° C. The precursor contained approximately 5% by weight copper.

Preparation of silver precursor: $AgNO_3$ (0.159 g) was added to a 100 ml beaker containing deionized water (60 ml) to form a solution which was contacted with the carbon support slurry. The pH of the carbon support slurry was maintained at from about 4.0 to about 4.5 by co-addition of a 0.1 wt. % solution of nitric acid. Approximately 2 ml of nitric acid solution was added to the carbon slurry during addition of the silver solution. After addition of the silver solution to the carbon slurry was complete, the slurry was stirred for 30 minutes with pH of the slurry monitored using the pH meter and maintained at approximately 4.5 by addition of nitric acid solution (2 ml).

The resulting mixture was filtered and washed with a plentiful amount of deionized water (approximately 500 ml) and the wet cake was dried for approximately 16 hours in a vacuum oven at 120° C. The precursor contained approximately 1% by weight silver.

Metal-containing catalysts containing 1% by weight metal (in the case of copper, 5% by weight) were prepared from each of the catalyst precursors as described above in Example 23.

Example 31

Each of the catalysts prepared as described in Example 30 was tested in PMIDA oxidation under the conditions described in Example 24.

The maximum $CO_2$ percent composition in the exit gas and the total $CO_2$ generated during the 50 minutes of reaction were used to measure the catalysts' activity. The results are shown below in Table 16.

TABLE 16

First cycle reaction results for various MCN catalysts

| Catalyst | $CO_2$ max in offgas | Total $CO_2$ after 50 minutes (cm³) |
|---|---|---|
| 1% FeCN/C | 25.93 | 1624 |
| 1% CoCN/C | 36.5 | 1571 |
| 1% NiCN/C | 7.36 | 343 |
| 1% VCN/C | 11.69 | 676 |
| 1% CrCN/C | 34.88 | 1809 |
| 1% MnCN/C | 22.22 | 1526 |
| 5% CuCN/C | 28.45 | 1571 |
| 1% MoCN/C | 10.92 | 753 |
| 1% WCN/C | 11.8 | 684 |
| 1% MgCN/C | 13.4 | 830 |
| 1% TeCN/C | 10.12 | 648 |
| 1% AgCN/C | 12.09 | 817 |
| 1% RuCN/C | 17.77 | 1041 |
| 1% CeCN/C | 16.54 | 1282 |

The carbon-supported cobalt-containing catalyst and chromium-containing catalysts showed the highest PMIDA oxidation activity.

Example 32

This example details the effectiveness of various carbon-supported catalysts for the oxidation of formaldehyde and formic acid during PMIDA oxidation under the conditions described in Example 24.

Figure 15:
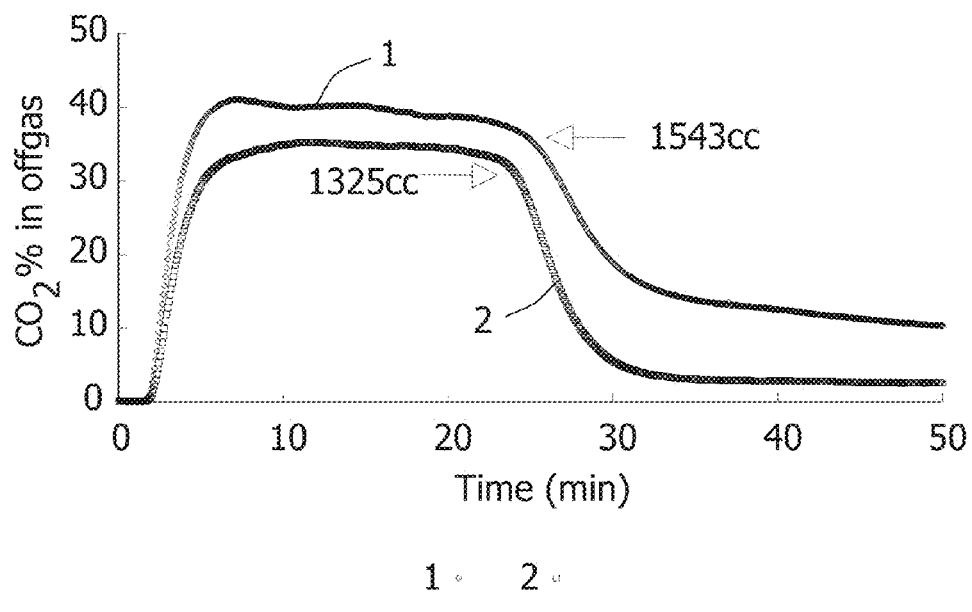
FIG. 15 shows the results of the carbon dioxide drop-point measurement comparison as described in Example 32.

Two methods were employed to evaluate the activity of various carbon-supported metal carbide-nitride catalysts in the oxidation of formaldehyde and formic acid: HPLC analysis of the reaction product and the $CO_2$ drop-point measurement. The drop-point measurement is the total amount of $CO_2$ that has passed through the exit gas at the moment a sudden reduction in exit gas $CO_2$ composition is observed. As shown in FIG. 15, a particulate carbon catalyst containing 5% Pt/1% Fe prepared in accordance with Ebner et al., U.S. Pat. No. 6,417,133 produces a $CO_2$ drop-point around 1500-1600 cm³ of total $CO_2$ under the PMIDA oxidation conditions of Example 24 (curve 1 of FIG. 15). Also shown in FIG. 15, a 1% cobalt-containing catalyst prepared as described above in Example 27 using acetonitrile, exhibits a $CO_2$ drop point around 1300 cm³ under the PMIDA oxidation conditions of Example 24 (curve 2 of FIG. 15).

The 200-300 cm³ increase in total $CO_2$ of the 5% Pt/1% Fe catalyst prepared in accordance with Ebner et al., U.S. Pat. No. 6,417,133 may be due to greater oxidation of formic acid as compared to the 1% cobalt catalyst.

Table 17 shows the HPLC results of the PMIDA oxidation product using various catalysts prepared as described above in Example 31: 1% by weight cobalt, 1% by weight manganese, 5% by weight copper, 1% by weight magnesium, 1% by weight chromium, 1% by weight molybdenum, and 1% by weight tungsten. The carbon-supported cobalt carbide-nitride catalyst showed the highest formaldehyde oxidation activity.

TABLE 17

HPLC results for various MCN catalysts after 50 minute runtime

| Catalyst | Loading | Cycle | PMIDA (%) | Gly (%) | FM (ppm) | FA (ppm) |
|---|---|---|---|---|---|---|
| 1% CoCN/C | 0.21 g | 1 | 0.016 | 3.81 | 1551 | 8243 |
|  | 0.21 g | 2 | 0.017 | 3.86 | 1316 | 8669 |
| 1% MnCN/C | 0.42 g | 1 | 0.021 | 3.28 | 4496 | 3711 |
| 5% CuCN/C | 0.21 g | 1 | 0.018 | 3.15 | 3143 | 5750 |
| 1% MgCN/C | 0.63 g | 1 | 0.028 | 3.01 | 5503 | 2338 |
| 1% CrCN/C | 0.21 g | 1 | 0.044 | 3.20 | 5846 | 2287 |
| 1% MoCN/C | 0.63 g | 1 | 0.058 | 3.51 | 4281 | 3230 |
| 1% WCN/C | 0.21 g | 1 | 2.654 | 1.90 | 1905 | 2223 |

Catalyst mixtures containing 50% by weight of the 1% by weight cobalt catalyst prepared as described in Example 27 using acetonitrile and 50% by weight of one of the 1% nickel, 1% vanadium, 1% magnesium, and 1% tellurium catalysts prepared in accordance with Example 31 were prepared and tested under the PMIDA oxidation conditions described in Example 24 to further test the activity toward oxidation of formaldehyde and formic acid. A drop point of approximately 1300 cm³ was observed for each of the 4 catalyst mixtures.

Example 33

This example details use of various promoters in combination with a 1% cobalt catalyst prepared as described above in Example 27 using acetonitrile in PMIDA oxidation under the conditions described in Example 24.

The promoters tested were: bismuth nitrate ($Bi(NO_3)_3$), bismuth oxide ($Bi_2O_3$), tellurium oxide ($TeO_2$), iron chloride ($FeCl_3$), nickel chloride ($NiCl_2$), copper sulfate ($CuSO_4$), ammonium molybdate (($NH_4)_2MoO_4$), and ammonium tungstate (($NH_4)_{10}W_{12}O_{41}$).

The promoters were introduced to the reaction mixture at the outset of the reaction cycle. The promoters were introduced to the reaction mixture at varying loadings as shown in Table 18.

The maximum $CO_2$ concentration in the exit gas stream and the cumulative $CO_2$ number were measured to determine the catalytic activity and the $CO_2$ drop-point measurement was recorded to determine the catalytic formic acid oxidation activity. Table 18 shows the maximum $CO_2$ in the exit gas and the total $CO_2$ generated during a first 50 minute reaction cycle. The $CO_2$ drop points for each of the catalysts were between about 1300 and 1350 cm³.

TABLE 18

First cycle reaction results from 1% CoCN/C (0.021 g) catalysts doped with promoters

| Promoter | $CO_2$ % max in offgas | Total $CO_2$ after 50 minutes |
|---|---|---|
| None | 36.5 | 1571 |
| 20 mg $Bi(NO_3)_3$ | 35.58 | 1571 |
| 25 mg $Bi_2O_3$ | 33.4 | 1654 |
| 10 mg $TeO_2$ | 36.31 | 1496 |
| 20 mg $TeO_2$ | 35.39 | 1580 |
| 50 mg $TeO_2$ | 37.81 | 1491 |
| 1 mg $FeCl_3$ | 36.2 | 1636 |
| 5 mg $FeCl_3$ | 35.97 | 1646 |
| 5 mg $NiCl_2$ | 34.69 | 1669 |
| 5 mg $CuSO_4$ | 33.18 | 1594 |
| 5 mg $(NH_4)_2MoO_4$ | 30.66 | 1635 |
| 5 mg $(NH_4)_{10}W_{12}O_{41}$ | 31.04 | 1569 |

Example 34

This example details preparation of bi-metallic carbon-supported carbide-nitride catalysts and their use in PMIDA oxidation.

A catalyst containing 1% by weight cobalt and 0.5% by weight iron was prepared in accordance with the process described above in Example 27 using acetonitrile. The precursor for the 1% cobalt and 0.5% iron catalyst was prepared by sequential deposition of each of the metals in accordance with the methods described above in Examples 26 and 22, respectively.

Similarly, a catalyst containing 1% cobalt and 0.5% cerium was prepared in accordance with the process described above in Example 27 using acetonitrile. The precursor for the 1% cobalt and 0.5% cerium catalyst was prepared by sequential deposition of each of the metals in accordance with the methods described above in Examples 26 and 30, respectively.

A catalyst containing 1% cobalt and 0.5% copper was prepared in accordance with the process described above in Example 27. The precursor for the 1% cobalt and 0.5% copper catalyst was prepared by sequential deposition of each of the metals in accordance with the methods described above in Examples 26 and 30, respectively.

Figure 16:
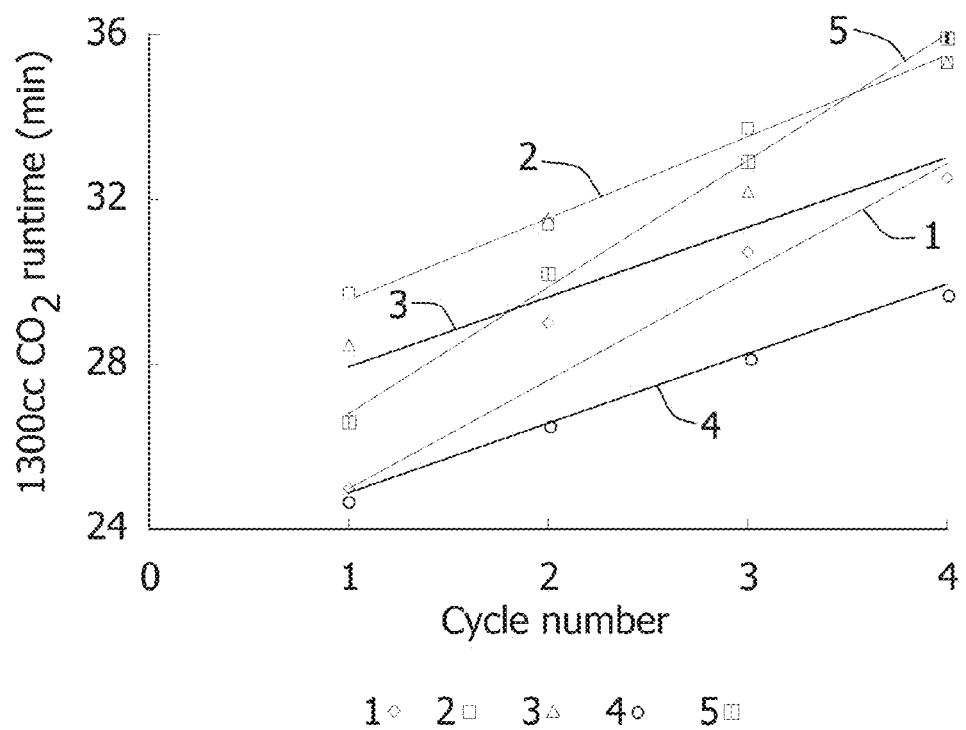
FIG. 16 shows carbon dioxide generation during PMIDA oxidation carried out as described in Example 34.

Each of the catalysts were tested in PMIDA oxidation under the conditions described in Example 24 over the course of four cycles. The time required to generate 1300 cm³ of $CO_2$ was determined for each of the cycles using each of the catalysts. For comparison purposes, a 1% by weight cobalt and 1.5% by weight cobalt catalyst, each prepared as described in Example 28, were also tested in this manner. The results are shown in FIG. 16. As shown in FIG. 16, the 1.5% cobalt catalyst had lower activity than the 1% cobalt catalyst but exhibited greater stability. The cobalt-cerium catalyst exhibited improved stability as compared to each of the cobalt catalysts but lower activity. Overall, the results indicated that the cobalt, cobalt-iron, and cobalt-cerium catalysts had similar formaldehyde oxidation activity.

HPLC results for the product when using the 1.5% cobalt catalyst and 1.5% cobalt/0.5% copper catalyst are set forth in Table 19. The carbon-supported cobalt-copper catalyst converted more formaldehyde to formic acid than the carbon-supported cobalt carbide-nitride catalyst.

A mixture (0.210 g) was prepared containing 50% by weight of a particulate carbon catalyst containing 5% by weight platinum and 0.5% by weight iron prepared in accordance with Ebner et al., U.S. Pat. No. 6,417,133 and the 1% by weight cobalt catalyst (0.105 g). The catalyst mixture was tested in PMIDA oxidation under the conditions set forth above in Example 24 over the course of six reaction cycles. A particulate carbon catalyst 5% by weight platinum and 0.5% by weight iron prepared in accordance with Ebner et al., U.S. Pat. No. 6,417,133 was also tested in PMIDA oxidation under the conditions set forth above in Example 24 over the course of six reaction cycles.

The maximum $CO_2$ proportion in the exit gas, total $CO_2$ generated during each of the reaction cycles, remaining formaldehyde content in the reaction, formic acid content in the reaction mixture, and platinum leaching are summarized below in Table 20.

TABLE 20

| Catalyst | Cycle No. | $CO_2$ % Max in offgas | Total $CO_2$ after 50 min (cc) | FM (ppm) | FA (ppm) | Pt Leaching (ppm) |
|---|---|---|---|---|---|---|
| 6,417,133 catalyst (0.21 g) | 1 | 39.37 | 1987 | 2021 | 3341 | 0.01 |
| | 2 | 35.58 | 1921 | 2016 | 3736 | 0.02 |
| | 3 | 35.92 | 1897 | | | |
| | 4 | 34.72 | 1852 | 2357 | 4164 | 0.02 |
| | 5 | 33.38 | 1836 | | | |
| | 6 | 32.94 | 1800 | 2485 | 4078 | 0.02 |
| 50/50 mixture (0.21 g) | 1 | 40.3 | 1736 | 1900 | 5986 | <0.01 |
| | 2 | 37.36 | 1650 | | | |
| | 3 | 32.71 | 1538 | 1738 | 6985 | 0.01 |
| | 4 | 27.59 | 1535 | | | |
| | 5 | 24.61 | 1499 | 1228 | 8280 | 0.01 |
| | 6 | 22.65 | 1424 | | | |

The catalyst mixture performed similarly to the 5% Pt/1% Fe catalyst in the first cycle except the catalyst mixture exhibited a lower cumulative $CO_2$ number possibly due to less oxidation of formic acid. During the remaining cycles, the catalyst mixture performed in a similar manner as the 1% by weight cobalt catalyst and exhibited deactivation with the accumulation of formic acid. Metal analysis showed minimal Pt leaching, indicating the platinum had been deactivated.

TABLE 19

HPLC results from 1.5% CO/C and 1.5% Cu/C catalysts after 50 min runtime

| | Cycle | PMIDA (%) | Gly (%) | FM (ppm) | FA (ppm) | IDA (%) | (M)AMPA (ppm) | NMG (ppm) | Iminobis (ppm) | $PO_4$ (ppm) | NFG (ppm) | Glycine (ppm) |
|---|---|---|---|---|---|---|---|---|---|---|---|---|
| 1.5% Co | 1 | 0.013 | 4.22 | 1683 | 8476 | 0.007 | 842 | 355 | 232 | 309 | 1758 | 128 |
| | 2 | 0.016 | 4.45 | 1634 | 9261 | 0.009 | 795 | 269 | 244 | 376 | 2254 | 161 |
| | 3 | 0.016 | 4.47 | 1569 | 9665 | 0.010 | 696 | 322 | 242 | 416 | 2240 | 180 |
| | 4 | 0.015 | 4.39 | 1495 | 9516 | 0.009 | 622 | 266 | 238 | 427 | 2248 | 187 |
| 1.5% Co). 5% Cu | 1 | 0.009 | 4.27 | 1729 | 8930 | 0.007 | 1232 | 236 | 249 | 284 | 2134 | 134 |
| | 2 | 0.014 | 4.36 | 1442 | 9774 | 0.008 | 898 | 237 | 241 | 381 | 2314 | 182 |
| | 3 | 0.016 | 4.35 | 1302 | 9975 | 0.009 | 750 | 201 | 234 | 444 | 2371 | 209 |
| | 4 | 0.014 | 4.25 | 1237 | 9661 | 0.010 | 626 | 214 | 231 | 469 | 2181 | 214 |

Example 35

This example details the use of a 1:1 mixture of 5% Pt/0.5% Fe catalyst prepared in accordance with Ebner et al., U.S. Pat. No. 6,417,133, and carbon-supported catalysts containing 1% by weight cobalt in the oxidation of N-(phosphonomethyl)iminodiacetic acid prepared as described above in Example 27 using acetonitrile.

Example 36

This example details deposition of platinum onto a catalyst containing 1% by weight cobalt prepared as described above in Example 27 using acetonitrile.

A sample of the 1% by weight cobalt catalyst prepared in accordance with the method described above in Example 27

(4.72 g) was added to a 1 liter flask containing deionized water (400 ml) to form a slurry.

$H_2PtCl_6 \cdot 2H_2O$ (0.282) was dissolved in deionized water (80 ml) to form a clear solution. The platinum solution was added to the slurry incrementally over the course of 40 minutes (i.e., at a rate of approximately 2 ml/minute). The pH of the slurry was maintained at from approximately 3.8-4.4 by co-addition of a 0.1 wt. % sodium hydroxide solution. Approximately 2 ml of 0.1 wt % sodium hydroxide solution was added to the slurry during addition of the platinum solution.

After addition of the solution to the slurry was complete, the slurry was stirred for 30 minutes with the pH of the slurry maintained at approximately 4.4 by addition of 0.1 wt. % sodium hydroxide solution.

The slurry was then heated under a nitrogen blanket to 70° C. at a rate of about 2° C. per minute while its pH was maintained at 4.4. Upon reaching 70° C., the slurry pH was increased by addition of a 0.1 wt. % sodium hydroxide solution according to the following profile: the pH was maintained at approximately 5.0 for 10 minutes after addition of 1 ml of sodium hydroxide solution, increased to 5.5 by addition of 1 ml of sodium hydroxide solution and maintained at that level for approximately 20 minutes, and stirred for approximately 20 minutes, increased to 6.0 by addition of 1 ml of 0.1 wt. % sodium hydroxide solution and maintained for 10 minutes. A 12 wt. % solution of $NaBH_4$ (0.38 g) in deionized water (10 ml) was added to the slurry at a rate of 2 ml/minute. The slurry was then heated to 70° C. under a nitrogen blanket while agitated.

The resulting mixture was filtered and washed with a plentiful amount of deionized water and the wet cake was dried for approximately 16 hours in a vacuum oven at 120° C.

After precursor deposition, platinum-containing catalyst (5.0 g) was charged into the tube reactor described above in Example 23. The reactor was purged with argon introduced to the reactor at a rate of approximately 100 cm$^3$/min at approximately 20° C. for approximately 15 minutes. A thermocouple was inserted into the center of the reactor for charging the catalyst.

The temperature of the reactor was then increased to approximately 850° C. over the course of 120 minutes during which time a 5%/95% (v/v) mixture of hydrogen and argon was introduced to the reactor at a rate of approximately 100 cm$^3$/minute.

The catalyst contained approximately 2.5% by weight platinum and 1% by weight cobalt.

Example 37

This example details deposition of platinum and iron onto a catalyst containing 1% by weight cobalt prepared as described above in Example 27 using acetonitrile.

A sample of the 1% by weight cobalt catalyst (4.72 g) was added to a 1 liter flask containing deionized water (400 ml) to form a slurry.

$H_2PtCl_6 \cdot 2H_2O$ (0.282) and $FeCl_3 \cdot 6H_2O$ (0.071 g) were dissolved in deionized water (80 ml) to form a clear solution. The iron and platinum solution was added to the slurry incrementally over the course of 40 minutes (i.e., at a rate of approximately 2 ml/minute). The pH of the slurry was maintained at from approximately 4.0-4.4 by co-addition of a 0.1 wt. % sodium hydroxide solution. Approximately 2 ml of sodium hydroxide solution was added to the slurry during addition of the platinum and iron solution.

After addition of the solution to the slurry was complete, the slurry was stirred for 30 minutes with the pH of the slurry maintained at approximately 4.4.

The slurry was then heated under a nitrogen blanket to 70° C. at a rate of about 2° C. per minute while its pH was maintained at 4.4. Upon reaching 70° C., the slurry pH was increased by addition of a 0.1 wt. % sodium hydroxide solution according to the following profile: the pH was maintained at approximately 5.0 for 10 minutes after addition of 1 ml of 0.1 wt. % sodium hydroxide solution, increased to 5.5 by addition of 2 ml of 0.1 wt. % sodium hydroxide solution and maintained at that level for approximately 20 minutes, and stirred for approximately 20 minutes during which time a constant pH of 6.0 was reached. A 12 wt. % solution of $NaBH_4$ (0.38 g) in deionized water (10 ml) was added to the slurry at a rate of 2 ml/minute. The slurry was then heated to 70° C. under a nitrogen blanket while agitated.

The resulting mixture was filtered and washed with a plentiful amount of deionized water and the wet cake was dried for approximately 16 hours in a vacuum oven at 120° C.

After precursor deposition, platinum/iron-containing catalyst (5.0 g) was charged into the tube reactor described above in Example 22 and treated in a hydrogen/argon atmosphere as described in Example 36.

The catalyst contained approximately 2.5% by weight platinum, 0.3% by weight iron, and 1% by weight cobalt.

Example 38

This example details deposition of platinum and cobalt onto a catalyst containing 1% by weight cobalt prepared as described above in Example 27 using acetonitrile.

A sample of the 1% by weight cobalt catalyst (5.055 g) was added to a 1 liter flask containing deionized water (400 ml) to form a slurry.

$H_2PtCl_6 \cdot 2H_2O$ (0.302) and $CoCl_2 \cdot 2H_2O$ (0.044 g) were dissolved in deionized water (80 ml) to form a clear solution. The platinum solution was added to the slurry incrementally over the course of 40 minutes (i.e., at a rate of approximately 2 ml/minute). The pH of the slurry was maintained at from approximately 3.5-4.0 by co-addition of a 0.1 wt. % sodium hydroxide solution. Approximately 2 ml of sodium hydroxide was added to the slurry during addition of the platinum solution.

After addition of the solution to the slurry was complete, the slurry was stirred for 30 minutes with the pH of the slurry maintained at approximately 4.4 by addition of 1 ml of a 0.1 wt. % sodium hydroxide solution.

The slurry was then heated under a nitrogen blanket to 70° C. at a rate of about 2° C. per minute while its pH was maintained at 4.4. Upon reaching 70° C., the slurry pH was increased by addition of a 0.1 wt. % sodium hydroxide solution according to the following profile: the pH was maintained at approximately 5.0 for 10 minutes after addition of 1 ml of 0.1 wt. % sodium hydroxide solution, increased to 5.5 by addition of 2 ml of 0.1 wt. % sodium hydroxide solution and maintained at that level for approximately 20 minutes, and stirred for approximately 20 minutes during which time a constant pH of 6.0 was reached. The pH was then increased to approximately 8.0 by addition of 1 ml of 0.1 wt. % sodium hydroxide solution and heated to 70° C. under a nitrogen blanket.

The resulting mixture was filtered and washed with a plentiful amount of deionized water and the wet cake was dried for approximately 16 hours in a vacuum oven at 120° C.

After precursor deposition, platinum/cobalt-containing catalyst (5.0 g) was charged into the tube reactor described above in Example 27 and treated in a hydrogen/argon atmosphere as described in Example 36.

The catalyst contained approximately 2.5% by weight platinum and 1.3% by weight cobalt (1% from the preparation procedure described above in Example 27 and 0.3% from the deposition procedure detailed in the present example).

Example 39

This example details use of the catalysts prepared in Examples 36 to 38 in PMIDA oxidation under the conditions described in Example 24.

The 2.5% platinum, 1% cobalt catalyst prepared in Example 36 was tested under the PMIDA oxidation conditions described above in Example 24 over the course of 3 reaction cycles.

The 2.5% platinum, 1% cobalt catalyst also containing an additional 0.3% by weight cobalt prepared in Example 38 was tested under the PMIDA oxidation conditions described above in Example 24 over the course of 3 reaction cycles.

The 2.5% platinum, 0.3% iron, 1% cobalt catalyst prepared in Example 37 was tested under the PMIDA oxidation conditions described above in Example 24 over the course of 2 reaction cycles.

The 2.5% platinum, 0.3% iron, 1% cobalt catalyst prepared in Example 37 was also tested under the PMIDA oxidation conditions described above in Example 24 during a reaction cycle in which a bismuth oxide promoter ($Bi_2O_3$) (10 mg) was added to the reaction mixture.

The 2.5% platinum, 0.3% iron, 1% cobalt catalyst prepared in Example 37 was also tested under the PMIDA oxidation conditions described above in Example 24 during 4 reaction cycles in which a bismuth oxide promoter ($Bi_2O_3$) (10 mg) was added to the reaction mixture during the fourth cycle.

The maximum $CO_2$ proportion in the exit gas, total $CO_2$ generated during each of the reaction cycles, remaining formaldehyde content in the reaction, formic acid content in the reaction mixture, and platinum leaching for each of the testings are summarized below in Table 21.

The performance of each of the catalysts was similar to that of the catalyst mixture prepared and tested in Example 35. The first cycle performance of each of the catalysts was similar to the performance of the platinum and iron catalyst prepared in accordance with Ebner et al., U.S. Pat. No. 6,417,133 tested above in Example 35, even though the catalysts tested in the present example contained half the platinum loading. However, the catalysts tested in the present example declined in subsequent cycles in both stability and activity toward formaldehyde and formic acid oxidation. Eventually the catalysts tested in the present example behaved similar to the 1% cobalt-containing catalysts described and tested above in Example 28 in terms of an increase in formic acid content without its further oxidation to $CO_2$. Each of the catalysts exhibited minimal platinum leaching, evidence that the Pt had become inactive.

The bismuth promoter was introduced in certain reaction cycles to determine if the platinum was initially inactive in the fresh mixed catalyst or whether it became inactive in subsequent cycles.

When bismuth was introduced to the reaction mixture in the 1st reaction cycle, catalyst performance was at least equal to that of the platinum and iron-containing catalyst prepared in accordance with Ebner et al., U.S. Pat. No. 6,417,133 described and tested above in Example 35 in terms of formaldehyde and formic acid oxidation. This indicated that the Pt was active in the first reaction cycle.

When bismuth was added in the 4th reaction cycle, catalyst performance was not affected. The platinum/iron-containing catalyst responded to inclusion of a bismuth promoter the same manner as the 1% cobalt catalyst described and tested above in Example 28. This suggested that the initially active Pt in the platinum/iron-containing catalyst was rendered inactive in subsequent reaction cycles.

Example 40

Various carbon-supported cobalt carbide-nitride catalysts were prepared in accordance with the process described above in Example 27 generally by varying the atmosphere introduced to the reactor.

Methane/hydrogen environment: A carbon-supported cobalt carbide-nitride catalyst containing 1% by weight cobalt was prepared as described in Example 27 under a methane/hydrogen environment from the precursor prepared in accordance with the procedure set forth above in Example 26. Catalyst precursor (5.0 g) was treated in the reactor using a flow of 100 $cm^3$/minute of a 50%/50% (v/v) mixture of methane and hydrogen.

TABLE 21

Reaction results from different catalysts

| Catalyst | Cycle No. | Doped prometer | $CO_2$% Max in offgas | Total $CO_2$ after 50 minutes (cc) | FM (ppm) | FA (ppm) | Pt leaching (ppm) |
|---|---|---|---|---|---|---|---|
| 2.5% Pt/1% CoCN/C | 1 | | 45.67 | 1922 | 1430 | 5003 | 0.02 |
| | 2 | | 32.01 | 1551 | 989 | 8738 | 0.03 |
| | 3 | | 26.76 | 1524 | 963 | 9206 | 0.02 |
| 2.5% Pt—0.3% Co/1% CoCN/C | 1 | | 42.49 | 1776 | | | |
| | 2 | | 36.16 | 1578 | | | |
| | 3 | | 31.96 | 1537 | | | |
| 2.5% Pt—0.3% Fe/1% CoCN/C | 1 | | 39.37 | 1767 | 1461 | 6436 | 0.06 |
| | 2 | | 32.39 | 1590 | 1293 | 8242 | 0.06 |
| 2.5% Pt—0.3% Fe/1% CoCN/C | 1 | 10 mg $Bi_2O_3$ | 39.5 | 2047 | 1368 | 2891 | 0.02 |
| 2.5% Pt—0.3% Fe/1% CoCN/C | 1 | | 43.8 | 1787 | | | 0.02 |
| | 2 | | 37.03 | 1618 | | | 0.02 |
| | 3 | | 32.53 | 1563 | | | 0.02 |
| | 4 | 10 mg$Bi_2O_3$ | 29.98 | 1539 | | | 0.01 |

Ammonia reactor environment: A carbon-supported cobalt carbide-nitride catalyst containing 1% by weight cobalt was prepared as described in Example 27 under an $NH_3$ environment from the precursor prepared in accordance with the procedure set forth above in Example 26. Catalyst precursor (5.0 g) was treated in the reactor using a flow of 50 $cm^3$/minute $NH_3$ and 100 $cm^3$/minute of argon.

Ammonia reactor environment: A carbon-supported cobalt carbide-nitride catalyst containing 1% by weight cobalt was prepared as described in Example 27 under an $NH_3$ environment from the precursor prepared in accordance with the procedure set forth above in Example 26. Catalyst precursor (5.0 g) was treated in the reactor using a flow of 50 $cm^3$/minute $NH_3$, 20 $cm^3$/minute hydrogen, and 100 $cm^3$/minute of argon.

Ammonia/methane reactor environment: A carbon-supported cobalt carbide-nitride catalyst containing 1% by weight cobalt was prepared as described in Example 27 under an $NH_3/CH_4$ environment from the precursor prepared in accordance with the procedure set forth above in Example 26. Catalyst precursor (5.0 g) was treated in the reactor using a flow of 25 $cm^3$/minute $NH_3$, 25 $cm^3$/minute of a 50%/50% (v/v/) mixture of hydrogen/methane, and 100 $cm^3$/minute of argon.

Acetonitrile reactor environment: A carbon-supported cobalt carbide-nitride catalyst containing 1% by weight cobalt was prepared as described in Example 27 under an acetonitrile-containing environment from the precursor prepared in accordance with the procedure set forth above in Example 26. Catalyst precursor (5.0 g) was treated in the reactor using a flow of 100 $cm^3$/minute argon and approximately 10 $cm^3$/minute of acetonitrile vapor.

Butylamine environment: A carbon-supported cobalt carbide-nitride catalyst containing 1% by weight cobalt was prepared as described in Example 27 under a butylamine-containing environment from the precursor prepared in accordance with the procedure set forth above in Example 26. Catalyst precursor (5.0 g) was treated in the reactor using a flow of 100 $cm^3$/minute argon and approximately 15 $cm^3$/minute of butylamine vapor.

Pyridine environment: A carbon-supported cobalt carbide-nitride catalyst containing 1% by weight cobalt was prepared as described in Example 27 under a pyridine-containing environment from the precursor prepared in accordance with the procedure set forth above in Example 26. Catalyst precursor (5.0 g) was treated in the reactor using a flow of 100 $cm^3$/minute argon and approximately 3 $cm^3$/minute of pyridine vapor.

Pyrrole environment: A carbon-supported cobalt carbide-nitride catalyst containing 1% by weight cobalt was prepared as described in Example 27 under a pyrrole-containing environment from the precursor prepared in accordance with the procedure set forth above in Example 26. Catalyst precursor (5.0 g) was treated in the reactor using a flow of 100 $cm^3$/minute argon and approximately 2 $cm^3$/minute of pyrrole vapor.

Picolonitrile environment: A carbon-supported cobalt carbide-nitride catalyst containing 1% by weight cobalt was prepared as described in Example 27 under a picolonitrile-containing environment from the precursor prepared in accordance with the procedure set forth above in Example 26. Catalyst precursor (5.0 g) and picolonitrile (3 g) were treated in the reactor using a flow of 100 $cm^3$/minute argon.

Melamine environment: A carbon-supported cobalt carbide-nitride catalyst containing 1% by weight cobalt was prepared as described in Example 27 under a melamine-containing environment from the precursor prepared in accordance with the procedure set forth above in Example 26. Catalyst precursor (5.0 g) and melamine (1 g) were treated in the reactor using a flow of 100 $cm^3$/minute argon.

A carbon-supported cobalt containing catalyst was prepared using an organometallic compound (cobalt(II)phthalocyanine).

A particulate carbon support (5.0 g) having a Langmuir surface area of approximately 1500 $m^2$/g and acetone (200 ml) (Aldrich, Milwaukee, Wis.) were added to a 1 liter flask to form a slurry. Cobalt(II)phthalocyanine (0.490 g) was dissolved in acetone (200 ml) contained in a 1 liter flask. The cobalt-containing solution was added to the carbon support slurry over the course of approximately 30 to 40 minutes.

The slurry was stirred using a mechanical stirring rod at 50% output at approximately 20° C. for 48 hours under a nitrogen blanket. The slurry was filtered and dried in a vacuum oven for approximately 16 hours at 120° C. under a small nitrogen flow of approximately 20 $cm^3$/minute. The resulting precursor contained approximately 1% by weight cobalt.

Dried catalyst precursor (5.0 g) was charged to the Hastelloy C tube reactor described in Example 23. The reactor was purged with argon introduced at a rate of approximately 100 $cm^3$/minute at approximately 20° C. for approximately 15 minutes. A thermocouple was inserted into the center of the reactor for charging the precursor material.

The temperature of the reactor was then increased to approximately 950° C. over the course of approximately 45 minutes under a flow of argon of 100 cc/min. The temperature of the reactor was maintained at approximately 950° C. for approximately 120 minutes. The resulting catalyst contained approximately 1% by weight cobalt.

Example 41

This example details the results of PMIDA oxidations carried out under the conditions described above in Example 24 using each of the catalysts prepared described above in Example 40 using the various environments. The results are shown in Table 22.

TABLE 22

Reaction results from catalysts synthesized at 950° C. under different environments

| Catalyst | C and/or N sources | Cat. charge (g) | $CO_2$ % Max in offgas | Total $CO2$ % after 50 min (cc) | PMIDA (%) | Gly (%) | FM (ppm) | FA (ppm) |
|---|---|---|---|---|---|---|---|---|
| 1% CoC/C | 50/50 $CH_4/H_2$ gas$^a$ | 0.21 | 6.89 | 450 | | | | |
| | | 0.84 | 17.68 | 1246 | 0.962 | 3.19 | 1021 | 6180 |
| 1% CoCN/C | $NH_3$ | 0.21 | 10.38 | 689 | | | | |
| | | 0.84 | 29.33 | 1658 | 0.049 | 3.65 | 651 | 9119 |

TABLE 22-continued

Reaction results from catalysts synthesized at 950° C. under different environments

| Catalyst | C and/or N sources | Cat. charge (g) | $CO_2$ % Max in offgas | Total $CO_2$ % after 50 min (cc) | PMIDA (%) | Gly (%) | FM (ppm) | FA (ppm) |
|---|---|---|---|---|---|---|---|---|
| 1% CoCN/C | $NH_3 + H_2$ | 0.21 | 8.24 | 556 | | | | |
| | | 0.84 | 18.48 | 1389 | 0.607 | 3.23 | 530 | 7224 |
| 1% CoCN/C | $CH_4/H_2 + NH_3$ | 0.21 | 15.97 | 1231 | 1.116 | 2.72 | 1143 | 6139 |
| 1% CoCN/C | $CH_3CN$ | 0.21 | 34.6 | 1650 | 0.016 | 3.81 | 1551 | 8243 |
| 1% CoCN/C | Butylamine ($C_4H_{11}N$) | 0.21 | 28.96 | 1625 | 0.04 | 3.74 | 1035 | 8348 |
| 1% CoCN/C | Pyridine ($C_5H_5N$) | 0.21 | 28.9 | 1608 | 0 | 3.52 | 669 | 8783 |
| 1% CoCN/C | Pyrrole ($C_4H_5N$) | 0.21 | 25.39 | 1622 | 0 | 3.31 | 500 | 8971 |
| 1% CoCN/C | Picolinonitrile ($C_6H_4N_2$) | 0.21 | 38.03 | 1577 | 0.08 | 3.28 | 866 | 7715 |
| 1% CoCN/C | Melamine ($C_3H_6N_6$) | 0.21 | 44.69 | 1712 | 0.017 | 3.43 | 2557 | 6624 |
| 1% CoCN/C | Cobalt phthalocyanine ($C_{32}H_{16}N_8$)Co | 0.21 | 32.83 | 1620 | 0.054 | 3.78 | 895 | 8791 |

As shown in Table 22, catalysts prepared from $CH_4/H_2$, $NH_3$, ($NH_3$ and $H_2$), and ($CH_4/H_2$ and $NH_3$) exhibited lower activity as compared to catalysts made from $CH_3CN$, butylamine, pyridine, pyrrole, picolinonitrile, melamine, and cobalt phthalocyanine. Each cobalt catalyst exhibited formaldehyde oxidation activity when the reaction was driven to greater than 80% PMIDA conversion.

Example 42

This example details preparation of cobalt-containing catalysts having varying metal loadings and their use in PMIDA oxidation to N-(phosphonomethyl)glycine.

Each of the catalysts were synthesized using an acetonitrile environment in accordance with the procedure set forth above in Example 40. Each of the catalysts was then tested in PMIDA oxidation under the conditions described above in Example 24. The results of each of the PMIDA oxidations are set out below in Table 23.

TABLE 23

Reaction results from CoCN/C synthesized by $CH_3CN$ treatment

| Catalyst | Calcination | Calcination | Cycle # | $CO_2$ % Max in | Total $CO_2$ at 50 | PMIDA (%) | Gly (%) | FM (ppm) | FA (ppm) |
|---|---|---|---|---|---|---|---|---|---|
| 1.0% CoCN/C | 950 | 2 | 1 | 36.59 | 1557 | 0.016 | 3.81 | 1551 | 8243 |
| | | | 2 | 31.9 | 1514 | 0.017 | 3.86 | 1316 | 8669 |
| | | | 3 | 29.8 | 1521 | 0.021 | 4.03 | 1263 | 9174 |
| | | | 4 | 28.18 | 1533 | 0.017 | 4.05 | 1239 | 9340 |
| 1.0% CoCN/C | 950 | 2 | 1 | 39.24 | 1678 | 0.046 | 3.46 | 1577 | 6908 |
| 1.5% CoCN/C | 950 | 2 | 1 | 38.45 | 1611 | 0.013 | 4.22 | 1683 | 8476 |
| | | | 2 | 33.63 | 1571 | 0.016 | 4.45 | 1634 | 9261 |
| | | | 3 | 31.97 | 1556 | 0.016 | 4.47 | 1569 | 9665 |
| | | | 4 | 30.97 | 1550 | 0.015 | 4.39 | 1495 | 9516 |
| 1.5% C0CN/C | 950 | 3 | 1 | 31.28 | 1544 | 0.013 | 4.08 | 2029 | 7825 |
| | | | 2 | 30.69 | 1509 | 0 | 4.14 | 1836 | 8487 |
| | | | 3 | 28.24 | 1490 | 0 | 4.11 | 1758 | 8595 |
| 2.0% CoCN/C | 950 | 2 | 1 | 36.89 | 1532 | 0.010 | 4.18 | 1628 | 8781 |
| | | | 2 | 32.41 | 1522 | 0.015 | 4.42 | 1361 | 9711 |
| 5.0% CoCN/C | 950 | 2 | 1 | 34.12 | 1627 | 0.017 | 3.49 | 1095 | 8232 |
| | | | 2 | 28.94 | 1606 | 0.018 | 3.85 | 1067 | 9234 |
| | | | 3 | 26.38 | 1595 | 0.017 | 3.79 | 1068 | 9142 |
| 5.0% CoCN/C | 950 | 4 | 1 | 34.22 | 1655 | 0.045 | 3.64 | 1315 | 7626 |
| 10% CoCN/C | 950 | 2 | 1 | 23.85 | 1615 | 0.066 | 3.58 | 1025 | 8200 |

As shown in Table 23, all carbon-supported cobalt carbide-nitride catalysts exhibited good PMIDA oxidation activity. The catalysts also demonstrated higher formaldehyde oxidation activity and much better stability compared to the carbon-supported iron carbide-nitride catalyst. The carbon-supported cobalt carbide-nitride catalyst containing 1-2% by weight cobalt exhibited the best overall reaction performance.

Example 43

This example details the preparation of a carbon-supported iron carbide-nitride precursor from tetraphenylporphyrin (FeTPP) precursor.

A carbon support (8.0 g) was added to a 1 liter flask and charged with 400 ml of acetone to form a slurry. A solution (200 ml) containing iron (III) tetraphenylporphyrin chloride (FeTPP) (2.0 g) in acetone was added drop wise to the carbon slurry for 30-40 minutes. The slurry was then stirred at room temperature for 48 hours under a nitrogen blanket.

The resulting mixture was filtered and dried overnight in a vacuum oven at 120° C. under a small nitrogen flow. The resulting precursor contained approximately 1.1% by weight iron.

Example 44

This example details subjecting catalysts prepared in accordance with the procedures set forth above in Example 23 and 43 to the PMIDA oxidation conditions described in Example 24. Results are shown in Table 24.

TABLE 24

Reaction results from iron catalysts synthesized under different environment

| Catalyst | C and N sources | Calcination Temp. (° C.) | Cycle | $CO_2$ % Max in offgas | Total $CO_2$ at 50 min (cc) | PMIDA (%) | Gly (%) | FM (ppm) | FA (ppm) |
|---|---|---|---|---|---|---|---|---|---|
| 0.5% FeCN/C | $CH_3CN$ | 850 | 1 | 33.24 | 1670 | 0.014 | 3.34 | 6281 | 1663 |
| | | | 2 | 22.57 | 1515 | | | | |
| 0.5% FeCN/C | $CH_3CN$ | 950 | 1 | 33.34 | 1740 | 0.017 | 3.71 | 6169 | 1349 |
| | | | 2 | 24.48 | 1555 | | | | |
| 0.75% FeCN/C | $CH_3CN$ | 850 | 1 | 31.15 | 1682 | 0.011 | 3.50 | 6162 | 1857 |
| | | | 2 | 21.58 | 1477 | | | | |
| 1.0% FeCN/C | $CH_3CN$ | 850 | 1 | 25.93 | 1624 | 0 | 3.63 | 6115 | 1976 |
| | | | 2 | 19.42 | 1344 | 0.355 | 3.50 | 4775 | 2156 |
| | | | 3 | 17.68 | 1105 | 1.279 | 3.11 | 4285 | 1986 |
| | | | 4 | 16.06 | 1005 | 1.721 | 2.92 | 3948 | 1925 |
| 2.0% FeCN/C | $CH_3CN$ | 850 | 1 | 21.56 | 1470 | 0.009 | 3.82 | 5010 | 2208 |
| 1.1% FeCN/C | FeTPP $Fe(C_{44}H_{28}N_4)Cl$ | 800 | 1 | 57.09 | 2150 | 0.014 | 2.98 | 7748 | 530 |
| | | | 2 | 43.06 | 1708 | 0.017 | 3.07 | 7092 | 821 |
| | | | 3 | 36.25 | 1597 | 0.018 | 3.38 | 6968 | 1028 |
| | | | 4 | 31.84 | 1571 | | | | |

All of the carbon-supported iron carbide-nitride catalysts suffered from catalyst deactivation. Both the maximum $CO_2$ concentration and the cumulative $CO_2$ decreased with subsequent reaction cycles. The catalyst synthesized from iron (III) tetraphenylporphyrin showed high PMIDA oxidation activity but produces a large amount of formaldehyde, aminomethylphosphonic acid, and N-methyl-aminophosphonic acid and exhibited little activity toward the oxidation of formaldehyde and formic acid. The catalyst synthesized from $CH_3CN$ exhibited PMIDA oxidation activity and formaldehyde oxidation activity.

Example 45

This examples details preparation of molybdenum and tungsten-containing catalysts in different carbiding environments and their use in PMIDA oxidation under the conditions described in Example 24.

Molybdenum and tungsten-containing catalysts were prepared as described above in Example 3 from precursors prepared as described in Example 2 using a flow of approximately 100 $cm^3$/min in place of the 50%/50% (v/v) mixture of methane and hydrogen as described in Example 3.

Catalysts containing 1% by weight molybdenum and 1% by weight tungsten prepared in accordance with the present Example were tested under the PMIDA oxidation conditions described in Example 24. A catalyst containing 10% by weight molybdenum carbide prepared as described in Example 3 and catalysts containing 10% by weight tungsten nitride prepared as described in Example 3 at varying temperatures were also tested.

TABLE 25

Reaction results from catalysts synthesized under different environment

| Catalyst | c(&N) source | Calcination Temp. (° C.) | Cat. charge (g) | $CO_2$ % Max in offgas | Total $CO_2$ at 50 min (cc) | PMIDA (%) | Gly (%) | FM (ppm) | FA (ppm) |
|---|---|---|---|---|---|---|---|---|---|
| 1% MoCN/C | $CH_3CN$ | 950 | 0.21 | 10.92 | 753 | | | | |
| | | | 0.63 | 22.53 | 1664 | 0.058 | 3.51 | 4281 | 3230 |
| 1% WCN/C | $CH_3CN$ | 950 | 0.21 | 11.8 | 684 | | | | |
| | | | 0.63 | 22.04 | 1638 | 0 | 3.52 | 3288 | 4534 |
| 10% $Mo_2C$/C | $CH_4 + H_2$ | 650 | 0.21 | 5.19 | 350 | | | | |
| | | | 1.05 | 12.51 | 870 | | | | |
| 10% $W_2C$/C | $CH_4 + H_2$ | 700 | 0.21 | 4.63 | 293 | | | | |
| | | | 1.05 | 15.07 | 1084 | 1.353 | 2.30 | 3100 | 1413 |
| 10% WC/C | $CH_4 + H_2$ | 850 | 0.21 | 4.21 | 284 | | | | |
| | | | 1.05 | 6.43 | 435 | 3.664 | 0.9 | 1271 | 561 |

The catalysts prepared using $CH_3CN$ treatment had superior PMIDA oxidation activity and formaldehyde oxidation activity as compared to the catalysts prepared by $CH_4/H_2$ treatment.

Example 46

This example details electroless copper plating on a 1% by weight cobalt catalyst prepared as described above in Example 27 prepared using acetonitrile.

1% by weight cobalt catalyst (15.5 g) was added to a 1 liter flask containing nitrogen-sparged water (364 ml) to form a slurry. The flask was fitted with a thermocouple, a nitrogen flow inlet, and mechanical stirrer.

A copper plating solution was prepared by adding reagant grade copper sulfate ($CuSO_4.5H_2O$) (20.65 g) (Aldrich Chemical Co., Milwaukee, Wis.) and 91.2% tetrasodium ethylenediamine tetraacetate ($EDTANa_4$) (41.82 g) to nitrogen-sparged water (950 ml). The mixture was cooled to approximately 10° C. and plating solution was added to the catalyst-containing slurry. A solution of 37% by weight formalin (20.13) in nitrogen-sparged water (305 ml) was prepared and added dropwise to the plating mixture over the course of 90 minutes.

The pH of the plating solution was monitored using a pH meter during addition of the formalin-containing solution. During the 90 minutes of addition of formalin-containing solution, the pH of the plating mixture changed from 13.65 (at 9.4° C.), to 13.4 (at 10.8° C.) and finally to 13.2 (at 11.7° C.). The plating mixture was agitated for approximately 30 minutes.

Plated catalyst was allowed to settle out of the plating mixture and the catalyst was recovered from the mixture by filtration under a nitrogen atmosphere. A filtrate (1533 g) was recovered from the mixture. The resulting wet cake was dried in nitrogen purged vacuum for approximately 8 hours. The dried catalyst weighed approximately 20.21 grams and Inductively Coupled Plasma (ICP) analysis provided a copper content of approximately 22.5% by weight.

Example 47

The example details use of the copper-containing catalyst prepared as described in Example 46 for the dehydrogenation of diethanolamine.

Dehydrogenation of diethanolamine was conducted in a 300 ml autoclave reactor constructed of Hastelloy C (high strength nickel-based alloy) and equipped with a back pressure regulator, $H_2$ mass flow meters, and a charge pot which allowed reagents and rinse water to be added to the reactor under inert gas.

The reactor was first flushed with argon (when conducting this reaction on a commercial scale, $N_2$ would be preferred). A mixture containing a 50 wt. % solution of sodium hydroxide (99.81 g) (Aldrich Chemical Co., Milwaukee, Wis.), diethanolamine (62.50 g) (Huntsman Chemicals), 22.5% copper/1% cobalt catalyst prepared as described in Example 46 (12.4 g), and deionized water (75 ml) to produce a total reaction mixture of 250 grams. The reactor was purged with nitrogen and pressurized to 135 psig with nitrogen. The reaction mixture was then heated to 150° C. while agitated over the course of two hours. Based on the amount of hydrogen generated during the reaction, conversion of diethanolamine to disodium iminodiacetic was approximately 1%.

Example 48

Various carbon-supported transition metal-containing catalysts and their supports were analyzed to determine their Langmuir surface areas. Catalysts and supports tested included: the carbon support described above in Example 22, a 1% FeCN/C catalyst prepared in accordance with Example 23, a 1% CoCN/C catalyst prepared in accordance with Example 27, a carbon support having a surface area of approximately 1600 $m^2$/g, and a 1% FeTPP/C catalyst prepared in accordance with Coleman et al., International Publication No. WO 03/068387 A1. The overall surface area, surface area attributed to pores having a diameter less than 20 Å (i.e., micropores), and surface area attributed to pores having a diameter greater than 20 Å (i.e., mesopores and micropores) were determined. The results of the surface area measurements are shown in Table 26.

TABLE 26

| Surface Area (SA) ($m^2$/g) | Example 22 Support | 1% FeCN/C | 1% CoCN/C | Example 48 support | 1.1% FeTPP/ C |
|---|---|---|---|---|---|
| Overall SA | 1584 | 1142 | 1263 | 1623 | 888 |
| Micropore SA | 1329 | 937 | 1051 | 1365 | 717 |
| Meso- & Macropore SA | 256 | 205 | 212 | 258 | 171 |

Figure 17:
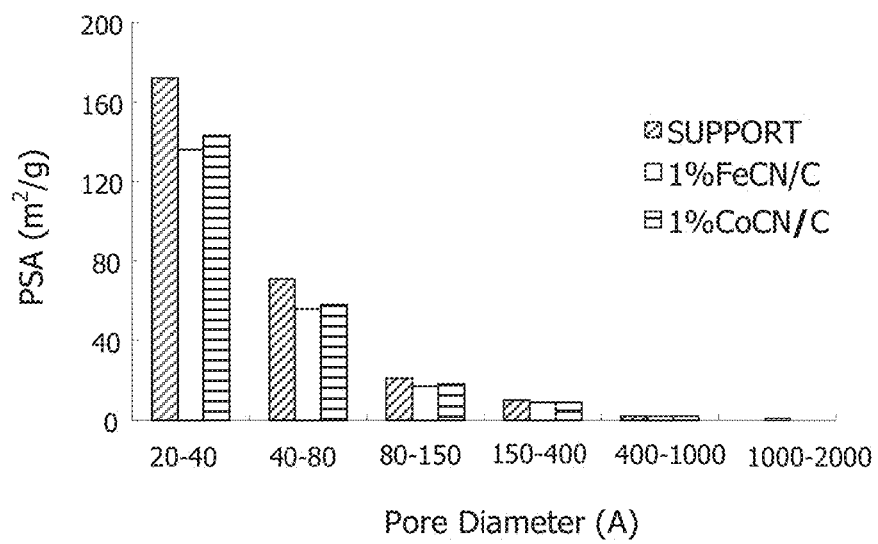
FIG. 17 shows a comparison of the pore surface area of various catalysts as described in Example 48.

FIG. 17 shows a comparison of the pore surface area of the of the 1% Fe, 1% Co catalysts, and the carbon support. FIG.

Figure 18:
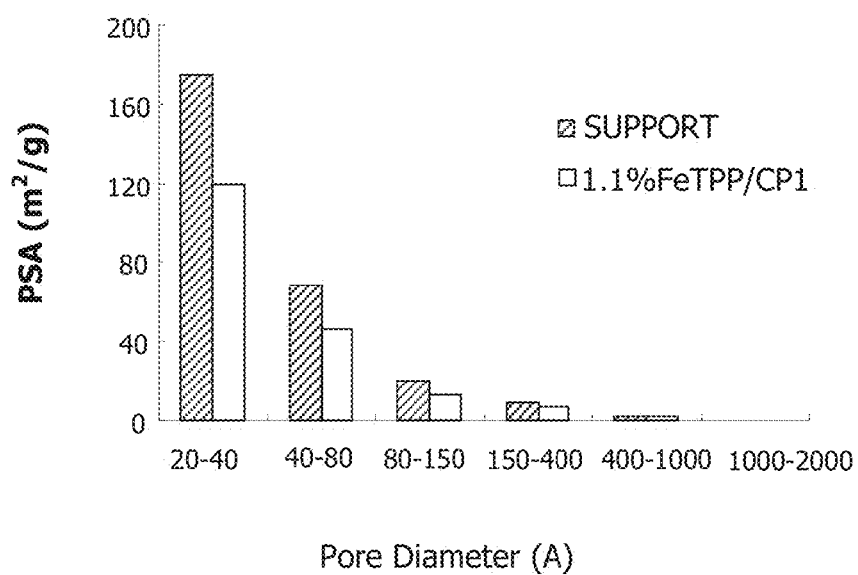
FIG. 18 shows a comparison of the pore surface area of various catalysts as described in Example 48.
Figure 19:
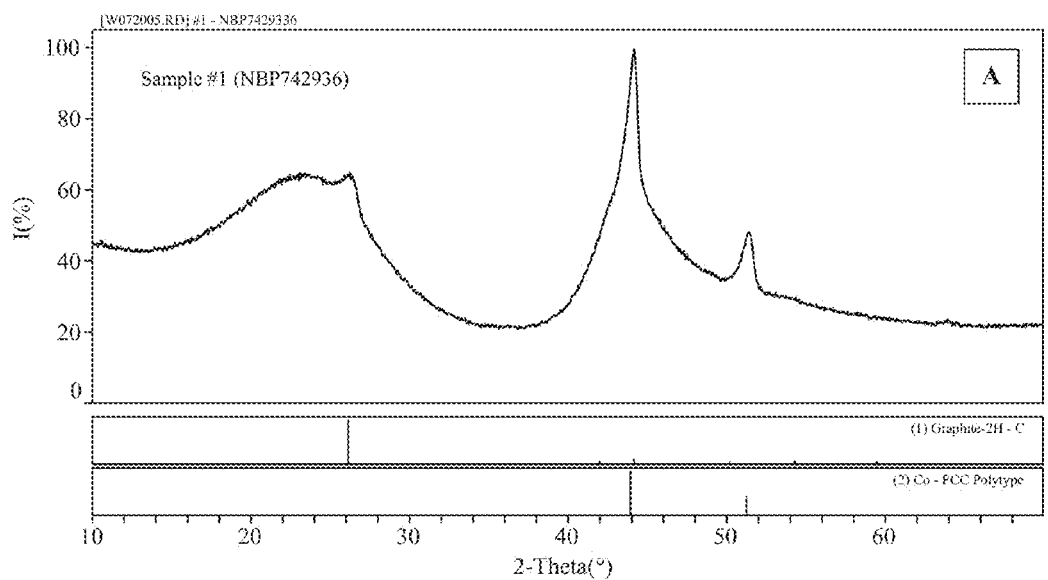
FIGS. 19-30 show X-ray diffraction (XRD) results for catalyst samples analyzed as described in Example 50.
Figure 20:
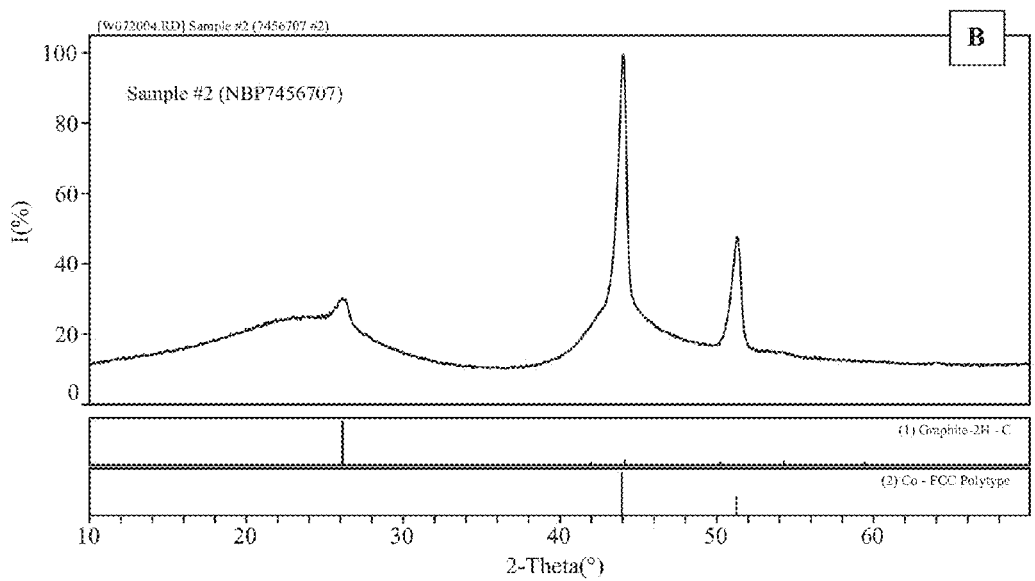
Figure 21:
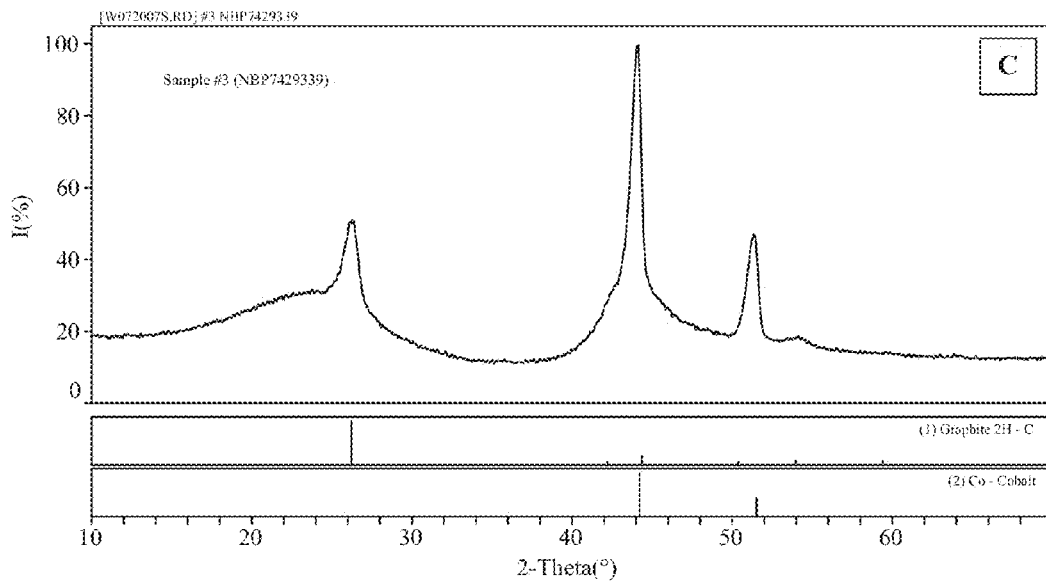
Figure 22:
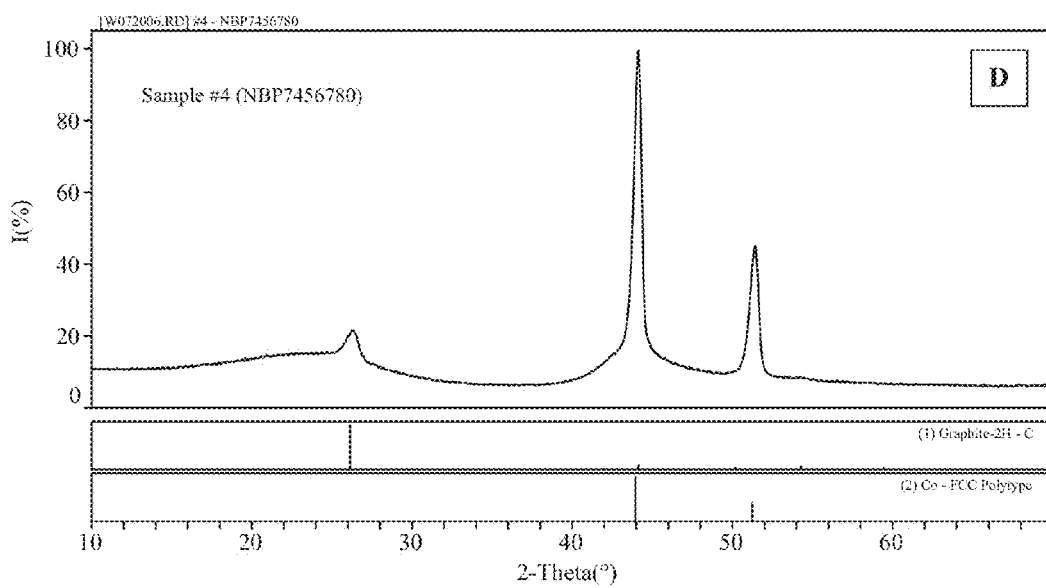
Figure 23:
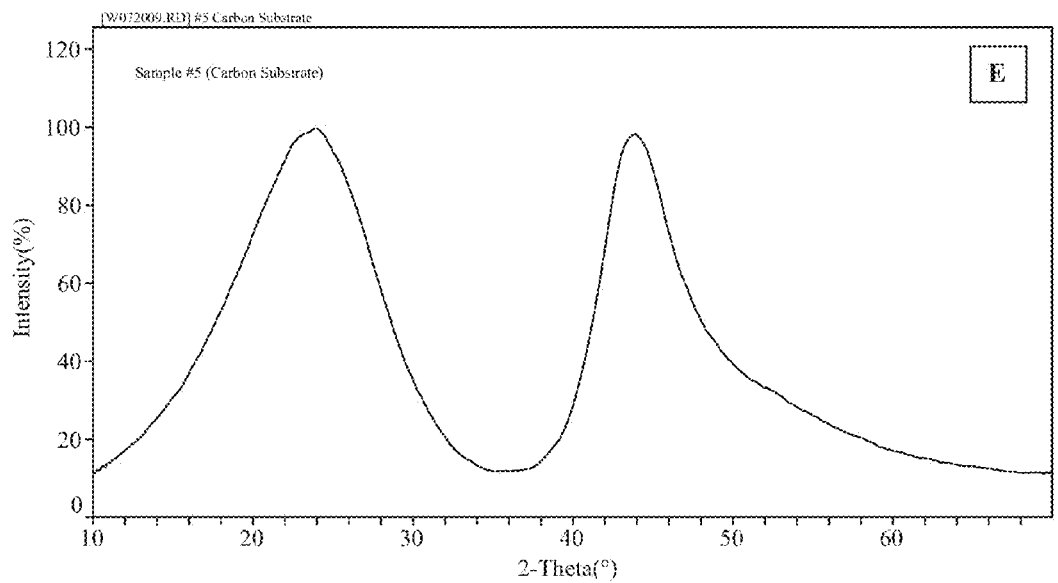
Figure 24:
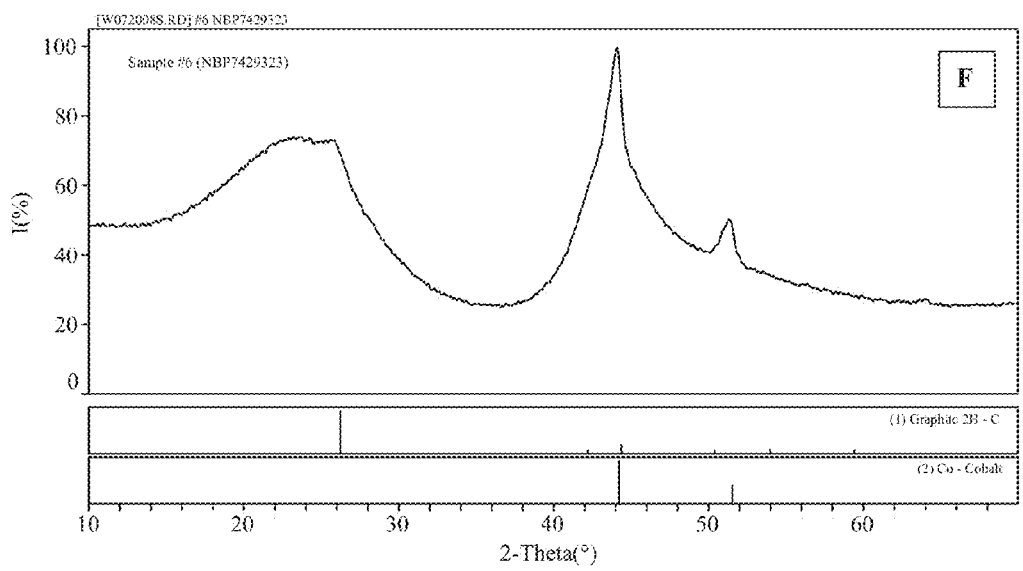
Figure 25:
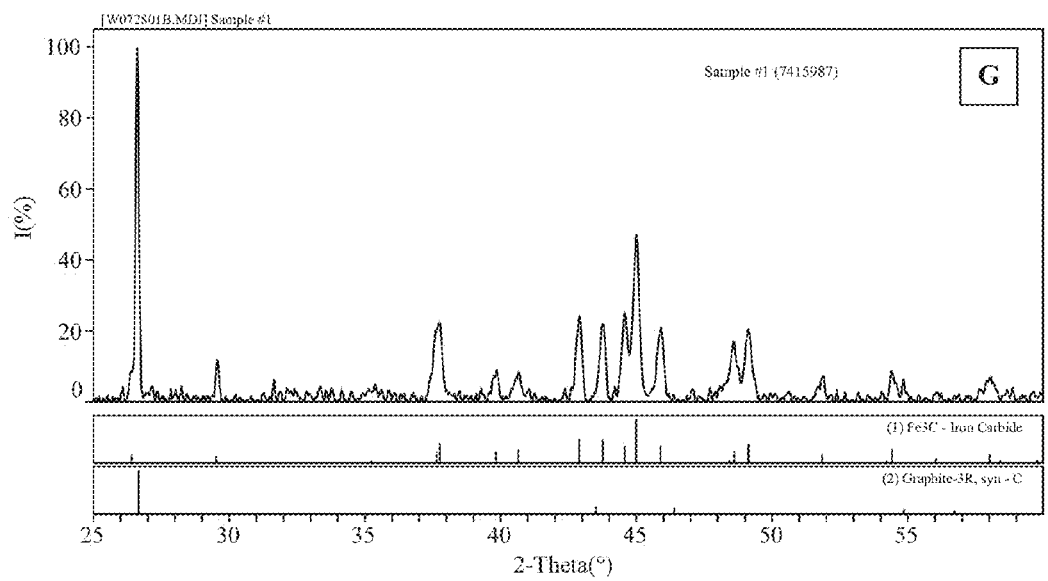
Figure 26:
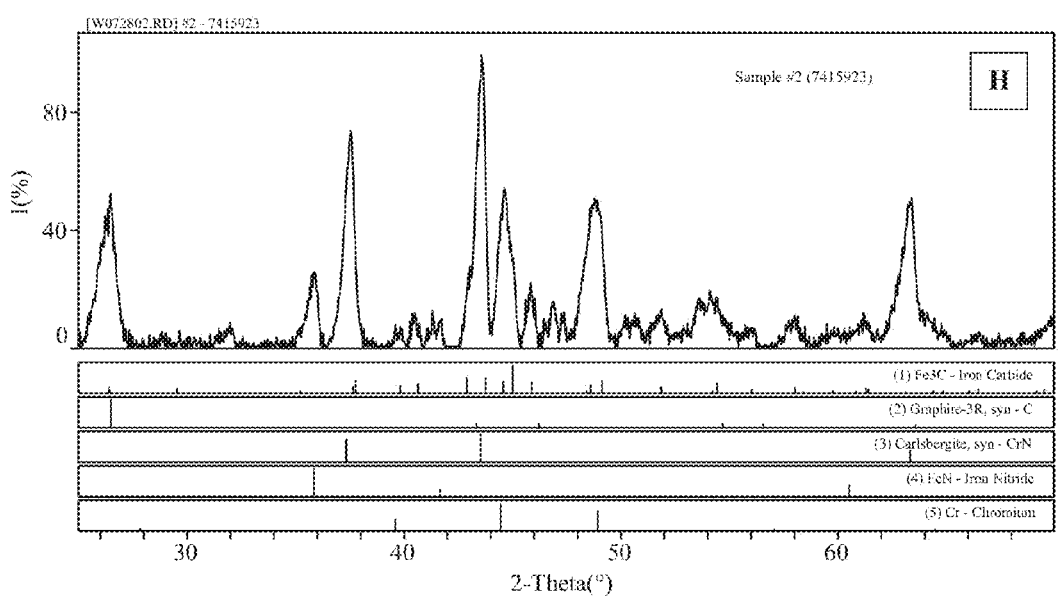

18 compares the pore surface area of the 1.1% FeTPP catalyst and its carbon support. As shown in FIG. 17, the 1% Fe catalyst has a surface area approximately 80% the total surface area of its carbon support while the 1% Co catalyst has a surface area approximately 72% the total surface area of the catalyst support. As shown in FIG. 18, the 1.1% FeTPP catalyst has a surface area approximately 55% of the total surface area of its carbon support.

Example 49

1% CoCN/C and 1.5% CoCN/C catalysts prepared as described in Example 28 were analyzed by Inductively Coupled Plasma (ICP) analysis to determine their nitrogen and transition metal content. The results are shown in Table 27.

TABLE 27

|  | Co (wt. %) | N (wt. %) | C + O + H (wt. %) |
|---|---|---|---|
| Example 22 support |  | <0.1% |  |
| 1% CoCN/C | 1.0 | 1.4 | 97.6 |
| 1.5% CoCN/C | 1.5 | 1.7 | 96.8 |

Example 50

This example details X-ray powder diffraction analysis (XRD) analysis of various catalysts prepared under different conditions. The catalysts were generally prepared in accordance with the procedure set forth above in Example 23, 27, 40, or 43 above. The samples and conditions for their preparation are described below in Table 28.

TABLE 28

| Catalyst Sample | Processing conditions |
|---|---|
| 1) 1.5% CoCN/C | $CH_3CN$ treated at 950° C. for 2 hours |
| 2) 5% CoCN/C | $CH_3CN$ treated at 950° C. for 2 hours |
| 3) 5% CoCN/C | $CH_3CN$ treated at 950° C. for 4 hours |
| 4) 10% CoCN/C | $CH_3CN$ treated at 950° C. for 2 hours |
| 5) Example 22 support | $CH_3CN$ treated at 950° C. for 2 hours |
| 6) 1% Co-phthalocyanine (PLCN) CN/C | Argon treated at 950° C. for 2 hours |
| 7) 1.1% FeTPP/C | Argon treated at 800° C. for 2 hours |
| 8) 1% FeCN/C | $CH_3CN$ treated at 950° C. for 2 hours |

The powder samples were analyzed by placing them directly onto a zero background holder and then placing them directly into a Philips PW 1800 Θ/Θ diffractometer using Cu radiation at 40 KV/30 mA and equipped with a diffracted beam monochromator to remove the flourscent radiation from the cobalt.

The resulting diffraction patterns for samples 1-8 are shown in FIGS. 19-26, respectively. The diffraction patterns for samples 1-4, and 6 (FIGS. 19-22, and 24) detected graphite and the face centered cubic (FCC) form of cobalt. Particle size analysis of the cobalt and graphite phases was performed through broadening of the diffraction lines which is sensitive to particles in the 100 Å to 2000 Å range. The results are summarized below in Table 29.

TABLE 29

|  | Particle Size (Å) | |
|---|---|---|
| Sample # | FCC cobalt | Graphite |
| 1 | 122 | 101 |
| 2 | 145 | 100 |
| 3 | 125 | 83 |
| 4 | 153 | 110 |
| 6 | 120 | 77 |

The diffraction patterns for sample 7 (FIG. 25) detected graphite and iron carbide ($Fe_3C$) Particle size analysis provided a particle size of the graphite of >1000 Å and approximately 505 Å. The diffraction patterns for sample 8 (FIG. 26) detected graphite, chromium nitride (CrN), iron nitide (FeN), chromium, and iron carbide ($Fe_3C$). Particle size analysis provided a particle size of graphite of approximately 124 Å, chromium nitride of approximately 183 Å, and iron nitride of approximately 210 Å.

Figure 27:
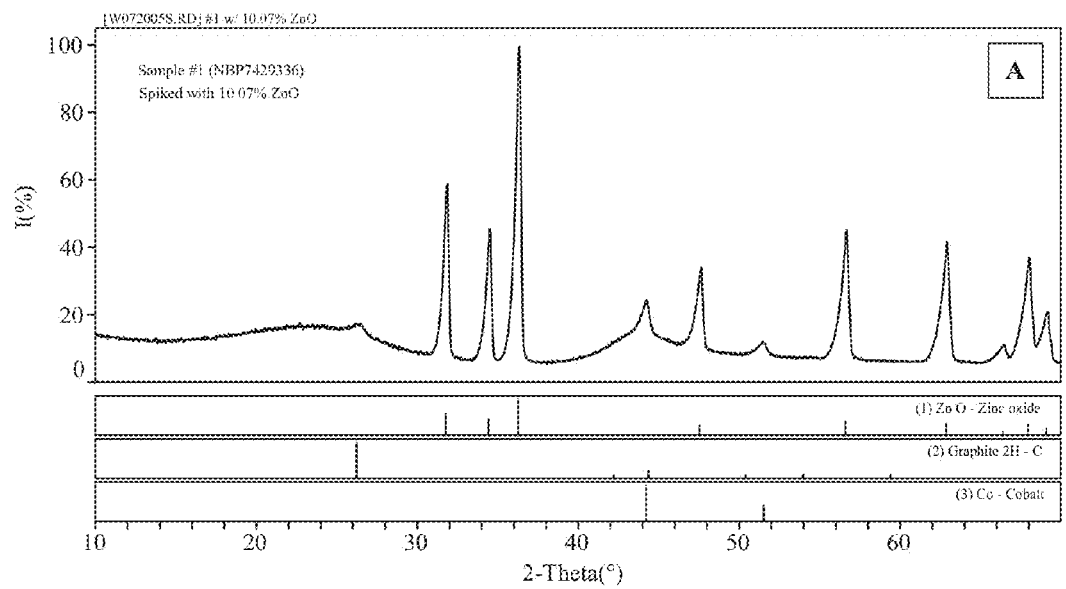
Figure 28:
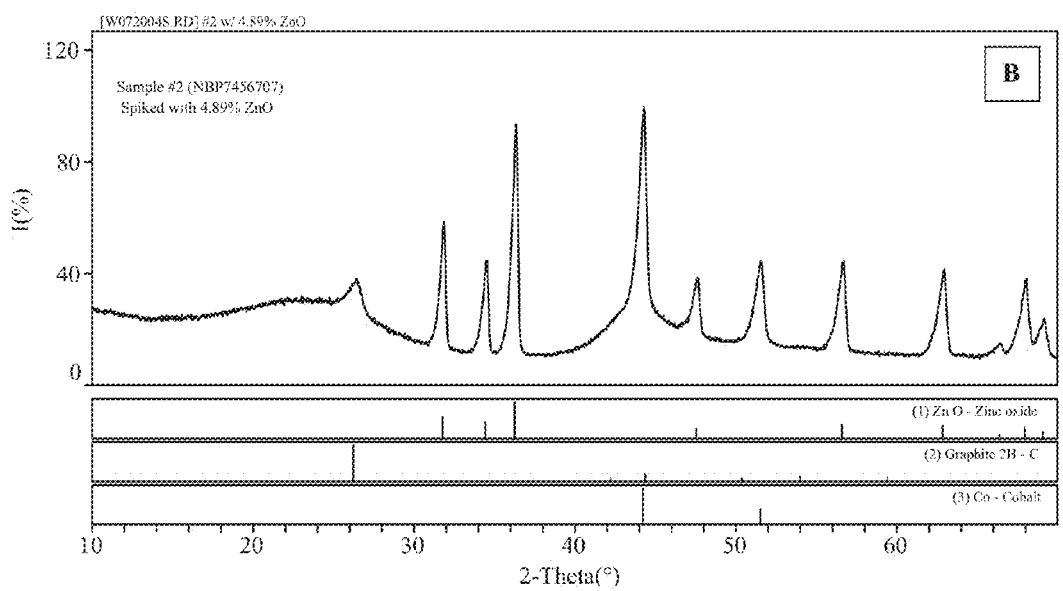

Quantitative analysis was carried out on Samples 1 and 2. The preferred internal standard was ZnO since it is well characterized and has no lines that overlap the peaks of interest. Approximately 100 mg of samples 1 and 2 were mixed with 10.7% ZnO (Sample 1) and 4.89% ZnO (Sample 2) and tested using the XRD procedure described above. The resulting diffraction for patterns for Samples 1 and 2 are provided in FIGS. 27 and 28, respectively.

Quantitative analysis was then carried out on Samples 1 and 2 using Rivetfeld refinement to determine the amount of each phase. The Rivetfeld refinement is a whole pattern-fitting program that computes a diffraction pattern based on first principles, compares it to the experimental pattern, computes an error between the two patterns, and then modifies the theoretical pattern until the residual error is minimized. In both cases, the Rivetfeld refinement gave loq residual errors in the 5-7% range. The results of the Rivetfeld refinement are set forth below in Table 30.

TABLE 30

|  | Weight Fractions (%) | |
|---|---|---|
| Sample # | Cobalt (FCC) | Graphite |
| 1 | 1.2 +/- 0.2% | 4.2 +/- 0.3% |
| 2 | 3.7 +/- 0.3% | 4.6 +/- 0.2% |

An estimate of the weight fractions of Samples 3 and 6 are provided in Table 31.

TABLE 31

|  | Weight Fractions (%) | |
|---|---|---|
| Sample # | Cobalt (FCC) | Graphite |
| 3 | 3.0% | 12.0% |
| 6 | 0.5% | 1.4% |

Figure 29:
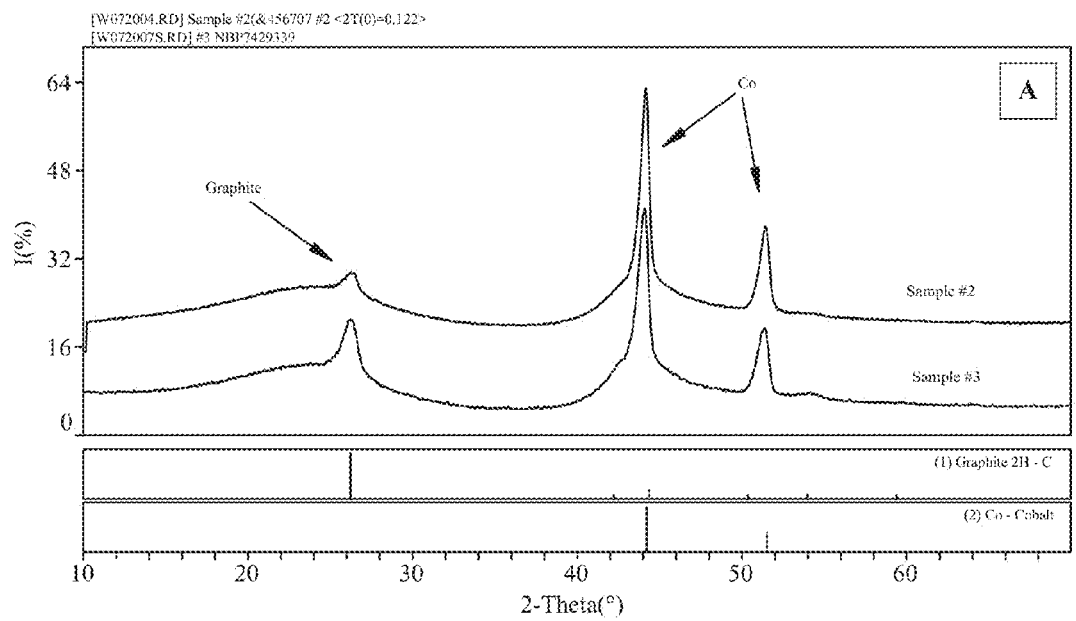
Figure 30:
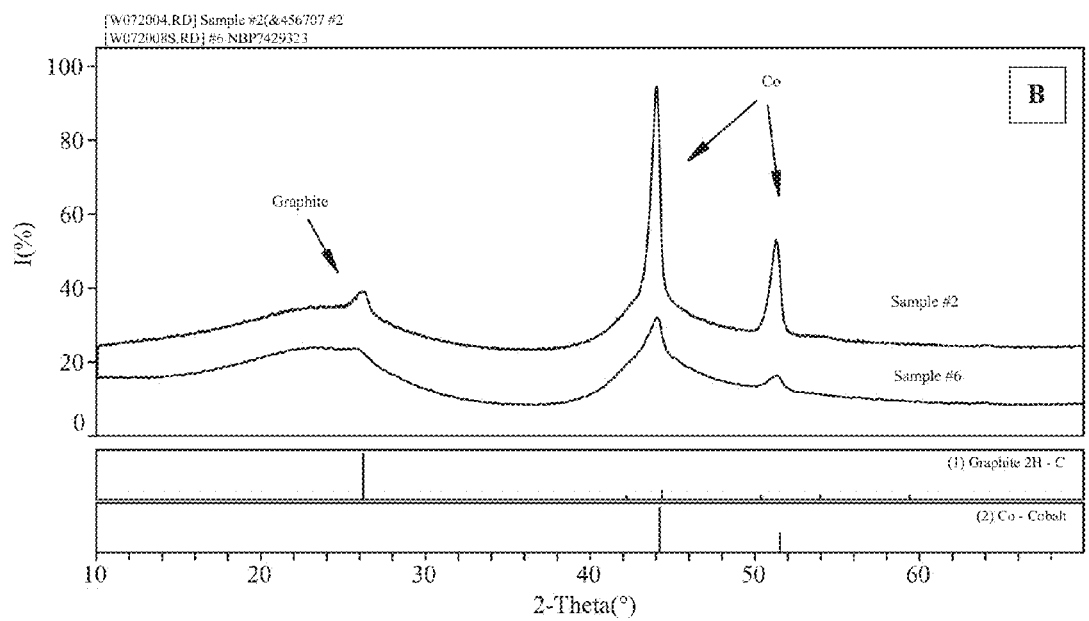

FIGS. 29 and 30 provide comparisons of the diffraction patterns of Samples 2 and 3, and Samples 3 and 6, respectively.

Example 51

This example details scanning electron microscopy (SEM) and transmission electron microscopy (TEM) analysis of Samples 1, 2, 4, 7, and 8 described above in Example 50. The SEM analysis was performed using a JEOL JSM 6460LV scanning electron microscope operated at 30 kV. The TEM characterizations were carried out using a JEOL 1200 EX TEM operated at 120 keV and/or JEOL 2000 EX TEM operated at 200 keV.

Figure 31:
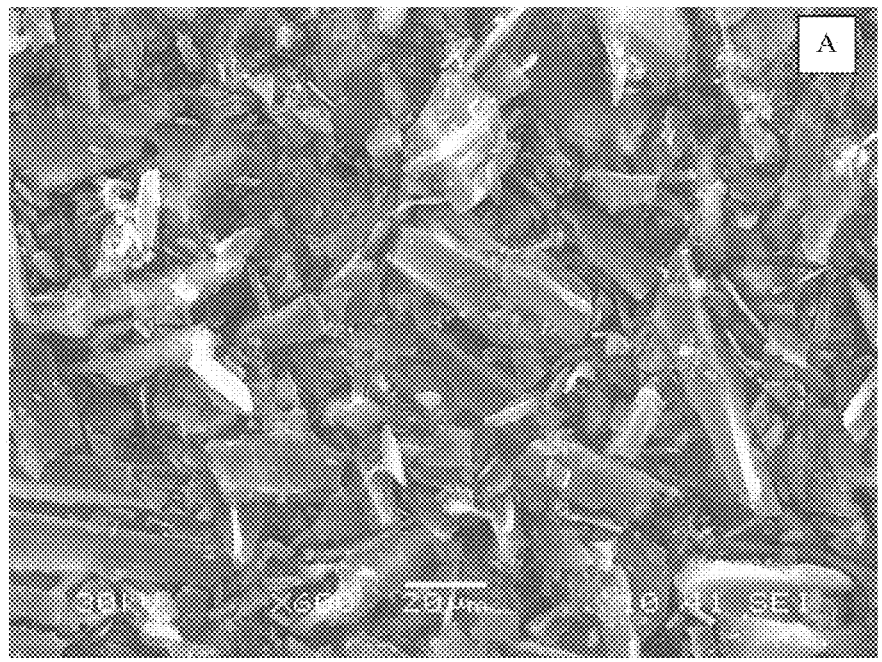
FIGS. 31-41 are SEM images of catalyst samples analyzed as described in Example 51.
Figure 32:
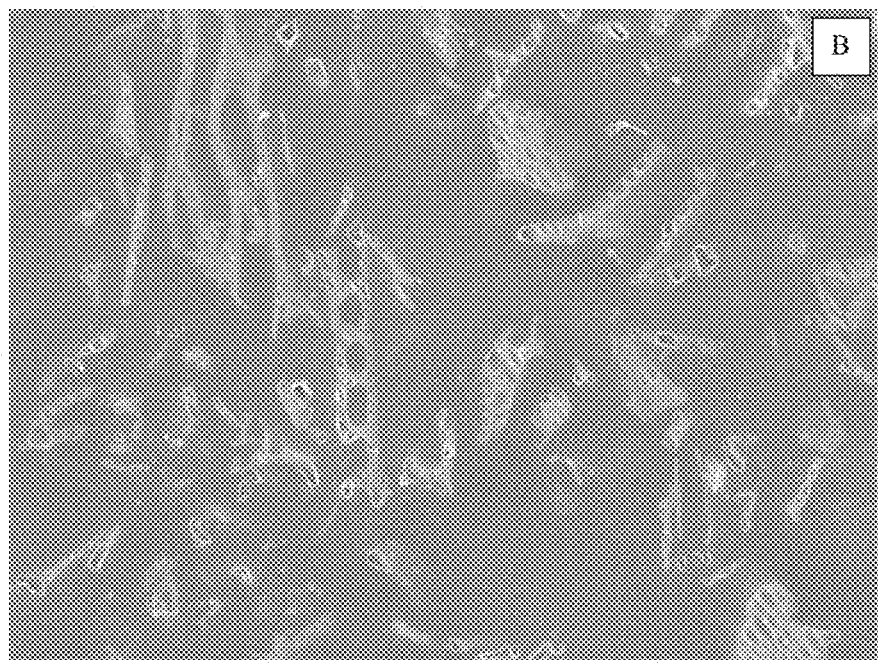
Figure 33:
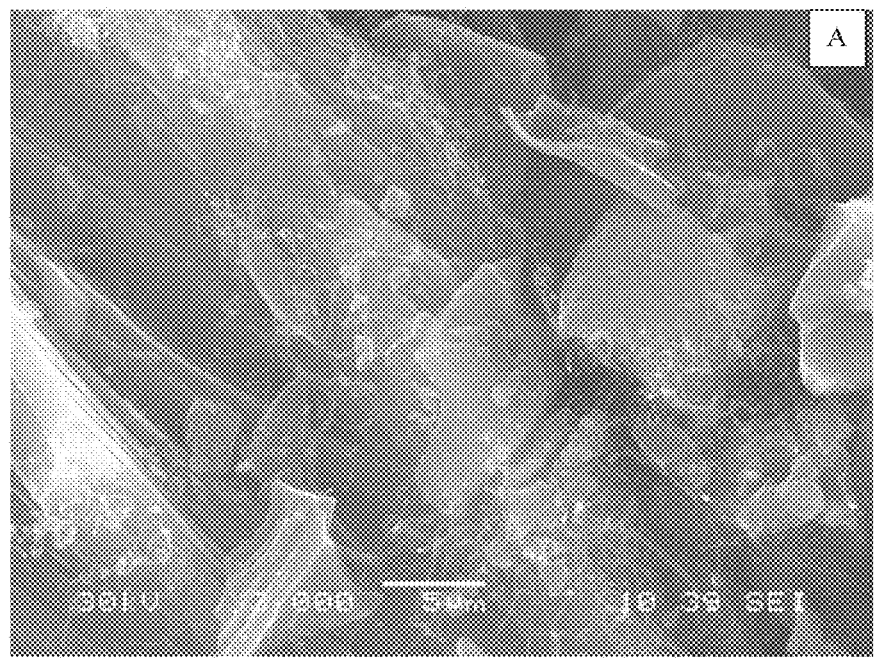
Figure 34:
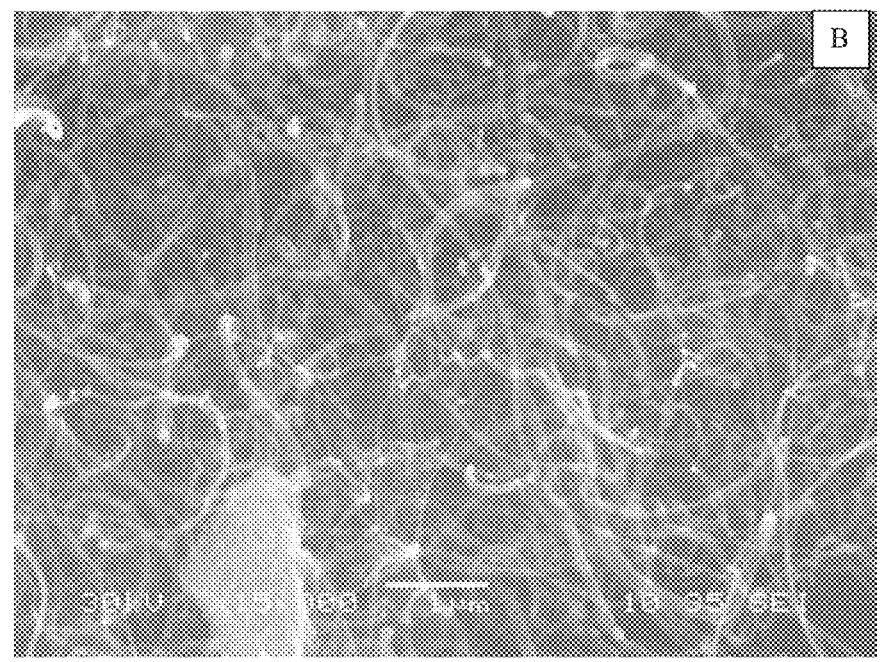
Figure 35:
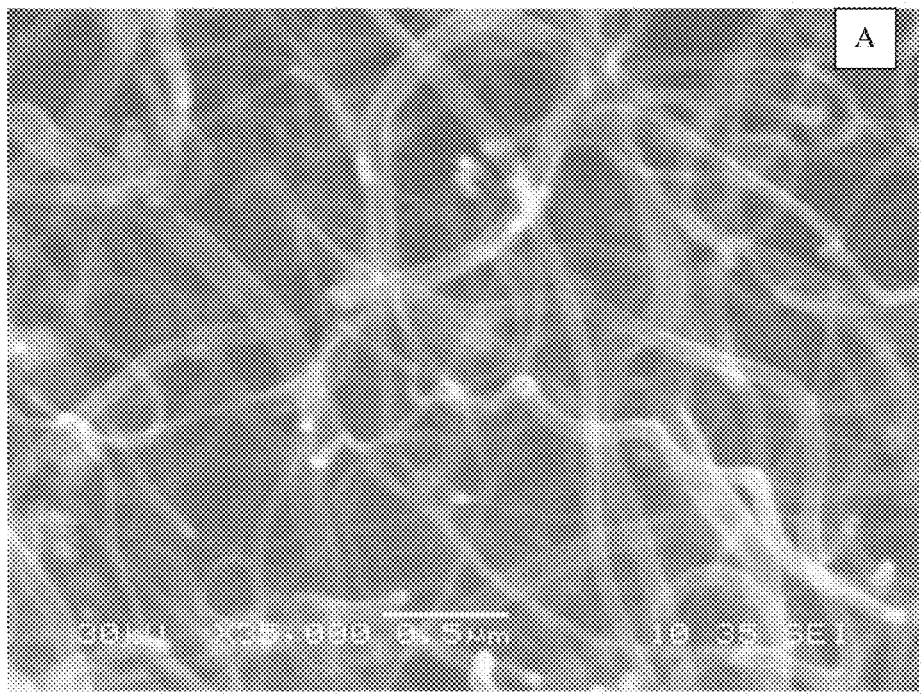
Figure 36:

FIGS. 31 and 32 are SEM images showing a view of the powder of Sample 1 and a cross-sectional view, respectively. FIGS. 33 and 34 are SEM images showing the distribution of carbon nanotubes on the surface of the carbon substrate and the morphology of the carbon nanotubes, respectively. FIGS. 35 and 36 are SEM images showing the carbon nanoutubes of the powder sample of Sample 1.

Figure 37:
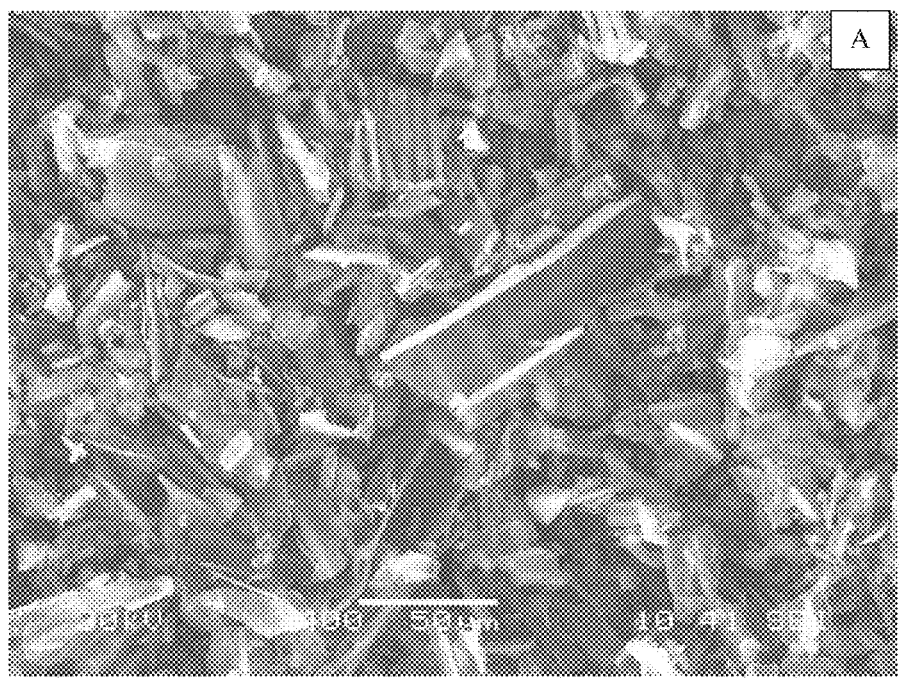
Figure 38:
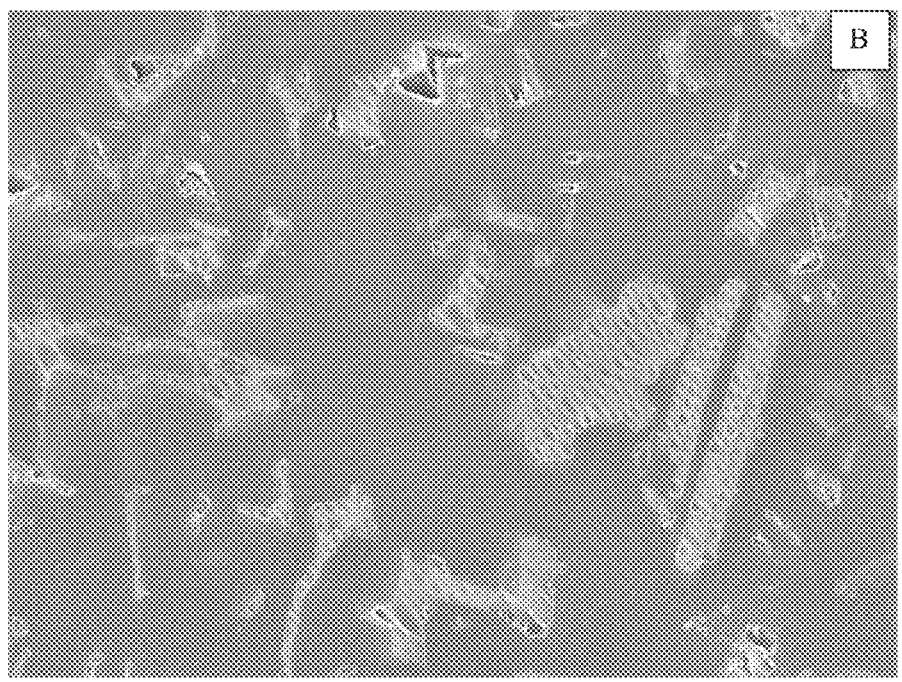
Figure 39:
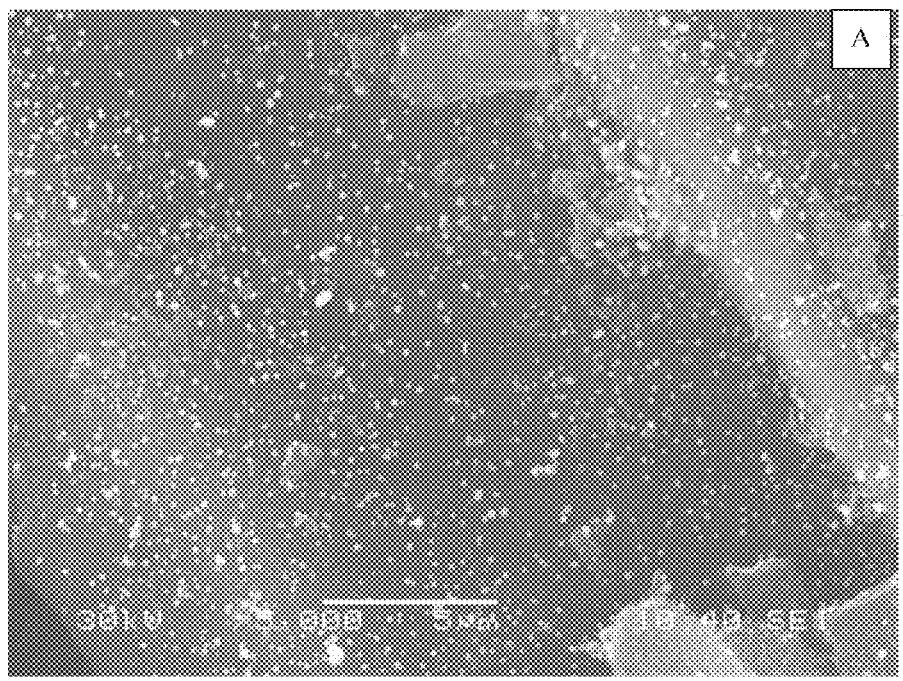
Figure 40:
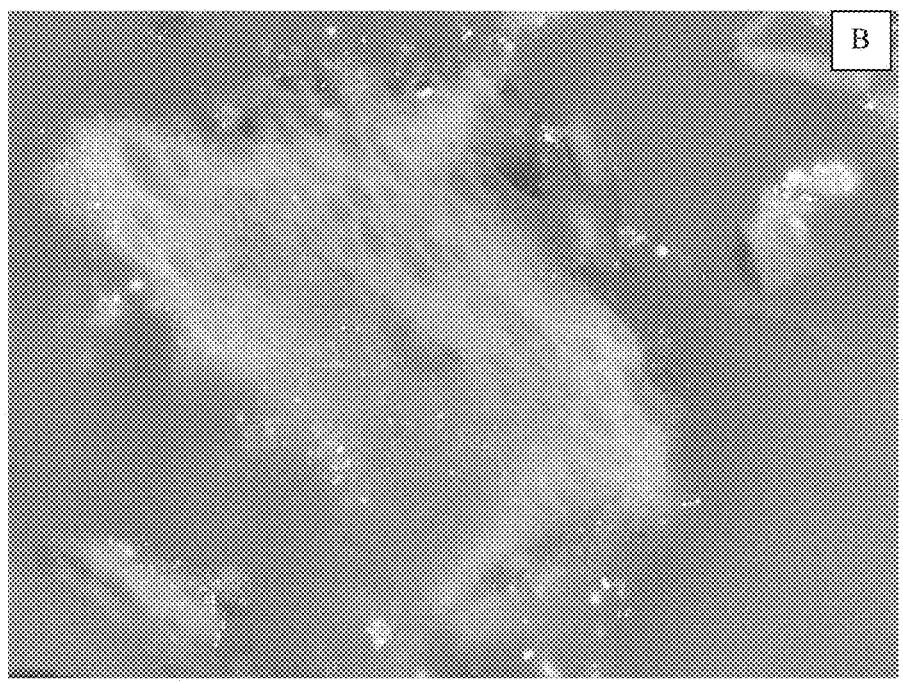
Figure 41:
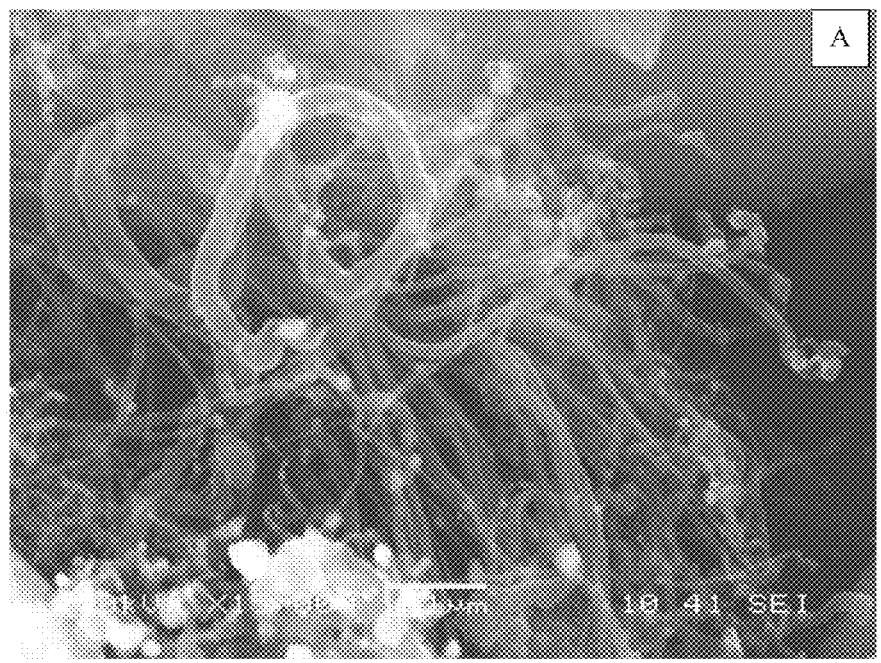
Figure 42:
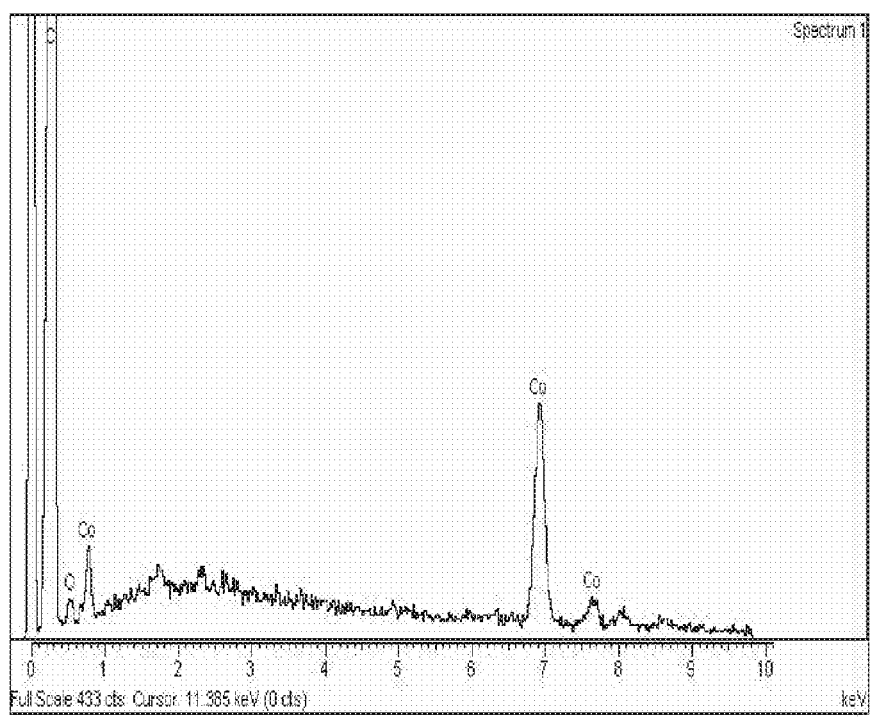
FIG. 42 is an Energy dispersive X-ray analysis spectroscopy (EDS) spectrum of a catalyst sample analyzed as described in Example 51.

FIGS. 37 and 38 are SEM images showing a view of the powder of Sample 2 and a cross-sectional view, respectively. FIGS. 39 and 40 are SEM images showing the distribution of the cobalt particles on the powder sample of Sample 2 and cross-sectional view, respectively. FIG. 41 is an SEM image showing the carbon nanotubes on the surface of the carbon support. FIG. 42 is an Energy dispersive X-ray analysis spectroscopy (EDS) spectrum of the powder sample of Sample 2. The EDS spectrum of Sample 2 was determined using an Oxford energy dispersive X-ray spectroscopy system.

Figure 43:
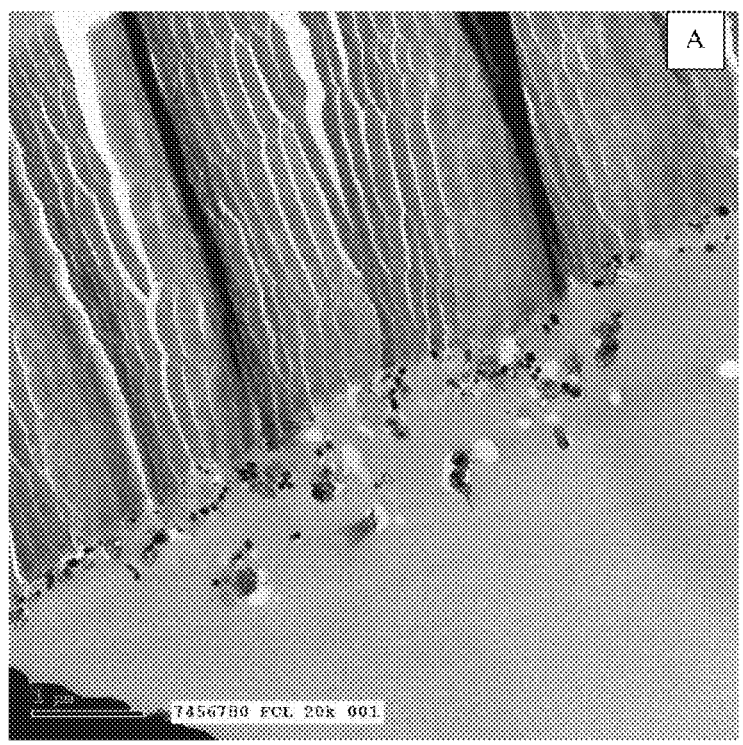
FIGS. 43 and 44 are TEM images of catalyst samples analyzed as described in Example 51.
Figure 44:
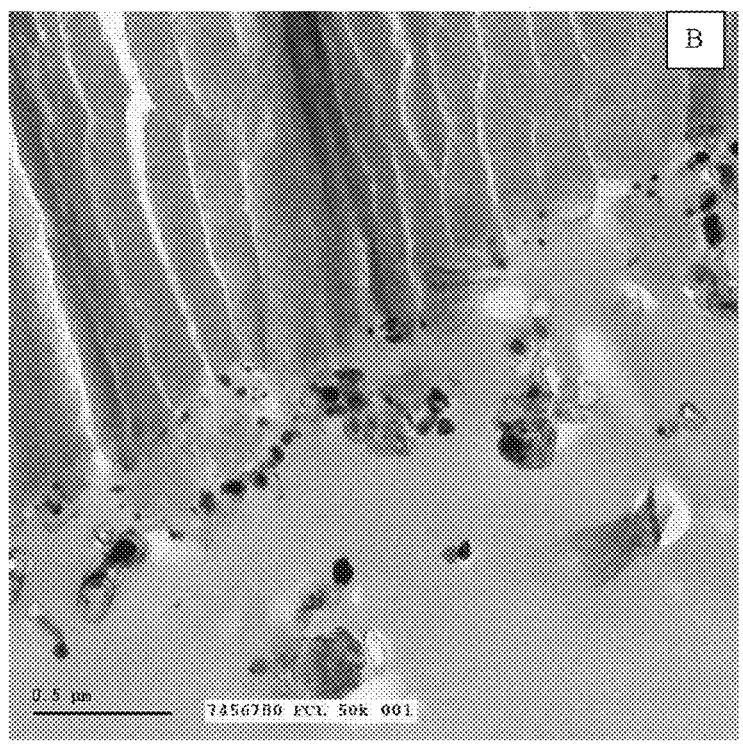

FIGS. 43 and 44 are TEM image images of Sample 4 at low and high magnification, respectively.

Figure 45:
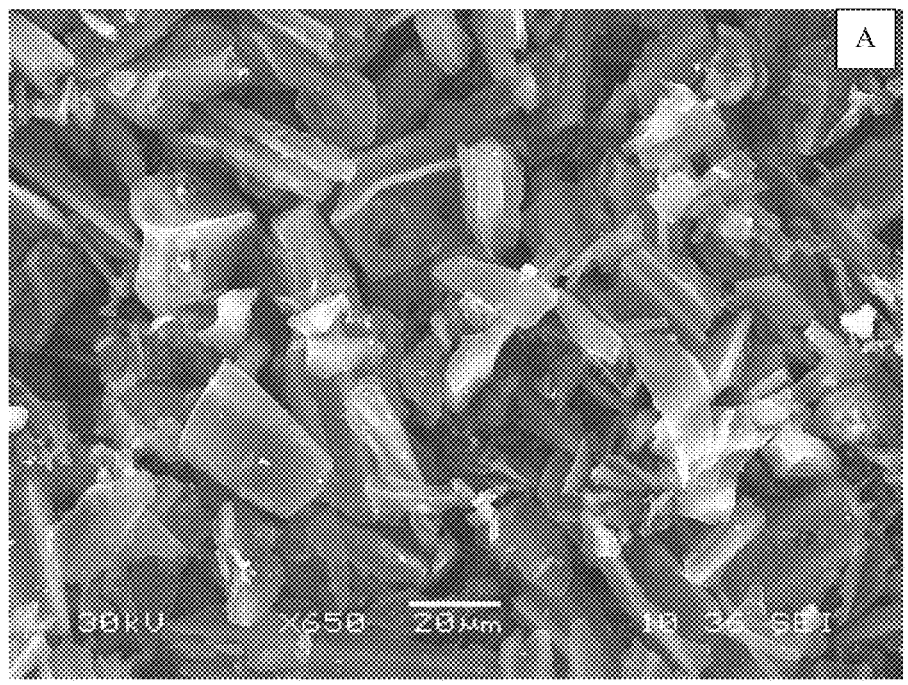
FIGS. 45 and 46 are SEM Images of catalyst samples analyzed as described in Example 51.
Figure 46:
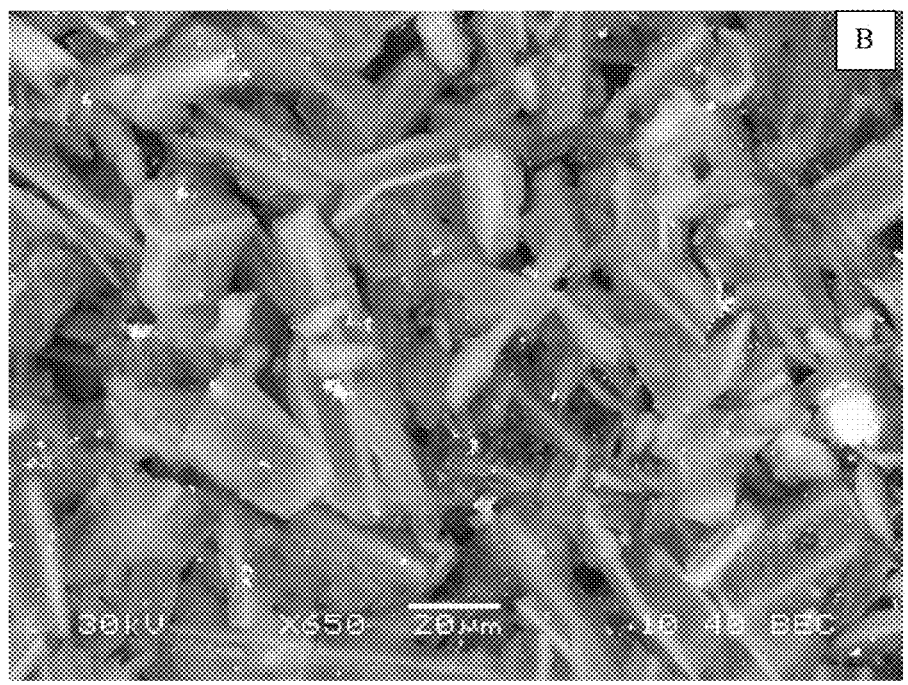

FIG. 45 is an SEM image of a powder sample of Sample 7. FIG. 46 is a backscattered electron image of the powder sample of Sample 7.

Figure 47:
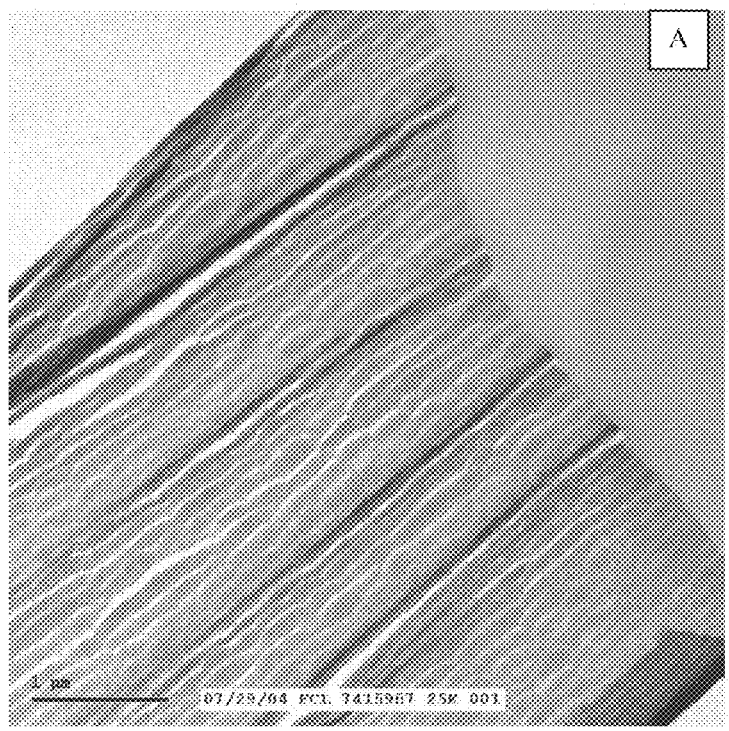
FIGS. 47 and 48 are TEM images of catalyst samples analyzed as described in Example 51.
Figure 48:
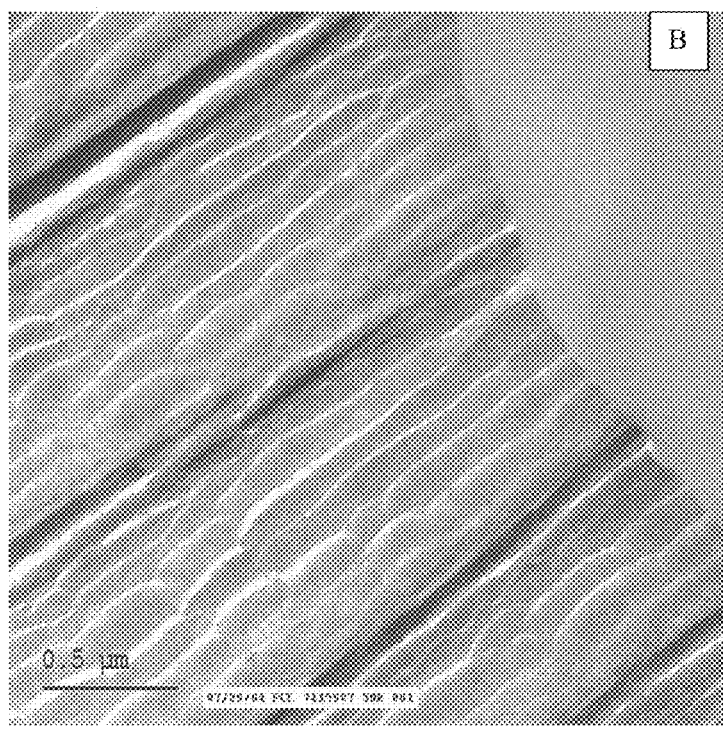

FIGS. 47 and 48 are TEM images showing a cross-sectional view of Sample 7.

Figure 49:
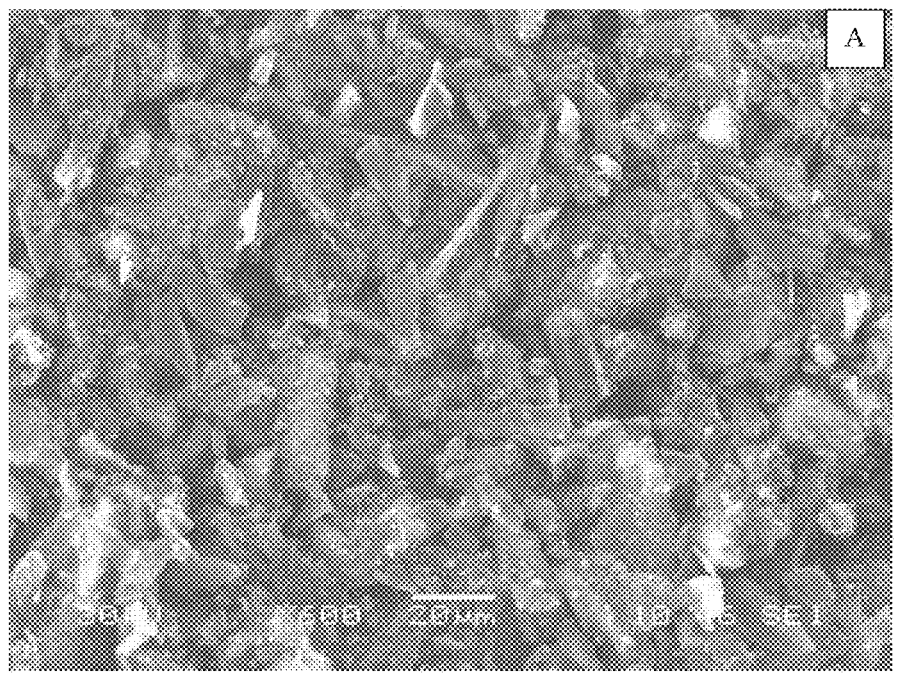
FIGS. 49-52 are SEM Images of catalyst samples analyzed as described in Example 51.
Figure 50:
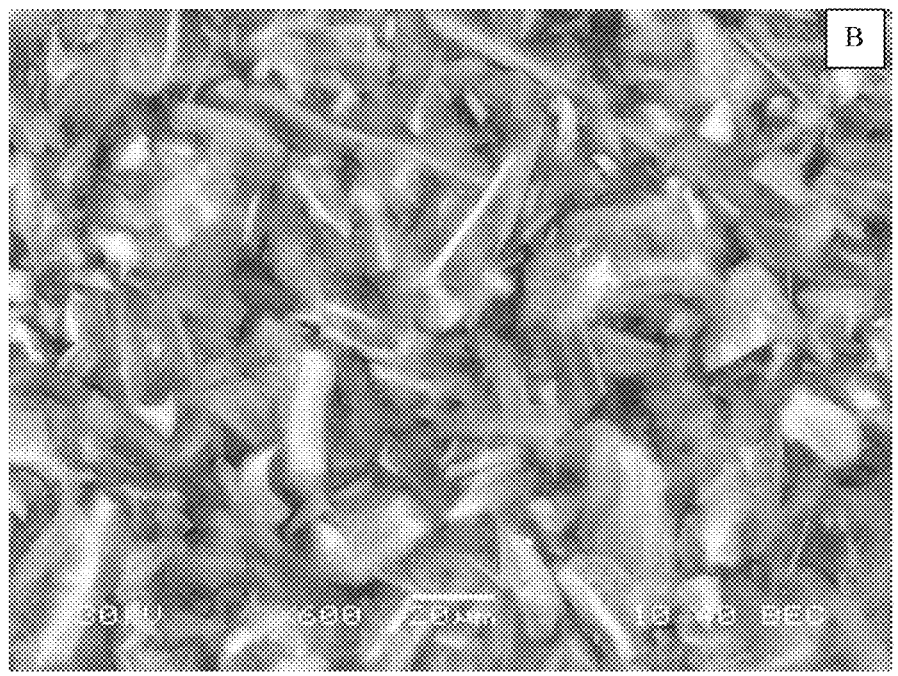
Figure 51:
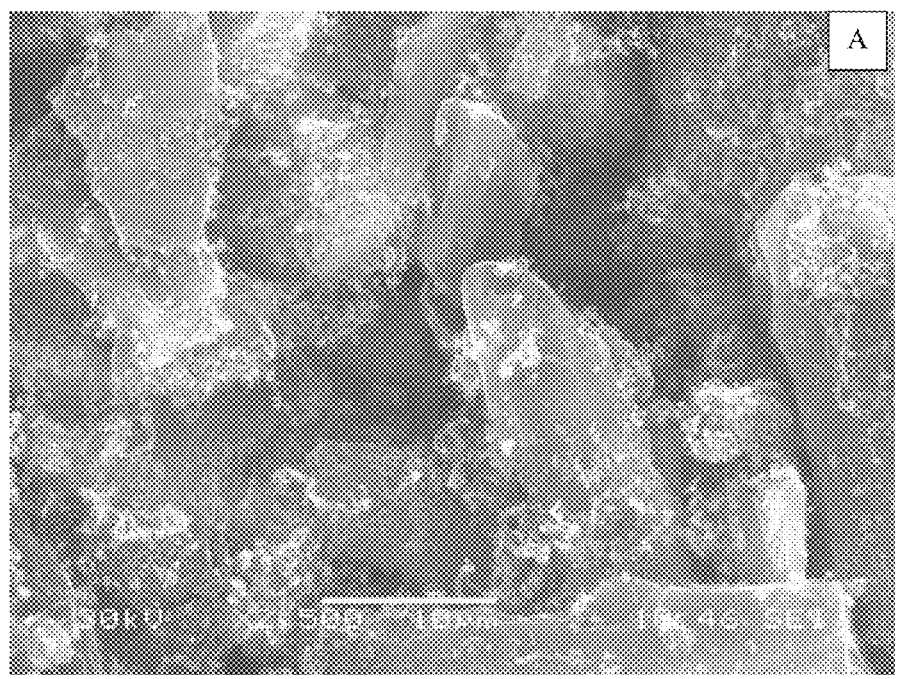
Figure 52:
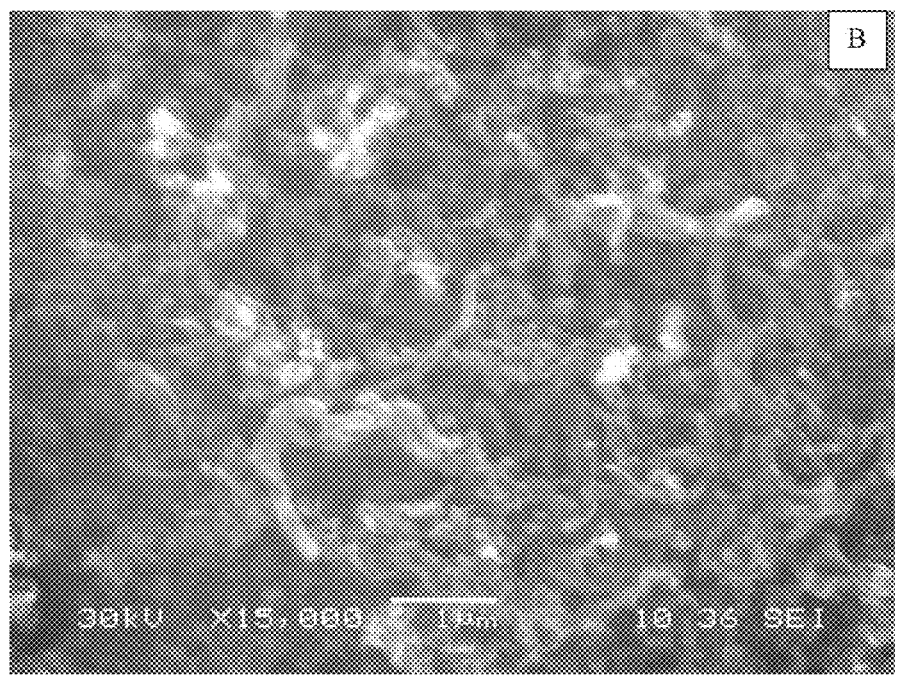
Figure 53:
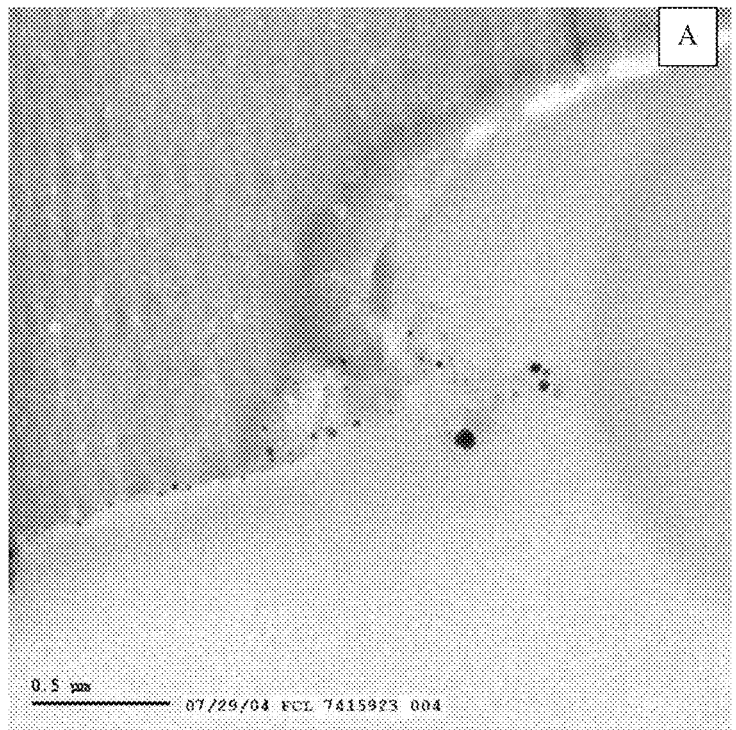
FIGS. 53 and 54 are TEM images of catalyst samples analyzed as described in Example 51.
Figure 54:
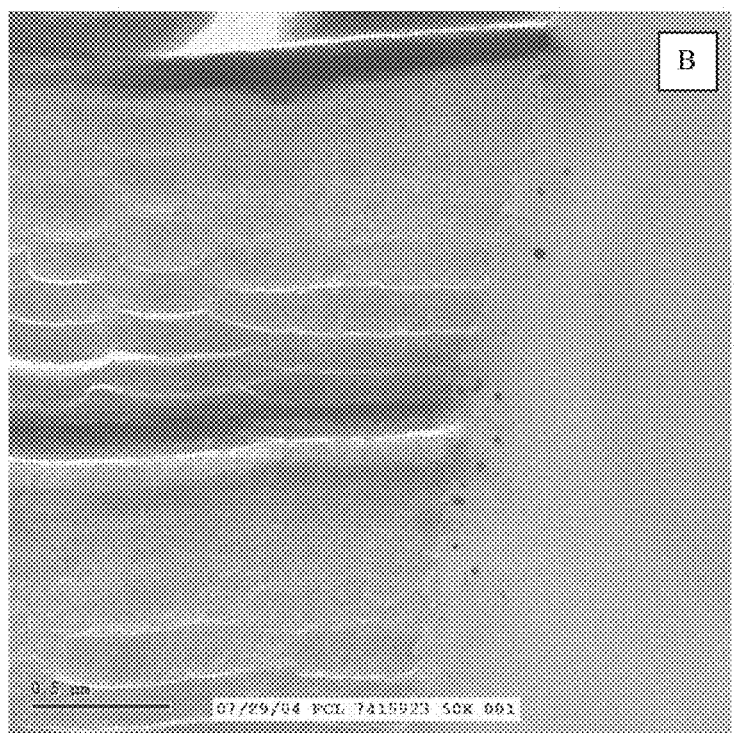

FIG. 49 is an SEM image of a powder sample of Sample 8. FIG. 50 is a backscattered electron image of the powder sample of Sample 8. FIGS. 51 and 52 are high magnification SEM images of powder sample 8 showing the growth of carbon nanotubes on the carbon support. FIGS. 53 and 54 are TEM images providing a cross-sectional view of Sample 8.

Example 52

This examples details X-ray Photoelectron Spectroscopy Analysis (XPS) of the samples described above in Example 50 (detailed in Table 28).

The XPS analysis was performed under the analytical conditions set forth in Table 32.

TABLE 32

| Instrument | Physical Electronics Quantum 2000 Scanning XPS |
|---|---|
| X-ray source | Monochromatic Al Kα |
| Analysis areas | 0.4 mm × 0.4 mm |
| Take-off angle | 45 degrees |
| Charge correction | C-C, C-H in C1s spectra set to 284.8 eV |
| Charge Neutralization | Low energy electron and ion floods |

Surface concentration results (area comment) for Samples 1-6 in terms of Atomic % and Weight % are detailed below in Tables 33 and 34, respectively.

TABLE 33

| Sample | C | N | O | Cl | Co |
|---|---|---|---|---|---|
| 1 | 97.3 | 1.2 | 1.0 | 0.07 | 0.42 |
| 2 | 97.9 | 0.2 | 1.3 | 0.09 | 0.52 |
| 3 | 97.9 | 0.7 | 0.9 | 0.05 | 0.41 |
| 4 | 97.7 | 0.4 | 1.2 | 0.08 | 0.73 |

TABLE 33-continued

| Sample | C | N | O | Cl | Co |
|---|---|---|---|---|---|
| 5 | 97.3 | 1.8 | 0.8 | 0.07 | — |
| 6 | 98.5 | 0.4 | 0.8 | 0.10 | 0.19 |

TABLE 34

| Sample | C | N | O | Cl | Co |
|---|---|---|---|---|---|
| 1 | 95.1 | 1.4 | 1.3 | 0.2 | 2.0 |
| 2 | 95.4 | 0.3 | 1.6 | 0.3 | 2.5 |
| 3 | 95.9 | 0.8 | 1.2 | 0.1 | 2.0 |
| 4 | 94.4 | 0.4 | 1.5 | 0.2 | 3.5 |
| 5 | 96.6 | 2.1 | 1.1 | 0.2 | — |
| 6 | 97.3 | 0.5 | 1.0 | 0.3 | 0.9 |

The cobalt 2p3 curve fit results for samples 1-4 and 6 are summarized below in Table 35.

TABLE 35

| Sample | % Co as metal | % Co as oxide |
|---|---|---|
| 1 | 27 | 73 |
| 2 | 47 | 53 |
| 3 | 35 | 65 |
| 4 | 35 | 65 |
| 6 | 61 | 39 |

Surface concentration results (area comment) for Samples 7-8 in terms of Atomic % and Weight % are detailed below in Tables 36 and 37, respectively.

TABLE 36

| Sample | C | N | O | Na | Cl | Fe |
|---|---|---|---|---|---|---|
| 7 | 97.6 | 0.7 | 1.5 | 0.0 | 0.1 | 0.2 |
| 8 | 95.2 | 0.6 | 2.6 | 0.7 | 0.2 | 0.8 |

TABLE 37

| Sample | C | N | O | Na | Cl | Fe |
|---|---|---|---|---|---|---|
| 7 | 96.2 | 0.7 | 2.0 | 0.0 | 0.3 | 0.7 |
| 8 | 90.8 | 0.6 | 3.3 | 1.3 | 0.6 | 3.3 |

The iron curve fit results (% of Fe) for samples 7-8 are summarized below in Table 38.

TABLE 38

| Sample | % Fe as metal | % Fe as oxide/hydroxide |
|---|---|---|
| 7 | 7 | 93 |
| 8 | 43 | 57 |

Figure 55:
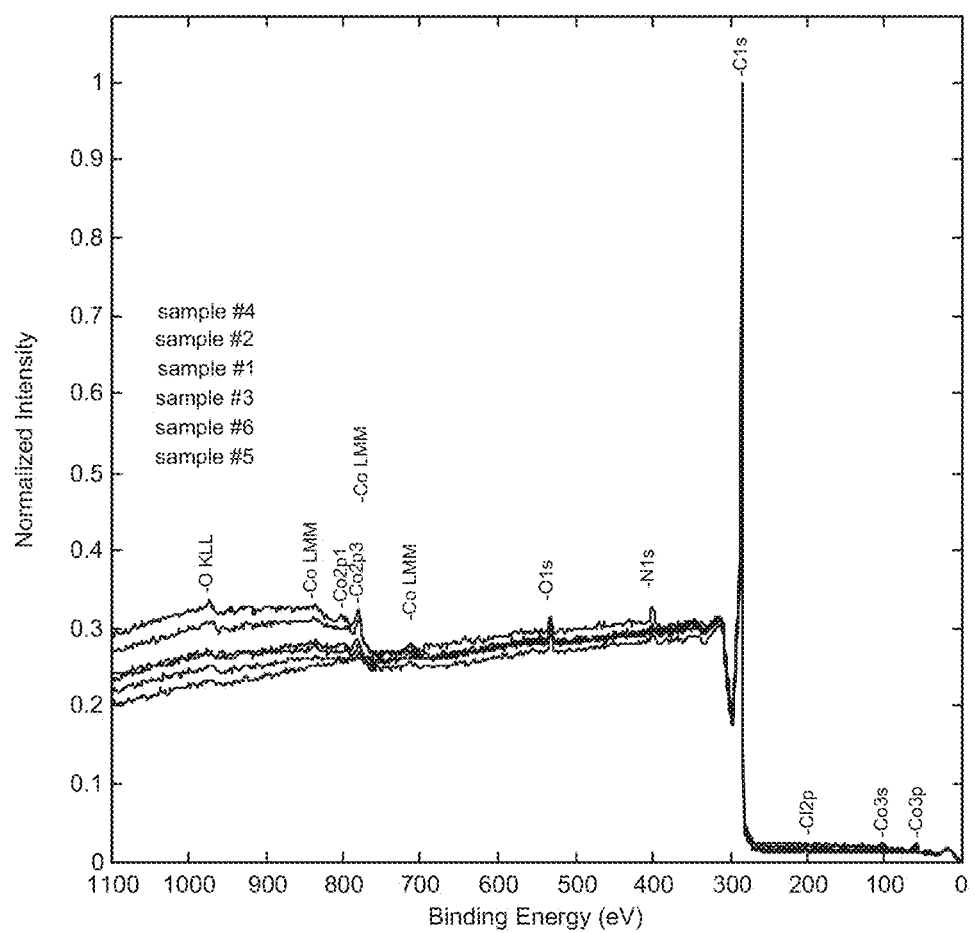
FIGS. 55 and 56 are X-ray Photoelectron Spectroscopy (XPS) results for samples analyzed as described in Example 52.
Figure 56:
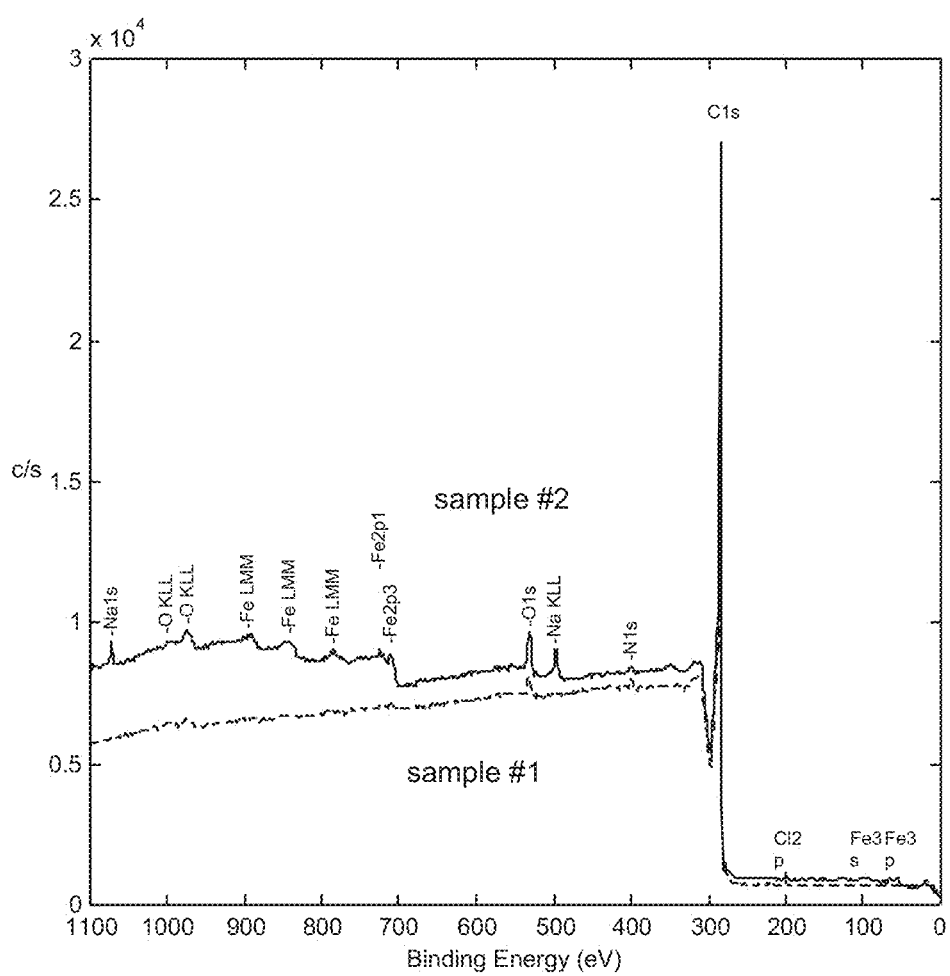

FIG. 54 is the XPS spectra for samples 1-6. FIG. 55 shows the XPS spectra for samples 7 and 8.

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

What is claimed is:

1. An oxidation catalyst, the catalyst comprising a particulate carbon support having formed thereon a transition metal composition comprising a transition metal and nitrogen, wherein:
   the transition metal composition comprises a transition metal nitride, transition metal carbide-nitride, or a combination thereof;
   the total Langmuir surface area of the catalyst is at least about 1000 $m^2/g$;
   the transition metal is selected from the group consisting of iron, cobalt, and combinations thereof;
   the transition metal constitutes from about 0.5 to about 10% by weight of the catalyst; and
   the oxidation catalyst further comprises carbon nanotubes at the surface of the carbon support.

2. The catalyst of claim 1 wherein the transition metal composition comprises a transition metal nitride.

3. The catalyst of claim 1 wherein the transition metal composition comprises a transition metal carbide-nitride.

4. The catalyst of claim 1 wherein the transition metal composition comprises a transition metal nitride and a transition metal carbide-nitride.

5. The catalyst of claim 1 wherein the total Langmuir surface area of the catalyst is at least about 1100 $m^2/g$.

6. The catalyst of claim 1 wherein the total Langmuir surface area of the catalyst is at least about 1200 $m^2/g$.

7. The catalyst of claim 1 wherein the total Langmuir surface area of the catalyst is from about 1000 $m^2/g$ to about 1400 $m^2/g$.

8. The catalyst of claim 1 wherein the total Langmuir surface area of the catalyst is from about 1100 $m^2/g$ to about 1400 $m^2/g$.

9. The catalyst of claim 1 wherein the total Langmuir surface area of the catalyst is from about 1200 $m^2/g$ to about 1400 $m^2/g$.

10. The catalyst of claim 1 wherein the carbon nanotubes contain a portion of the transition metal of the transition metal composition.

11. The catalyst of claim 1 wherein the carbon nanotubes contain a portion of the nitrogen of the transition metal composition.

12. The catalyst of claim 1 wherein the catalyst is substantially devoid of a noble metal active phase.

13. An oxidation catalyst, the catalyst comprising a particulate carbon support having formed thereon a transition metal composition comprising a transition metal and nitrogen, wherein:
    the total Langmuir surface area of the catalyst is at least about 1000 $m^2/g$;
    the transition metal is selected from the group consisting of iron, cobalt, and combinations thereof;
    the transition metal constitutes from about 0.5 to about 10% by weight of the catalyst;
    the oxidation catalyst further comprises carbon nanotubes at the surface of the carbon support; and
    at least about 40% by weight of the transition metal is present in a non-zero oxidation state.

14. The catalyst of claim 13 wherein the total Langmuir surface area of the catalyst is at least about 1100 $m^2/g$.

15. The catalyst of claim 13 wherein the total Langmuir surface area of the catalyst is at least about 1200 $m^2/g$.

16. The catalyst of claim 13 wherein the total Langmuir surface area of the catalyst is from about 1000 $m^2/g$ to about 1400 $m^2/g$.

17. The catalyst of claim 16 wherein the total Langmuir surface area of the catalyst is from about 1100 $m^2/g$ to about 1400 $m^2/g$.

18. The catalyst of claim 13 wherein the total Langmuir surface area of the catalyst is from about 1200 $m^2/g$ to about 1400 $m^2/g$.

19. The catalyst of claim 13 wherein the carbon nanotubes contain a portion of the transition metal of the transition metal composition.

20. The catalyst of claim 13 wherein the carbon nanotubes contain a portion of the nitrogen of the transition metal composition.

21. The catalyst of claim 13 wherein the catalyst is substantially devoid of a noble metal active phase.

* * * * *